US008362221B2

(12) United States Patent
Berka et al.

(10) Patent No.: US 8,362,221 B2
(45) Date of Patent: Jan. 29, 2013

(54) METHODS FOR MONITORING MULTIPLE GENE EXPRESSION

(75) Inventors: Randy M. Berka, Davis, CA (US); Ib Groth Clausen, Hillerød (DK); Alexandre Bolotine, Vandoeuvre (FR); Alexei Sorokine, Gif sur Yvette (FR); Alla Lapidus, Walnut Creek, CA (US)

(73) Assignees: Novozymes, Inc., Davis, CA (US); Novozymes A/S, Bagsvaerd (DK)

( * ) Notice: Subject to any disclaimer, the term of this patent is extended or adjusted under 35 U.S.C. 154(b) by 0 days.

(21) Appl. No.: 13/421,682

(22) Filed: Mar. 15, 2012

(65) Prior Publication Data

US 2012/0171749 A1 Jul. 5, 2012

Related U.S. Application Data

(60) Continuation of application No. 12/753,000, filed on Apr. 1, 2010, now Pat. No. 8,168,773, which is a division of application No. 11/203,606, filed on Aug. 12, 2005, now Pat. No. 7,691,574, which is a division of application No. 09/974,300, filed on Oct. 5, 2001, now Pat. No. 7,018,794, which is a continuation-in-part of application No. 09/680,598, filed on Oct. 6, 2000, now abandoned.

(60) Provisional application No. 60/279,526, filed on Mar. 27, 2001.

(51) Int. Cl.
*C07H 21/02* (2006.01)
(52) U.S. Cl. ...................................................... 536/23.1
(58) Field of Classification Search .................. None
See application file for complete search history.

(56) References Cited

U.S. PATENT DOCUMENTS

| 5,807,522 | A | 9/1998 | Brown et al. |
| 7,018,794 | B2 | 3/2006 | Berka et al. |
| 7,691,574 | B2 | 4/2010 | Berka et al. |
| 8,168,773 | B2 | 5/2012 | Berka et al. |
| 2001/0053519 | A1 | 12/2001 | Fodor et al. |

FOREIGN PATENT DOCUMENTS

| DE | 10 2004 030 938 A1 | 1/2006 |
| EP | 0805205 A1 | 5/1996 |
| EP | 0786519 A2 | 1/1997 |

OTHER PUBLICATIONS

Richards, F.M., "Protein stability: still an unsolved problem," CMLS, Cell. mol. life. sci. (1997), vol. 53, pp. 790-802.*
Fawcett, 2000, PNAS 97(14), 8063-8068.
Hoffmann et al, 1991, Genbank Access No. X91819.
Maghnouj, 1998, J Bacteriol, 180(24), 6468-6475.
Watson et al., "Technology for microarray analysis of gene expression" 1998, Current Opinion in Biotechnology 9: 609-614.
Chu et al., The Transcriptional Program of Sporulation in Budding Yeast, 1998, Science 282: 699-705.
Ruan et al., Towards *Arabidopsis* genome analysis: monitoring expression profiles of 1400 genes using cDNA microarrays, 1998, The Plant Journal 15: 821-833.
Iyer et al., The Transcriptional Progam in the Response of Human Fibroblasts to Serum, 1999, Science 283: 83-87.
Hayward et al., Shotgun DNA microarrays and stage-specific gene expression in *Plasmodium falciparum* malaria, 2000, Molecular Microbiology 35: 6-14.
Ye et al., "Global gene expression profiles of *Bacillus subtilis* grown under anaerobic conditions," Journal of Bacteriology, v. 182, No. 16, Aug. 2000, pp. 4458-4465.
Waldeck et al., "Isolation and molecular characterization of chitinase-deficient *Bacillus licheniformis* strains capable of deproteinization of shrimp shell waste to obtain highly viscous chitin," Applied and Environmental Microbiology, v. 72, No. 12, Dec. 2006, pp. 7879-7885.
Frank et al, 1996, Biosis Access No. A27094.
Attwood et al, 2000, Science, V. 290, Issue 5491, 471-473.
Bork et al, 1998, J. Mol. Biol., 288, 707-725.
Derisi et al., 1997, Science, vol. 278, 680-686.

* cited by examiner

*Primary Examiner* — Young J Kim
(74) *Attorney, Agent, or Firm* — Robert L. Stames; Eric J. Fechter

(57) ABSTRACT

The present invention relates to methods for monitoring differential expression of a plurality of genes in a first *Bacillus* cell relative to expression of the same genes in one or more second *Bacillus* cells using microarrays containing *Bacillus* genomic sequenced tags. The present invention also relates to computer readable media and computer-based systems. The present invention further relates to substrates containing an array of *Bacillus licheniformis* or *Bacillus clausii* GSTs.

13 Claims, 1 Drawing Sheet

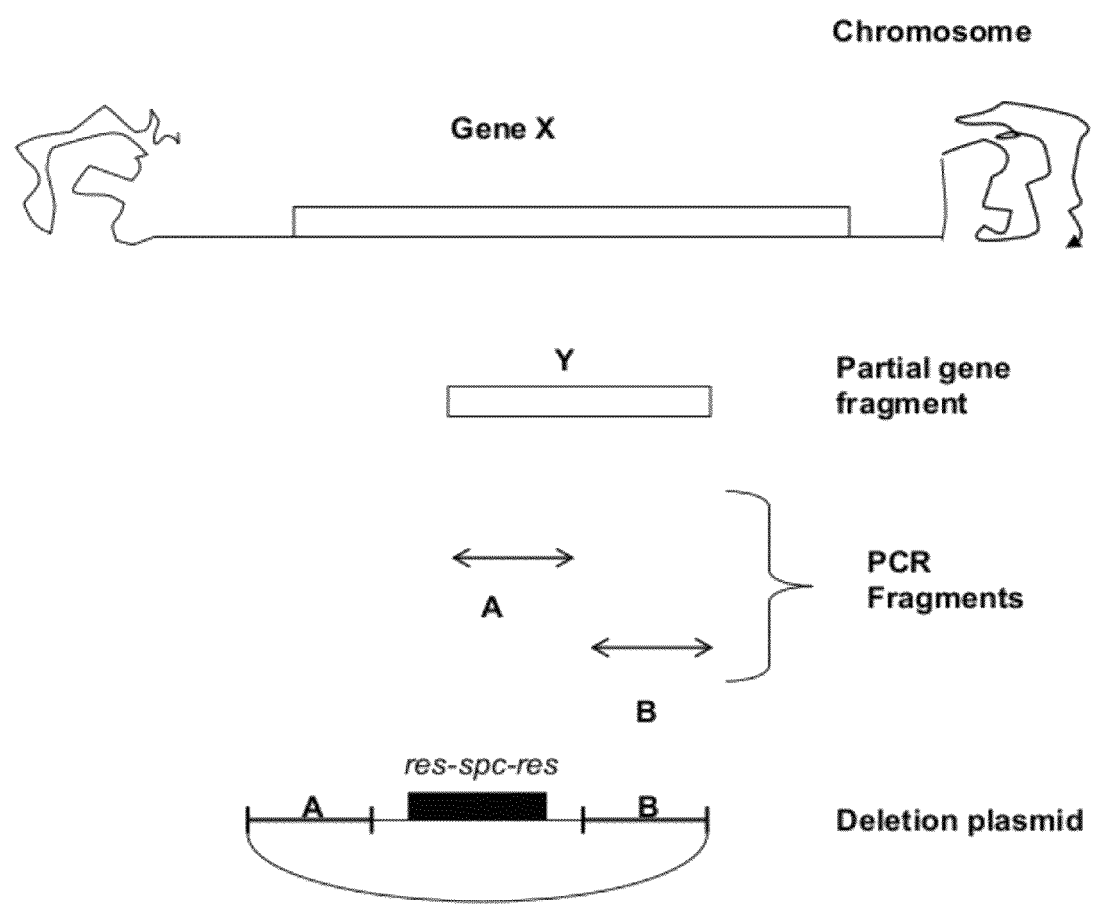

METHODS FOR MONITORING MULTIPLE GENE EXPRESSION

CROSS-REFERENCE TO RELATED APPLICATIONS

This application is a continuation of U.S. application Ser. No. 12/753,000, filed Apr. 1, 2010, which is a divisional of U.S. application Ser. No. 11/203,606, filed Aug. 12, 2005, now U.S. Pat. No. 7,691,574, which is a divisional of U.S. application Ser. No. 09/974,300 filed on Oct. 5, 2001, now U.S. Pat. No. 7,018,794, which is a continuation-in-part of U.S. application Ser. No. 09/680,598 filed on Oct. 6, 2000, now abandoned. U.S. application Ser. No. 09/974,300, filed on Oct. 5, 2001, now U.S. Pat. No. 7,018,794, claims priority benefit of U.S. Provisional Application Ser. No. 60/279,526, filed Mar. 27, 2001.

BACKGROUND OF THE INVENTION

1. Field of the Invention

The present invention relates to methods for monitoring expression of a plurality of genes in Bacillus cells. The present invention also relates to Bacillus genomic sequenced tags and to substrates and computer readable media containing such genomic sequenced tags.

2. Description of the Related Art

Microarray technology is increasingly becoming the method of choice for the quantitative and simultaneous analysis of the expression levels of many thousands of genes. Microarray analyses typically follow the steps of gene selection, microarray synthesis, sample preparation, array hybridization, detection, and data analysis (Watson et al., 1998, Current Opinion in Biotechnology 9: 609-614).

PCR-amplified coding sequences of genomic DNA from an organism are particularly useful in microarrays for obtaining global expression profiles where the genome of the organism has been fully sequenced.

Chu et al., 1998, Science 282: 699-705 disclose the use of microarrays containing PCR-amplified genomic coding sequences for determining the temporal expression of Saccharomyces cerevisiae genes during sporulation.

For other organisms whose genomes have not been sequenced, global expression profiles may be obtained with arraying (1) random genomic DNA segments or clones (e.g., from a genomic DNA library); (2) random cDNA clones (e.g., from one or more cDNA libraries) that are uncharacterized at the DNA sequence level; or (3) random cDNA clones that have been sequenced and partially characterized with respect to putative identification and function.

Genomic sequenced tags (GSTs) are partial genomic DNA sequences. Simply stated, a GST is a segment of a sequence from a random genomic DNA clone that corresponds to part of a specific gene. The use of sequenced GSTs in microarrays compared to genomic clones or random cDNA clones provides several advantages especially for organisms whose genomes have not been fully sequenced. First, since sequence information is available, redundancy and follow-up characterization is minimized. Second, GST microarrays can be organized based on function of the gene products to facilitate analysis of the results (e.g., GSTs encoding enzymes from the same metabolic pathway can be arranged or grouped accordingly).

Ruan et al., 1998, The Plant Journal 15: 821-833, disclose the use of microarrays containing Arabidopsis thaliana EST sequences for determining the temporal expression of Arabidopsis thaliana genes in root, leaf, and two stages of floral development.

Iyer et al., 1999, Science 283; 83-87, disclose the use of microarrays containing human EST sequences for determining the temporal expression of human fibroblast cells in response to serum.

Hayward et al., 2000, Molecular Microbiology 35: 6-14, disclose shotgun DNA microarrays and stage-specific gene expression in Plasmodium falciparum malaria.

Bacteria are used as host microorganisms for the industrial production of enzymes and other proteins whether endogenous or heterogenous to the microorganisms. There is a need in the art to provide methods for monitoring the global expression of genes from Bacillus cells to improve the production potential of these microorganisms.

It is an object of the present invention to provide alternative methods for monitoring expression of a plurality of genes in Bacillus cells.

SUMMARY OF THE INVENTION

The present invention relates to methods for monitoring differential expression of a plurality of genes in a first Bacillus cell relative to expression of the same or similar genes in one or more second Bacillus cells, comprising:

(a) adding a mixture of labeled nucleic acid probes isolated from the Bacillus cells to a substrate containing an array of Bacillus GSTs under conditions where the nucleic acids hybridize to complementary sequences of the Bacillus GSTs in the array, wherein the nucleic acids from the first Bacillus cell and the one or more second Bacillus cells are labeled with a first reporter and one or more different second reporters, respectively; and (b) examining the array under conditions wherein the relative expression of the genes in the Bacillus cells is determined by the observed hybridization reporter signal of each spot in the array in which (i) the Bacillus GSTs in the array that hybridize to the nucleic acids obtained from either the first or the one or more second Bacillus cells produce a distinct first hybridization reporter signal or one or more second hybridization reporter signals, respectively, and (ii) the GSTs in the array that hybridize to the nucleic acids obtained from both the first and one or more second Bacillus cells produce a distinct combined hybridization reporter signal. In a preferred embodiment, the Bacillus GSTs are the Bacillus licheniformis GSTs of SEQ ID NOs. 1-4448. In another preferred embodiment, the Bacillus GSTs are the Bacillus clausii GSTs of SEQ ID NOs. 4449-8481.

The present invention also relates to computer readable media, substrates containing an array of Bacillus GSTs, and computer-based systems.

BRIEF DESCRIPTION OF THE FIGURE

FIG. 1 shows a method to make deletions at specific loci of the Bacillus licheniformis or Bacillus clausii chromosome utilizing the Bacillus licheniformis or Bacillus clausii GST sequences described herein.

DETAILED DESCRIPTION OF THE INVENTION

The present invention relates to methods for monitoring differential expression of a plurality of genes in a first Bacillus cell relative to expression of the same genes in one or more second Bacillus cells. The methods comprise (a) adding a mixture of labeled nucleic acid probes isolated from two or more *Bacillus* cells in culture to a substrate containing an array of *Bacillus* GSTs under conditions where the nucleic acids hybridize to complementary sequences of the *Bacillus* GSTs in the array; and (b) examining the array under conditions wherein the relative expression of the genes in the two or more cells is determined by the observed hybridization reporter signal of each spot in the array.

The methods of the present invention may be used to monitor global expression of a plurality of genes from a *Bacillus* cell, discover new genes, identify possible functions of unknown open reading frames, and monitor gene copy number variation and stability. For example, the global view of changes in expression of genes may be used to provide a picture of the way in which *Bacillus* cells adapt to changes in culture conditions, environmental stress, or other physiological provocation. Other possibilities for monitoring global expression include spore morphogenesis, recombination, metabolic or catabolic pathway engineering.

The methods of the present invention are particularly advantageous when one spot on an array equals one gene or open reading frame because extensive follow-up characterization is unnecessary since sequence information is available, and *Bacillus* GST microarrays can be organized based on function of the gene products. However, one spot may contain more than one gene especially if random genomic sequences are used.

Genomic Sequenced Tags

The term "genomic sequenced tag" or "GST" is defined herein as a segment of a sequence from a random genomic DNA clone of an expressed *Bacillus* genome. The term "GST" will be understood to also include two or more *Bacillus* GSTs assembled into a contig. *Bacillus* GSTs are generally generated as follows: Total cellular DNA is isolated from a *Bacillus* cell, digested with a restriction endonuclease or cleaved by sonication, nebulization, or physical methods, size-selected by agarose gel electrophoresis, isolated, and ligated into a vector, e.g., pSGMU2 (Errington, 1986, *Journal of General Microbiology* 132: 2953-2961). The ligation mixture is used to transform competent *E. coli* cells and transformants are selected under selective pressure, e.g., ampicillin selection. Plasmids from the genomic DNA libraries are generated from random selected transformants, isolated, and partially sequenced. The partial sequences are then compared to sequences in various publicly available databases, for example GenBank, EMBL, Swissprot etc., for identification of function and annotated accordingly.

In the methods of the present invention, the *Bacillus* GSTs are preferably at least about 50 bp in length, more preferably at least about 100 bp in length, even more preferably at least about 150 bp in length, and most preferably at least about 200 bp in length.

The *Bacillus* GSTs may be obtained from any *Bacillus* cell but preferably from a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus,* or *Bacillus thuringiensis* cells. In a preferred embodiment, the *Bacillus* cell is a *Bacillus clausii* cell.

In a preferred embodiment, the *Bacillus* GSTs are obtained from a *Bacillus licheniformis* cell. In a more preferred embodiment, the *Bacillus licheniformis* GSTs are obtained from *Bacillus licheniformis* ATCC 14580. In a most preferred embodiment, the *Bacillus licheniformis* GSTs are selected from the group consisting of SEQ ID NOs. 1-4448, nucleic acid fragments of SEQ ID NOs. 1-4448, and nucleic acid sequences having at least 85%, more preferably at least 90%, and most preferably at least 95% homology to SEQ ID NOs. 1-4448.

In another preferred embodiment, the *Bacillus* GSTs are obtained from a *Bacillus clausii* cell. In another more preferred embodiment, the *Bacillus clausii* GSTs are obtained from *Bacillus clausii* NCIB 10309. In another most preferred embodiment, the *Bacillus clausii* GSTs are selected from the group consisting of SEQ ID NOs. 4449-8481, nucleic acid fragments of SEQ ID NOs. 4449-8481, and nucleic acid sequences having at least 85%, more preferably at least 90%, and most preferably at least 95% homology to SEQ ID NOs. 4449-8481.

Microarrays

The term "an array of *Bacillus* GSTs" is defined herein as a linear or two-dimensional array of preferably discrete elements of *Bacillus* GSTs, each having a finite area, formed on the surface of a solid support.

The term "microarray" is defined herein as an array of *Bacillus* GST elements having a density of discrete GST elements of at least about 100/cm$^2$, and preferably at least about 1000/cm$^2$. The GST elements in a microarray have typical dimensions, e.g., diameters, in the range of between about 10 to about 250 µm, preferably in the range of between about 10 to about 200 µm, more preferably in the range of between about 20 to about 150 µm, even more preferably in the range of between about 20 to about 100 µm, most preferably in the range of between about 50 to about 100 µm, and even most preferably in the range of between about 80 to about 100 µm, and are separated from other GST elements in the microarray by about the same distance.

Methods and instruments for forming microarrays on the surface of a solid support are well known in the art. See, for example, U.S. Pat. No. 5,807,522; U.S. Pat. No. 5,700,637; and U.S. Pat. No. 5,770,151. The instrument may be an automated device such as described in U.S. Pat. No. 5,807,522.

The term "a substrate containing an array of *Bacillus* GSTs" is defined herein as a solid support having deposited on the surface of the support one or more of a plurality of *Bacillus* GSTs for use in detecting binding of labeled nucleic acids to the *Bacillus* GSTs.

The substrate may, in one aspect, be a glass support (e.g., glass slide) having a hydrophilic or hydrophobic coating on the surface of the support, and an array of distinct *Bacillus* GSTs bound to the coating, where each distinct GST is disposed at a separate, defined position.

Each microarray in the substrate preferably contains at least 10$^3$ distinct *Bacillus* GSTs in a surface area of less than about 5 or 6 cm$^2$. Each distinct *Bacillus* GST (i) is disposed at a separate, defined position in the array, (ii) has a length of at least 50 bp, and (iii) is present in a defined amount between about 0.1 femtomoles and 100 nanomoles or higher if necessary.

For a hydrophilic coating, the glass slide is coated by placing a film of a polycationic polymer with a uniform thickness on the surface of the slide and drying the film to form a dried coating. The amount of polycationic polymer added should be sufficient to form at least a monolayer of polymers on the glass surface. The polymer film is bound to the surface via electrostatic binding between negative silyl-OH groups on the surface and charged cationic groups in the polymers. Such polycationic polymers include, but are not limited to, polylysine and polyarginine.

Another coating strategy employs reactive aldehydes to couple DNA to the slides (Schena et al., 1996, *Proceedings of* the *National Academy of Science USA* 93: 10614-10619; Heller at al., 1997, *Proceedings of the National Academy of Science USA* 94: 2150-2155).

Alternatively, the surface may have a relatively hydrophobic character, i.e., one that causes aqueous medium deposited on the surface to bead. A variety of known hydrophobic polymers, such as polystyrene, polypropylene, or polyethylene, have desirable hydrophobic properties, as do glass and a variety of lubricant or other hydrophobic films that may be applied to the support surface. A support surface is "hydrophobic" if an aqueous droplet applied to the surface does not spread out substantially beyond the area size of the applied droplet, wherein the surface acts to prevent spreading of the droplet applied to the surface by hydrophobic interaction with the droplet.

In another aspect, the substrate may be a multi-cell substrate where each cell contains a microarray of *Bacillus* GSTs, and preferably an identical microarray, formed on a porous surface. For example, a 96-cell array may typically have array dimensions between about 12 and 244 mm in width and 8 and 400 mm in length, with the cells in the array having width and length dimension of I/12 and I/8 the array width and length dimensions, respectively, i.e., between about 1 and 20 in width and 1 and 50 mm in length.

The solid support may include a water-impermeable backing such as a glass slide or rigid polymer sheet, or other non-porous material. Formed on the surface of the backing is a water-permeable film which is formed of porous material. Such porous materials include, but are not limited to, nitrocellulose membrane nylon, polypropylene, and polyvinylidene difluoride (PVDF) polymer. The thickness of the film is preferably between about 10 and 1000 µm. The film may be applied to the backing by spraying or coating, or by applying a preformed membrane to the backing.

Alternatively, the solid support may be simply a filter composed of nitrocellulose, nylon, polypropylene, or polyvinylidene difluoride (PVDF) polymer, or for that matter any material suitable for use.

The film surface may be partitioned into a desirable array of cells by water-impermeable grid lines typically at a distance of about 100 to 2000 µm above the film surface. The grid lines can be formed on the surface of the film by laying down an uncured flowable resin or elastomer solution in an array grid, allowing the material to infiltrate the porous film down to the backing, and then curing the grid lines to form the cell-array substrate.

The barrier material of the grid lines may be a flowable silicone, wax-based material, thermoset material (e.g., epoxy), or any other useful material. The grid lines may be applied to the solid support using a narrow syringe, printing techniques, heat-seal stamping, or any other useful method known in the art.

Each well preferably contains a microarray of distinct *Bacillus* GSTs. "Distinct *Bacillus* GSTs" as applied to the GSTs forming a microarray is defined herein as an array member which is distinct from other array members on the basis of a different GST sequence, and/or different concentrations of the same or distinct GSTs, and/or different mixtures of distinct GSTs or different-concentrations of GSTs. Thus an array of "distinct *Bacillus* GSTs" may be an array containing, as its members, (i) distinct GSTs, which may have a defined amount in each member, (ii) different, graded concentrations of given-sequence GSTs, and/or (iii) different-composition mixtures of two or more distinct GSTs.

However, any type of substrate known in the art may be used in the methods of the present invention.

The delivery of a known amount of a selected *Bacillus* GST to a specific position on the support surface is preferably performed with a dispensing device equipped with one or more tips for insuring reproducible deposition and location of the GSTs and for preparing multiple arrays. Any dispensing device known in the art may be used in the methods of the present invention. See, for example, U.S. Pat. No. 5,807,522.

For liquid-dispensing on a hydrophilic surface, the liquid will have less of a tendency to bead, and the dispensed volume will be more sensitive to the total dwell time of the dispenser tip in the immediate vicinity of the support surface.

For liquid-dispensing on a hydrophobic surface, flow of fluid from the tip onto the support surface will continue from the dispenser onto the support surface until it forms a liquid bead. At a given bead size, i.e., volume, the tendency of liquid to flow onto the surface will be balanced by the hydrophobic surface interaction of the bead with the support surface, which acts to limit the total bead area on the surface, and by the surface tension of the droplet, which tends toward a given bead curvature. At this point, a given bead volume will have formed, and continued contact of the dispenser tip with the bead, as the dispenser tip is being withdrawn, will have little or no effect on bead volume.

The desired deposition volume, i.e., bead volume, formed is preferably in the range 2 pl (picoliters) to 2 nl (nanoliters), although volumes as high as 100 nl or more may be dispensed. It will be appreciated that the selected dispensed volume will depend on (i) the "footprint" of the dispenser tip(s), i.e., the size of the area spanned by the tip(s), (ii) the hydrophobicity of the support surface, and (iii) the time of contact with and rate of withdrawal of the tip(s) from the support surface. In addition, bead size may be reduced by increasing the viscosity of the medium, effectively reducing the flow time of liquid from the dispensing device onto the support surface. The drop size may be further constrained by depositing the drop in a hydrophilic region surrounded by a hydrophobic grid pattern on the support surface.

At a given tip size, bead volume can be reduced in a controlled fashion by increasing surface hydrophobicity, reducing time of contact of the tip with the surface, increasing rate of movement of the tip away from the surface, and/or increasing the viscosity of the medium. Once these parameters are fixed, a selected deposition volume in the desired picoliter to nanoliter range can be achieved in a repeatable fashion.

After depositing a liquid droplet of a *Bacillus* GST sample at one selected location on a support, the tip may be moved to a corresponding position on a second support, the GST sample is deposited at that position, and this process is repeated until the GST sample has been deposited at a selected position on a plurality of supports.

This deposition process may then be repeated with another GST sample at another microarray position on each of the supports.

The diameter of each *Bacillus* GST region is preferably between about 20-200 µm. The spacing between each region and its closest (non-diagonal) neighbor, measured from center-to-center, is preferably in the range of about 20-400 µm. Thus, for example, an array having a center-to-center spacing of about 250 µm contains about 40 regions/cm or 1,600 regions/cm$^2$. After formation of the array, the support is treated to evaporate the liquid of the droplet forming each region, to leave a desired array of dried, relatively flat GST regions. This drying may be done by heating or under vacuum. The DNA can also be UV-crosslinked to the polymer coating.

Bacterial Cells

In the methods of the present invention, the two or more *Bacillus* cells may be any *Bacillus* cell where one of the cells is used as a reference for identifying differences in expression of the same or similar complement of genes in the other cell(s). In one aspect, the two or more cells are the same cell. For example, they may be compared under different growth conditions, e.g., oxygen limitation, nutrition, and/or physiology. In another aspect, one or more cells are mutants of the reference cell. For example, the mutant(s) may have a different phenotype. In a further aspect, the two or more cells are of different species (e.g., *Bacillus clausii* and *Bacillus subtilis*). In another further aspect, the two or more cells are of different genera. In an even further aspect, one or more cells are transformants of the reference cell, wherein the one or more transformants exhibit a different property. For example, the transformants may have an improved phenotype relative to the reference cell and/or one of the other transformants. The term "phenotype" is defined herein as an observable or outward characteristic of a cell determined by its genotype and modulated by its environment. Such improved phenotypes may include, but are not limited to, improved secretion or production of a protein or compound, reduced or no secretion or production of a protein or compound, improved or reduced expression of a gene, desirable morphology, an altered growth rate under desired conditions, relief of over-expression mediated growth inhibition, or tolerance to low oxygen conditions.

The *Bacillus* cells may be any *Bacillus* cells, but preferably *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* cells.

In a preferred embodiment, the *Bacillus* cells are *Bacillus alkalophilus* cells. In another preferred embodiment, the *Bacillus* cells are *Bacillus amyloliquefaciens* cells. In another preferred embodiment, the *Bacillus* cells are *Bacillus brevis* cells. In another preferred embodiment, the *Bacillus* cells are *Bacillus circulans* cells. In another preferred embodiment, the *Bacillus* cells are *Bacillus clausii* cells. In another preferred embodiment, the *Bacillus* cells are *Bacillus coagulans* cells. In another preferred embodiment, the *Bacillus* cells are *Bacillus firmus* cells. In another preferred embodiment, the *Bacillus* cells are *Bacillus lautus* cells. In another preferred embodiment, the *Bacillus* cells are *Bacillus lentus* cells. In another preferred embodiment, the *Bacillus* cells are *Bacillus licheniformis* cells. In another preferred embodiment, the *Bacillus* cells are *Bacillus megaterium* cells. In another preferred embodiment, the *Bacillus* cells are *Bacillus pumilus* cells. In another preferred embodiment, the *Bacillus* cells are *Bacillus stearothermophilus* cells. In another preferred embodiment, the *Bacillus* cells are *Bacillus subtilis* cells. In another preferred embodiment, the *Bacillus* cells are *Bacillus thuringiensis* cells.

In a more preferred embodiment, the *Bacillus* cells are *Bacillus licheniformis* cells. In a most preferred embodiment, the *Bacillus licheniformis* cells are *Bacillus licheniformis* ATCC 14580 cells.

In another more preferred embodiment, the *Bacillus* cells are *Bacillus clausii* cells. In another most preferred embodiment, the *Bacillus clausii* cells are *Bacillus clausii* NCIB 10309 cells.

In the methods of the present invention, the cells are cultivated in a nutrient medium suitable for growth using methods well known in the art for isolation of the nucleic acids to be used as probes. For example, the cells may be cultivated by shake flask cultivation, small-scale or large-scale fermentation (including continuous, batch, fed-batch, or solid state fermentations) in laboratory or industrial fermentors performed in a suitable medium. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection).

Nucleic Acid Probes

The nucleic acid probes from the two or more *Bacillus* cells may be any nucleic acid including genomic DNA, cDNA, and RNA, and may be isolated using standard methods known in the art. For example, cDNA probes may be obtained from total RNA isolated from the cells using standard methods and reverse transcribed into total cDNA.

The populations of isolated nucleic acid probes may be labeled with colorimetric, radioactive (for example, $^{32}P$, $^{33}P$, or $^{35}S$), fluorescent reporters, or other reporters using methods known in the art (Chen et al., 1998, Genomics 51: 313-324; DeRisi et al., 1997, *Science* 278: 680-686; U.S. Pat. No. 5,770,367).

In a preferred embodiment, the probes are labeled with fluorescent reporters. For example, the cDNA probes may be labeled during reverse transcription from the respective RNA pools by incorporation of fluorophores as dye-labeled nucleotides (DeRisi et al., 1997, supra), e.g., Cy5-labeled deoxyuridine triphosphate, or the isolated cDNAs may be directly labeled with different fluorescent functional groups. Fluorescent-labeled nucleotides include, but are not limited to, fluorescein conjugated nucleotide analogs (green fluorescence), lissamine nucleotide analogs (red fluorescence). Fluorescent functional groups include, but are not limited to, Cy3 (a green fluorescent dye) and Cy5 (red fluorescent dye).

Array Hybridization

The labeled nucleic acids from the two or more *Bacillus* cells are then added to a substrate containing an array of *Bacillus* GSTs under conditions where the nucleic acid pools from the two or more *Bacillus* cells hybridize to complementary sequences of the GSTs in the array. For purposes of the present invention, hybridization indicates that the labeled nucleic acids from the two or more cells hybridize to the GSTs under very low to very high stringency conditions.

A small volume of the labeled nucleic acids mixture is loaded onto the substrate. The solution will spread to cover the entire microarray. In the case of a multi-cell substrate, one or more solutions are loaded into each cell which stop at the barrier elements.

For nucleic acid probes of at least about 100 nucleotides in length, miroarray hybridization conditions described by Eisen and Brown, 1999, *Methods of Enzymology* 303: 179-205, may be used. Hybridization is conducted under a coverslip at 65° C. in 3×SSC for 4-16 hours followed by post-hybridization at room temperature after removal of the coverslip in 2×SSC, 0.1% SDS by plunging the array two or three times in the solution, followed by successive washes in 1×SSC for 2 minutes and 0.2×SSC wash for to or more minutes.

Conventional conditions of very low to very high stringency conditions may also be used. Very low to very high stringency conditions are defined as prehybridization and hybridization at 42° C. in 5×SSPE, 0.3% SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures.

The carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For shorter nucleic acid probes which are less than 50 nucleotides, microarray hybridization conditions described by Kane et al., 2000, *Nucleic Acids Research* 28: 4552-4557, may be used. Hybridization is conducted under a supported coverslip at 42° C. for 16-18 hours at high humidity in 50% formamide, 4.1×Denhardts, 4.4×SSC, and 100 µg/ml of herring sperm DNA. Arrays are washed after removal of the coverslip in 4×SSC by immersion into 1×SSC, 0.1% SDS for 10 minutes, 0.1×SSC, 0.1% SDS twice for 10 minutes, and 0.1×SSC twice for 10 minutes.

For shorter nucleic acid probes which are about 50 nucleotides to about 100 nucleotides in length, conventional stringency conditions may be used. Such stringency conditions are defined as prehybridization, hybridization, and washing post-hybridization at 5° C. to 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

The carrier material is finally washed once in 6×SSC plus 0.1% SDS for 15 minutes and twice each for 15 minutes using 6×SSC at 5° C. to 10° C. below the calculated $T_m$.

The choice of hybridization conditions will depend on the degree of homology between the *Bacillus* GSTs and the nucleic acids obtained from the two or more *Bacillus* cells. For example, where the nucleic acid probes and the GSTs are obtained from identical *Bacillus* cells, high stringency conditions may be most suitable. Where the cells are from a genus or species different from which the GSTs were obtained, low or medium stringency conditions may be more suitable.

In a preferred embodiment, the hybridization is conducted under low stringency conditions. In a more preferred embodiment, the hybridization is conducted under medium stringency conditions. In a most preferred embodiment, the hybridization is conducted under high stringency conditions.

The entire solid support is then reacted with detection reagents if needed and analyzed using standard calorimetric, radioactive, or fluorescent detection means. All processing and detection steps are performed simultaneously to all of the microarrays on the solid support ensuring uniform assay conditions for all of the microarrays on the solid support.

Detection

Any detection method known in the art may be used. The most common detection method is laser-induced fluorescence detection using confocal optics (Cheung et al., 1998, *Nat. Genet.* 18: 225-230). The array is examined under fluorescence excitation conditions such that (i) the *Bacillus* GSTs in the array that hybridize to the nucleic acid probes obtained from one of the first cell and one or more second cells produces a distinct first fluorescence emission color or one or second fluorescence emission colors, respectively, and (ii) the *Bacillus* GSTs in the array that hybridize to substantially equal numbers of nucleic acid probes obtained from the first cell and one of the one or more second cells produce a distinct combined fluorescence emission color, respectively; wherein the relative expression of the genes in the two or more cells can be determined by the observed fluorescence emission color of each spot in the array.

The fluorescence excitation conditions are based on the selection of the fluorescence reporters. For example, Cy3 and Cy5 reporters are detected with solid state lasers operating at 532 nm and 632 nm, respectively.

Other methods of detection may be used employing colorimetric and radioactive (for example, $^{32}P$, $^{33}P$, or $^{35}S$) reporters, or other reporters using methods known in the art (Chen et al., 1998, supra; DeRisi et al., 1997, supra; U.S. Pat. No. 5,770,367).

Data Analysis

The fluorescence data obtained from the scanned image may then be analyzed using any of the commercially available image analysis software. The software preferably identifies array elements, subtracts backgrounds, deconvolutes multicolor images, flags or removes artifacts, verifies that controls have performed properly, and normalizes the signals (Chen et al., 1997, *Journal of Biomedical Optics* 2: 364-374).

Several computational methods have been described for the analysis and interpretation of microarray-based expression profiles including cluster analysis (Eisen et al., 1998, *Proc. Nat. Acad. Sci. USA* 95: 14863-14868), parametric ordering of genes (Spellman et al., 1998, *Mol. Biol. Cell* 9: 3273-3297), and supervised clustering methods based on representative hand-picked or computer-generated expression profiles (Chu et al., 1998. *Science* 282: 699-705).

Computer Readable Media

The *Bacillus* GSTs described herein may be "provided" in a variety of media to facilitate their use. The term "provided" refers to a manufacture comprising an array of *Bacillus* GSTs. Such manufactures provide a large portion of the genome of *Bacillus* and parts thereof (e.g., an open reading frame (ORF)) in a form which allows one skilled in the art to examine the manufacture using means not directly applicable to examining the genome or a subset thereof as it exists in nature or in purified form.

Thus, the present invention also relates to such a manufacture in the form of a computer readable medium comprising an array of *Bacillus* GSTs selected from the group consisting of SEQ ID NOs. 1-8481, nucleic acid fragments of SEQ ID NOs. 1-8481, and nucleic acid sequences having preferably at least 85%, more preferably at least 90%, and most preferably at least 95% homology to SEQ ID NOs. 1-8481.

In a preferred embodiment, the computer readable medium comprises an array of *Bacillus licheniformis* GSTs consisting of nucleic acid sequences of SEQ ID NOs. 1-4448.

In another preferred embodiment, the computer readable medium comprises an array of *Bacillus licheniformis* GSTs consisting of nucleic acid fragments of SEQ ID NOs. 1-4448.

In another preferred embodiment, the computer readable medium comprises an array of *Bacillus licheniformis* GSTs consisting of nucleic acid sequences having preferably at least 85%, more preferably at least 90%, and most preferably at least 95% homology to SEQ ID NOs. 1-4448.

In another preferred embodiment, the computer readable medium comprises an array of *Bacillus clausii* GSTs consisting of nucleic acid sequences of SEQ ID NOs. 4449-8481.

In another preferred embodiment, the computer readable medium comprises an array of *Bacillus clausii* GSTs consisting of nucleic acid fragments of SEQ ID NOs. 4449-8481.

In another preferred embodiment, the computer readable medium comprises an array of *Bacillus clausii* GSTs consisting of nucleic acid sequences having preferably at least 85%, more preferably at least 90%, and most preferably at least 95% homology to SEQ ID NOs. 4449-8481

In one application of this embodiment, the *Bacillus* GSTs of the present invention can be recorded on computer readable media. The term "computer readable media" is defined herein as any medium which can be read and accessed by a computer. Such computer readable media include, but are not limited to, magnetic storage media, e.g., floppy discs, hard disc storage medium, and magnetic tape; optical storage media, e.g., CD-ROM, DVD; electrical storage media, e.g., RAM and ROM; and hybrids of these categories, e.g., magnetic/optical storage media. One skilled in the art can readily appreciate how any of the presently known computer readable media can be used to create a manufacture comprising computer readable medium having recorded thereon a nucleotide sequence of the present invention. Likewise, it will be clear to those of skill how additional computer readable media that may be developed also can be used to create analogous manufactures having recorded thereon a nucleotide sequence of the present invention.

As used herein, "recorded" refers to a process for storing information on computer readable medium. One skilled in the art can readily adopt any of the presently known methods for recording information on computer readable medium to generate manufactures comprising the nucleotide sequence information of the present invention.

A variety of data storage structures are available for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. A skilled artisan can readily adapt any number of data-processor structuring formats (e.g., text file or database) in order to obtain computer readable medium having recorded thereon the nucleotide sequence information of the present invention.

Various computer software are publicly available that allow a skilled artisan to access sequence information provided in a computer readable medium. Thus, by providing in computer readable form an array of *Bacillus clausii* GSTs selected from the group consisting of SEQ ID NOs. 4449-8481, nucleic acid fragments of SEQ ID NOs. 4449-8481, and nucleic acid sequences having preferably at least 85%, more preferably at least 90%, and most preferably at least 95% homology to SEQ ID NOs. 4449-8481 enables one skilled in the art to routinely access the provided sequence information for a wide variety of purposes.

Software utilizing the BLAST (Altschul et al., 1990, *Journal of Molecular Biology* 215: 403-410), BLAZE (Brutlag et al., 1993, *Comp. Chem.* 17: 203-207), GENEMARK (Lukashin and Borodovsky, 1998, *Nucleic Acids Research* 26: 1107-1115), GENSCAN (Burge and Karlin, 1997, *Journal of Molecular Biology* 268: 78-94), GLIMMER (Salzberg et al., 1998, *Nucleic Acids Research* 26: 544-548), and GRAIL (Xu et al., 1994, *Comput. Appl. Biosci.* 10: 613-623) search algorithms may be used to identify open reading frames (ORFs) within a genome of interest, which contain homology to ORFs or proteins from both *Bacillus licheniformis* and *Bacillus clausii* and from other organisms. Among the ORFs discussed herein are protein encoding fragments of the *Bacillus licheniformis* and *Bacillus clausii* genomes useful in producing commercially important proteins, such as enzymes used in fermentation reactions and in the production of commercially useful metabolites.

The present invention further provides systems, particularly computer-based systems, which contain the sequence information described herein. Such systems are designed to identify, among other things, genes and gene products—many of which could be products themselves or used to genetically modify an industrial expression host through increased or decreased expression of a specific gene sequence(s).

The term "a computer-based system" is herein defined as the hardware means, software means, and data storage means used to analyze the nucleotide sequence information of the present invention. The minimum hardware means of the computer-based systems of the present invention comprises a central processing unit (CPU), input means, output means, and data storage means. One skilled in the art can readily appreciate that any currently available computer-based system is suitable for use in the present invention.

As stated above, the computer-based systems of the present invention comprise a data storage means having stored therein a nucleotide sequence of the present invention and the necessary hardware means and software means for supporting and implementing a search means.

The term "data storage means" is defined herein as memory which can store nucleotide sequence information of the present invention, or a memory access means which can access manufactures having recorded thereon the nucleotide sequence information of the present invention.

The term "search means" refers is defined herein as one or more programs which are implemented on the computer-based system to compare a target sequence or target structural motif with the sequence information stored within the data storage means. Search means are used to identify fragments or regions of the present genomic sequences which match a particular target sequence or target motif. A variety of known algorithms are disclosed publicly and a variety of commercially available software for conducting search means are and can be used in the computer-based systems of the present invention. Examples of such software includes, but is not limited to, MacPattern (Fuchs, 1991, *Comput. Appl. Biosci.* 7: 105-106), BLASTN and BLASTX National Center for Biotechnology Information (NCBI). One skilled in the art can readily recognize that any one of the available algorithms or implementing software packages for conducting homology searches can be adapted for use in the present computer-based systems.

The term "target sequence" is defined here as any DNA (genomic DNA, cDNA) or amino acid sequence of six or more nucleotides or two or more amino acids. One skilled in the art can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that searches for commercially important fragments, such as sequence fragments involved in gene expression and protein processing, may be of shorter length.

The term "a target structural motif" or "target motif" is defined herein as any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences, substrate and cofactor binding domains, transmembrane domains, and sites for post-translational modifications. Nucleic acid target motifs include, but are not limited to, promoter sequences, hairpin structures and inducible expression elements (protein binding sequences), repeats, palindromes, dyad symmetries, and transcription and translation start and stop sites.

A variety of structural formats for the input and output means can be used to input and output the information in the computer-based systems of the present invention. A preferred format for an output means ranks fragments of the *Bacillus licheniformis* or *Bacillus* clausii genomic sequences possessing varying degrees of homology to the target sequence or target motif. Such presentation provides one skilled in the art with a ranking of sequences which contain various amounts of the target sequence or target motif and identifies the degree of homology contained in the identified fragment.

A variety of comparing means can be used to compare a target sequence or target motif with the data storage means to identify sequence fragments of the *Bacillus licheniformis* and *Bacillus* clausii genomes. For example, implementing software which utilize the BLAST and BLAZE algorithms, described in Altschul et al., 1990, *Journal of Molecular Biology* 215: 403-410, may be used to identify open reading frames within the *Bacillus licheniformis* or *Bacillus* clausii genome or the genomes of other organisms. A skilled artisan can readily recognize that any one of the publicly available homology search programs can be used as the search means for the computer-based systems of the present invention. Of course, suitable proprietary systems that may be known to those of skill also may be employed in this regard.

Substrates

The present invention also relates to substrates as described herein comprising an array of *Bacillus* GSTs.

In a preferred embodiment, the substrate comprises an array of *Bacillus licheniformis* GSTs selected from the group consisting of SEQ ID NOs. 1-4448, nucleic acid fragments of SEQ ID NOs. 1-4448, and nucleic acid sequences having preferably at least 85%, more preferably at least 90%, and most preferably at least 95% homology to SEQ ID NOs. 1-4448. In a more preferred embodiment, the substrate comprises an array of *Bacillus licheniformis* GSTs selected from the group consisting of SEQ ID NOs. 1-4448. In another more preferred embodiment, the substrate comprises an array of *Bacillus licheniformis* GSTs selected from the group consisting of nucleic acid fragments of SEQ ID NOs. 1-4448. In another more preferred embodiment, the substrate comprises an array of *Bacillus licheniformis* GSTs selected from the group consisting of nucleic acid sequences having preferably at least 85%, more preferably at least 90%, and most preferably at least 95% homology to SEQ ID NOs. 1-4448.

In a preferred embodiment, the substrate comprises an array of *Bacillus clausii* GSTs selected from the group consisting of SEQ ID NOs. 4449-8481, nucleic acid fragments of SEQ ID NOs. 4449-8481, and nucleic acid sequences having preferably at least 85%, more preferably at least 90%, and most preferably at least 95% homology to SEQ ID NOs. 4449-8481. In a more preferred embodiment, the substrate comprises an array of *Bacillus clausii* GSTs selected from the group consisting of SEQ ID NOs. 4449-8481. In another more preferred embodiment, the substrate comprises an array of *Bacillus clausii* GSTs selected from the group consisting of nucleic acid fragments of SEQ ID NOs. 4449-8481. In another more preferred embodiment, the substrate comprises an array of *Bacillus clausii* GSTs selected from the group consisting of nucleic acid sequences having preferably at least 85%, more preferably at least 90%, and most preferably at least 95% homology to SEQ ID NOs. 4449-8481.

Co-Linearity of *Bacillus licheniformis* and *Bacillus subtilis* Chromosomes

The complete nucleotide sequence of the *Bacillus subtilis* chromosome was recently published (Kunst et al., 1997, *Nature* 390: 249-256) and reveals the exact position of more than 4000 genes in this genome. Several public databases are available for searching and graphic representations of the entire genome.

The method of shot-gun sequencing of the *Bacillus licheniformis* chromosome which is conducted herein does not directly address the specific arrangement of genes on the chromosome. However, since *Bacillus subtilis* and *Bacillus licheniformis* are very closely related organisms according to the literature (Ash et al., 1991, *Letters in Applied Microbiology* 13: 202-206) the linear arrangement of genes on the two chromosomes might be similar.

To investigate this hypothesis, a series of long range PCR amplifications were made using primers to *Bacillus licheniformis* sequences which were identified as homologues to specific genes in *Bacillus subtilis*. Each PCR reaction employs *Bacillus licheniformis* chromosomal DNA as template for primer pairs that hybridizes to two genes in *Bacillus licheniformis* which has a known location, orientation and distance in the *Bacillus subtilis* homologs. If a PCR product of the expected size is synthesized, according to the *Bacillus subtilis* chromosomal map, it can be concluded that the two target genes are placed in the same orientation and at the same distance on both chromosomes.

Multiple PCR reactions as described herein were performed on *Bacillus licheniformis* to investigate the degree of co-linearity to the model organism *Bacillus subtilis*. The results of the PCR mapping indicate that approximately 75% of the *Bacillus subtilis* and *Bacillus licheniformis* gene content are similar or collinear (Lapidus et al., Poster P67 at The $10^{th}$ International Conference on Bacilli, Baveno, Italy).

This high degree of co-linearity between these two organisms can be exploited when yet unidentified genes or part of genes from the *Bacillus licheniformis* chromosome are to be cloned. By using the *Bacillus subtilis* chromosomal map as model for the *Bacillus licheniformis* chromosome, it is possible to amplify specific genome regions of *Bacillus licheniformis* where a certain gene of interest are predicted to be located according to the *Bacillus subtilis* chromosomal map. Flanking sequence tags to the region can be as far apart as 10-15 kb when long range PCR methods are employed. This method of PCR mapping was used for cloning several genes of specific interest that were not tagged in the primary shot-gun library.

Gene Disrupting/Deletion

FIG. 1 describes a method to make deletions at specific loci of the *Bacillus licheniformis* or *Bacillus* clausii chromosome utilizing the *Bacillus licheniformis* or *Bacillus* clausii GST sequences, respectively, described herein.

A plasmid denoted "Deletion plasmid" is constructed by cloning two PCR amplified fragments from given gene X region denoted "Y" on a temperature-sensitive parent plasmid. The PCR fragments are denoted "A" and "B", wherein A comprises the 5'-part of the Y fragment; and B comprises the 3'-part of DNA fragment Y. The deleted Y DNA between A and B may be varied depending of the size of the Y fragment. The size of the A and B fragment should be larger than 100 basepairs. A spectinomycin resistance gene flanked by resolvase (res) sites is introduced between fragments "A" and "B" on the plasmid. This spectinomycin resistance gene can later be removed by resolvase-mediated site-specific recombination.

The disrupting/deletion is transferred from the "Deletion plasmid" to the chromosome of a *Bacillus licheniformis* or *Bacillus clausii* target strain by double homologous recombination via fragments "A" and "B", mediated by integration and excision of the temperature-sensitive plasmid. The resulting strain is denoted "Deletion strain".

The present invention is further described by the following examples, which should not be construed as limiting the scope of the invention.

EXAMPLES

Chemicals used as buffers and substrates were commercial products of at least reagent grade.

Example 1

Construction of *Bacillus licheniformis* Library

*Bacillus licheniformis* ATCC 14580 was used as source of chromosomal DNA for constructing a library. Strain *E. coli* JJC 128F' araD139 Δ(ara-leu)7696 galE15 galK16 Δ(lac) X74 hsdr⁻ hsdm⁺ Str$^R$ F'[lacI$^q$ Δ(lacZ)M15 traD36] was used as a host to construct the genomic bank (Sorokin et al., 1996, *Microbiology* 142: 2005-2016).

Chromosomal DNA from *Bacillus licheniformis* ATCC 14580 was prepared as follows. *Bacillus licheniformis* strain ATCC 14580 was cultivated overnight at 37° C. in 125 ml shake flasks containing 25 ml of LB medium (Sambrook et al., Molecular Cloning: A Laboratory Manual, 2$^{nd}$ ed., Cold Spring Harbor Laboratory Press, NY, 1989). The cells were harvested and treated with 10 μg of lysozyme per ml of 50 mM Tris-HCl pH 8.0, 50 mM EDTA, 25% sucrose. SDS was then added to a final concentration of 0.5% followed by proteinase K to 100 μg/ml. The mixture was incubated at 50 for 4 hours, and then extracted three times with water-saturated phenol-chloroform (1:1 v/v) at pH 8.0. After precipitation with two volumes of ethanol in 0.3 M sodium acetate pH 4.8, the DNA was removed with a glass rod, washed in 70% ethanol, and stored at −20° C. in water at 100 μg/ml.

Plasmid pSGMU2 (Errington, 1986, *Journal of General Microbiology* 132: 2953-2961) was used as a vector for constructing the chromosomal bank. pSGMU2 was isolated as follows. Cells of *E. coli* JJC 128F', containing pSGMU2, were grown in 4 ml of 2×YT medium (Sambrook et al., 1989, supra) overnight. The cell pellet was resuspended in 100 μl of 50 mM glucose, 25 mM Tris/HCl pH 8.0, 10 mM EDTA solution (TE). Then a 100 μl volume of 10 mg/ml lysozyme was added. After 30 minutes 400 μl of 1% (w/v) SDS, 0.2 M NaOH were added. After cell lysis, 300 μl of 3 M sodium acetate pH 4.8, was added. After 30 minutes on ice, tubes were centrifuged at 13,000 rpm (5000×g) for 1 hour and 0.6 ml of isopropanol was added to the supernatant. After centrifugation as before for 10 minutes, the pellet was dissolved in 100 μl of water and then 100 μl of 9 M lithium chloride was added. After 1 hour at −20° C., tubes were centrifuged at 13,000 rpm (5000×g) for 10 minutes. The pellet was discarded and 500 μl of absolute ethanol was added to the supernatant. The pellet was redissolved in 300 μl of 0.3 M sodium acetate pH 4.8 and precipitated again. After dissolving the pellet in 100 μl of TE, the plasmid preparation was sufficiently pure for fluorescent sequencing.

A library with insert sizes in the range from 1 to 2 kb, was constructed by using pSGMU2. A 20 μg quantity of *Bacillus licheniformis* chromosomal DNA was sonicated using a VibraCell 72408 sonicator (Bioblock Scientific) at minimal amplitude for 10 seconds. The sonication was performed in 300 μl of Bal31 buffer (600 mM NaCl, 20 mM Tris-HCl pH 8.0, 12 mM CaCl$_2$, 12 mM MgCl$_2$, 1 mM EDTA) in a 1.5 ml Eppendorf tube. After sonication the chromosomal DNA was treated with Bal31 exonuclease (New England Biolabs, Inc., Beverly, Mass.) for 5 minutes at 25° C. After water-saturated phenol extraction and ethanol precipitation the DNA was treated by Klenow fragment of DNA polymerase I under the following conditions: 10 mM Tris HCl pH 7.6, 10 mM MgCl$_2$, 0.2 mM each dNTP, at 37° C. for 1 hour. After water-saturated phenol extraction and ethanol precipitation, the DNA was ligated with SmaI-digested pSGMU2 and treated with bacterial alkaline phosphatase. The ligation was performed in 10 mM Tris HCl pH 7.6, 10 mM MgCl$_2$, 1 mM DTT, 1 mM ATP at 10° C. for 6 hours. DNA from the ligation mixture was precipitated with ethanol in the presence of 1 mM glycogen at −20° C.

The DNA was then electroporated into *E. coli* JJC128F' cells using 2.5 kV and 25 mF. The cells were plated on LB agar medium containing 50 μg/ml of ampicillin for selection of transformants and 20 μg/ml of 5-bromo-4-chloro-3-indolyl beta-D-galactopyranoside (XGAL) and 20 μg/ml of isopropyl beta-D-thiogalactopyranoside (IPTG) for selection of inserts. The ratio of white to blue colonies in a successful experiment was 4 to 1. A total of 25.244 plasmids were extracted from the white colonies and were sequenced by forward (M13-21) primer and 877 plasmids by reverse (M13RP1) primer using a Perkin-Elmer Applied Biosystems Model 377 XL Automatic DNA Sequencer, Perkin-Elmer Applied Biosystems, Inc., Foster City, Calif.) with successful sequencing rate of about 90%. The sequencing produced a total of 13.227.856 bases. The total accumulated nonredundant contig length was 3.723.871 basepairs in 1.239 contigs randomly distributed over the chromosome.

Oligonucleotides were synthesized using a DNA Synthesizer "Oligo 1000" (Beckman-Coulter, Fullerton, Calif.). Primers used for Long Accurate PCR were 20-22-mers, chosen to contain 12 GC-bases.

Plasmid DNA for sequencing was prepared as described above. PCR products used for sequencing with dye terminators were purified by the Wizard™ PCR Preps kit (Promega, Madison, Wis.) or agarose gel electrophoresis. Forward and reverse PCR sequencing was performed using BigDye terminator Cycle Sequencing Ready Reaction Kit (Perkin-Elmer Applied Biosystems, Inc., Foster City, Calif.) and a "Perkin Elmer" 9600 thermal cycler or the "Catalyst" station (Perkin-Elmer Applied Biosystems, Inc., Foster City, Calif.). The fragment separation was conducted using an Applied Biosystems Model 377 XL Automatic DNA Sequencer.

The Long Accurate PCR reaction (50 μl) contained the following components as described by Sorokin et al. (1996, *Genome Research* 6: 448-453): 20 mM Tricine, pH 8.7; 85 mM potassium acetate; 1 mM magnesium acetate; 8% glycerol; 2% dimethylsulfoxide; 0.2 mM each dNTP; 0.2 μM each primer; 0.1 μg chromosomal DNA; 2 U rTth (Perkin-Elmer Applied Biosystems, Inc., Foster City, Calif.); and 0.05 U of Vent polymerase (New England Biolabs, Inc., Beverly, Mass.). The Long Accurate PCR used the following cycling conditions: One cycle at 94° C. for 5 minutes; 12 cycles of 10 second melting at 94° C., and 12 minutes annealing-polymerisation-repair at 68° C., and 24 cycles with increasing the extension time 15 seconds for each cycle.

The overall results are summarized in Table 1.

TABLE 1

Summary of whole-genome random clone
sequencing of *Bacillus licheniformis*
ATCC 14580

| | |
|---|---|
| Successful sequencing reactions | 22,468 |
| Total contig length (bp) | 3,723,871 |
| Number of contigs | 1,239 |
| Average contig length (bp) | 3,006 |

Example 2

DNA Sequencing and Analysis of Nucleotide Sequence Data of the *Bacillus licheniformis* GST Libraries Nucleotide sequence data were scrutinized for quality, and samples giving improper spacing or ambiguity levels exceeding 2% were discarded or re-run. Vector sequences were removed with the crossmatch program from the Phred/Phrap package (Ewing and Green, 1998, *Genome Research* 8: 186-194). The sequences were assembled with Phrap also from the Phred/Phrap package.

Annotation of a gene means assignment of a function to a given sequence. The protein encoded genes were found and annotated the following way: The assembled sequences were searched with BLASTX (Pearson and Lipman, 1988, *Proceedings of the National Academy of Science USA* 85: 2444-2448; Pearson, 1990, *Methods in Enzymology* 183: 63-98) against a customized database consisting of protein sequences from SWISSPROT, SWISSPROTNEW, TREMBL, TREMBLNEW, REMTREMBL, PDB and GeneSeqP. The matrix used was BL50. The start and stop position of each hit and the score of the hit where temporarily marked in the sequence. All open reading frames starting with ATG, GTG or TTG where temporarily marked with the start and stop position and a score. The score of the ORF was calculated as 0.5 times the length of the ORF for ORF starting with ATG and 0.25 times the length of the ORF for ORFs starting with GTG or TTG. A non overlapping set of regions with maximal score larger than 100 was found from the temporarily marked sequence. Each region represents a gene. The best hit for each gene is shown in Appendix 1. Functional category assignment was done by fastx homology search against clusters of orthologous genes from ncbi. In Appendix 1, the assignment to a particular functional category is represented by a single letter. "C" means energy production and conversion. "D" means cell division and chromosome partitioning. "E" means amino acid transport and metabolism. "F" means nucleotide transport and metabolism. "G" means carbohydrate transport and metabolism. "H" means coenzyme metabolism. "I" means lipid metabolism. "J" means translation, ribosomal structure and biogenesis. "K" means transcription. "L" means DNA replication, recombination and repair. "M" means cell envelope biogenesis, outer membrane. "N" means cell motility and secretion. "O" means posttranslational modification, protein turnover, chaperones. "P" means inorganic ion transport and metabolism. "Q" means secondary metabolites biosynthesis, transport and catabolism. "R" means general function prediction only. "S" means function unknown. "T" means signal transduction mechanisms.

Structural RNA encoding genes were found by homology (blastn) to tRNA and rRNA genes in *Bacillus subtilis*.

The *Bacillus licheniformis* GST sequences are designated SEQ ID NOs. 1-4448. An "N" in a nucleic acid sequence means that the nucleotide is an A, C, G, or T.

Example 3

Construction of *Bacillus clausii* Library

*Bacillus clausii* NCIB 10309 (National Collections of Industrial and Marine Bacteria Ltd., 23 St. Machar Drive, Aberdeen, Scotland, UK AB2 1RY) was used as source of chromosomal DNA for constructing a library. Strain *E. coli* JJC 128F' araD139 Δ(ara-leu)7696 galE15 galK16 Δ(lac) X74 hsdr⁻ hsdm⁺ Str$^R$ F'[lacI$^q$ Δ(lacZ)M15 traD36] was used as a host to construct the genomic bank (Sorokin et al., 1996, *Microbiology* 142: 2005-2016).

Chromosomal DNA from *Bacillus clausii* NCIB 10309 was prepared as follows. *Bacillus clausii* strain NCIB 10309 was cultivated overnight at 37° C. in 125 ml shake flasks containing 25 ml of LB medium (Sambrook et al., Molecular Cloning: A Laboratory Manual, 2$^{nd}$ ed., Cold Spring Harbor Laboratory Press, NY, 1989). The cells were harvested and treated with 10 µg of lysozyme per ml of 50 mM Tris-HCl pH 8.0, 50 mM EDTA, 25% sucrose. SDS was then added to a final concentration of 0.5% followed by proteinase K to 100 µg/ml. The mixture was incubated at 50° C. for 4 hours, and then extracted three times with water-saturated phenol-chloroform (1:1 v/v) at pH 8.0. After precipitation with two volumes of ethanol in 0.3 M sodium acetate pH 4.8, the DNA was removed with a glass rod, washed in 70% ethanol, and stored at −20° C. in water at 100 µg/ml.

Plasmid pSGMU2 (Errington, 1986, *Journal of General Microbiology* 132: 2953-2961) was used as a vector for constructing the chromosomal bank. pSGMU2 was isolated as follows. Cells of *E. coli* JJC 128F', containing pSGMU2, were grown in 4 ml of 2×YT medium (Sambrook et al., 1989, supra) overnight. The cell pellet was resuspended in 100 µl of 50 mM glucose, 25 mM Tris/HCl pH 8.0, 10 mM EDTA solution (TE). Then a 100 µl volume of 10 mg/ml lysozyme was added. After 30 minutes 400 µl of 1% (w/v) SDS, 0.2 M NaOH were added. After cell lysis, 300 µl of 3 M sodium acetate pH 4.8, was added. After 30 minutes on ice, tubes were centrifuged at 13,000 rpm (5000×g) for 1 hour and 0.6 ml of isopropanol was added to the supernatant. After centrifugation as before for 10 minutes, the pellet was dissolved in 100 µl of water and then 100 µl of 9 M lithium chloride was added. After 1 hour at −20° C., tubes were centrifuged at 13,000 rpm (5000×g) for 10 minutes. The pellet was discarded and 500 µl of absolute ethanol was added to the supernatant. The pellet was redissolved in 300 µl of 0.3 M sodium acetate pH 4.8 and precipitated again. After dissolving the pellet in 100 µl of TE, the plasmid preparation was sufficiently pure for fluorescent sequencing.

A library with insert sizes in the range from 1 to 2 kb, was constructed by using pSGMU2. A 20 µg quantity of *Bacillus clausii* chromosomal DNA was sonicated using a VibraCell 72408 sonicator (Bioblock Scientific) at minimal amplitude for 10 seconds. The sonication was performed in 300 µl of Bal31 buffer (600 mM NaCl, 20 mM Tris-HCl pH 8.0, 12 mM CaCl$_2$, 12 mM MgCl$_2$, 1 mM EDTA) in a 1.5 ml Eppendorf tube. After sonication the chromosomal DNA was treated with Bal31 exonuclease (New England Biolabs, Inc., Beverly, Mass.) for 5 minutes at 25° C. After water-saturated phenol extraction and ethanol precipitation the DNA was treated by Klenow fragment of DNA polymerase I under the following conditions: 10 mM Tris HCl pH 7.6, 10 mM MgCl$_2$, 0.2 mM each dNTP, at 37° C. for 1 hour. After water-saturated phenol extraction and ethanol precipitation, the DNA was ligated with SmaI-digested pSGMU2 and treated with bacterial alkaline phosphatase. The ligation was performed in 10 mM Tris HCl pH 7.6, 10 mM MgCl$_2$, 1 mM DTT, 1 mM ATP at 10° C. for 6 hours. DNA from the ligation mixture was precipitated with ethanol in the presence of 1 mM glycogen at −20° C.

The DNA was then electroporated into E. coli JJC128F' cells using 2.5 kV and 25 mF. The cells were plated on LB agar medium containing 50 µg/ml of ampicillin for selection of transformants and 20 µg/ml of 5-bromo-4-chloro-3-indolyl beta-D-galactopyranoside (XGAL) and 20 µg/ml of isopropyl beta-D-thiogalactopyranoside (IPTG) for selection of inserts. The ratio of white to blue colonies in a successful experiment was 4 to 1. A total of 6.554 plasmids were extracted from the white colonies and were sequenced by forward (M13-21) primer using a Perkin-Elmer Applied Biosystems Model 377 XL Automatic DNA Sequencer, Perkin-Elmer Applied Biosystems, Inc., Foster City, Calif.) with successful sequencing rate of about 90%. The sequencing produced 3,191.401 bp. The total accumulated nonredundant contig length was 2.022.840 bp in 2.232 contigs randomly distributed over the chromosome.

Oligonucleotides were synthesized using a DNA Synthesizer "Oligo 1000" (Beckman-Coulter, Fullerton, Calif.). Primers used for Long Accurate PCR were 20-22-mers, chosen to contain 12 GC-bases.

The overall results are summarized in Table 2.

TABLE 2

Summary of whole-genome random clone sequencing of Bacillus clausii

| | |
|---|---|
| Successful sequencing reactions | 5,899 |
| Total characters in gel readings (bp) | 3,191,401 |
| Average gel read length (bp) | 541 |
| Total contig length (bp) | 2,022,840 |
| Number of contigs | 2,232 |

Example 4

Analysis of Nucleotide Sequence Data of the Bacillus clausii GST Libraries

Nucleotide sequence data were scrutinized for quality, and samples giving improper spacing or ambiguity levels exceeding 2% were discarded or re-run. Vector sequences were removed with the crossmatch program from the Phred/Phrap package (Ewing and Green, 1998, Genome Research 8: 186-194). The sequences were assembled with Phrap also from the Phred/Phrap package.

Annotation of a gene means assignment of a function to a given sequence. The protein encoded genes were found and annotated the following way: The assembled sequences were searched with BLASTX (Pearson and Lipman, 1988, Proceedings of the National Academy of Science USA 85: 2444-2448; Pearson, 1990, Methods in Enzymology 183: 63-98) against a customized database consisting of protein sequences from SWISSPROT, SWISSPROTNEW, TREMBL, TREMBLNEW, REMTREMBL, PDB and GeneSeqP. The matrix used was BL50. The start and stop position of each hit and the score of the hit where temporarily marked in the sequence. All open reading frames starting with ATG, GTG or TTG where temporarily marked with the start and stop position and a score. The score of the ORF was calculated as 0.5 times the length of the ORF for ORF starting with ATG and 0.25 times the length of the ORF for ORFs starting with GTG or TTG. A non overlapping set of regions with maximal score larger than 100 was found from the temporarily marked sequence. Each region represents a gene. The best hit for each gene is shown in Appendix 2. Functional category assignment was done by fastx homology search against clusters of orthologous genes from ncbi. In Appendix 2, the assignment to a particular functional category is represented by a single letter. "C" means energy production and conversion. "D" means cell division and chromosome partitioning. "E" means amino acid transport and metabolism. "F" means nucleotide transport and metabolism. "G" means carbohydrate transport and metabolism. "H" means coenzyme metabolism. "I" means lipid metabolism. "J" means translation, ribosomal structure and biogenesis. "K" means transcription. "L" means DNA replication, recombination and repair. "M" means cell envelope biogenesis, outer membrane. "N" means cell motility and secretion. "O" means posttranslational modification, protein turnover, chaperones. "P" means inorganic ion transport and metabolism. "Q" means secondary metabolites biosynthesis, transport and catabolism. "R" means general function prediction only. "S" means function unknown. "T" means signal transduction mechanisms.

Structural RNA encoding genes were found by homology (blastn) to tRNA and rRNA genes in Bacillus subtilis.

The Bacillus clausii GST sequences, which encode proteins are designated SEQ ID NOs. 4449-8481. An "N" in a nucleic acid sequence means that the nucleotide is an A, C, G, or T.

Example 5

DNA Microarrays

Details of the construction of a typical microarrayer can be found on the world wide web site of Professor Patrick Brown of Stanford University. Scanners and computer software for analysis of DNA microarrays are available from several commercial sources such as General Scanning Inc. (Watertown, Mass.), or Axon Instruments (Foster City, Calif.). Individual Bacillus GST clones were purified as plasmid minipreps using Qiagen Biorobot 9600 (QIAGEN, Inc., Valencia, Calif.). The plasmid minipreps were precipitated with isopropanol, aliquoted and stored as described on the web site of Professor Patrick Brown of Stanford University.

The amplified GST targets prepared in this manner were spotted individually onto polylysine-coated glass slides using a microarrayer device as described by DeRisi et al. (1997, Science 278: 680-686). The microarrays were probed with fluorescently labeled cDNA prepared by reverse transcription of polyadenylated mRNA (DeRisi et al., 1997, supra) extracted from Bacillus cells (Example 2 or Example 4). Conditions for pretreatment of the microarrays, hybridization and washing conditions have been described previously (DeRisi et al., 1997, supra).

To increase the reliability with which changes in expression levels could be discerned, probes prepared from induced or treated cells were labeled with the red fluorescent dye, Cy5 (Amersham Corporation, Arlington Heights, Ill.), and mixed with probes from uninduced, untreated, or "reference" cells were labeled with a green fluorescent dye, Cy3 (Amersham Corporation, Arlington Heights, Ill.). The relative ratio of fluorescence intensity measured for the Cy3 and Cy5 fluorophors corresponding to each GST target in the arrays was determined using ScanAlyze software. This provides a reliable measure of the relative abundance of the corresponding mRNA in the two cell populations (e.g., treated cells versus reference cells).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

APPENDIX 1

*Bacillus licheniformis* Annotation and Divisions into Functional Categories

Information Storage and Processing
J 1154-1309 Translation, ribosomal structure and biogenesis
K 1310-1521 Transcription
L 1522-1665 DNA replication, recombination and repair
Cellular Processes
D 174-218 Cell division and chromosome partitioning
O 1925-2015 Posttranslational modification, protein turnover, chaperones
M 1666-1835 Cell envelope biogenesis, outer membrane
N 1836-1924 Cell motility and secretion
P 2016-2165 Inorganic ion transport and metabolism
T 4337-4360 Signal transduction mechanisms
Metabolism
C 1-173 Energy production and conversion
G 642-967 Carbohydrate transport and metabolism
E 219-554 Amino acid transport and metabolism
F 555-641 Nucleotide transport and metabolism
H 968-1073 Coenzyme metabolism
I 1074-1153 Lipid metabolism
Q 2166-2287 Secondary metabolites biosynthesis, transport and catabolism
Structural RNA
Z 4361-4448 tRNA and rRNA
Functional Category not Assigned
R 2288-2621 Functional category not assigned
S 2622-4236 Functional category not assigned
ID0001C NITRATE REDUCTASE ALPHA CHAIN (EC 1.7.99.4).
ID0002C PYRUVATE CARBOXYLASE (EC 6.4.1.1).
ID0003C QUINOL OXIDASE POLYPEPTIDE I (EC 1.9.3.-) (QUINOL OXIDASE AA
ID0004C NITRITE REDUCTASE [NAD(P)H] (EC 1.6.6.4).
ID0005C HYPOTHETICAL 79.2 KDA PROTEIN IN ACDA 5'REGION.
ID0006C FORMATE DEHYDROGENASE ALPHA CHAIN.
ID0007C 2-OXOGLUTARATE DEHYDROGENASE E1 COMPONENT (EC 1.2.4.2) (ALPH
ID0008C FORMATE ACETYLTRANSFERASE.
ID0009C PUTATIVE FORMATE DEHYDROGENASE.
ID0010C 68% IDENTITY PROTEIN TO 1-PYRROLINE-5-CARBOXYLATE DEHYDROGEN
ID0011C L-RIBULOKINASE (EC 2.7.1.16).
ID0012C YVFW PROTEIN.
ID0013C ATP SYNTHASE BETA CHAIN (EC 3.6.1.34) (VEGETATIVE PROTEIN 31
ID0014C CYTOCHROME CAA3 OXIDASE (SUBUNIT I).
ID0015C ATP SYNTHASE ALPHA CHAIN (EC 3.6.1.34) (VEGETATIVE PROTEIN 1
ID0016C PTS SYSTEM, MANNITOL-SPECIFIC IIABC COMPONENT (EIIABC-MTL)
ID0017C L-LACTATE PERMEASE.
ID0018C FUMARATE HYDRATASE, CLASS-II (EC 4.2.1.2) (FUMARASE).
ID0019C AEROBIC GLYCEROL-3-PHOSPHATE DEHYDROGENASE (EC 1.1.99.5).
ID0020C ALCOHOL-ACETALDEHYDE DEHYDROGENASE.
ID0021C CitM protein.
ID0022C ISOCITRATE DEHYROGENASE.
ID0023C ASSIMILATORY NITRATE REDUCTASE CATALYTIC SUBUNIT (EC 1.7.99.
ID0024C HOMOLOGUE OF SUCCINATE SEMIALDEHYDE DEHYDROGENASE GABD OF E.
ID0025C HYPOTHETICAL 50.9 KDA PROTEIN.
ID0026C PROTON GLUTAMATE SYMPORT PROTEIN (GLUTAMATE-ASPARTATE CARRIE
ID0027C NADP-DEPENDENT ALDEHYDE DEHYDROGENASE (EC 1.2.1.3).
ID0028C PROBABLE NADH-DEPENDENT BUTANOL DEHYDROGENASE 1 (EC 1.1.1.-)
ID0029C NADH DEHYDROGENASE-LIKE PROTEIN.
ID0030C HYPOTHETICAL 47.8 KDA PROTEIN.
ID0031C PROBABLE MALATE OXIDOREDUCTASE [NAD] (EC 1.1.1.38) (MALIC EN
ID0032C HYPOTHETICAL 54.6 KDA PROTEIN.
ID0033C HYPOTHETICAL NA+/H+ ANTIPORTER IN ANSB-SPOIIM INTERGENIC REG
ID0034C *Staphylococcus aureus* mutant P10B2 virulence gene product.
ID0035C CYTOCHROME D UBIQUINOL OXIDASE SUBUNIT I (EC 1.10.3.-).
ID0036C SUCCINYL-COA SYNTHETASE BETA CHAIN (EC 6.2.1.5) (SCS-ALPHA)
ID0037C CITRATE SYNTHASE II (EC 4.1.3.7).
ID0038C DIHYDROLIPOAMIDE DEHYDROGENASE COMPONENT OF PYRUVATEDEHYDROG
ID0039C METHYLMALONATE-SEMIALDEHYDE DEHYDROGENASE.
ID0040C HYPOTHETICAL 44.9 KDA PROTEIN.
ID0041C PROBABLE NAD-DEPENDENT MALIC ENZYME (EC 1.1.1.38) (NAD-ME).
ID0042C ASSIMILATORY NITRATE REDUCTASE ELECTRON TRANSFER SUBUNIT.
ID0043C PUTATIVE BUTYRATE KINASE (EC 2.7.2.7) (BK).
ID0044C HYPOTHETICAL 37.1 KDA PROTEIN IN ARALACA INTERGENIC REGION.
ID0045C 2-OXOISOVALERATE DEHYDROGENASE ALPHA SUBUNIT (EC 1.2.4.4) (B
ID0046C PYRUVATE DEHYDROGENASE E2 (DIHYDROLIPOAMIDE ACETYLTRANSFERAS
ID0047C IOLS PROTEIN (VEGETATIVE PROTEIN 147) (VEG147).
ID0048C 2-OXOISOVALERATE DEHYDROGENASE BETA SUBUNIT (EC 1.2.4.4) (BR
ID0049C GLYCEROL KINASE (EC 2.7.1.30) (ATP:GLYCEROL 3-PHOSPHOTRANSFE
ID0050C CYTOCHROME C OXIDASE POLYPEPTIDE II PRECURSOR (EC 1.9.3.1)

ID0051C SUCCINYL-COA SYNTHETASE (ALPHA SUBUNIT).
ID0052C PROBABLE NADH-DEPENDENT FLAVIN OXIDOREDUCTASE YQJM (EC 1.-.-
ID0053C HOMOLOGOUS TO CITRATE-SODIUM SYMPORT.
ID0054C YFMT.
ID0055C ELECTRON TRANSFER FLAVOPROTEIN ALPHA-SUBUNIT (ALPHA-ETF) (EL
ID0056C MALATE DEHYDROGENASE (EC 1.1.1.37) (VEGETATIVE PROTEIN 69)
ID0057C SUCCINATE DEHYDROGENASE FLAVOPROTEIN SUBUNIT (EC 1.3.99.1).
ID0058C *Corynebacterium thermoaminogenes* acn protein.
ID0059C PYRUVATE DEHYDROGENASE E1 COMPONENT, ALPHA SUBUNIT (EC 1.2.4
ID0060C PYRUVATE DEHYDROGENASE BETA SUBUNIT PDHB (EC 1.2.4.1).
ID0061C PROTON/SODIUM-GLUTAMATE SYMPORT PROTEIN (GLUTAMATE-ASPARTATE
ID0062C GLYCEROL-3-PHOSPHATE DEHYDROGENASE [NAD(P)+] (EC 1.1.1.94)
ID0063C SUCCINATE DEHYDROGENASE IRON-SULFUR PROTEIN (EC 1.3.99.1).
ID0064C LIPOAMIDE ACYLTRANSFERASE COMPONENT OF BRANCHED-CHAIN ALPHA-
ID0065C QUINOL OXIDASE POLYPEPTIDE II PRECURSOR (EC 1.9.3.-) (QUINOL
ID0066C PHOSPHATE ACETYLTRANSFERASE (EC 2.3.1.8) (PHOSPHOTRANSACETYL
ID0067C *Bacillus subtilis* ypgA Glade protein.
ID0068C H(+)/SODIUM-GLUTAMATE SYMPORTER.
ID0069C ACETATE KINASE (EC 2.7.2.1) (ACETOKINASE).
ID0070C HYPOTHETICAL 49.2 KDA PROTEIN.
ID0071C PUTATIVE L-LACTATE PERMEASE YVFH.
ID0072C PUTATIVE MALATE DEHYDROGENASE (EC 1.1.1.37).
ID0073C L-LACTATE DEHYDROGENASE (EC 1.1.1.27).
ID0074C CITRATE SYNTHASE I (EC 4.1.3.7).
ID0075C PUTATIVE MALOLACTIC ENZYME (EC 1.-.-.-) [INCLUDES: MALIC ENZ
ID0076C FDHD PROTEIN HOMOLOG.
ID0077C HYPOTHETICAL 37.6 KDA PROTEIN.
ID0078C HYPOTHETICAL 35.0 KDA PROTEIN IN RAPJ-OPUAA INTERGENIC REGIO
ID0079C NITRATE REDUCTASE GAMMA CHAIN (EC 1.7.99.4).
ID0080C HYPOTHETICAL 36.6 KDA PROTEIN IN QOXD-VPR INTERGENIC REGION.
ID0081C HYPOTHETICAL 49.0 KDA PROTEIN.
ID0082C MALATE SYNTHASE (EC 4.1.3.2).
ID0083C YTHA.
ID0084C Glycerol dehydrogenase.
ID0085C FERRIC LEGHEMOGLOBIN REDUCTASE-2 PRECURSOR.
ID0086C OXIDOREDUCTASE, N5,N10-METHYLENE-TETRAHYDROMETHANOPTERINREDUC
ID0087C NITRO/FLAVIN REDUCTASE (EC 1.-.-.-).
ID0088C *Corynebacterium thermoaminogenes* acn protein.
ID0089C HYPOTHETICAL 48.5 KDA PROTEIN.
ID0090C ISOCITRATE LYASE (EC 4.1.3.1).
ID0091C ARABINOSE OPERON PROTEIN ARAM.
ID0092C HYPOTHETICAL 48.1 KDA PROTEIN.
ID0093C PHOSPHOENOLPYRUVATE CARBOXYKINASE.
ID0094C HMP (FLAVOHEMOGLOBIN).
ID0095C ATP SYNTHASE A CHAIN (EC 3.6.1.34) (PROTEIN 6).
ID0096C GLYCEROPHOSPHORYL DIESTER PHOSPHODIESTERASE (EC 3.1.4.46) (GL
ID0097C PUTATIVE MALOLACTIC ENZYME (EC 1.-.-.-) [INCLUDES: MALIC ENZ
ID0098C HYPOTHETICAL 27.9 KDA PROTEIN IN PHRC-GDH INTERGENIC REGION.
ID0099C FDRA PROTEIN.
ID0100C ATP SYNTHASE GAMMA CHAIN.
ID0101C (PYRUVATE).
ID0102C DIHYDROLIPOYL TRANSACETYLASE AND LIPOAMIDE DEHYDROGENASE OF
ID0103C PROTOPORPHYRIN OXIDASE.
ID0104C PROBABLE PHOSPHATE BUTYRYLTRANSFERASE (EC 2.3.1.19) (PHOSPHOT
ID0105C BH1977 PROTEIN.
ID0106C ASSIMILATORY NITRATE REDUCTASE ELECTRON TRANSFER SUBUNIT.
ID0107C ACONITATE HYDRATASE (EC 4.2.1.3) (CITRATE HYDRO-LYASE) (ACON
ID0108C *Arabidopsis* aldehyde dehydrogenase (ALDH)-1.
ID0109C METHYLMALONATE-SEMIALDEHYDE DEHYDROGENASE (EC 1.2.1.27) (METH
ID0110C PUTATIVE NAD(P)H NITROREDUCTASE YDFN (EC 1.-.-.-).
ID0111C YTHB.
ID0112C NIFU-LIKE PROTEIN.
ID0113C ISOCITRATE LYASE.
ID0114C ALDEHYDE DEHYDROGENASE (ALDHT) (EC 1.2.1.3).
ID0115C PUTATIVE DEHYDROGENASE SUBUNIT.
ID0116C ATTL.
ID0117C YTHA.
ID0118C PROBABLE NAD-DEPENDENT MALIC ENZYME (EC 1.1.1.38) (NAD-ME).
ID0119C ORF starting with ATG of length 1209
ID0120C HYPOTHETICAL 27.0 KDA PROTEIN IN SPOOA-MMGA INTERGENIC REGIO
ID0121C PHOSPHOENOLPYRUVATE CARBOXYKINASE (ATP) (EC 4.1.1.49).
ID0122C CITRATE SYNTHASE-LIKE PROTEIN.
ID0123C NITRATE REDUCTASE DELTA CHAIN (EC 1.7.99.4).
ID0124C ORF starting with ATG of length 1167
ID0125C MALATE DEHYDROGENASE I (EC 1.1.1.37) (EC 1.1.1.82).
ID0126C 2-OXOGLUTARATE DEHYDROGENASE (FRAGMENT).
ID0127C HYPOTHETICAL OXIDOREDUCTASE IN CSTA-AHPC INTERGENIC REGION.
ID0128C ORF starting with ATG of length 1134
ID0129C YFHC PROTEIN.
ID0130C HYPOTHETICAL 49.2 KDA PROTEIN.
ID0131C GLYCEROPHOSPHORYL DIESTER PHOSPHODIESTERASE.
ID0132C PROBABLE ALDEHYDE DEHYDROGENASE YWDH (EC 1.2.1.3).
ID0133C ALCOHOL-ACETALDEHYDE DEHYDROGENASE.
ID0134C ELECTRON TRANSFER FLAVOPROTEIN BETA-SUBUNIT (BETA-ETF) (ELEC
ID0135C PROBABLE NADH-DEPENDENT FLAVIN OXIDOREDUCTASE YQIG (EC 1.-.-
ID0136C CYTOCHROME OXIDASE SUBUNIT II.
ID0137C ORF starting with ATG of length 854

ID0138C PUTATIVE NAD(P)H NITROREDUCTASE YFKO (EC 1.-.-.-).
ID0139C PUTATIVE SECRETED HYDROLASE.
ID0140C SA0799 PROTEIN.
ID0141C PUTATIVE NAD(P)H NITROREDUCTASE 12C (EC 1.-.-.-) (VEGETATIVE
ID0142C PUTATIVE ACYLPHOSPHATASE (EC 3.6.1.7) (ACYLPHOSPHATEPHOSPHOH
ID0143C Corynebacterium glutamicum MCT protein SEQ ID NO:544.
ID0144C MANGANESE-DEPENDENT INORGANIC PYROPHOSPHATASE (EC 3.6.1.1) (P
ID0145C FOF1-ATP SYNTHASE EPSILON SUBUNIT.
ID0146C ORF starting with ATG of length 624
ID0147C ORF starting with ATG of length 615
ID0148C GLYCEROL-3-PHOSPHATE DEHYDROGENASE [NAD(P)+] (EC 1.1.1.94)
ID0149C PUTATIVE FLAVODOXIN.
ID0150C PROBABLE FLAVODOXIN 2.
ID0151C BH0367 PROTEIN.
ID0152C ELECTRON TRANSFER FLAVOPROTEIN (BETA SUBUNIT).
ID0153C ORF starting with ATG of length 555
ID0154C HYPOTHETICAL 17.0 KDA PROTEIN.
ID0155C ATP SYNTHASE C CHAIN (EC 3.6.1.34) (LIPID-BINDING PROTEIN).
ID0156C ATP SYNTHASE B CHAIN.
ID0157C HYPOTHETICAL OXIDOREDUCTASE IN ANSR-BMRU INTERGENIC REGION.
ID0158C ACETOIN DEHYDROGENASE (TPP-DEPENDENT) ALPHA CHAIN.
ID0159C HYPOTHETICAL 45.4 KDA PROTEIN IN SSPB-PRSA INTERGENIC REGION
ID0160C MENAQUINOL-CYTOCHROME C REDUCTASE CYTOCHROME B SUBUNIT.
ID0161C ORF starting with ATG of length 399
ID0162C MENAQUINOL-CYTOCHROME C REDUCTASE CYTOCHROME B/C SUBUNIT.
ID0163C ORF starting with ATG of length 330
ID0164C ORF starting with ATG of length 294
ID0165C ORF starting with ATG of length 225
ID0166C ORF starting with ATG of length 210
ID0167C HYPOTHETICAL 50.9 KDA PROTEIN.
ID0168CHR YVCT PROTEIN.
ID0169CHR 376AA LONG HYPOTHETICAL DEHYDROGENASE.
ID0170CP YUFT PROTEIN.
ID0171CP HYPOTHETICAL 52.1 KDA PROTEIN.
ID0172CP NADH DEHYDROGENASE SUBUNIT 5 (EC 1.6.5.3) (NADH-UBIQUINONEOX
ID0173CR ORF starting with ATG of length 803
ID0174D CHROMOSOME PARTITION PROTEIN SMC.
ID0175D YUKA PROTEIN.
ID0176D GLUCOSE INHIBITED DIVISION PROTEIN A.
ID0177D YHAN PROTEIN.
ID0178D STAGE III SPORULATION PROTEIN E.
ID0179D STAGE V SPORULATION PROTEIN E.
ID0180D CELL DIVISION PROTEIN FTSZ.
ID0181 D HYPOTHETICAL 53.5 KDA PROTEIN IN SPOIIE-HPT INTERGENIC REGIO
ID0182D CELL DIVISION PROTEIN FTSA.
ID0183D ROD SHAPE-DETERMINING PROTEIN MREB.
ID0184D MREBH PROTEIN.
ID0185D MRP PROTEIN HOMOLOG.
ID0186D MREB-LIKE PROTEIN (MBL PROTEIN).
ID0187D PROTEIN GID.
ID0188D STAGE II SPORULATION PROTEIN D.
ID0189D YTPT.
ID0190D CELL DIVISION PROTEIN FTSX HOMOLOG.
ID0191D SPOIIIE PROTEIN.
ID0192D STAGE V SPORULATION PROTEIN E.
ID0193D ORF starting with ATG of length 1990
ID0194D HYPOTHETICAL 33.2 KDA PROTEIN IN FLHF-CHEB INTERGENIC REGION
ID0195D CELL-DIVISION ATP-BINDING PROTEIN.
ID0196D MINICELL-ASSOCIATED PROTEIN DIVIVA.
ID0197D STAGE V SPORULATION PROTEIN E.
ID0198D Neisseria meningitidis ORF 567 protein sequence SEQ ID NO:16
ID0199D ORF starting with ATG of length 1410
ID0200D MAF PROTEIN.
ID0201 D SEPTUM SITE-DETERMINING PROTEIN MINC.
ID0202D HYPOTHETICAL 43.3 KDA PROTEIN IN QOXD-VPR INTERGENIC REGION.
ID0203D AMIDASE ENHANCER PRECURSOR (MODIFIER PROTEIN OF MAJOR AUTOLY
ID0204D SEPTUM SITE-DETERMINING PROTEIN MIND (CELL DIVISION INHIBITO
ID0205D HYPOTHETICAL 43.3 KDA PROTEIN IN QOXD-VPR INTERGENIC REGION.
ID0206D CAPSULAR POLYSACCHARIDE BIOSYNTHESIS.
ID0207D DIARRHEAL TOXIN.
ID0208D HYPOTHETICAL 13.9 KDA PROTEIN.
ID0209D HYPOTHETICAL PROTEIN H11677.
ID0210D CHROMOSOME PARTITION PROTEIN SMC.
ID0211D HYDROXYPROLINE-RICH GLYCOPROTEIN DZ-HRGP PRECURSOR.
ID0212D ORF starting with ATG of length 510
ID0213D ORF starting with ATG of length 477
ID0214D BH2986 PROTEIN.
ID0215D ORF starting with ATG of length 417
ID0216D Arabidopsis thaliana protein fragment SEQ ID NO: 42012.
ID0217D HYPOTHETICAL 43.3 KDA PROTEIN IN QOXD-VPR INTERGENIC REGION.
ID0218D ORF starting with ATG of length 273
ID0219E GLUTAMATE SYNTHASE [NADPH] LARGE CHAIN (EC 1.4.1.13) (NADPH-
ID0220E 5-METHYLTETRAHYDROFOLATE S-HOMOCYSTEINE METHYLTRANSFERASE (EC
ID0221E 5-METHYLTETRAHYDROPTEROYLTRI-GLUTAMATE-HOMOCYSTEINE METHYLTR
ID0222E ASPARAGINE SYNTHETASE [GLUTAMINE-HYDROLYZING] 3 (EC 6.3.5.4)
ID0223E PERMEASE.
ID0224E PROBABLE PEPTIDASE YUXL (EC 3.4.21.-).
ID0225E PROBABLE GLYCINE DEHYDROGENASE [DECARBOXYLATING] SUBUNIT 2(E
ID0226E HYPOTHETICAL 54.1 KDA PROTEIN IN DEOD-ARGE INTERGENIC REGION
ID0227E ASPARAGINE SYNTHETASE [GLUTAMINE-HYDROLYZING] 1 (EC 6.3.5.4)
ID0228E ARGININOSUCCINATE LYASE (EC 4.3.2.1) (ARGINOSUCCINASE) (ASAL
ID0229E YBGF PROTEIN.
ID0230E PROBABLE GLYCINE DEHYDROGENASE [DECARBOXYLATING] SUBUNIT 1(E
ID0231E HYPOTHETICAL PROTEIN YWRD.
ID0232E Gamma glutamyl transpeptidase.
ID0233E YVBW PROTEIN.

ID0234E PROBABLE ASPARTOKINASE (EC 2.7.2.4) (ASPARTATE KINASE).
ID0235E HOMOSERINE DEHYDROGENASE (EC 1.1.1.3) (HDH).
ID0236E YUSX PROTEIN.
ID0237E AMINO-ACID PERMEASE ROCE.
ID0238E PUTATIVE L-AMINO ACID OXIDASE PRECURSOR.
ID0239E LEUCINE DEHYDROGENASE (EC 1.4.1.9) (LEUDH).
ID0240E ACETYLORNITINE DEACETYLASE (YOKP).
ID0241E TRYPTOPHAN SYNTHASE BETA CHAIN (EC 4.2.1.20).
ID0242E ORNITHINE CARBAMOYLTRANSFERASE, CATABOLIC (EC 2.1.3.3) (OTCA
ID0243E YKBA PROTEIN.
ID0244E AMINOPEPTIDASE AMPS (EC 3.4.11.-).
ID0245E ORNITHINE AMINOTRANSFERASE (EC 2.6.1.13).
ID0246E CHORISMATE SYNTHASE (EC 4.6.1.4) (5-ENOLPYRUVYLSHIKIMATE-3-P
ID0247E HYPOTHETICAL 39.7 KDA PROTEIN IN GLNQ-ANSR INTERGENIC REGION
ID0248E AMINO ACID CARRIER PROTEIN ALST.
ID0249E 2,4-DIAMINOBUTYRATE DECARBOXYLASE.
ID0250E THREONINE SYNTHASE (EC 4.2.99.2).
ID0251E HISTIDINOL DEHYDROGENASE (EC 1.1.1.23) (HDH).
ID0252E CARBAMATE KINASE (EC 2.7.2.2).
ID0253E 3-ISOPROPYLMALATE DEHYDRATASE LARGE SUBUNIT (EC 4.2.1.33) (IS
ID0254E PEPTIDASE T (EC 3.4.11.-) (AMINOTRIPEPTIDASE) (TRIPEPTIDASE)
ID0255E PREPHENATE DEHYDROGENASE (EC 1.3.1.12) (PDH).
ID0256E NAD-SPECIFIC GLUTAMATE DEHYDROGENASE (EC 1.4.1.2) (NAD-GDH).
ID0257E ARGININOSUCCINATE SYNTHASE (EC 6.3.4.5) (CITRULLINE-ASPARTA
ID0258E YBGH PROTEIN.
ID0259E YKVY PROTEIN.
ID0260E PUTATIVE AMINOTRANSFERASE B (EC 2.6.1.-).
ID0261E Peptide with glutamine synthetase activity.
ID0262E YURG PROTEIN.
ID0263E ARGININE DEIMINASE (EC 3.5.3.6) (ARGININE DIHYDROLASE).
ID0264E THREONINE DEHYDRATASE (EC 4.2.1.16).
ID0265E ASPARTOKINASE 2 (EC 2.7.2.4) (ASPARTOKINASE II) (ASPARTATE K
ID0266E YDFO PROTEIN.
ID0267E PUTATIVE PEPTIDASE IN GCVT-SPOIIIAA INTERGENIC REGION (EC 3.
ID0268E PROBABLE AMINOMETHYLTRANSFERASE (EC 2.1.2.10) (GLYCINE CLEAV
ID0269E 2,4-DIAMINOBUTYRATE DECARBOXYLASE.
ID0270E HYPOTHETICAL TRANSPORT PROTEIN IN EXPZ-DINB INTERGENIC REGIO
ID0271E PROBABLE CYSTEINE SYNTHASE (EC 4.2.99.8) (O-ACETYLSERINESULF
ID0272E YJCJ PROTEIN.
ID0273E PROBABLE 4-AMINOBUTYRATE AMINOTRANSFERASE (EC 2.6.1.19) (GAM
ID0274E DNA FOR 25-36 DEGREE REGION CONTAINING THE AMYE-SRFA REGION,
ID0275E PROJ.
ID0276E B. subtilis AnsB homologue.
ID0277E AROMATIC AMINO ACID TRANSPORTER.
ID0278E YFLA PROTEIN.
ID0279E GLYCINE OXIDASE (EC 1.5.3.-).
ID0280E PUTATIVE INNER MEMBRANE PROTEIN.
ID0281E HYDANTOIN UTILIZATION PROTEIN A (ORF2).
ID0282E HYPOTHETICAL 38.3 KDA PROTEIN IN PEPT-KATB INTERGENIC REGION
ID0283E HYPOTHETICAL 58.2 KDA PROTEIN IN KDGT-XPT INTERGENIC REGION.
ID0284E HYPOTHETICAL 43.4 KDA PROTEIN IN SODA-COMGA INTERGENIC REGIO
ID0285E GLYCINE BETAINE TRANSPORT SYSTEM PERMEASE PROTEIN OPUAB.
ID0286E TIORF195 PROTEIN.
ID0287E HOMOSERINE KINASE (EC 2.7.1.39) (HK).
ID0288E YRVO PROTEIN.
ID0289E PZ-PEPTIDASE.
ID0290E TARTRATE DEHYDROGENASE.
ID0291E CYSTATHIONINE GAMMA-LYASE.
ID0292E ASPARTATE AMINOTRANSFERASE (EC 2.6.1.1) (TRANSAMINASE A) (AS
ID0293E DIPEPTIDE TRANSPORT PROTEIN DPPA.
ID0294E D-3-PHOSPHOGLYCERATE DEHYDROGENASE (EC 1.1.1.95) (PGDH).
ID0295E PROBABLE AMINO-ACID ABC TRANSPORTER ATP-BINDING PROTEIN YCKI
ID0296E YNGG PROTEIN.
ID0297E PUTATIVE HYDANTOIN UTILIZATION PROTEIN.
ID0298E HISTIDINOL-PHOSPHATE AMINOTRANSFERASE/TYROSINE AND PHENYLALA
ID0299E BUSAA.
ID0300E L-2,4-DIAMINOBUTYRATE DECARBOXYLASE (EC 4.1.1.).
ID0301E ANTHRANILATE PHOSPHORIBOSYLTRANSFERASE (EC 2.4.2.18).
ID0302E HISF PROTEIN (CYCLASE).
ID0303E N-ACETYLORNITHINE AMINOTRANSFERASE (EC 2.6.1.11).
ID0304E YURW PROTEIN.
ID0305E 2-ISOPROPYLMALATE SYNTHASE (EC 4.1.3.12).
ID0306E PROBABLE AMINO-ACID ABC TRANSPORTER EXTRACELLULAR BINDING PR
ID0307E L-SERINE DEHYDRATASE ALPHA SUBUNIT.
ID0308E Bacillus subtilis metalloprotease YurH.
ID0309E PROBABLE ABC TRANSPORTER EXTRACELLULAR BINDING PROTEIN YCKB
ID0310E YNBB.
ID0311E HYPOTHETICAL 57.1 KDA PROTEIN.
ID0312E LYSINE DECARBOXYLASE (EC 4.1.1.18) (LDC).
ID0313E HYPOTHETICAL 53.2 KDA PROTEIN IN XPAC-ABRB INTERGENIC REGION
ID0314E OLIGOENDOPEPTIDASE F HOMOLOG (EC 3.4.24.-).
ID0315E SERINE HYDROXYMETHYLTRANSFERASE (EC 2.1.2.1) (SERINE METHYLA
ID0316E PUTATIVE AMINOTRANSFERASE A (EC 2.6.1.-).
ID0317E ORF starting with ATG of length 2001
ID0318E GLYCINE BETAINE/CARNITINE/CHOLINE TRANSPORT SYSTEM PERMEASE
ID0319E TRANSCARBAMYLASE ID0320E SHIKIMATE 5-DEHYDROGENASE (EC 1.1.1.25).
ID0321E COME OPERON PROTEIN 4.
ID0322E ORF starting with ATG of length 1971
ID0323E Bacillus subtilis Class II EPSPS.
ID0324E PHOSPHORIBOSYLFORMIMINO-5-AMINOIMIDAZOLE CARBOXAMIDE RIBOTID
ID0325E SERINE ACETYLTRANSFERASE (EC 2.3.1.30) (SAT).
ID0326E GLYCINE BETAINE/CARNITINE/CHOLINE TRANSPORT SYSTEM PERMEASE
ID0327E GLUTAMYL ENDOPEPTIDASE PRECURSOR (EC 3.4.21.19) (GLUTAMATE S
ID0328E ASPARTOKINASE 1 (EC 2.7.2.4) (ASPARTOKINASE I) (ASPARTATE KI
ID0329E BH0994 PROTEIN.
ID0330E HYPOTHETICAL 40.8 KDA PROTEIN IN PCP-LMRB INTERGENIC REGION
ID0331E HYPOTHETICAL 39.4 KDA OXIDOREDUCTASE IN HOM-MRGA INTERGENIC
ID0332E CYSTEINE SYNTHASE.
ID0333E 3-ISOPROPYLMALATE DEHYDRATASE SMALL SUBUNIT (EC 4.2.1.33) (IS
ID0334E IMIDAZOLEGLYCEROL-PHOSPHATE DEHYDRATASE (EC 4.2.1.19) (IGPD)
ID0335E ASPARTATE-SEMIALDEHYDE DEHYDROGENASE (EC 1.2.1.11) (ASA DEHY
ID0336E YBEC PROTEIN (ORF3).
ID0337E GLYCINE BETAINE-BINDING PROTEIN PRECURSOR.
ID0338E ORF starting with ATG of length 1797
ID0339E 3-ISOPROPYLMALATE DEHYDROGENASE (EC 1.1.1.85) (BETA-IPM DEHY
ID0340E PROBABLE AMINO-ACID ABC TRANSPORTER PERMEASE PROTEIN YCKA.
ID0341E ORF starting with ATG of length 1740
ID0342E GLUTAMATE SYNTHASE [NADPH] LARGE CHAIN (EC 1.4.1.13) (NADPH—
ID0343E PYRROLINE-5-CARBOXYLATE REDUCTASE HOMOLOG 1.
ID0344E ALANINE DEHYDROGENASE (EC 1.4.1.1) (STAGE V SPORULATION PROT
ID0345E HISTIDINE BIOSYNTHESIS BIFUNCTIONAL PROTEIN HISIE [INCLUDES:
ID0346E NIFS2.
ID0347E ACETYLGLUTAMATE KINASE (EC 2.7.2.8) (NAG KINASE) (AGK) (N-AC
ID0348E BH1629 PROTEIN.
ID0349E HYPOTHETICAL 27.6 KDA LIPOPROTEIN IN NUCB-AROD INTERGENIC RE
ID0350E HYPOTHETICAL TRANSPORT PROTEIN IN NDHF-CSGA INTERGENIC REGIO
ID0351E BH0591PROTEIN.
ID0352E ALANINE DEHYDROGENASE (STAGE V SPORULATION PROTEIN N) (EC 1.
ID0353E 5-METHYLTETRAHYDROFOLATE S-HOMOCYSTEINE METHYLTRANSFERASE (EC
ID0354E BRANCH-CHAIN AMINO ACID TRANSPORTER.
ID0355E HYPOTHETICAL 63.8 KDA PROTEIN IN SIPU-PBPC INTERGENIC REGION
ID0356E B. subtilis hydrolase protein YTMA.
ID0357E ATP PHOSPHORIBOSYLTRANSFERASE (EC 2.4.2.17).
ID0358E AMINO ACID TRANSPORTER.
ID0359E Alanine dehydrogenase amino acid sequence.
ID0360E YEST PROTEIN.
ID0361E HYPOTHETICAL 69.3 KDA PROTEIN.
ID0362E 314AA LONG HYPOTHETICAL CARBAMATE KINASE (FUCOXANTHIN CHLORO
ID0363E YEBA.
ID0364E AMIDOTRANSFERASE HISH (EC 2.4.2.-).
ID0365E PYRROLINE-5-CARBOXYLATE REDUCTASE HOMOLOG 2.
ID0366E YCGF PROTEIN.
ID0367E HYPOTHETICAL 28.9 KDA PROTEIN IN ILVA 3'REGION.
ID0368E ORF starting with ATG of length 1512
ID0369E GAMMA-GLUTAMYL PHOSPHATE REDUCTASE.
ID0370E SPERMIDINE SYNTHASE (EC 2.5.1.16) (PUTRESCINE AMINOPROPYLTRA
ID0371E AMINO ACID CARRIER PROTEIN.
ID0372E AMINO ACID TRANSPORTER.
ID0373E ORF starting with ATG of length 1404
ID0374E ORF starting with ATG of length 1404
ID0375E NADP-SPECIFIC GLUTAMATE DEHYDROGENASE (EC 1.4.1.4) (GLUTAMAT
ID0376E PROBABLE AMINO-ACID ABC TRANSPORTER EXTRACELLULAR BINDING PR
ID0377E HYPOTHETICAL 30.2 KDA PROTEIN IN HTRA-DPPA INTERGENIC REGION
ID0378E YJCI PROTEIN.
ID0379E DIAMINOBUTYRATE-PYRUVATE AMINOTRANSFERASE (EC 2.6.1.76) (L—
ID0380E VALINE-PYRUVATE AMINOTRANSFERASE.
ID0381E N-ACETYL-GAMMA-GLUTAMYL-PHOSPHATE REDUCTASE (EC 1.2.1.38) (A
ID0382E BH3963 PROTEIN.
ID0383E HYPOTHETICAL 23.6 KDA PROTEIN IN KIPR-PBPC INTERGENIC REGION
ID0384E Region of tryptophan synthase A.
ID0385E ARGININE DEIMINASE (EC 3.5.3.6) (ARGININE DIHYDROLASE).
ID0386E PROBABLE L-SERINE DEHYDRATASE, BETA CHAIN (EC 4.2.1.13) (L-S
ID0387E DIHYDRODIPICOLINATE REDUCTASE (EC 1.3.1.26) (DHPR).
ID0388E RHBA DIAMINOBUTYRATE-PYRUVATE AMINOTRANSFERASE (EC2.6.1.46).
ID0389E SHIKIMATE KINASE (EC 2.7.1.71) (SK).
ID0390E Neisseria gonorrheae ORF 705 protein sequence SEQ ID NO:2358
ID0391E YFLA PROTEIN.
ID0392E HOMOSERINE O-SUCCINYLTRANSFERASE (EC 2.3.1.46) (HOMOSERINE 0
ID0393E SODIUM/ALANINE SYMPORTER.
ID0394E 376AA LONG HYPOTHETICAL DEHYDROGENASE.
ID0395E 3-ISOPROPYLMALATE DEHYDRATASE LARGE SUBUNIT (EC 4.2.1.33) (IS
ID0396E HYPOTHETICAL 32.4 KDA PROTEIN.
ID0397E ORF starting with ATG of length 1104
ID0398E THERMOSTABLE DIPEPTIDASE BDP.
ID0399E 3-DEHYDROQUINATE DEHYDRATASE (EC 4.2.1.10) (3-DEHYDROQUINASE
ID0400E ORF starting with ATG of length 1020
ID0401E UGPC.
ID0402E HYPOTHETICAL 14.8 KDA PROTEIN IN TDK-PRFA INTERGENIC REGION.
ID0403E HYPOTHETICAL 23.4 KDA PROTEIN IN AAPA-SIGV INTERGENIC REGION
ID0404E Arabidopsis thaliana protein fragment SEQ ID NO: 18888.

ID0405E ASPARAGINE SYNTHETASE [GLUTAMINE-HYDROLYZING] 1 (EC 6.3.5.4)
ID0406E N-(5'-PHOSPHORIBOSYL)ANTHRANILATE ISOMERASE (EC 5.3.1.24) (P
ID0407E INDOLE-3-GLYCEROL PHOSPHATE SYNTHASE.
ID0408E AROA(G) PROTEIN [INCLUDES: PHOSPHO-2-DEHYDRO-3-DEOXYHEPTONAT
ID0409E BH1818 PROTEIN.
ID0410E D-ALANINE GLYCINE PERMEASE.
ID0411E ORF starting with ATG of length 906
ID0412E YNDN PROTEIN.
ID0413E PUTATIVE ASPARTATE AMINOTRANSFERASE (EC 2.6.1.1).
ID0414E HYPOTHETICAL 53.2 KDA PROTEIN IN XPAC-ABRB INTERGENIC REGION
ID0415E ORF starting with ATG of length 870
ID0416E HOMOSERINE KINASE (EC 2.7.1.39) (HK).
ID0417E PROBABLE 3-DEHYDROQUINATE DEHYDRATASE (EC 4.2.1.10) (3-DEHYD
ID0418E ASPARTOKINASE II ALPHA AND BETA SUBUNITS (EC 2.7.2.4).
ID0419E 5-ENOLPYRUVYLSHIKMATE 3-P SYNTHASE (FRAGMENT).
ID0420E HYPOTHETICAL 61.8 KDA PROTEIN IN GLNQ-ANSR INTERGENIC REGION
ID0421E YKCA PROTEIN.
ID0422E ORF starting with ATG of length 801
ID0423E GLUTAMINE SYNTHETASE (EC 6.3.1.2) (GLUTAMATE-AMMONIA LIGASE
ID0424E HYPOTHETICAL 14.4 KDA PROTEIN IN TETB-EXOA INTERGENIC REGION
ID0425E *Arabidopsis thaliana* protein fragment SEQ ID NO: 12719.
ID0426E ORF starting with ATG of length 1431
ID0427E HYPOTHETICAL 14.4 KDA PROTEIN IN EPR-GALK INTERGENIC REGION.
ID0428E HYPOTHETICAL 15.2 KDA PROTEIN IN GLNQ-ANSR INTERGENIC REGION
ID0429E 3-DEHYDROQUINATE SYNTHASE (EC 4.6.1.3).
ID0430E YDAO PROTEIN.
ID0431E ORF starting with ATG of length 654
ID0432E ORF starting with ATG of length 617
ID0433E YUSH PROTEIN.
ID0434E ORF starting with ATG of length 573
ID0435E DIAMINOPIMELATE DECARBOXYLASE (EC 4.1.1.20) (DAP DECARBOXYLA
ID0436E YKRV PROTEIN.
ID0437E ORF starting with ATG of length 536
ID0438E MALTOSE PERMEASE (MALA).
ID0439E ORF starting with TTG or GTG of length 1038
ID0440E METAL-ACTIVATED PYRIDOXAL ENZYME.
ID0441E *Staphylococcus aureus* mutant P7C18 virulence gene product.
ID0442E CYSTEINE SYNTHASE A (EC 4.2.99.8).
ID0443E BRANCHED-CHAIN AMINO ACID TRANSPORTER.
ID0444E ORF starting with ATG of length 465
ID0445E YDAO PROTEIN.
ID0446E 3-PHOSPHOGLYCERATE DEHYDROGENASE (EC 1.1.1.95).
ID0447E NITROGEN REGULATORY PROTEIN P-II (GLNB-2).
ID0448E GLYCINE CLEAVAGE SYSTEM PROTEIN H (AMINOMETHYL CARRIER).
ID0449E Human ORFX ORF544 polypeptide sequence SEQ ID NO:1088.
ID0450E 307AA LONG HYPOTHETICAL PHOSPHOGLYCERATE DEHYDROGENASE.
ID0451E ORF starting with ATG of length 387
ID0452E ORF starting with ATG of length 837
ID0453E ORF starting with ATG of length 360
ID0454E YEBA.
ID0455E PROBABLE 3-DEHYDROQUINATE DEHYDRATASE (EC 4.2.1.10) (3-DEHYD
ID0456E BH3810 PROTEIN.
ID0457E ORF starting with ATG of length 321
ID0458E AMINO ACID CARRIER PROTEIN.
ID0459E Human ORFX ORF618 polypeptide sequence SEQ ID NO:1236.
ID0460E HYPOTHETICAL PROTEIN XF2305.
ID0461E AGAE.
ID0462E ORF starting with ATG of length 237
ID0463E ORF starting with ATG of length 237
ID0464E ORF starting with ATG of length 231
ID0465E HOMOCITRATE SYNTHASE (EC 4.1.3.21).
ID0466E ORF starting with ATG of length 225
ID0467E ORF starting with ATG of length 225
ID0468E YNDN PROTEIN.
ID0469E YEST PROTEIN.
ID0470E BH1818 PROTEIN.
ID0471E HISF PROTEIN (CYCLASE).
ID0472EF CARBAMOYL-PHOSPHATE SYNTHETASE (CATALYTIC SUBUNIT).
ID0473EF CARBAMOYL-PHOSPHATE SYNTHASE, ARGININE-SPECIFIC, LARGE CHAIN
ID0474EF CARBAMOYL-PHOSPHATE SYNTHASE, PYRIMIDINE-SPECIFIC, SMALL CHA
ID0475EF ORF starting with ATG of length 3213
ID0476EF CARBAMOYLPHOSPHATE SYNTHETASE HEAVY SUBUNIT.
ID0477EF CARBAMOYL-PHOSPHATE SYNTHASE, ARGININE-SPECIFIC, SMALL CHAIN
ID0478EF GLUTAMINE-DEPENDENT CARBAMOYL PHOSPHATE SYNTHASE (EC 6.3.5.5
ID0479EH PROBABLE MALONIC SEMIALDEHYDE OXIDATIVE DECARBOXYLASE (EC 1.
ID0480EH YDAP PROTEIN.
ID0481EH *B. subtilis* acetohydroxyacid synthetase subunit, IlvB.
ID0482EH PARA-AMINOBENZOATE SYNTHASE COMPONENT I (EC 4.1.3.-) (ADC SY
ID0483EH KETOL-ACID REDUCTOISOMERASE (EC 1.1.1.86) (ACETOHYDROXY-ACID
ID0484EH ALPHA-ACETOLACTATE SYNTHASE PROTEIN, ALSS.
ID0485EH PHOSPHOADENOSINE PHOSPHOSULFATE REDUCTASE (EC 1.8.99.4) (PAP
ID0486EH ANTHRANILATE SYNTHASE COMPONENT I (EC 4.1.3.27).
ID0487EH PROBABLE PHOSPHOADENOSINE PHOSPHOSULFATE REDUCTASE (EC 1.8.9
ID0488EH 4-AMINO-4-DEOXYCHORISMATE LYASE (EC 4.-.-.-) (ADC LYASE) (AD
ID0489EH PARA-AMINOBENZOATE/ANTHRANILATE SYNTHASE GLUTAMINE AMIDOTRAN
ID0490EH ORF starting with ATG of length 1746
ID0491EH ANTHRANILATE SYNTHASE.
ID0492EH PUTATIVE BRANCHED-CHAIN AMINO ACID AMINOTRANSFERASE (EC 2.6.
ID0493EH ORF starting with ATG of length 1539
ID0494EH D-ALANINE AMINOTRANSFERASE.

ID0495EH *B. subtilis* IlvE homologue #1.
ID0496EHR HYPOTHETICAL 55.0 KDA PROTEIN IN EPR-GALK INTERGENIC REGION.
ID0497EHR NA+/MYO-INOSITOL COTRANSPORTER.
ID0498EHR HYPOTHETICAL 40.1 KDA PROTEIN IN SIPU-KIPI INTERGENIC REGION
ID0499EHR YOLC.
ID0500EHR OSMOREGULATED PROLINE TRANSPORTER (SODIUM/PROLINE SYMPORTER)
ID0501EHR Mouse high affinity choline transporter protein.
ID0502EHR HOMOLOGUE OF PROLINE PERMEASE OF *E. COLI.*
ID0503EHR HOMOLOGUE OF PROLINE PERMEASE OF *E. COLI.*
ID0504EHR HOMOLOGUE OF PROLINE PERMEASE OF *E. COLI.*
ID0505EJ L-ASPARAGINASE (EC 3.5.1.1) (L-ASPARAGINE AMIDOHYDROLASE).
ID0506EJ L-ASPARAGINASE.
ID0507EM PROBABLE 5-DEHYDRO-4-DEOXYGLUCARATE DEHYDRATASE (EC 4.2.1.41
ID0508EM DIHYDRODIPICOLINATE SYNTHASE (EC 4.2.1.52) (DHDPS) (VEGETATI
ID0509EM DIHYDRODIPICOLINATE SYNTHASE.
ID0510EM DIHYDRODIPICOLINATE SYNTHASE (EC 4.2.1.52) (DHDPS) (VEGETATI
ID0511EM ORF starting with ATG of length 606
ID0512EP OLIGOPEPTIDE-BINDING PROTEIN APPA PRECURSOR.
ID0513EP *B. subtilis* oppD ATPase.
ID0514EP DIPEPTIDE-BINDING PROTEIN DPPE PRECURSOR.
ID0515EP OLIGOPEPTIDE TRANSPORT ATP-BINDING PROTEIN APPF.
ID0516EP DIPEPTIDE TRANSPORTER PROTEIN DPPA (FRAGMENT).
ID0517EP OLIGOPEPTIDE TRANSPORT ATP-BINDING PROTEIN APPD.
ID0518EP OLIGOPEPTIDE TRANSPORT SYSTEM PERMEASE PROTEIN APPB.
ID0519EP OLIGOPEPTIDE TRANSPORT SYSTEM PERMEASE PROTEIN APPC.
ID0520EP YKFD.
ID0521EP OLIGOPEPTIDE TRANSPORT SYSTEM PERMEASE PROTEIN OPPC.
ID0522EP DIPEPTIDE TRANSPORT SYSTEM PERMEASE PROTEIN DPPC.
ID0523EP DIPEPTIDE ABC TRANSPORTER (PERMEASE).
ID0524EP *B. subtilis* oppA ligand binding protein.
ID0525EP NICKEL TRANSPORT SYSTEM (PERMEASE).
ID0526EP NICKEL TRANSPORT SYSTEM (PERMEASE).
ID0527EP NICKEL ABC TRANSPORTER (PERMEASE).
ID0528EP DIPEPTIDE TRANSPORT SYSTEM PERMEASE PROTEIN DPPC.
ID0529EP DIPEPTIDE TRANSPORT ATP-BINDING PROTEIN DPPD.
ID0530EP OLIGOPEPTIDE ABC TRANSPORTER (ATP-BINDING PROTEIN).
ID0531EP OLIGOPEPTIDE ABC TRANSPORTER (ATP-BINDING PROTEIN).
ID0532EP OLIGOPEPTIDE TRANSPORT ATP-BINDING PROTEIN AMIF.
ID0533EP NICKEL ABC TRANSPORTER (PERMEASE).
ID0534EP NICKEL ABC TRANSPORTER (NICKEL-BINDING PROTEIN).
ID0535EP OLIGOPEPTIDE TRANSPORT SYSTEM PERMEASE PROTEIN OPPB.
ID0536EP OLIGOPEPTIDE ABC TRANSPORTER (ATP-BINDING PROTEIN).
ID0537EP OLIGOPEPTIDE ABC TRANSPORTER (ATP-BINDING PROTEIN).
ID0538EP DIPEPTIDE TRANSPORTER DPPD HOMOLOG.
ID0539EP *B. subtilis* oppB membrane protein.
ID0540EP 420AA LONG HYPOTHETICAL OLIGOPEPTIDE TRANSPORT ATP-BINDING P
ID0541EP *B. subtilis* oppA ligand binding protein.
ID0542EP ATPASE OPPD.
ID0543EP ORF starting with ATG of length 240
ID0544EP ORF starting with ATG of length 213
ID0545EP ORF starting with ATG of length 210
ID0546ER HYPOTHETICAL 64.1 KDA PROTEIN.
ID0547ER GLUTAMATE SYNTHASE (EC 1.4.1.13) (GLUTAMATE SYNTHASE (NADPH)
ID0548ER YTVP.
ID0549ER NAD ALCOHOL DEHYDROGENASE.
ID0550ER *Pyrococcus horikoshii* thermophilic dehydrogenase.
ID0551ER L-IDITOL 2-DEHYDROGENASE (EC 1.1.1.14).
ID0552ER ZINC-CONTAINING ALCOHOL DEHYDROGENASE.
ID0553ER ORF starting with ATG of length 1140
ID0554ER ORF starting with ATG of length 321
ID0555F YFKN PROTEIN.
ID0556F PHOSPHORIBOSYLFORMYLGLYCINAMIDINE SYNTHASE II (EC 6.3.5.3)
ID0557F HYPOTHETICAL 132.7 KDA PROTEIN IN CSPB-GLPP INTERGENIC REGIO
ID0558F RIBONUCLEOSIDE-DIPHOSPHATE REDUCTASE ALPHA CHAIN (EC 1.17.4.
ID0559F GMP SYNTHASE [GLUTAMINE-HYDROLYZING] (EC 6.3.5.2) (GLUTAMINE
ID0560F BIFUNCTIONAL PURINE BIOSYNTHESIS PROTEIN PURH [INCLUDES:PHOS
ID0561F TRANSFERASE (GLUTAMINE AMIDOTRANSFERASE)
ID0562F ADENYLOSUCCINATE LYASE (EC 4.3.2.2) (ADENYLOSUCCINASE) (ASL)
ID0563F ADENINE DEAMINASE (EC 3.5.4.2) (ADENASE) (ADENINE AMINASE).
ID0564F HYPOTHETICAL 66.6 KDA PROTEIN IN PURD-PCRB INTERGENIC REGION
ID0565F PHOSPHORIBOSYLAMINE-GLYCINE LIGASE (EC 6.3.4.13) (GARS) (GL
ID0566F DIHYDROOROTASE (EC 3.5.2.3) (DHOASE).
ID0567F PYRIMIDINE NUCLEOSIDE TRANSPORT PROTEIN.
ID0568F URACIL PERMEASE (URACIL TRANSPORTER).
ID0569F PHOSPHORIBOSYLAMINOIMIDAZOLE CARBOXYLASE ATPASE SUBUNIT (EC
ID0570F ORF starting with ATG of length 2985
ID0571F HYPOTHETICAL 43.7 KDA PROTEIN IN PEPT-KATB INTERGENIC REGION
ID0572F DIHYDROOROTATE DEHYDROGENASE, CATALYTIC SUBUNIT (EC 1.3.3.1)
ID0573F PUTATIVE PURINE PERMEASE YWDJ.
ID0574F ALLANTOINASE (EC 3.5.2.5).

ID0575F A formate transport associated protein, PurU.
ID0576F CTP SYNTHASE (EC 6.3.4.2) (UTP-AMMONIA LIGASE) (CTP SYNTHET
ID0577F IMPDH.
ID0578F PYRIMIDINE NUCLEOSIDE PHOSPHORYLASE.
ID0579F YJBT PROTEIN.
ID0580F YJBT PROTEIN.
ID0581F PURINE NUCLEOSIDE PHOSPHORYLASE I (EC 2.4.2.1) (PNP I) (PU-N
ID0582F XANTHINE PERMEASE.
ID0583F PHOSPHORIBOSYLAMINOIMIDAZOLE-SUCCINOCARBOXAMIDE SYNTHASE (EC
ID0584F SA2078 PROTEIN.
ID0585F RIBONUCLEOSIDE-DIPHOSPHATE REDUCTASE BETA CHAIN (EC 1.17.4.1
ID0586F MTA/SAH NUCLEOSIDASE [INCLUDES: 5'-METHYLTHIOADENOSINE NUCLE
ID0587F DEOXYRIBOSE-PHOSPHATE ALDOLASE (EC 4.1.2.4) (PHOSPHODEOXYRIB
ID0588F ORF starting with ATG of length 1776
ID0589F ADENYLATE KINASE (EC 2.7.4.3) (ATP-AMP TRANSPHOSPHORYLASE) (S
ID0590F CYTIDYLATE KINASE (EC 2.7.4.14) (CK) (CYTIDINE MONOPHOSPHATE
ID0591F PHOSPHORIBOSYLFORMYLGLYCINAMIDINE CYCLO-LIGASE (EC 6.3.3.1)
ID0592F COME OPERON PROTEIN 2.
ID0593F FORMYLTETRAHYDROFOLATE SYNTHETASE.
ID0594F OROTATE PHOSPHORIBOSYLTRANSFERASE (EC 2.4.2.10) (OPRT) (OPRT
ID0595F YUND PROTEIN.
ID0596F ADENINE PHOSPHORIBOSYLTRANSFERASE (EC 2.4.2.7) (APRT).
ID0597F ASPARTATE TRANSCARBAMOYLASE.
ID0598F HYPOTHETICAL 24.1 KDA PROTEIN IN SERS-DNAZ INTERGENIC REGION
ID0599F PHOSPHORIBOSYLFORMYLGLYCINAMIDINE SYNTHETASE I.
ID0600F XANTHINE PHOSPHORIBOSYLTRANSFERASE (EC 2.4.2.-).
ID0601F PHOSPHORIBOSYLAMINOIMIDAZOLE CARBOXYLASE CATALYTIC SUBUNIT (E
ID0602F HYPOTHETICAL 25.4 KDA PROTEIN IN SERS-DNAZ INTERGENIC REGION
ID0603F THYMIDINE KINASE (EC 2.7.1.21).
ID0604F Thymidylate kinase-2.
ID0605F URIDYLATE KINASE (EC 2.7.4.-) (UK) (URIDINE MONOPHOSPHATE KI
ID0606F ORF starting with ATG of length 1146
ID0607F C-1-TETRAHYDROFOLATE SYNTHASE, MITOCHONDRIAL PRECURSOR (C1-T
ID0608F PurR protein sequence.
ID0609F URIDINE KINASE (EC 2.7.1.48) (URIDINE MONOPHOSPHOKINASE).
ID0610F XANTHINE PERMEASE.
ID0611F Nucleoside phosphorylase.
ID0612F DEOXYRIBOSE-PHOSPHATE ALDOLASE.
ID0613F THYMIDYLATE SYNTHASE A (EC 2.1.1.45) (TS A) (TSASE A).
ID0614F ORF starting with ATG of length 870
ID0615F YUND PROTEIN.
ID0616F *Corynebacterium glutamicum* MP protein sequence SEQ ID NO:948
ID0617F PYRIMIDINE OPERON REGULATORY PROTEIN PYRR.
ID0618F NUCLEOSIDE DIPHOSPHATE KINASE (EC 2.7.4.6) (NDK) (NDP KINASE
ID0619F PHOSPHORIBOSYLGLYCINAMIDE FORMYLTRANSFERASE (EC 2.1.2.2) (GA
ID0620F CYTIDINE DEAMINASE (EC 3.5.4.5).
ID0621F ORF starting with ATG of length 591
ID0622F THYMIDYLATE SYNTHASE A (EC 2.1.1.45) (TS A) (TSASE A).
ID0623F HYPOTHETICAL 9.7 KDA PROTEIN IN PURC-PURL INTERGENIC REGION.
ID0624F PUTATIVE ADENYLOSUCCINATE SYNTHETASE (EC 6.3.4.4).
ID0625F GUANYLATE KINASE (EC 2.7.4.8) (GMP KINASE).
ID0626F *Zea mays* protein fragment SEQ ID NO: 40074.
ID0627F *Corynebacterium glutamicum* MP protein sequence SEQ ID NO:998
ID0628F GARS-AIRS-GART (FRAGMENT).
ID0629F PURINE NUCLEOSIDE PHOSPHORYLASE II (EC 2.4.2.1) (PNP II) (PU
ID0630F PHOSPHORIBOSYLGLYCINAMIDE FORMYLTRANSFERASE (EC 2.1.2.2) (GA
ID0631F ORF starting with ATG of length 261
ID0632F DIHYDROOROTASE (EC 3.5.2.3) (DHOASE).
ID0633FE RIBOSE-PHOSPHATE PYROPHOSPHOKINASE (EC 2.7.6.1) (PHOSPHORIBO
ID0634FE PRPP SYNTHETASE (EC 2.7.6.1).
ID0635FGR HIT PROTEIN.
ID0636FGR HYPOTHETICAL HIT-LIKE PROTEIN MJ0866.
ID0637FH HYPOTHETICAL 54.0 KDA PROTEIN IN NRGA-USD INTERGENIC REGION.
ID0638FH HYPOTHETICAL 54.0 KDA PROTEIN IN NRGA-USD INTERGENIC REGION.
ID0639FJ HYPOTHETICAL 17.8 KDA PROTEIN IN SERS-DNAH INTERGENIC REGION
ID0640FJ YKOA.
ID0641 FR BH0185 PROTEIN.
ID0642G PEP SYNTHASE.
ID0643G GLYCOGEN PHOSPHORYLASE (EC 2.4.1.1).
ID0644G *Bacillus species* alpha-glucosidase.
ID0645G LEVANASE PRECURSOR (EC 3.2.1.65) (2,6-BETA-D-FRUCTANFRUCTANO
ID0646G CHITINASE.
ID0647G PEP SYNTHASE.
ID0648G PHOSPHOENOLPYRUVATE-PROTEIN PHOSPHOTRANSFERASE (EC 2.7.3.9)
ID0649G GLUCOSIDASE.
ID0650G Arabinose isomerase from *Bacillus licheniformis*, deduced amo
ID0651G YESZ PROTEIN.
ID0652G HYPOTHETICAL 88.3 KDA PROTEIN IN CLPP-CRH INTERGENIC REGION.
ID0653G 1,4-ALPHA-GLUCAN BRANCHING ENZYME (EC 2.4.1.18) (GLYCOGEN BR
ID0654G HYPOTHETICAL 68.9 KDA PROTEIN.
ID0655G *Bacillus* sp. exo-alpha-1,4-glucosidase, AMY1084
ID0656G HYPOTHETICAL 79.2 KDA PROTEIN.
ID0657G TREHALOSE-6-PHOSPHATE HYDROLASE (EC 3.2.1.93) (ALPHA,ALPHA-P
ID0658G 6-PHOSPHOGLUCONATE DEHYDROGENASE, DECARBOXYLATING II (EC 1.1
ID0659G HYPOTHETICAL 70.6 KDA LIPOPROTEIN IN FEUA-SIGW INTERGENIC RE
ID0660G BETA-D-GALACTOSIDASE.
ID0661G CHITINASE PRECURSOR (EC 3.2.1.14).

ID0662G GLUCOSE-6-PHOSPHATE ISOMERASE (GPI) (EC 5.3.1.9) (PHOSPHOGLU
ID0663G LIPOPROTEIN LPLA PRECURSOR.
ID0664G ENOLASE (EC 4.2.1.11) (2-PHOSPHOGLYCERATE DEHYDRATASE) (2-PH
ID0665G Amino acid sequence of a *Staphylococcus aureus* tktA polypept
ID0666G GLUCOSE-6-PHOSPHATE 1-DEHYDROGENASE (EC 1.1.1.49) (G6PD) (VE
ID0667G XYLOSE ISOMERASE (EC 5.3.1.5).
ID0668G PROBABLE BETA-GLUCOSIDASE (EC 3.2.1.21) (GENTIOBIASE) (CELLO
ID0669G PROBABLE PHOSPHOMANNOMUTASE (EC 5.4.2.8) (PMM).
ID0670G HYPOTHETICAL 48.5 KDA PROTEIN.
ID0671G GLUCAN-GLUCOHYDROLASE (EC 3.2.1.74) (GLUCAN 1,4-BETA-GLUCOSI
ID0672G YDHP PROTEIN.
ID0673G HYPOTHETICAL 47.3 KDA PROTEIN.
ID0674G ALPHA-GALACTOSIDASE (EC 3.2.1.22) (MELIBIASE).
ID0675G XYLULOKINASE.
ID0676G 6-PHOSPHO-GLUCOSIDASE MALH.
ID0677G PUTATIVE PTS SYSTEM IIBC COMPONENT YWBA (EC 2.7.1.69).
ID0678G HYPOTHETICAL SYMPORTER IN COTT-RAPA INTERGENIC REGION.
ID0679G YTCQ.
ID0680G *Bacillus subtilis* araN gene product.
ID0681G ALTRONATE HYDROLASE (EC 4.2.1.7) (ALTRONIC ACID HYDRATASE).
ID0682G YBBT PROTEIN.
ID0683G YKRW PROTEIN.
ID0684G CELLULASE.
ID0685G PTS SYSTEM, SUCROSE-SPECIFIC IIBC COMPONENT (EIIBC-SCR) (SUC
ID0686G YESO PROTEIN.
ID0687G Amino acid sequence of tac promoter and *Bacillus subtilis* BR
ID0688G RIBOSE TRANSPORT ATP-BINDING PROTEIN RBSA.
ID0689G PUTATIVE FAMILY 31GLUCOSIDASE YICI.
ID0690G PTS SYSTEM, N-ACETYLGLUCOSAMINE-SPECIFIC ENZYME II, ABC COMP
ID0691G GLUCONOKINASE (EC 2.7.1.12) (GLUCONATE KINASE).
ID0692G HYPOTHETICAL 34.0 KDA PROTEIN IN RHO-MURA INTERGENIC REGION
ID0693G YTOP.
ID0694G YTBD.
ID0695G IOLH PROTEIN.
ID0696G 2,3-BISPHOSPHOGLYCERATE-INDEPENDENT PHOSPHOGLYCERATE MUTASE.
ID0697G 6-PHOSPHOGLUCONATE DEHYDROGENASE, DECARBOXYLATING (EC 1.1.1.
ID0698G D-MANNONATE HYDROLASE.
ID0699G L-ARABINOSE MEMBRANE PERMEASE.
ID0700G HYPOTHETICAL 39.2 KDA PROTEIN.
ID0701G LPLB PROTEIN.
ID0702G SA2434 PROTEIN.
ID0703G GLYCEROL-3-PHOSPHATE TRANSPORTER.
ID0704G MEMBRANE TRANSPORT PROTEIN.
ID0705G LIPOPROTEIN.
ID0706G GLUCOSE-1-PHOSPHATE ADENYLYL-TRANSFERASE (EC 2.7.7.27) (ADP-G
ID0707G YJDE PROTEIN.
ID0708G PROBABLE ABC TRANSPORTER PERMEASE PROTEIN YESP.
ID0709G SUGAR-BINDING PROTEIN.
ID0710G HYPOTHETICAL 35.0 KDA PROTEIN.
ID0711G IOLE PROTEIN.
ID0712G YBBF.
ID0713G PHOSPHOPENTOMUTASE (EC 5.4.2.7) (PHOSPHODEOXYRIBOMUTASE).
ID0714G LPLC PROTEIN.
ID0715G SUGAR ABC TRANSPORTOR (ATP-BINDING PROTEIN).
ID0716G BIFUNCTIONAL PGK/TIM [INCLUDES: PHOSPHOGLYCERATE KINASE (EC
ID0717G PROBABLE 6-PHOSPHO-BETA-GLUCOSIDASE (EC 3.2.1.86).
ID0718G HYPOTHETICAL ALTRONATE OXIDOREDUCTASE.
ID0719G HYPOTHETICAL 30.9 KDA PROTEIN.
ID0720G IOLI PROTEIN.
ID0721G TEICHOIC ACID TRANSLOCATION ATP-BINDING PROTEIN TAGH.
ID0722G D-MANNONATE DEHYDROLASE.
ID0723G HYPOTHETICAL 45.5 KDA PROTEIN.
ID0724G ORF starting with ATG of length 2513
ID0725G endo 1,5 alpha-L-arabinase
ID0726G HYPOTHETICAL 31.3 KDA PROTEIN.
ID0727G ABC TRANSPORTER (PERMIASE).
ID0728G YKRP PROTEIN.
ID0729G 6-PHOSPHO-BETA-GLUCOSIDASE BGLB (EC 3.2.1.86).
ID0730G PROBABLE FRUCTOSE-BISPHOSPHATE ALDOLASE 2 (EC 4.1.2.13).
ID0731G PROBABLE FRUCTOSE-BISPHOSPHATE ALDOLASE 1 (EC 4.1.2.13).
ID0732G SUGAR TRANSPORTER.
ID0733G PUTATIVE INTEGRAL PROTEIN.
ID0734G SAC OPERON RELATED REGULATION PROTEIN (FRAGMENT).
ID0735G HYPOTHETICAL 59.0 KDA PROTEIN.
ID0736G D-RIBOSE-BINDING PROTEIN PRECURSOR.
ID0737G ALPHA-L-ARABINOFURANOSIDASE 1 (EC 3.2.1.55) (ARABINOSIDASE).
ID0738G YFHI.
ID0739G PYRUVATE KINASE (EC 2.7.1.40) (PK).
ID0740G GLYCOGEN BIOSYNTHESIS PROTEIN GLGD.
ID0741G YUTF PROTEIN.
ID0742G 2-DEHYDRO-3-DEOXYGLUCONOKINASE (EC 2.7.1.45) (2-KETO-3-DEOXY
ID0743G PUTATIVE CARBOXYVINYL-CARBOXYPHOSPHONATE PHOSPHORYLMUTASE (EC
ID0744G PTS SYSTEM, GLUCOSE-SPECIFIC ENZYME II, A COMPONENT.
ID0745G YFJS PROTEIN.
ID0746G PROBABLE D-GALACTARATE DEHYDRATASE (EC 4.2.1.42) (GALCD).
ID0747G RIBOKINASE (EC 2.7.1.15).
ID0748G HYPOTHETICAL 42.1 KDA PROTEIN.
ID0749G MANNITOL-1-PHOSPHATE 5-DEHYDROGENASE (EC 1.1.1.17).
ID0750G HYPOTHETICAL 29.9 KDA PROTEIN IN SIGY-CYDD INTERGENIC REGION
ID0751G HYPOTHETICAL 48.4 KDA PROTEIN.
ID0752G FRUCTOSE SPECIFIC PERMEASE.
ID0753G SUGAR TRANSPORTER.
ID0754G HYPOTHETICAL 28.3 KDA PROTEIN IN KBAA-FEUC INTERGENIC REGION ID0755G PHOSPHO-BETA-GLUCOSIDASE.
ID0756G PROBABLE ABC TRANSPORTER PERMEASE PROTEIN YESQ.
ID0757G GLYCOGEN SYNTHASE.
ID0758G 6-PHOSPHO-BETA-GLUCOSIDASE A.
ID0759G B. licheniformis acid stable and thermostable alpha-amylase.
ID0760G PTS SYSTEM, N-ACETYLGLUCOSAMINE-SPECIFIC ENZYME II, ABC COMP
ID0761G MULTIPLE SUGAR TRANSPORT SYSTEM (MULTIPLE SUGAR-BINDING PROT
ID0762G SUCROSE-6-PHOSPHATE HYDROLASE E1 (EC 3.2.1.26) (SUCRASE E1)
ID0763G Bacillus sp. OC187 4(R)-hydroxy-2-ketoglutaric acid aldolase
ID0764G GALACTOKINASE (EC 2.7.1.6) (GALACTOSE KINASE).
ID0765G SUCRASE (EC 3.2.1.26).
ID0766G XYLAN BETA-1,4-XYLOSIDASE (EC 3.2.1.37).
ID0767G N-ACETYLGLUCOSAMINE-6-PHOSPHATE DEACETYLASE (EC 3.5.1.25) (G
ID0768G GLUCONOKINASE (EC 2.7.1.12) (GLUCONATE KINASE).
ID0769G RIBULOSE-PHOSPHATE 3-EPIMERASE (EC 5.1.3.1) (PENTOSE-5-PHOSP
ID0770G SUGAR KINASE.
ID0771G HOMOLOGOUS TO SWISSPROT:YADE_E-COLI.
ID0772G PTS SYSTEM, ARBUTIN-LIKE IIBC COMPONENT (PHOSPHOTRANSFERASE
ID0773G SUGAR ABC TRANSPORTER (SUGAR-BINDING PROTEIN).
ID0774G GLYCERALDEHYDE 3-PHOSPHATE DEHYDROGENASE 2 (EC 1.2.1.12) (GA
ID0775G PUTATIVE SUGAR-TRANSPORT ATP BINDING PROTEIN.
ID0776G URONATE ISOMERASE (EC 5.3.1.12) (GLUCURONATE ISOMERASE) (URO
ID0777G PUTATIVE PTS SYSTEM IIBC COMPONENT YWBA (EC 2.7.1.69).
ID0778G URONATE ISOMERASE (EC 5.3.1.12) (GLUCURONATE ISOMERASE) (URO
ID0779G 6-PHOSPHOGLUCONATE DEHYDROGENASE, DECARBOXYLATING (EC 1.1.1.
ID0780G ORF starting with ATG of length 1998
ID0781G HYPOTHETICAL 52.5 KDA PROTEIN IN HUTP-BGLP INTERGENIC REGION
ID0782G PROBABLE HEXULOSE-6-PHOSPHATE SYNTHASE (EC 4.1.2.-) (HUMPS)
ID0783G PROBABLE GALACTARATE TRANSPORTER (D-GALACTARATE PERMEASE).
ID0784G TRANSALDOLASE (PENTOSE PHOSPHATE).
ID0785G 6-PHOSPHO-BETA-GLUCOSIDASE BGLA (EC 3.2.1.86).
ID0786G L-RIBULOSE-5-PHOSPHATE 4-EPIMERASE.
ID0787G KBAY.
ID0788G FRUCTOSE 1-PHOSPHATE KINASE.
ID0789G YTEQ PROTEIN.
ID0790G BH0592 PROTEIN.
ID0791G HYPOTHETICAL 54.3 KDA PROTEIN.
ID0792G L-RIBULOSE-5-PHOSPHATE 4-EPIMERASE.
ID0793G endo 1,5 alpha-L-arabinase
ID0794G CONSERVED HYPOTHETICAL PROTEIN, POSSIBLE OXIDOREDUCTASE.
ID0795G HYPOTHETICAL 21.3 KDA PROTEIN IN BLTR-SPOIIIC INTERGENIC REG
ID0796G 358AA LONG HYPOTHETICAL TRANSPORTER ATP-BINDING PROTEIN.
ID0797G IOLC PROTEIN.
ID0798G PHOSPHOTRANSFERASE ENZYME II (EC 2.7.1.69) (PROTEIN-N(PI)-PHO
ID0799G PTS SYSTEM ENZYME II ABC (ASC), CRYPTIC, TRANSPORTS SPECIFIC
ID0800G PTS SYSTEM, FRUCTOSE-SPECIFIC IIB COMPONENT (EIIB-FRU) (FRUC
ID0801G HYPOTHETICAL 22.0 KDA PROTEIN.
ID0802G N-ACETYLGLUCOSAMINE-6-PHOSPHATE ISOMERASE (EC 5.3.1.10).
ID0803G PUTATIVE XYLANASE (FRAGMENT).
ID0804G PUTATIVE ATP/GTP-BINDING PROTEIN.
ID0805G HYPOTHETICAL 37.2 KDA PROTEIN IN PBP-GGT INTERGENIC REGION.
ID0806G D-XYLOSE-BINDING PERIPLASMIC PROTEIN PRECURSOR.
ID0807G PEP-DEPENDENT PHOSPHOTRANSFERASE ENZYME II FOR CELLOBIOSE.
ID0808G ORF starting with ATG of length 1332
ID0809G B. subtilis cysteine protease CP3 protein sequence.
ID0810G HYPOTHETICAL LACA/RPIB FAMILY PROTEIN IN SPOIIR-GLYC INTERGE
ID0811G MALTOSE/MALTODEXTRIN-BINDING PROTEIN.
ID0812G ORF starting with ATG of length 1284
ID0813G PUTATIVE PTS SYSTEM IIA COMPONENT YPQE (EC 2.7.1.69).
ID0814G N-ACETYLGLUCOSAMINE-6-PHOSPHATE ISOMERASE (EC 5.3.1.10).
ID0815G HYPOTHETICAL 48.4 KDA PROTEIN.
ID0816G KHG/KDPG ALDOLASE [INCLUDES: 4-HYDROXY-2-OXOGLUTARATE ALDOLA
ID0817G PTS SYSTEM, FRUCTOSE-SPECIFIC IIA COMPONENT (EIIA-FRU) (FRUC
ID0818G ABC TRANSPORTER SUGAR PERMEASE.
ID0819G NODB-LIKE PROTEIN.
ID0820G ORF starting with ATG of length 1098
ID0821G 2-KETO-3-DEOXY-GLUCONATE KINASE.
ID0822G ENZYME II SUCROSE PROTEIN (EC 2.7.1.69).
ID0823G AMYX PROTEIN.
ID0824G HYPOTHETICAL 79.2 KDA PROTEIN.
ID0825G HYPOTHETICAL 44.9 KDA PROTEIN.
ID0826G ABC TRANSPORTER SUGAR PERMEASE.
ID0827G HYPOTHETICAL 31.7 KDA PROTEIN.
ID0828G ORF starting with ATG of length 993
ID0829G ORF starting with ATG of length 975
ID0830G HYPOTHETICAL ABC TRANSPORTER PERMEASE PROTEIN YURM.
ID0831G TRANSKETOLASE.
ID0832G PUTATIVE ABC TRANSPORTER, SUGAR PERMEASE PROTEIN.
ID0833G ORF starting with ATG of length 960
ID0834 G ENDO-1,4-BETA-XYLANASE.
ID0835G ORF starting with ATG of length 957
ID0836G ORF starting with ATG of length 936
ID0837G ORF starting with ATG of length 1050
ID0838G PTS SYSTEM ENZYME II ABC (ASC), CRYPTIC, TRANSPORTS SPECIFIC
ID0839G ORF starting with ATG of length 888
ID0840G MALP.
ID0841G SA1198 PROTEIN.
ID0842G AMYX PROTEIN.
ID0843G ORF starting with ATG of length 843
ID0844G TRANSKETOLASE C-TERMINAL SECTION.

ID0845G Arabinose isomerase from *Bacillus licheniformis*, deduced amo
ID0846G ORF starting with ATG of length 822
ID0847G ORF starting with ATG of length 1231
ID0848G ORF starting with ATG of length 816
ID0849G BETA-GLUCOSIDE PERMEASE IIABC COMPONENT.
ID0850G *Bacillus subtilis* L-arabinose isomerase.
ID0851G PUTATIVE TRANSALDOLASE.
ID0852G RHAMNOSE TRANSPORTER (FRAGMENT).
ID0853G PTS SYSTEM, CELLOBIOSE-SPECIFIC IIA COMPONENT (EIIA-CEL) (CE
ID0854G MALTOSE/MALTODEXTRIN TRANSPORT SYSTEM (MALTOSE/MALTODEXTRIN-
ID0855G ORF starting with ATG of length 1239
ID0856G HPR PROTEIN.
ID0857G PTS SYSTEM, GLUCOSE-SPECIFIC ENZYME II, A COMPONENT.
ID0858G ORF starting with ATG of length 705
ID0859G PHOSPHOPENTOMUTASE (EC 5.4.2.7) (PHOSPHODEOXYRIBOMUTASE).
ID0860G ORF starting with ATG of length 687
ID0861G FRUCTOSE 1-PHOSPHATE KINASE.
ID0862G GLYCEROL-3-PHOSPHATE TRANSPORTER.
ID0863G PROBABLE PTS SYSTEM, TREHALOSE-SPECIFIC IIBC COMPONENT (EIIB
ID0864G PHOSPHOCARRIER PROTEIN HPR (CATABOLITE REPRESSION).
ID0865G ORF starting with ATG of length 576
ID0866G PUTATIVE MALTOSE PHOSPHORYLASE (EC 2.4.1.8) (FRAGMENT).
ID0867G HYPOTHETICAL 87.9 KDA PROTEIN.
ID0868G HYPOTHETICAL 38.4 KDA PROTEIN IN DPPE-HMP INTERGENIC REGION.
ID0869G C4-DICARBOXYLATE TRANSPORT SYSTEM (C4-DICARBOXYLATE-BINDING
ID0870G PTS SYSTEM, CELLOBIOSE-SPECIFIC IIA COMPONENT (EIIA-CEL) (CE
ID0871G METHYLGLYOXAL SYNTHASE (EC 4.2.99.11) (MGS).
ID0872G *S. pneumoniae* derived protein #352.
ID0873G ORF starting with ATG of length 516
ID0874G C4-DICARBOXYLATE TRANSPORT SYSTEM (C4-DICARBOXYLATE-BINDING
ID0875G SUCRASE-6-PHOSPHATE HYDROLASE.
ID0876G *Enterococcus faecalis* protein EF092.
ID0877G SA0255 PROTEIN.
ID0878G *Enterococcus faecalis* protein EF092.
ID0879G *S. pneumoniae* cellobiose phosphotransferase system celA.
ID0880G YTEP.
ID0881G GLYCEROL UPTAKE FACILITATOR PROTEIN.
ID0882G ORF starting with ATG of length 2513
ID0883G ORF starting with ATG of length 429
ID0884G ORF starting with ATG of length 402
ID0885G 6-PHOSPHOFRUCTOKINASE, MUSCLE TYPE (EC 2.7.1.11) (PHOSPHOFRU
ID0886G ORF starting with ATG of length 351
ID0887G MYO-INOSITOL CATABOLISM, IOLC.
ID0888G HYPOTHETICAL 35.3 KDA PROTEIN.
ID0889G ORF starting with ATG of length 321
ID0890G ORF starting with ATG of length 315
ID0891G ORF starting with ATG of length 303
ID0892G ORF starting with TTG or GTG of length 561
ID0893G ORF starting with ATG of length 1368
ID0894G ORF starting with ATG of length 264
ID0895G PHOSPHOTRANSFERASE EII (GLUCOSE) (FRAGMENT).
ID0896G PROBABLE D-GALACTARATE DEHYDRATASE (EC 4.2.1.42) (GALCD).
ID0897GC HYPOTHETICAL 43.0 KDA PROTEIN.
ID0898GC HYPOTHETICAL GLYCOSYL TRANSFERASE.
ID0899GC HYPOTHETICAL 43.0 KDA PROTEIN.
ID0900GC HYPOTHETICAL GLYCOSYL TRANSFERASE.
ID0901GE GLUCONATE PERMEASE.
ID0902GE HYPOTHETICAL PROTEIN H10092.
ID0903GEPR HYPOTHETICAL 58.3 KDA PROTEIN IN GLPD-CSPB INTERGENIC REGION
ID0904GEPR MYO-INOSITOL TRANSPORT PROTEIN.
ID0905GEPR BICYCLOMYCIN RESISTANCE PROTEIN.
ID0906GEPR HYPOTHETICAL 48.7 KDA PROTEIN.
ID0907GEPR HYPOTHETICAL METABOLITE TRANSPORT PROTEIN IN GLVBC 3'REGION.
ID0908GEPR YBFB PROTEIN.
ID0909GEPR BH2528 PROTEIN.
ID0910GEPR YFMO.
ID0911GEPR HOMOLOGUE OF MULTIDRUG RESISTANCE PROTEIN B, EMRB, OF E. COL
ID0912GEPR MULTIDRUG TRANSPORTER.
ID0913GEPR HYPOTHETICAL 48.2 KDA PROTEIN IN COTF-TETB INTERGENIC REGION
ID0914GEPR HYPOTHETICAL.
ID0915GEPR LMRB.
ID0916GEPR HYPOTHETICAL 52.7 KDA PROTEIN.
ID0917GEPR PROBABLE GALACTARATE TRANSPORTER (D-GALACTARATE PERMEASE).
ID0918GEPR MYO-INOSITOL TRANSPORT PROTEIN.
ID0919GEPR MELY.
ID0920GEPR BENZOATE TRANSPORT PROTEIN.
ID0921GEPR YVMA.
ID0922GEPR HEXURONATE TRANSPORTER.
ID0923GEPR HYPOTHETICAL 39.1 KDA PROTEIN IN KAPD-PBPD INTERGENIC REGION
ID0924GEPR ORF starting with ATG of length 1452
ID0925GEPR YITG PROTEIN.
ID0926GEPR ORF starting with ATG of length 1434
ID0927GEPR HYPOTHETICAL 43.1 KDA PROTEIN.
ID0928GEPR HYPOTHETICAL 44.7 KDA PROTEIN IN GLNQ-ANSR INTERGENIC REGION
ID0929GEPR ORF starting with ATG of length 1368
ID0930GEPR MULTIDRUG RESISTANCE PROTEIN 2 (MULTIDRUG-EFFLUX TRANSPORTER
ID0931GEPR HYPOTHETICAL 44.7 KDA PROTEIN IN GLNQ-ANSR INTERGENIC REGION
ID0932GEPR ORF starting with ATG of length 1266
ID0933GEPR ORF starting with ATG of length 1257
ID0934GEPR LMRB.
ID0935GEPR HEXURONATE TRANSPORTER.
ID0936GEPR ORF starting with ATG of length 1098
ID0937GEPR ORF starting with ATG of length 1047
ID0938GEPR ORF starting with ATG of length 993
ID0939GEPR ORF starting with ATG of length 918
ID0940GEPR HYPOTHETICAL 44.2 KDA PROTEIN IN COTF-TETB INTERGENIC REGION
ID0941GEPR ORF starting with ATG of length 843
ID0942GEPR YFKF PROTEIN.
ID0943GEPR ORF starting with ATG of length 747
ID0944GEPR PARTIAL PUTATIVE MEMBRANE TRANSPORT PROTEIN.
ID0945GEPR GLUCOSE TRANSPORTER 3.

ID0946GEPR SA2300 PROTEIN.
ID0947GEPR ORF starting with ATG of length 456
ID0948GEPR SIMILAR TO METABOLITE TRANSPORT PROTEINS.
ID0949GEPR BH0884 PROTEIN.
ID0950GER HYPOTHETICAL 37.8 KDA PROTEIN.
ID0951GER HYPOTHETICAL 33.8 KDA PROTEIN IN GLPT-PURT INTERGENIC REGION
ID0952GER HYPOTHETICAL 34.0 KDA PROTEIN IN GLTP-PCP INTERGENIC REGION
ID0953GER BH1931PROTEIN.
ID0954GER HYPOTHETICAL 30.5 KDA PROTEIN IN GDHI 5'REGION (ORF 2).
ID0955GER HYPOTHETICAL 33.0 KDA PROTEIN IN PELB-PENP INTERGENIC REGION
ID0956GER BH2747 PROTEIN.
ID0957GER ORF starting with ATG of length 939
ID0958GER ORF starting with ATG of length 912
ID0959GER ORF starting with ATG of length 369
ID0960GER ORF starting with ATG of length 345
ID0961GR YVRK PROTEIN.
ID0962GR YOAN.
ID0963GT YJDC PROTEIN.
ID0964GT PUTATIVE CEL OPERON REGULATOR.
ID0965GT FRUCTOSE SPECIFIC PERMEASE (FRAGMENT).
ID0966GT BH0220 PROTEIN.
ID0967GT ORF starting with ATG of length 459
ID0968H HYPOTHETICAL 53.0 KDA PROTEIN IN SFP-GERKA INTERGENIC REGION
ID0969H YUEK PROTEIN.
ID0970H MENAQUINONE BIOSYNTHESIS PROTEIN MEND [INCLUDES: 2-SUCCINYL-
ID0971H THIAMINE BIOSYNTHESIS PROTEIN THIC.
ID0972H S-ADENOSYLMETHIONINE SYNTHETASE (EC 2.5.1.6) (METHIONINEADEN
ID0973H PROBABLE GLUCARATE DEHYDRATASE (EC 4.2.1.40) (GDH) (GLUCD).
ID0974H GLUTAMYL-TRNA REDUCTASE (EC 1.2.1.-) (GLUTR).
ID0975H GLUTAMATE-1-SEMIALDEHYDE 2,1-AMINOMUTASE (EC 5.4.3.8) (GSA)
ID0976H B. subtilis rib operon protein translated from reading frame
ID0977H MOLYBDOPTERIN BIOSYNTHESIS PROTEIN.
ID0978H PROTOPORPHYRINOGEN OXIDASE (EC 1.3.3.4) (PPO).
ID0979H PROBABLE AMINOTRANSFERASE YODT (EC 2.6.-.-).
ID0980H BIOTIN SYNTHASE (EC 2.8.1.6) (BIOTIN SYNTHETASE).
ID0981H 2-AMINO-3-KETOBUTYRATE COENZYME A LIGASE (EC 2.3.1.29) (AKB
ID0982H BH1152 PROTEIN.
ID0983H GLUTAMATE-1-SEMIALDEHYDE 2,1-AMINOMUTASE 2 (EC 5.4.3.8) (GSA
ID0984H YLOI PROTEIN.
ID0985H UROPORPHYRINOGEN DECARBOXYLASE (EC 4.1.1.37) (URO-D) (UPD).
ID0986H YTFD.
ID0987H PROBABLE OXYGEN-INDEPENDENT COPROPORPHYRINOGEN III OXIDASE (E
ID0988H HYPOTHETICAL 38.0 KDA PROTEIN.
ID0989H QUINOLINATE SYNTHETASE.
ID0990H FOLYLPOLYGLUTAMATE SYNTHASE (EC 6.3.2.17) (FOLYLPOLY-GAMMA-G
ID0991H MOLYBDENUM COFACTOR BIOSYNTHESIS PROTEIN A (NARA PROTEIN).
ID0992H DIHYDROXYNAPHTHOATE SYNTHASE.
ID0993H 8-AMINO-7-OXONONANOATE SYNTHASE (EC 2.3.1.47) (AONS) (8-AMIN
ID0994H MOLYBDOPTERIN BIOSYNTHESIS PROTEIN.
ID0995H YKFB.
ID0996H DENOSYLMETHIONINE-8-AMINO-7-OXONONANOATE AMINOTRANSFERASE.
ID0997H YJBU PROTEIN.
ID0998H FOLD BIFUNCTIONAL PROTEIN [INCLUDES: METHYLENETETRAHYDROFOLA
ID0999H HEPTAPRENYL DIPHOSPHATE SYNTHASE COMPONENT II (EC 2.5.1.30)
ID1000H PORPHOBILINOGEN DEAMINASE (EC 4.3.1.8) (PBG) (HYDROXYMETHYLB
ID1001H B. subtilis pantothenate kinase, CoaA#1.
ID1002H DGOA PROTEIN [INCLUDES: 2-DEHYDRO-3-DEOXYPHOSPHOGALACTONATE
ID1003H YITF PROTEIN.
ID1004H DELTA-AMINOLEVULINIC ACID DEHYDRATASE (EC 4.2.1.24) (PORPHOB
ID1005H NH(3)-DEPENDENT NAD(+) SYNTHETASE (EC 6.3.5.1) (SPORE OUTGRO
ID1006H 3-METHYL-2-OXOBUTANOATE HYDROXYMETHYLTRANSFERASE (EC 2.1.2.1
ID1007H DIHYDROPTEROATE SYNTHASE (EC 2.5.1.15) (DHPS) (DIHYDROPTEROA
ID1008H PROBABLE THIAMINE BIOSYNTHESIS PROTEIN THII.
ID1009H SUPEROXIDE-INDUCIBLE PROTEIN.
ID1010H LYASE (NITROGEN-HYDROGEN)
ID1011H PUTATIVE S-ADENOSYL L-METHIONINE: UROPORPHYRINOGEN IIIMETHYL
ID1012H MENAQUINONE BIOSYNTHESIS METHYLTRANSFERASE (EC 2.1.1.-) (SPO
ID1013H THIAMINE-MONOPHOSPHATE KINASE (EC 2.7.4.16) (THIAMINE-PHOSPH
ID1014H FERROCHELATASE.
ID1015H GERANYLTRANSTRANSFERASE (EC 2.5.1.10) (FARNESYL-DIPHOSPHATE
ID1016H RIBOFLAVIN BIOSYNTHESIS PROTEIN RIBC [INCLUDES: RIBOFLAVIN K
ID1017H METHYLTRANSFERASE/UROPORPHYRINOGEN-III SYNTHASE.
ID1018H YJBV PROTEIN.
ID1019H HYDROXYETHYLTHIAZOLE KINASE (EC 2.7.1.50) (4-METHYL-S-BETA-H
ID1020H TRANSCRIPTIONAL REPRESSOR OF THE BIOTIN OPERON.
ID1021H HYPOTHETICAL 21.4 KDA PROTEIN IN DACA-SERS INTERGENIC REGION
ID1022H DIPICOLINATE SYNTHASE, B CHAIN.
ID1023H HYPOTHETICAL 31.4 KDA PROTEIN IN PTA 3'REGION.
ID1024H PROBABLE NICOTINATE-NUCLEOTIDE PYROPHOSPHORYLASE [CARBOXYLAT
ID1025H Polypeptide encoded by rib operon of *Bacillus subtilis*.
ID1026H HOMOLOGUE OF PHENYLACRYLIC ACID DECARBOXYLASE PAD1 OF YEAST.
ID1027H RIBOFLAVIN SYNTHASE ALPHA CHAIN (EC 2.5.1.9).
ID1028H DETHIOBIOTIN SYNTHETASE (EC 6.3.3.3) (DETHIOBIOTIN SYNTHASE)
ID1029H COMQ.

ID1030H UROPORPHYRINOGEN-III SYNTHASE (EC 4.2.1.75) (UROS) (UROPORPH
ID1031H YLOS PROTEIN.
ID1032H THIAMIN BIOSYNTHESIS
ID1033H BH2162 PROTEIN.
ID1034H PROBABLE NICOTINATE-NUCLEOTIDE ADENYLYLTRANSFERASE (EC 2.7.7
ID1035H PANTOATE-BETA-ALANINE LIGASE (EC 6.3.2.1) (PANTOTHENATE SYN
ID1036H MOLYBDOPTERIN-GUANINE DINUCLEOTIDE BIOSYNTHESIS PROTEIN B.
ID1037H DEPHOSPHO-COA KINASE (EC 2.7.1.24) (DEPHOSPHOCOENZYME A KINA
ID1038H MOLYBDOPTERIN CONVERTING FACTOR (SUBUNIT 2).
ID1039H 6,7-DIMETHYL-8-RIBITYLLUMAZINE SYNTHASE (EC 2.5.1.9) (DMRL S
ID1040H Bradykinin gene product from plasmid pBLAK1.
ID1041H UNKNOWN (PYRIDOXAL PHOSPHATE BIOSYNTHETIC PROTEIN).
ID1042H ASPARTATE 1-DECARBOXYLASE PRECURSOR (EC 4.1.1.11) (ASPARTATE
ID1043H PROBABLE 1,4-DIHYDROXY-2-NAPHTHOATE OCTAPRENYLTRANSFERASE (E
ID1044H ORF starting with ATG of length 984
ID1045H 6-PYRUVOYL TETRAHYDROBIOPTERIN SYNTHASE HOMOLOGUE.
ID1046H ASPARTATE OXIDASE (NADB) (EC 1.4.3.16).
ID1047H PROBABLE LIPOIC ACID SYNTHETASE (LIP-SYN) (LIPOATE SYNTHASE)
ID1048H DIHYDRONEOPTERIN ALDOLASE (EC 4.1.2.25).
ID1049H LIPOIC ACID SYNTHASE.
ID1050H ORF starting with ATG of length 675
ID1051H 6-CARBOXYHEXANOATE-COA LIGASE (EC 6.2.1.14) (PIMELOYL-COASY
ID1052H 2-AMINO-4-HYDROXY-6-HYDROXYMETHYLDIHYDROPTERIDINE PYROPHOSPH
ID1053H Protein product of *Lactococcus* lactis DNA fragment.
ID1054H MOLYBDOPTERIN-GUANINE DINUCLEOTIDE BIOSYNTHESIS PROTEIN A.
ID1055H PYRIDOXAL PHOSPHATE BIOSYNTHETIC PROTEIN, PDXA.
ID1056H ORF starting with ATG of length 513
ID1057H YJBS PROTEIN.
ID1058H HYPOTHETICAL 21.4 KDA PROTEIN IN SODA-COMGA INTERGENIC REGIO
ID1059H *B. subtilis* pantothenate synthetase.
ID1060H ORF starting with ATG of length 354
ID1061H Sirohem synthase protein.
ID1062H ORF starting with ATG of length 303
ID1063H ORF starting with ATG of length 406
ID1064H THIAMINE-MONOPHOSPHATE KINASE (EC 2.7.4.16) (THIAMINE-PHOSPH
ID1065HC HYPOTHETICAL 54.4 KDA PROTEIN.
ID1066HC 4-HYDROXYBENZOATE 3-MONOOXYGENASE (EC 1.14.13.2) (P-HYDROXYB
ID1067HE PHOSPHOSERINE AMINOTRANSFERASE (EC 2.6.1.52) (PSAT) (VEGETAT
ID1068HI *Synechocystis* sp. 6803 DXP synthase protein sequence.
ID1069HI ORF starting with ATG of length 1536
ID1070HI *Bacillus subtilis* DXP synthase protein sequence.
ID1071HI *Synechocystis* sp. 6803 DXP synthase protein sequence.
ID1072HQ ISOCHORISMATE SYNTHASE DHBC (EC 5.4.99.6).
ID1073HQ MENAQUINONE-SPECIFIC ISOCHORISMATE SYNTHASE (EC 5.4.99.6).
ID1074I YUSL PROTEIN.
ID1075I YNGE PROTEIN.
ID1076I HYPOTHETICAL 72.2 KDA PROTEIN.
ID1077I YTCI.
ID1078I PROBABLE CARDIOLIPIN SYNTHETASE 2 (EC 2.7.8.-) (CARDIOLIPIN
ID1079I SQUALENE-HOPENE CYCLASE.
ID1080I YUSK PROTEIN.
ID1081I YNGH.
ID1082I BUTYRYL-COA DEHYDROGENASE.
ID1083I 1-DEOXY-D-XYLULOSE 5-PHOSPHATE REDUCTOISOMERASE (EC 1.1.1.-)
ID1084I METHYLMALONYL-COA DECARBOXYLASE ALPHA SUBUNIT (EC 6.4.1.3).
ID1085I ACETYL-COENZYME A CARBOXYLASE CARBOXYL TRANSFERASE SUBUNIT A
ID1086I MALONYL COA-ACYL CARRIER PROTEIN TRANSACYLASE (EC 2.3.1.39)
ID1087I ACSA (FRAGMENT).
ID1088I 4-DIPHOSPHOCYTIDYL-2-C-METHYL-D-ERYTHRITOL KINASE (EC 2.7.1.
ID1089I FATTY ACID/PHOSPHOLIPID SYNTHESIS PROTEIN PLSX.
ID1090I ACYL-COA DEHYDROGENASE (EC 1.3.99.).
ID1091I ACETYL-COA ACETYLTRANSFERASE (EC 2.3.1.9).
ID1092I ORF starting with ATG of length 1977
ID1093I HYPOTHETICAL 45.8 KDA PROTEIN IN ACDA-NARI INTERGENIC REGION
ID1094I YVAB PROTEIN.
ID1095I YDBM PROTEIN.
ID1096I 3-HYDROXYBUTYRYL-COA DEHYDROGENASE (EC 1.1.1.157).
ID1097I PHOSPHATIDATE CYTIDYLYLTRANSFERASE (EC 2.7.7.41) (CDP-DIGLYC
ID1098I FATTY ACID DESATURASE.
ID1099I UNDECAPRENYL PYROPHOSPHATE SYNTHETASE (EC 2.5.1.31) (UPP SYN
ID1100I BUTYRATE ACETOACETATE-COA TRANSFERASE.
ID1101I ORF starting with ATG of length 1716
ID1102I YUSJ PROTEIN.
ID1103I 4-DIPHOSPHOCYTIDYL-2C-METHYL-D-ERYTHRITOL SYNTHASE (EC 2.7.7
ID1104I FATTY ACID DESATURASE.
ID1105I PHAGE SHOCK PROTEIN A HOMOLOG.
ID1106I ACETYL-COA CARBOXYLASE BIOTIN CARBOXYLASE SUBUNIT (EC 6.4.1.
ID1107I TYPE B CARBOXYLESTERASE (EC 3.1.1.1).
ID1108I PYRUVATE CARBOXYLASE (FRAGMENT).
ID1109I HYPOTHETICAL 30.7 KDA PROTEIN IN MCPC-KINA INTERGENIC REGION
ID1110I HYPOTHETICAL 19.9 KDA PROTEIN IN ILVD-THYB INTERGENIC REGION
ID1111I HYPOTHETICAL 25.7 KDA PROTEIN IN GERAC-FHUC INTERGENIC REGIO
ID1112I BUTYRYL-COA DEHYDROGENASE (EC 1.1.1.35) (3-HYDROXYACYL-COADE
ID1113I *B. subtilis* hydrolase protein YTPA.
ID1114I HYPOTHETICAL 18.7 KDA PROTEIN IN HOM-MRGA INTERGENIC REGION.
ID1115I CG5044 PROTEIN.

ID1116I SIMILAR TO HYDROXYMYRISTOYL-(ACYL CARRIER PROTEIN) DEHYDRATA
ID1117I PHOSPHATIDYLSERINE DECARBOXYLASE PROENZYME (EC 4.1.1.65).
ID1118I YHAR PROTEIN.
ID1119I HYPOTHETICAL 35.4 KDA PROTEIN.
ID1120I ORF starting with ATG of length 1089
ID1121I 3-HYDROXYBUTYRYL-COA DEHYDRATASE.
ID1122I BUTYRATE-ACETOACETATE COA-TRANSFERASE SUBUNIT B (EC 2.8.3.9)
ID1123I 3-HYDROXYACYL-COA DEHYDROGENASE/ENOYL COA HYDRATASE (EC 1.1.
ID1124I 2C-METHYL-D-ERYTHRITOL 2,4-CYCLODIPHOSPHATE SYNTHASE (MECPS)
ID1125I ACETYL-COA SYNTHETASE (ACS-3).
ID1126I TYPE B CARBOXYLESTERASE (EC 3.1.1.1).
ID1127I CDP-DIACYLGLYCEROL-GLYCEROL-3-PHOSPHATE 3-PHOSPHATIDYLTRANS
ID1128I ORF starting with ATG of length 897
ID1129I ORF starting with ATG of length 888
ID1130I ACETYL-COA CARBOXYLASE TRANSFERASE BETA SUBUNIT (EC 6.4.1.2)
ID1131I ORF starting with ATG of length 855
ID1132I BH2687 PROTEIN.
ID1133I PUTATIVE ACYL-COA THIOESTER HYDROLASE YKHA (EC 3.1.2.-).
ID1134I CFR-ASSOCIATED PROTEIN P70.
ID1135I ORF starting with ATG of length 630
ID1136I ORF starting with ATG of length 627
ID1137I BH1133 PROTEIN.
ID1138I YDBM PROTEIN.
ID1139I HYPOTHETICAL 19.6 KDA PROTEIN IN SIPU-PBPC INTERGENIC REGION
ID1140I ORF starting with ATG of length 342
ID1141I CG4784 PROTEIN.
ID1142I ACYL-COA DEHYDROGENASE (FRAGMENT).
ID1143I MALONYL COA-ACYL CARRIER PROTEIN TRANSACYLASE (EC 2.3.1.39)
ID1144I ACSA (FRAGMENT).
ID1145IM LYTB PROTEIN HOMOLOG.
ID1146IQ YJAY PROTEIN.
ID1147IQ OSB-COA SYNTHASE.
ID1148IQ LONG-CHAIN-FATTY-ACID-COA LIGASE.
ID1149IQ LONG-CHAIN-FATTY-ACID-COA LIGASE (FADD-7).
ID1150IQ DNA encoding human synthetase #8.
ID1151IQ ORF starting with ATG of length 1386
ID1152IQ LONG-CHAIN-FATTY-ACID-COA LIGASE (FADD-7).
ID1153IQ D-ALANYL CARRIER PROTEIN (DCP).
ID1154J VALYL-TRNA SYNTHETASE (EC 6.1.1.9).
ID1155J THREONYL-TRNA SYNTHETASE 1 (EC 6.1.1.3) (THREONINE-TRNA LIG
ID1156J ISOLEUCYL-TRNA SYNTHETASE (EC 6.1.1.5) (ISOLEUCINE-TRNA LIG
ID1157J TRANSLATIONAL ELONGATION FACTOR G.
ID1158J ARGINYL-TRNA SYNTHETASE (EC 6.1.1.19) (ARGININE-TRNA LIGASE
ID1159J PHENYLALANYL-TRNA SYNTHETASE BETA SUBUNIT (EC 6.1.1.20).
ID1160J TRANSLATION INITIATION FACTOR IF-2.
ID1161J HYPOTHETICAL 58.2 KDA PROTEIN IN KLB-COTE INTERGENIC REGION.
ID1162J PROLYL-TRNA SYNTHETASE.
ID1163J CYSTEINYL-TRNA SYNTHETASE (EC 6.1.1.16) (CYSTEINE-TRNA LIGA
ID1164J GLUTAMYL-TRNA (GLN) AMIDOTRANSFERASE SUBUNIT A.
ID1165J ASPARAGINYL-TRNA SYNTHETASE (EC 6.1.1.22) (ASPARAGINE-TRNA
ID1166J THREONYL-TRNA SYNTHETASE 2 (EC 6.1.1.3) (THREONINE-TRNA LIG
ID1167J HYPOTHETICAL 51.7 KDA PROTEIN IN DNAJ-RPSU INTEREGENIC REGIO
ID1168J SERYL-TRNA SYNTHETASE (EC 6.1.1.11) (SERINE-TRNA LIGASE) (S
ID1169J YFJO PROTEIN.
ID1170J GLYCYL-TRNA SYNTHETASE BETA CHAIN (EC 6.1.1.14) (GLYCINE-TR
ID1171J TYROSYL-TRNA SYNTHETASE 1 (EC 6.1.1.1) (TYROSINE-TRNA LIGAS
ID1172J HISTIDYL-TRNA SYNTHETASE (EC 6.1.1.21) (HISTIDINE-TRNA LIGA
ID1173J ALANYL-TRNA SYNTHETASE (EC 6.1.1.7) (ALANINE-TRNA LIGASE)
ID1174J TYROSYL-TRNA SYNTHETASE 2 (EC 6.1.1.1) (TYROSINE-TRNA LIGAS
ID1175J PROBABLE TRNA (5-METHYLAMINOMETHYL-2-THIOURIDYLATE)-METHYLTR
ID1176J PEPTIDE CHAIN RELEASE FACTOR 1 (RF-1).
ID1177J GLUTAMYL-TRNA (GLN) AMIDOTRANSFERASE SUBUNIT B (EC 6.3.5.-)
ID1178J GLUTAMYL-TRNA SYNTHETASE (EC 6.1.1.17) (GLUTAMATE-TRNA LIGA
ID1179J LEUCYL-TRNA SYNTHETASE (EC 6.1.1.4).
ID1180J PUTATIVE TRANSLATION INITIATION FACTOR EIF-2B (EIF-2B GDP-GT
ID1181J LYSYL-TRNA SYNTHETASE (EC 6.1.1.6) (LYSINE-TRNA LIGASE) (LY
ID1182J PROBABLE METHYLTRANSFERASE (EC 2.1.1.-).
ID1183J LEUCYL-TRNA SYNTHETASE (EC 6.1.1.4) (LEUCINE-TRNA LIGASE)
ID1184J ATP PHOSPHORIBOSYLTRANSFERASE REGULATORY SUBUNIT.
ID1185J ELONGATION FACTOR TS (EF-TS).
ID1186J TRYPTOPHANYL-TRNA SYNTHETASE (EC 6.1.1.2) (TRYPTOPHAN-TRNA
ID1187J POLYRIBONUCLEOTIDE NUCLEOTIDYL-TRANSFERASE (EC 2.7.7.8) (POLY
ID1188J POLY(A) POLYMERASE (EC 2.7.7.19) (PAP).
ID1189J DIMETHYLADENOSINE TRANSFERASE (EC 2.1.1.-) (S-ADENOSYLMETHIO
ID1190J QUEUINE TRNA-RIBOSYLTRANSFERASE (EC 2.4.2.29) (TRNA-GUANINET
ID1191J 30S RIBOSOMAL PROTEIN S2 (BS1) (VEGETATIVE PROTEIN 209) (VEG
ID1192J *Streptococcus pneumoniae* glycyl tRNA synthetase alpha.
ID1193J HYPOTHETICAL TRNA/RRNA METHYLTRANSFERASE YACO (EC 2.1.1.-).
ID1194J YFLG PROTEIN.
ID1195J METHIONINE AMINOPEPTIDASE (EC 3.4.11.18) (MAP).
ID1196J 30S RIBOSOMAL PROTEIN S3 (BS3) (BS2).
ID1197J RIBONUCLEASE PH (FRAGMENT).
ID1198J TRNA PSEUDOURIDINE SYNTHASE A (EC 4.2.1.70) (PSEUDOURIDYLATE
ID1199J Aspartyl-tRNA synthetase from *Staph. aureus*.
ID1200J HYPOTHETICAL 29.7 KDA PROTEIN IN FOLD-AHRC INTERGENIC REGION
ID1201J HEMK PROTEIN HOMOLOG.

ID1202J HYPOTHETICAL 33.7 KDA PROTEIN IN CSPB-GLPP INTERGENIC REGION
ID1203J HYPOTHETICAL P20 PROTEIN.
ID1204J TRNA PSEUDOURIDINE SYNTHASE B (EC 4.2.1.70) (TRNA PSEUDOURID
ID1205J HYPOTHETICAL 31.5 KDA PROTEIN IN MECA-TENA INTERGENIC REGION
ID1206J PEPTIDYL-TRNA HYDROLASE (EC 3.1.1.29) (PTH) (STAGE V SPORULA
ID1207J METHIONYL-TRNA FORMYLTRANSFERASE (EC 2.1.2.9).
ID1208J POLYRIBONUCLEOTIDE NUCLEOTIDYL-TRANSFERASE (EC 2.7.7.8) (POLY
ID1209J HYPOTHETICAL 37.0 KDA PROTEIN IN SPOIIR-GLYC INTERGENIC REGI
ID1210J Methionyl-tRNA synthetase from *Staph. aureus.*
ID1211J POLYPEPTIDE DEFORMYLASE 2 (EC 3.5.1.31) (PDF 2) (FORMYLMETHI
ID1212J HYPOTHETICAL 22.0 KDA PROTEIN IN FLIT-SECA INTERGENIC REGION
ID1213J 30S RIBOSOMAL PROTEIN S7 (BS7).
ID1214J HYPOTHETICAL 22.5 KDA PROTEIN IN RPLL-RPOB INTERGENIC REGION
ID1215J PHENYLALANYL-TRNA SYNTHETASE ALPHA CHAIN (EC 6.1.1.20) (PHEN
ID1216J 50S RIBOSOMAL PROTEIN L10 (BL5) (COLD ACCLIMATIZATION PROTEI
ID1217J ORF starting with ATG of length 1479
ID1218J 50S RIBOSOMAL PROTEIN L3 (BL3).
ID1219J 50S RIBOSOMAL PROTEIN L13.
ID1220J 50S RIBOSOMAL PROTEIN L16.
ID1221J 50S RIBOSOMAL PROTEIN L15.
ID1222J S-ADENOSYLMETHIONINE:TRNA RIBOSYL-TRANSFERASE-ISOMERASE (EC 5
ID1223J YJCG PROTEIN.
ID1224J ERM2 PROTEIN.
ID1225J 16S PSEUDOURIDYLATE SYNTHASE.
ID1226J 30S RIBOSOMAL PROTEIN S11 (BS11).
ID1227J 30S RIBOSOMAL PROTEIN S9 (BS10).
ID1228J GLYCYL-TRNA SYNTHETASE BETA CHAIN (EC 6.1.1.14) (GLYCINE-TR
ID1229J PUTATIVE REGULATOR OF PURINE BIOSYNTHESIS.
ID1230J S-ADENOSYLMETHIONINE TRNA RIBOSYL-TRANSFERASE.
ID1231J RRNA METHYLASE HOMOLOG.
ID1232J AT1G08980/F7G19_15.
ID1233J 30S RIBOSOMAL PROTEIN S13.
ID1234J 50S RIBOSOMAL PROTEIN L14.
ID1235J GENERAL STRESS PROTEIN CTC.
ID1236J RIBOSOME-BINDING FACTOR A (P15B PROTEIN).
ID1237J 50S RIBOSOMAL PROTEIN L17.
ID1238J ELONGATION FACTOR P (EF-P).
ID1239J 50S RIBOSOMAL PROTEIN L6 (BL10).
ID1240J 6-AMINOHEXANOATE-CYCLIC-DIMER HYDROLASE.
ID1241J 50S RIBOSOMAL PROTEIN L24 (BL23) (12 KDA DNA-BINDING PROTEIN
ID1242J ORF starting with ATG of length 989
ID1243J ORF starting with ATG of length 964
ID1244J SA0330 PROTEIN.
ID1245J BH1243 PROTEIN.
ID1246J 30S RIBOSOMAL PROTEIN S19 (BS19).
ID1247J HYPOTHETICAL 37.0 KDA PROTEIN IN SPOIIR-GLYC INTERGENIC REGI
ID1248J 30S RIBOSOMAL PROTEIN 51 HOMOLOG.
ID1249J ORF starting with ATG of length 873
ID1250J HYPOTHETICAL 18.7 KDA PROTEIN.
ID1251J Glutamyl-tRNA (Gln) amidotransferase subunit ratC subunit.
ID1252J 30S RIBOSOMAL PROTEIN S17 (BS16).
ID1253J 50S RIBOSOMAL PROTEIN L27 (BL30) (BL24).
ID1254J 30S RIBOSOMAL PROTEIN S8 (BS8).
ID1255J 50S RIBOSOMAL PROTEIN L20.
ID1256J RHIZOBACTIN SIDEROPHORE BIOSYNTHESIS PROTEIN RHSD.
ID1257J ALANYL-TRNA SYNTHETASE (ALAS).
ID1258J 30S RIBOSOMAL PROTEIN S18 (BS21).
ID1259J A formate transport associated protein, FMD.
ID1260J HYPOTHETICAL 9.7 KDA PROTEIN IN MFD-DIVIC INTERGENIC REGION.
ID1261J HYPOTHETICAL 21.1 KDA PROTEIN IN AMYX-OPUD INTERGENIC REGION
ID1262J TRANSLATION INITIATION FACTOR IF-1.
ID1263J 30S RIBOSOMAL PROTEIN S20 (BS20).
ID1264J YJCK PROTEIN.
ID1265J ORF starting with ATG of length 705
ID1266J BH1498 PROTEIN.
ID1267J PHE-TRNA SYNTHETASE ALPHA CHAIN.
ID1268J SPERMIDINE N1-ACETYLTRANSFERASE (EC 2.3.1.57) (DIAMINEACETYL
ID1269J CG8684 PROTEIN.
ID1270J 30S RIBOSOMAL PROTEIN S6 (BS9).
ID1271J TRNA-GUANINE TRANSGLYCOSYLASE.
ID1272J ORF starting with ATG of length 600
ID1273J 6-AMINOHEXANOATE-CYCLIC-DIMER HYDROLASE.
ID1274J HYPOTHETICAL 12.3 KDA PROTEIN IN RPLU-RPMA INTERGENIC REGION
ID1275J 50S RIBOSOMAL PROTEIN L5 (BL6).
ID1276J YFKH PROTEIN.
ID1277J 50S RIBOSOMAL PROTEIN L30 (BL27).
ID1278J SA1699 PROTEIN.
ID1279J ORF starting with ATG of length 537
ID1280J ORF starting with ATG of length 510
ID1281J ORF starting with ATG of length 507
ID1282J TRANSLATION INITIATION FACTOR IF-3.
ID1283J 50S RIBOSOMAL PROTEIN L7/L12 (BL9) ('A' TYPE) (VEGETATIVE PR
ID1284J RIBOSOMAL PROTEIN S15 (BS18).
ID1285J 50S RIBOSOMAL PROTEIN L2 (BL2).
ID1286J SPERMIDINE N1-ACETYLTRANSFERASE (EC 2.3.1.57) (DIAMINEACETYL
ID1287J ORF starting with ATG of length 477
ID1288J TRANSLATION INITIATION INHIBITOR, PUTATIVE.
ID1289J 50S RIBOSOMAL PROTEIN L22.
ID1290J PROTEIN SYNTHESIS INHIBITOR, PUTATIVE.
ID1291J ASPARTYL-TRNA SYNTHETASE (EC 6.1.1.12) (ASPARTATE-TRNA LIGA
ID1292J BH0940 PROTEIN.
ID1293J 50S RIBOSOMAL PROTEIN L28.
ID1294J 50S RIBOSOMAL PROTEIN L22.
ID1295J ELONGATION FACTOR-P HOMOLOG (FRAGMENT).
ID1296J THREONYL-TRNA SYNTHETASE 1 (EC 6.1.1.3) (THREONINE-TRNA LIG
ID1297J HYPOTHETICAL 29.7 KDA PROTEIN IN FOLD-AHRC INTERGENIC REGION
ID1298J PEPTIDE CHAIN RELEASE FACTOR 2 (RF-2) (FRAGMENT).
ID1299J GLUTAMYL-TRNA SYNTHETASE (EC 6.1.1.17).

ID1300J ORF starting with ATG of length 318
ID1301 J GLUTAMINYL-TRNA SYNTHETASE (EC 6.1.1.18) (GLUTAMINE-TRNA L1
ID1302J ORF starting with ATG of length 270
ID1303J ORF starting with TTG or GTG of length 497
ID1304J ORF starting with ATG of length 228
ID1305J ORF starting with ATG of length 225
ID1306J ORF starting with TTG or GTG of length 438
ID1307J HYPOTHETICAL 18.7 KDA PROTEIN.
ID1308J RIBONUCLEASE PH (FRAGMENT).
ID1309JE ELONGATION FACTOR TU (EF-TU) (P-40).
ID1310K DNA-DIRECTED RNA POLYMERASE BETA CHAIN (EC 2.7.7.6) (TRANSCR
ID1311K DNA-DIRECTED RNA POLYMERASE BETA' CHAIN (EC 2.7.7.6) (TRANSC
ID1312K YTDP PROTEIN.
ID1313K RNA POLYMERASE SIGMA FACTOR RPOD (SIGMA-A) (SIGMA-43).
ID1314K N UTILIZATION SUBSTANCE PROTEIN A HOMOLOG.
ID1315K DNA-DIRECTED RNA POLYMERASE ALPHA CHAIN (EC 2.7.7.6) (TRANSC
ID1316K TRANSCRIPTION TERMINATION FACTOR RHO.
ID1317K CENTRAL GLYCOLYTIC GENES REGULATOR.
ID1318K HEAT-INDUCIBLE TRANSCRIPTION REPRESSOR HRCA.
ID1319K DEOXYRIBONUCLEOSIDE REGULATOR.
ID1320K VIRULENCE-ASSOCIATED PROTEIN.
ID1321K HYPOTHETICAL TRANSCRIPTIONAL REGULATOR IN CLPP-CRH INTERGENI
ID1322K SIGMA-B GENERAL STRESS TRANSCRIPTION FACTOR.
ID1323K HYPOTHETICAL TRANSCRIPTIONAL REGULATOR YKUM.
ID1324K TRANSCRIPTIONAL REGULATORY PROTEIN GLTC.
ID1325K RNA POLYMERASE SIGMA-54 FACTOR.
ID1326K *B. subtilis* novel pantothenate kinase encoded by the gene co
ID1327K STAGE 0 SPORULATION PROTEIN J.
ID1328K PROBABLE HTH_ARAC_FAMILY OF TRANSCRIPTIONAL REGULATOR.
ID1329K RNA POLYMERASE SIGMA-E FACTOR PRECURSOR (SIGMA-29) (P31) (ST
ID1330K YKVZ PROTEIN.
ID1331K PUTATIVE FIBRONECTIN-BINDING PROTEIN (YLOA PROTEIN).
ID1332K YKOZ PROTEIN.
ID1333K XYL REPRESSOR.
ID1334K LACI REPRESSOR-LIKE PROTEIN (YJMH PROTEIN).
ID1335K RNA POLYMERASE SIGMA-28 FACTOR PRECURSOR.
ID1336K PUTATIVE FIBRONECTIN-BINDING PROTEIN (YLOA PROTEIN).
ID1337K HOMOLOGUE OF ALS OPERON REGULATORY PROTEIN ALSR OF B. SUBTIL
ID1338K ALS OPERON REGULATORY PROTEIN.
ID1339K RNA POLYMERASE SIGMA-G FACTOR (STAGE III SPORULATION PROTEIN
ID1340K HYPOTHETICAL 37.7 KDA PROTEIN.
ID1341K KDG OPERON REPRESSOR.
ID1342K TRANSCRIPTIONAL ACTIVATOR TENA.
ID1343K HYPOTHETICAL TRANSCRIPTIONAL REGULATOR IN GLTP-CWLJ INTERGEN
ID1344K HYPOTHETICAL TRANSCRIPTIONAL REGULATOR IN SPOIIIE-PGSA INTER
ID1345K LACI-FAMILY TRANSCRIPTION REGULATOR.
ID1346K RNA POLYMERASE SIGMA-H FACTOR (SIGMA-30).
ID1347K CATABOLITE CONTROL PROTEIN A (GLUCOSE-RESISTANCE AMYLASE REG
ID1348K HYPOTHETICAL 33.3 KDA PROTEIN IN FEUA-SIGW INTERGENIC REGION
ID1349K PUTATIVE FRUCTOKINASE (EC 2.7.1.4).
ID1350K RNA POLYMERASE SIGMA-D FACTOR (SIGMA-28).
ID1351K TREHALOSE OPERON TRANSCRIPTIONAL REPRESSOR.
ID1352K HYPOTHETICAL TRANSCRIPTIONAL REGULATOR IN SIPU-PBPC INTERGEN
ID1353K HYPOTHETICAL 29.3 KDA PROTEIN IN GLVA-GLVC INTERGENIC REGION
ID1354K RNA POLYMERASE SIGMA FACTOR SIGW.
ID1355K HYPOTHETICAL TRANSCRIPTIONAL REGULATOR YWFK.
ID1356K TRANSCRIPTIONAL ACTIVATOR OF MULTIDRUG-EFFLUX TRANSPORTER GE
ID1357K HYPOTHETICAL TRANSCRIPTIONAL REGULATOR YWBI.
ID1358K HYPOTHETICAL TRANSCRIPTIONAL REGULATOR IN MRGA-CITG INTERGEN
ID1359K PROTEASE PRODUCTION REGULATORY PROTEIN HPR.
ID1360K TRANSCRIPTIONAL REPRESSOR OF THE XYLOSE OPERON.
ID1361K STAGE V SPORULATION PROTEIN T.
ID1362K HYPOTHETICAL 24.3 KDA PROTEIN (YVFI PROTEIN).
ID1363K YDHQ PROTEIN.
ID1364K Gene product which inhibits production of coenzymes and intr
ID1365K RNA POLYMERASE SIGMA FACTOR SIGX.
ID1366K YUGG PROTEIN.
ID1367K HYPOTHETICAL TRANSCRIPTIONAL REGULATOR IN HEMY-GLTT INTERGEN
ID1368K YEEK PROTEIN.
ID1369K BH0411PROTEIN.
ID1370K HYPOTHETICAL PROTEIN YWRC.
ID1371K TRANSCRIPTION ELONGATION FACTOR GREA (TRANSCRIPT CLEAVAGE FA
ID1372K MEMBRANE-BOUND PROTEIN LYTR.
ID1373K HYPOTHETICAL 21.1 KDA PROTEIN IN GBSA-TLPB INTERGENIC REGION
ID1374K TRANSCRIPTIONAL REGULATOR (MARR FAMILY).
ID1375K PEPTIDE METHIONINE SULFOXIDE REDUCTASE REGULATOR.
ID1376K BH0391PROTEIN.
ID1377K HYPOTHETICAL 21.3 KDA PROTEIN (ORF-1).
ID1378K Modified penicillinase repressor peril gene product.
ID1379K HYPOTHETICAL TRANSCRIPTIONAL REGULATOR IN WPRA-DEGA INTERGEN
ID1380K RNA POLYMERASE SIGMA FACTOR SIGY.
ID1381K TRANSCRIPTIONAL REGULATOR LRPC.
ID1382K ATTENUATOR FOR LYTABC AND LYTR EXPRESSION.
ID1383K SIMILAR TO *B. SUBTILIS* YWGB GENE (BH0656 PROTEIN).
ID1384K YKVE PROTEIN.

ID1385K YWQ[A,B,C,D,E,F,G,H,I,J,K,L,M,N,O] GENES.
ID1386K PUTATIVE RNA POLYMERASE SIGMA FACTOR YLAC.
ID1387K YFMP.
ID1388K GLUCONATE OPERON TRANSCRIPTIONAL REPRESSOR.
ID1389K HYPOTHETICAL 16.6 KDA PROTEIN IN GLPD-SPOVR INTERGENIC REGIO
ID1390K HYPOTHETICAL 20.7 KDA PROTEIN IN BLTR-SPOIIIC INTERGENIC REG
ID1391K SINR PROTEIN.
ID1392K HYPOTHETICAL 14.5 KDA PROTEIN IN GAPB-MUTM INTERGENIC REGION
ID1393K REGULATORY PROTEIN.
ID1394K RNA POLYMERASE ECF-TYPE SIGMA FACTOR.
ID1395K RIBONUCLEASE R (EC 3.1.-.-) (RNASE R) (VACB PROTEIN HOMOLOG)
ID1396K ORF starting with ATG of length 1056
ID1397K RIBOSE OPERON REPRESSOR.
ID1398K N UTILIZATION SUBSTANCE PROTEIN B HOMOLOG (NUSB PROTEIN).
ID1399K ORF starting with ATG of length 1047
ID1400K HYPOTHETICAL 17.6 KDA PROTEIN.
ID1401K YRHO.
ID1402K SCGR GENE.
ID1403K BH3951PROTEIN.
ID1404K RIBONUCLEASE III (EC 3.1.26.3) (RNASE III).
ID1405K TRANSCRIPTIONAL REGULATOR LRPA.
ID1406K HYPOTHETICAL 14.7 KDA PROTEIN.
ID1407K HYPOTHETICAL TRANSCRIPTIONAL REGULATOR YTLI.
ID1408K HYPOTHETICAL 32.8 KDA PROTEIN IN SPOOJ-GIDB INTERGENIC REGIO
ID1409K HYPOTHETICAL 15.9 KDA PROTEIN.
ID1410K YKOM.
ID1411K YKMA.
ID1412K 30S RIBOSOMAL PROTEIN S21.
ID1413K DNA-DIRECTED RNA POLYMERASE DELTA SUBUNIT (RNAP DELTA FACTOR
ID1414K BH1561PROTEIN.
ID1415K BH0575 PROTEIN.
ID1416K BH1889 PROTEIN.
ID1417K TRANSCRIPTIONAL REGULATOR (ICLR FAMILY).
ID1418K ORF starting with ATG of length 882
ID1419K YOZA PROTEIN.
ID1420K ORF starting with ATG of length 879
ID1421K HYPOTHETICAL 12.8 KDA PROTEIN IN ODHA-CTPA INTERGENIC REGION
ID1422K ORF starting with ATG of length 858
ID1423K HYPOTHETICAL TRANSCRIPTIONAL REGULATOR IN GNTR-HTPG INTERGEN
ID1424K ORF starting with ATG of length 855
ID1425K PUTATIVE TRANSITION STATE REGULATOR ABH.
ID1426K ORF starting with ATG of length 837
ID1427K TRANSCRIPTIONAL REPRESSOR (BETA-GALACTOSIDASE GENE).
ID1428K ORF starting with ATG of length 813
ID1429K ORF starting with ATG of length 804
ID1430K BH0353 PROTEIN.
ID1431K VIRULENCE-ASSOCIATED PROTEIN.
ID1432K YVNA.
ID1433K BH2909 PROTEIN.
ID1434K ORF starting with ATG of length 741
ID1435K RNA POLYMERASE SPORULATION FORESPORE-SPECIFIC (LATE) SIGMA-G
ID1436K HYPOTHETICAL 21.1 KDA PROTEIN IN TDK-PRFA INTERGENIC REGION.
ID1437K ORF starting with ATG of length 729
ID1438K PUTATIVE GNTR-FAMILY REGULATORY PROTEIN.
ID1439K SORBITOL OPERON REGULATOR (SOR OPERON ACTIVATOR).
ID1440K HYPOTHETICAL TRANSCRIPTIONAL REGULATOR IN DINB-PHOB INTERGEN
ID1441K TRANSCRIPTIONAL REGULATOR (GNTR FAMILY).
ID1442K TRANSCRIPTIONAL REPRESSOR (BETA-GALACTOSIDASE GENE).
ID1443K TRANSCRIPTIONAL REPRESSOR OF THE RIBOSE OPERON.
ID1444K HYPOTHETICAL 14.1 KDA PROTEIN IN TLPC-SRFAA INTERGENIC REGIO
ID1445K HYPOTHETICAL 8.2 KDA PROTEIN IN BLTR-SPOIIIC INTERGENIC REGI
ID1446K ARAR.
ID1447K ORF starting with ATG of length 624
ID1448K HYPOTHETICAL TRANSCRIPTIONAL REGULATOR IN SPOIIIC-CWLA INTER
ID1449K ORF starting with ATG of length 615
ID1450K HYPOTHETICAL TRANSCRIPTIONAL REGULATOR IN UVRX-ILVA INTERGEN
ID1451K ORF starting with ATG of length 606
ID1452K HYPOTHETICAL 14.5 KDA PROTEIN.
ID1453K ORF starting with ATG of length 600
ID1454K ORF starting with ATG of length 597
ID1455K ORF starting with ATG of length 585
ID1456K YDET PROTEIN.
ID1457K YVBA PROTEIN.
ID1458K ORF starting with ATG of length 573
ID1459K TRANSCRIPTIONAL REGULATOR OF EXTRACELLULAR ENZYME GENES.
ID1460K PUTATIVE TETR FAMILY TRANSCRIPTIONAL REGULATOR.
ID1461K YLOH PROTEIN.
ID1462K BH0406 PROTEIN.
ID1463K Barstar protein sequence.
ID1464K BH0521PROTEIN.
ID1465K ORF starting with ATG of length 519
ID1466K RNA POLYMERASE SIGMA-G FACTOR (STAGE III SPORULATION PROTEIN
ID1467K RNA POLYMERASE SIGMA FACTOR SIGV.
ID1468K HYPOTHETICAL 14.5 KDA PROTEIN.
ID1469K MERCURIC RESISTANCE OPERON REGULATORY PROTEIN.
ID1470K RPOC PROTEIN (DNA-DIRECTED RNA POLYMERASE BETA' SUBUNIT) (EC
ID1471K ACTIVATOR PROTEIN.
ID1472K ORF starting with ATG of length 477
ID1473K AUTOLYSIN ATLE AND PUTATIVE TRANSCRIPTIONAL REGULATOR ATLR G
ID1474K HYPOTHETICAL TRANSCRIPTIONAL REGULATOR IN LYSP-NFO INTERGENI
ID1475K ORF starting with ATG of length 783
ID1476K TRANSCRIPTIONAL REGULATOR (ARAC/XYLS FAMILY).
ID1477K ORF starting with ATG of length 396
ID1478K ORF starting with ATG of length 387
ID1479K BH3535 PROTEIN.
ID1480K HYPOTHETICAL PROTEIN MTH1285.
ID1481K HYPOTHETICAL 14.5 KDA PROTEIN.

ID1482K RRF2 PROTEIN.
ID1483K MLR8761PROTEIN.
ID1484K HYPOTHETICAL 46.4 KDA PROTEIN.
ID1485K YOZG PROTEIN.
ID1486K YORF[A,B,C,D,E], FTSL, PBPX AND REGR GENES.
ID1487K HYPOTHETICAL TRANSCRIPTIONAL REGULATOR MJ0272.
ID1488K ORF starting with ATG of length 342
ID1489K PUTATIVE TRANSCRIPTIONAL REGULATOR OF SORBOSE UPTAKE AND UTI
ID1490K ORF starting with ATG of length 315
ID1491K SINR PROTEIN.
ID1492K PROBABLE GNTR-FAMILY REGULATOR.
ID1493K YTCG (DNAB).
ID1494K RNA POLYMERASE SIGMA FACTOR SIGK.
ID1495K ORF starting with ATG of length 255
ID1496K ORF starting with ATG of length 225
ID1497K SIGMA-B GENERAL STRESS TRANSCRIPTION FACTOR.
ID1498KE HYPOTHETICAL 50.8 KDA PROTEIN IN SRFA4-SFP INTERGENIC REGION
ID1499KE YDEL PROTEIN.
ID1500KE HOMOLOGUE OF REGULATORY PROTEIN MOCR OF R. MELILOTI.
ID1501KE YDEL PROTEIN.
ID1502KE HYPOTHETICAL 48.9 KDA PROTEIN PH0207.
ID1503KG DNA-BINDING PROTEIN IOLR.
ID1504KG SIMILAR TO PHOSPHOTRANSFERASE SYSTEM REGULATOR.
ID1505KG DNA FOR 25-36 DEGREE REGION CONTAINING THE AMYE-SRFA REGION,
ID1506KG YTZE PROTEIN.
ID1507KG TRANSCRIPTIONAL REGULATOR (DEOR FAMILY).
ID1508KL YWQA PROTEIN (MEMBER OF THE SNF2 HELICASE FAMILY).
ID1509KL HYPOTHETICAL HELICASE IN SINI-GCVT INTERGENIC REGION.
ID1510KL YWQA PROTEIN (MEMBER OF THE SNF2 HELICASE FAMILY).
ID1511KN NEGATIVE REGULATOR OF FLAGELLIN SYNTHESIS (ANTI-SIGMA-D FACT
ID1512KR YBFA PROTEIN.
ID1513KR PROTEASE SYNTHASE AND SPORULATION NEGATIVE REGULATORY PROTEI
ID1514KR CGEE PROTEIN.
ID1515KR YJCF PROTEIN.
ID1516KR BH2157 PROTEIN.
ID1517KR BH1453 PROTEIN.
ID1518KR BH1582 PROTEIN.
ID1519KR ORF starting with ATG of length 552
ID1520KT LEXA REPRESSOR (EC 3.4.21.88) (SOS REGULATORY PROTEIN DINR).
ID1521KT YVLC.
ID1522L DNA POLYMERASE III POLC-TYPE (EC 2.7.7.7) (POLIII).
ID1523L EXCINUCLEASE ABC SUBUNIT A.
ID1524L DNA POLYMERASE I (EC 2.7.7.7) (POL I).
ID1525L ATP-DEPENDENT DNA HELICASE PCRA (EC 3.6.1.-).
ID1526L MUTS2 PROTEIN.
ID1527L EXCINUCLEASE ABC SUBUNIT B (DINA PROTEIN).
ID1528L DNA GYRASE SUBUNIT B (EC 5.99.1.3).
ID1529L ATP-DEPENDENT NUCLEASE SUBUNIT A.
ID1530L Amino acid sequence of a DnaE polypeptide.
ID1531L DNA TOPOISOMERASE IV SUBUNIT A.
ID1532L PROBABLE DNA TOPOISOMERASE III (EC 5.99.1.2) (RELAXING ENZYM
ID1533L YIRY PROTEIN (PUTATIVE_HOMOLOGY WITH SBCC FROM C. PERFRING
ID1534L DNA GYRASE SUBUNIT A (EC 5.99.1.3).
ID1535L PRIMOSOMAL REPLICATION FACTORY.
ID1536L DNA MISMATCH REPAIR PROTEIN MUTL.
ID1537L YJCD PROTEIN.
ID1538L DNA REPAIR PROTEIN RECN (RECOMBINATION PROTEIN N).
ID1539L YRRC PROTEIN.
ID1540L YVGS PROTEIN.
ID1541L PROBABLE ATP-DEPENDENT HELICASE DING HOMOLOG.
ID1542L DNA PRIMASE (EC 2.7.7.-).
ID1543L REPLICATIVE DNA HELICASE (EC 3.6.1.-).
ID1544L DNA MISMATCH REPAIR PROTEIN (MISMATCH RECOGNITION STEP).
ID1545L YKOU PROTEIN.
ID1546L DNA TOPOISOMERASE IV SUBUNIT B.
ID1547L SPORE PHOTOPRODUCT LYASE.
ID1548L PROBABLE EXODEOXYRIBONUCLEASE VII LARGE SUBUNIT (EC 3.1.11.6
ID1549L DNA POLYMERASE III SUBUNIT GAMMA/TAU (EC 2.7.7.7).
ID1550L REPLICATION INITIATION AND MEMBRANE ATTACHMENT PROTEIN.
ID1551L L. lactis HsdM subunit #2.
ID1552L EXCINUCLEASE ABC SUBUNIT C.
ID1553L HYPOTHETICAL 47.0 KDA PROTEIN IN GLNQ-ANSR INTERGENIC REGION
ID1554L DNA POLYMERASE III, BETA CHAIN (EC 2.7.7.7).
ID1555L RECQ HOMOLOG.
ID1556L PROBABLE ENDONUCLEASE IV (EC 3.1.21.2) (ENDODEOXYRIBONUCLEAS
ID1557L PROBABLE ATP-DEPENDENT HELICASE IN COTD-KDUD INTERGENIC REGI
ID1558L HYPOTHETICAL 40.5 KDA PROTEIN IN COMEC-RPST INTERGENIC REGIO
ID1559L EXONUCLEASE SBCD HOMOLOG (FRAGMENT).
ID1560L CHROMOSOMAL REPLICATION INITIATOR PROTEIN DNAA.
ID1561L PRIMOSOMAL PROTEIN DNAI.
ID1562L PROBABLE INTEGRASE/RECOMBINASE CODV.
ID1563L PUTATIVE DEOXYRIBONUCLEASE YABD (EC 3.1.21.-).
ID1564L PUTATIVE 5'-3' EXONUCLEASE (EC 3.1.11.-).
ID1565L YFJP PROTEIN.
ID1566L HYPOTHETICAL 46.8 KDA PROTEIN.
ID1567L ORF starting with ATG of length 2277
ID1568L FORMAMIDOPYRIMIDINE-DNA GLYCOSYLASE (EC 3.2.2.23) (FAPY-DNAG
ID1569L PROBABLE ENDONUCLEASE III (EC 4.2.99.18) (DNA-(APURINIC ORAP
ID1570L HYPOTHETICAL 37.4 KDA PROTEIN IN ACKA-SSPA INTERGENIC REGION
ID1571L ATP-DEPENDENT DNA HELICASE RECQ (EC 3.6.1.-) (RECOMBINATION
ID1572L HOLLIDAY JUNCTION DNA HELICASE RUVB.
ID1573L DNA REPAIR PROTEIN RADC HOMOLOG.
ID1574L SA1093 PROTEIN.

ID1575L HYPOTHETICAL 36.1 KDA PROTEIN IN SPOIIIC-CWLA INTERGENIC REG
ID1576L DNA REPAIR PROTEIN RECO (RECOMBINATION PROTEIN O).
ID1577L PHAGE-LIKE ELEMENT PBSX PROTEIN XKDC.
ID1578L YOQV PROTEIN.
ID1579L SIMILAR TO B. ANTHRACIS WEYAR ELEMENT ORFB.
ID1580L PROBABLE ATP-DEPENDENT HELICASE IN COTD-KDUD INTERGENIC REGI
ID1581L YRVE PROTEIN.
ID1582L Staphylococcus aureus CcrB1 protein sequence SEQ ID NO:8.
ID1583L YFHQ PROTEIN.
ID1584L ORF starting with ATG of length 1809
ID1585L DNA GYRASE A (FRAGMENT).
ID1586L UV-DAMAGE REPAIR PROTEIN.
ID1587L DNA REPLICATION AND REPAIR PROTEIN RECF.
ID1588L HYPOTHETICAL 48.0 KDA PROTEIN IN PONA-COTD INTERGENIC REGION
ID1589L ORF starting with ATG of length 1320
ID1590L TYPE IC RESTRICTION SUBUNIT.
ID1591L PROBABLE INTEGRASE/RECOMBINASE RIPX.
ID1592L SINGLE-STRAND DNA-SPECIFIC EXONUCLEASE.
ID1593L L. lactis HsdM subunit #1.
ID1594L PUTATIVE TYPE I RESTRICTION ENZYME R PROTEIN (EC 3.1.21.3).
ID1595L YRVN PROTEIN.
ID1596L SIMILAR TO B. ANTHRACIS WEYAR ELEMENT ORFB.
ID1597L ORF starting with ATG of length 1146
ID1598L ORF starting with ATG of length 1143
ID1599L SA0828 PROTEIN.
ID1600L HYPOTHETICAL 48.0 KDA PROTEIN IN PONA-COTD INTERGENIC REGION
ID1601L BH0056 PROTEIN.
ID1602L METALLOREGULATION DNA-BINDING STRESS PROTEIN.
ID1603L RECOMBINATION PROTEIN RECR.
ID1604L YLBH PROTEIN.
ID1605L COME OPERON PROTEIN 1.
ID1606L METHYLATED-DNA-PROTEIN-CYSTEINE METHYLTRANSFERASE (EC 2.1.1
ID1607L YADA PROTEIN.
ID1608L RIBONUCLEASE HII.
ID1609L DNA REPLICATION AND REPAIR PROTEIN RECF.
ID1610L SIMILAR TO E. COLI YJAF PROTEIN.
ID1611L 14.7 KDA RIBONUCLEASE H-LIKE PROTEIN.
ID1612L EXTRACELLULAR RIBONUCLEASE PRECURSOR (EC 3.1.-.-).
ID1613L Amino acid sequence of a DnaE polypeptide.
ID1614L YUSF PROTEIN.
ID1615L ORF starting with ATG of length 1197
ID1616L HOLLIDAY JUNCTION DNA HELICASE RUVA.
ID1617L MISMATCH BINDING PROTEIN (FRAGMENT).
ID1618L ORF starting with ATG of length 774
ID1619L SINGLE-STRAND BINDING PROTEIN (SSB) (HELIX-DESTABILIZING PRO
ID1620L HYPOTHETICAL 15.2 KDA PROTEIN IN UDK-ALAS INTERGENIC REGION.
ID1621L ORF starting with ATG of length 738
ID1622L RECQ HOMOLOG.
ID1623L ATP-DEPENDENT DNA HELICASE RECQ (EC 3.6.1.-) (RECOMBINATION
ID1624L SIMILAR TO B. ANTHRACIS WEYAR ELEMENT ORFB.
ID1625L YAZA PROTEIN.
ID1626L SIMILAR TO SINGLE STRAND BINDING PROTEIN.
ID1627L HYPOTHETICAL 43.5 KDA PROTEIN IN COTD-KDUD INTERGENIC REGION
ID1628L ORF starting with ATG of length 648
ID1629L ORF starting with ATG of length 645
ID1630L HYPOTHETICAL 43.8 KDA PROTEIN.
ID1631L 06-METHYLGUANINE DNA ALKYLTRANSFERASE.
ID1632L ORF starting with ATG of length 606
ID1633L DNA POLYMERASE III DELTA' SUBUNIT (EC 2.7.7.7).
ID1634L YIRY PROTEIN (PUTATIVE-HOMOLOGY WITH SBCC FROM C. PERFRING
ID1635L DNA-BINDING PROTEIN HU 1 (DNA-BINDING PROTEIN II) (HB).
ID1636L EXODEOXYRIBONUCLEASE VII (SMALL SUBUNIT).
ID1637L CHROMOSOMAL REPLICATION INITIATOR PROTEIN DNAA.
ID1638L Amino acid sequence of a DnaE polypeptide.
ID1639L SINGLE-STRAND BINDING PROTEIN (SSB) (HELIX-DESTABILIZING PRO
ID1640L YNEB.
ID1641L ORF starting with ATG of length 417
ID1642L HYPOTHETICAL 17.0 KDA PROTEIN.
ID1643L EXCINUCLEASE ABC (C) (FRAGMENT).
ID1644L INT PROTEIN.
ID1645L RIBONUCLEASE Hill (EC 3.1.26.-) (RNASE HIII).
ID1646L ORF starting with ATG of length 315
ID1647L ORF starting with ATG of length 258
ID1648L DNA HELICASE HOMOLOG (FRAGMENT).
ID1649L ORF starting with ATG of length 678
ID1650L ORF starting with ATG of length 201
ID1651L ORF starting with ATG of length 1143
ID1652LK TRANSCRIPTION-REPAIR COUPLING FACTOR (TRCF).
ID1653LK ATP-DEPENDENT DNA HELICASE RECG (EC 3.6.1.-).
ID1654LK TRANSCRIPTION-REPAIR COUPLING FACTOR (FRAGMENT).
ID1655LK ORF starting with ATG of length 657
ID1656LKJ PROBABLE RNA HELICASE IN CCCA-SODA INTERGENIC REGION.
ID1657LKJ COMF OPERON PROTEIN 1.
ID1658LKJ YFML PROTEIN.
ID1659LKJ COLD-SHOCK DEAD-BOX PROTEIN A HOMOLOG (ATP-DEPENDENT RNA HEL
ID1660LKJ HYPOTHETICAL 56.9 KDA PROTEIN.
ID1661LN SMF PROTEIN.
ID1662LR Amino acid sequence of activator YgkG of methanol dehydrogen
ID1663LR MUTATOR MUTT PROTEIN.
ID1664LR MUTATOR MUTT PROTEIN.
ID1665LR YTKD.
ID1666M STAGE V SPORULATION PROTEIN D (SPORULATION SPECIFIC PENICILL
ID1667M REGULATORY PROTEIN BLAR1.
ID1668M PENICILLIN-BINDING PROTEIN 1F (PBP-1F).

ID1669M GLUCOSAMINE-FRUCTOSE-6-PHOSPHATE AMINOTRANSFERASE [ISOMERIZ
ID1670M PENICILLIN-BINDING PROTEIN 2B (PBP-2B).
ID1671M PENICILLIN-BINDING PROTEIN 1A/1B (PBP1) [INCLUDES: PENICILLI
ID1672M HYPOTHETICAL 71.8 KDA PROTEIN.
ID1673M PENICILLIN-BINDING PROTEIN 4 PRECURSOR (PBP 4).
ID1674M PENICILLIN-BINDING PROTEIN 3 (PBP 3) (PSPB20).
ID1675M YFLE PROTEIN.
ID1676M YRRR PROTEIN.
ID1677M UDP-N-ACETYLGLUCOSAMINE 1-CARBOXYVINYLTRANSFERASE 1 (EC 2.5.
ID1678M TEICHOIC ACID BIOSYNTHESIS PROTEIN F.
ID1679M UDP-N-ACETYLGLUCOSAMINE 1-CARBOXYVINYLTRANSFERASE 2 (EC 2.5.
ID1680M HYPOTHETICAL 73.6 KDA PROTEIN IN DNAC-RPLI INTERGENIC REGION
ID1681M YVGJ PROTEIN.
ID1682M D-ALANYL-D-ALANINE CARBOXYPEPTIDASE PRECURSOR (EC 3.4.16.4)
ID1683M PROBABLE N-ACETYLMURAMOYL-L-ALANINE AMIDASE PRECURSOR (EC 3.
ID1684M B. subtilis yaeL polypeptide.
ID1685M UDP-N-ACETYLMURAMOYLALANINE-D-GLUTAMATE LIGASE (EC 6.3.2.9)
ID1686M HYPOTHETICAL 73.2 KDA PROTEIN IN SODA-COMGA INTERGENIC REGIO
ID1687M CARBOXY-TERMINAL PROCESSING PROTEASE.
ID1688M SPOIVB.
ID1689M B. subtilis glycosyl transferase catalytic domain.
ID1690M DLTB PROTEIN.
ID1691M PENICILLIN-BINDING PROTEIN 4* (PBP 4*) (PBP 4A).
ID1692M GCPE PROTEIN HOMOLOG.
ID1693M PENICILLIN-BINDING PROTEIN DACF PRECURSOR (D-ALANYL-D-ALANIN
ID1694M UDP-N-ACETYLGLUCOSAMINE-N-ACETYLMURAMYL-(PENTAPEPTIDE)PYROP
ID1695M HYPOTHETICAL 42.0 KDA PROTEIN IN DAPB-PAPS INTERGENIC REGION
ID1696M PUTATIVE UNDECAPRENYL-PHOSPHATE N-ACETYLGLUCOSAMINYLTRANSFER
ID1697M UDP-N-ACETYLGLUCOSAMINE PYROPHOSPHORYLASE (EC 2.7.7.23) (N-A
ID1698M YBBE PROTEIN (YBZA).
ID1699M UDP-N-ACETYLMURAMOYLALANYL-D-GLUTAMYL-2,6-DIAMINOPIMELATE L
ID1700M YKUA PROTEIN.
ID1701M UTP-GLUCOSE-1-PHOSPHATE URIDYLYLTRANSFERASE (EC 2.7.7.9) (U
ID1702M HYPOTHETICAL 43.6 KDA PROTEIN.
ID1703M GLYCINE BETAINE/CARNITINE/CHOLINE-BINDING PROTEIN PRECURSOR
ID1704M CSBB PROTEIN.
ID1705M TUAH PROTEIN.
ID1706M SIMILAR TO E. COLI NLPC PROTEIN AND TO LISTERIA SPECIES P60-R
ID1707M TUAC PROTEIN.
ID1708M YFNI.
ID1709M BETA-LACTAMASE (EC 3.5.2.6) (PENICILLINASE) (CEPHALOSPORINAS
ID1710M HYPOTHETICAL 37.4 KDA PROTEIN IN SPOIISA-HTRA INTERGENIC REG
ID1711M HYPOTHETICAL 50.1 KDA PROTEIN.
ID1712M YKON.
ID1713M N-ACETYLMURAMOYL-L-ALANINE AMIDASE CWLM (EC 3.5.1.28) (CELL
ID1714M PUTATIVE ALANINE RACEMASE (EC 5.1.1.1).
ID1715M HYPOTHETICAL 42.6 KDA PROTEIN.
ID1716M UDP-GLUCOSE 4-EPIMERASE (EC 5.1.3.2).
ID1717M GALE.
ID1718M HYPOTHETICAL 38.5 KDA PROTEIN IN TNRA-SSPD INTERGENIC REGION
ID1719M HYPOTHETICAL 37.2 KDA PROTEIN IN IDH-DEOR INTERGENIC REGION.
ID1720M YKCB PROTEIN.
ID1721M GLUTAMATE RACEMASE (EC 5.1.1.3).
ID1722M GENERAL STRESS PROTEIN A.
ID1723M HYPOTHETICAL 40.6 KDA PROTEIN IN SPOVID 3'REGION (ORF2).
ID1724M ORF starting with ATG of length 2235
ID1725M PROLIPOPROTEIN DIACYLGLYCERYL TRANSFERASE (EC 2.4.99.-) (SPO
ID1726M SPORE-CORTEX-LYTIC ENZYME PRECURSOR.
ID1727M HYPOTHETICAL 80.1 KDA PROTEIN IN SODA-COMGA INTERGENIC REGIO
ID1728M HYPOTHETICAL 32.7 KDA PROTEIN.
ID1729M ROD SHAPE-DETERMINING PROTEIN MREC.
ID1730M ALPHA-D-MANNOSE-ALPHA(1-6)PHOSPHATIDYL MYO-INOSITOL MONOMANN
ID1731M TEICHOIC ACID BIOSYNTHESIS PROTEIN B PRECURSOR.
ID1732M YUSA PROTEIN.
ID1733M GERMINATION-SPECIFIC N-ACETYLMURAMOYL-L-ALANINE AMIDASE (EC
ID1734M TUAG PROTEIN.
ID1735M DIVIB PROTEIN.
ID1736M HYPOTHETICAL 24.4 KDA PROTEIN.
ID1737M HYPOTHETICAL 42.5 KDA PROTEIN IN CITA-SSPB INTERGENIC REGION
ID1738M HYPOTHETICAL 39.8 KDA PROTEIN.
ID1739M ORF starting with ATG of length 1982
ID1740M CARBOXYPEPTIDASE.
ID1741M PHOSPHO-N-ACETYLMURAMOYL-PENTAPEPTIDE-TRANSFERASE (EC 2.7.8.
ID1742M YKFC.
ID1743M GALE.
ID1744M 455AA LONG HYPOTHETICAL VI POLYSACCHARIDE BIOSYNTHESIS PROTE
ID1745M Bacillus subtilis IFO 3336 PGA synthesising enzyme.
ID1746M YRVJ PROTEIN.
ID1747M D-alanine racemase from Bacillus licheniformis.
ID1748M UDP-N-ACETYLENOLPYRUVOYLGLUCOSAMINE REDUCTASE (EC 1.1.1.158)
ID1749M PLEIOTROPIC REGULATORY PROTEIN.
ID1750M PENICILLIN-BINDING PROTEIN 5* PRECURSOR (D-ALANYL-D-ALANINEC
ID1751M CARBOXY-TERMINAL PROCESSING PROTEASE.
ID1752M STAGE IV SPORULATION PROTEIN FA.
ID1753M PUTATIVE PENICILLIN BINDING PROTEIN PRECURSOR.
ID1754M ENDOPEPTIDASE LYTF PRECURSOR (CELL WALL-ASSOCIATED POLYPEPTI
ID1755M ORF starting with ATG of length 1527
ID1756M HYPOTHETICAL 23.1 KDA PROTEIN.

ID1757M ORF starting with ATG of length 1497
ID1758M D-ALANINE-D-ALANINE LIGASE (EC 6.3.2.4) (D-ALANYLALANINE SY
ID1759M YUNA PROTEIN.
ID1760M PUTATIVE ENDOPEPTIDASE LYTE PRECURSOR (PHOSPHATASE-ASSOCIATE
ID1761M HYPOTHETICAL 35.3 KDA PROTEIN IN FTSL 5'REGION (ORFB).
ID1762M GALE.
ID1763M ORF46.
ID1764M D-ALANINE-D-ALANINE LIGASE (EC 6.3.2.4) (D-ALANYLALANINE SY
ID1765M SIMILAR TO PSEUDOMONAS AERUGINOSA GDP-MANNOSE 6-DEHYDROGENAS
ID1766M HYPOTHETICAL 22.2 KDA PROTEIN IN SPOOA-MMGA INTERGENIC REGIO
ID1767M YUNA PROTEIN.
ID1768M HYPOTHETICAL 80.1 KDA PROTEIN IN SODA-COMGA INTERGENIC REGIO
ID1769M UDP-N-ACETYLMURAMOYLALANYL-D-GLUTAMYL-2,6-DIAMINOPIMELATE-D—
ID1770M ORF starting with ATG of length 1236
ID1771M ORF starting with ATG of length 1227
ID1772M N-ACETYLMURAMOYL-L-ALANINE AMIDASE CWLL PRECURSOR (EC 3.5.1.
ID1773M MINIMAL CHANGE NEPHRITIS TRANSMEMBRANE GLYCOPROTEIN (FRAGMEN
ID1774M ORF starting with ATG of length 1170
ID1775M GLUCOSE INHIBITED DIVISION PROTEIN B.
ID1776M ROD SHAPE-DETERMINING PROTEIN MRED.
ID1777M SIMILAR TO BACILLUS ANTHRACIS CAPA PROTEIN.
ID1778M TEICHOIC ACID BIOSYNTHESIS PROTEIN A.
ID1779M N-ACETYLMURAMOYL-L-ALANINE AMIDASE CWLM (EC 3.5.1.28) (CELL
ID1780M YTMP.
ID1781M HYPOTHETICAL 25.8 KDA PROTEIN IN EPRGALK INTERGENIC REGION.
ID1782M ORF starting with ATG of length 1062
ID1783M GLYCINE BETAINE TRANSPORTER OPUD.
ID1784M ORF starting with ATG of length 1035
ID1785M YNGB PROTEIN.
ID1786M PLEIOTROPIC REGULATORY PROTEIN DEGT.
ID1787M STAGE V SPORULATION PROTEIN G.
ID1788M UDP-N-ACETYLGLUCOSAMINE PYROPHOSPHORYLASE (EC 2.7.7.23).
ID1789M LARGE-CONDUCTANCE MECHANOSENSITIVE CHANNEL.
ID1790M STAGE II SPORULATION PROTEIN.
ID1791M *B. subtilis* hexylose phosphate isomerase.
ID1792M UDP-D-GLUCOSE-DEHYDROGENASE GDHGA.
ID1793M YNGB PROTEIN.
ID1794M Amino acid sequence of epsH of *L. delbrueckii bulgaricus* Lfi
ID1795M PUTATIVE UDP-N-ACETYLGLUCOSAMINE 2-EPIMERASE (EC 5.1.3.14)
ID1796M N-ACETYLMURAMOYL-L-ALANINE AMIDASE CWLL PRECURSOR (EC 3.5.1.
ID1797M ORF starting with ATG of length 810
ID1798M BH1600 PROTEIN.
ID1799M PUTATIVE UDP-N-ACETYLGLUCOSAMINE 2-EPIMERASE (EC 5.1.3.14)
ID1800M ORF starting with ATG of length 753
ID1801M PENICILLIN-BINDING PROTEIN 1A/1B (PBP1) [INCLUDES: PENICILLI
ID1802M *Staphylococcus aureus* ica A protein.
ID1803M TEICHOIC ACID TRANSLOCATION PERMEASE PROTEIN TAGG.
ID1804M PUTATIVE ALANINE RACEMASE (EC 5.1.1.1).
ID1805M ORF starting with ATG of length 654
ID1806M PHOSPHO-N-ACETYLMURAMOYL-PENTAPEPTIDE-TRANSFERASE (EC 2.7.8.
ID1807M HYPOTHETICAL 73.2 KDA PROTEIN IN SODA-COMGA INTERGENIC REGIO
ID1808M TUAA PROTEIN.
ID1809M HYPOTHETICAL 18.4 KDA PROTEIN.
ID1810M AMIDASE ENHANCER PRECURSOR (MODIFIER PROTEIN OF MAJOR AUTOLY
ID1811M PENICILLIN-BINDING PROTEIN 2B (INTERNAL REGION OF THE PENICIL
ID1812M CWLV.
ID1813M UDP-N-AACERYLMURAMATE-ALANINE LIGASE.
ID1814M ORF starting with ATG of length 498
ID1815M PHOSPHINOTHRICIN N-ACETYLTRANSFERASE.
ID1816M ORF starting with ATG of length 495
ID1817M ORF starting with ATG of length 483
ID1818M TEICHOIC ACID TRANSLOCATION PERMEASE PROTEIN TAGG.
ID1819M AMIDASE ENHANCER PRECURSOR (MODIFIER PROTEIN OF MAJOR AUTOLY
ID1820M MurF protein.
ID1821M HYPOTHETICAL 40.8 KDA PROTEIN IN SODA-COMGA INTERGENIC REGIO
ID1822M GLYCINE BETAINE TRANSPORTER OPUD.
ID1823M ORF starting with ATG of length 372
ID1824M ORF starting with TTG or GTG of length 705
ID1825M ORF starting with ATG of length 327
ID1826M HYPOTHETICAL 30.5 KDA PROTEIN.
ID1827M ORF starting with ATG of length 276
ID1828MG HYPOTHETICAL 66.3 KDA PROTEIN.
ID1829MG HYPOTHETICAL 28.2 KDA PROTEIN IN BIOI 3'REGION (ORF2).
ID1830MG PUTATIVE UDP-GLUCOSE 4-EPIMERASE (EC 5.1.3.2) (GALACTOWALDEN
ID1831 MG HYPOTHETICAL 66.3 KDA PROTEIN.
ID1832MG ORF starting with ATG of length 975
ID1833MG CONSERVED HYPOTHETICAL PROTEIN.
ID1834MG PUTATIVE SUGAR NUCLEOTIDE BIOSYNTHESIS PROTEIN.
ID1835MG YESF PROTEIN.
ID1836N GTP-BINDING PROTEIN LEPA.
ID1837N GTP-BINDING PROTEIN TYPA/BIPA HOMOLOG.
ID1838N PREPROTEIN TRANSLOCASE SECA SUBUNIT.
ID1839N CHEMOTAXIS PROTEIN CHEA (EC 2.7.3.-).
ID1840N *B. subtilis* secretion factor SecDF.
ID1841N METHYL-ACCEPTING CHEMOTAXIS PROTEIN MCPA (H1).
ID1842N YOAH.
ID1843N METHYL-ACCEPTING CHEMOTAXIS PROTEIN MCPB (H3).
ID1844N PREPROTEIN TRANSLOCASE SECY SUBUNIT.
ID1845N FLAGELLUM-SPECIFIC ATP SYNTHASE (EC 3.6.1.34).

ID1846N FLAGELLAR HOOK-ASSOCIATED PROTEIN 1 (HAP1).
ID1847N SIGNAL RECOGNITION PARTICLE PROTEIN (FIFTY-FOUR HOMOLOG).
ID1848N FLAGELLAR HOOK-ASSOCIATED PROTEIN 2 (HAP2) (FILAMENT CAP PRO
ID1849N FLAGELLAR MOTOR SWITCH PROTEIN FLIG.
ID1850N HYPOTHETICAL 48.8 KDA PROTEIN.
ID1851N FLAGELLAR BIOSYNTHETIC PROTEIN FLHB.
ID1852N *Bacillus subtilis* protein secretion chaperone FtsY.
ID1853N FLAGELLAR BIOSYNTHESIS PROTEIN FLHA.
ID1854N COMG OPERON PROTEIN 1.
ID1855N FLAGELLIN.
ID1856N METHYL-ACCEPTING CHEMOTAXIS PROTEIN MCPB (H3).
ID1857N FLAGELLAR M-RING PROTEIN.
ID1858N CHEMOTAXIS CHEV PROTEIN (EC 2.7.3.-).
ID1859N FLAGELLAR HOOK-ASSOCIATED PROTEIN 3 (HAP3).
ID1860N YFMS.
ID1861N FLAGELLA-ASSOCIATED PROTEIN.
ID1862N FLAGELLAR MOTOR SWITCH PROTEIN.
ID1863N HYPOTHETICAL 30.1 KDA PROTEIN IN ACUC 5'REGION (ORFA).
ID1864N FLAGELLAR BIOSYNTHESIS PROTEIN FLHF (FLAGELLA ASSOCIATED GTP
ID1865N CHEMOTAXIS MOTA PROTEIN (MOTILITY PROTEIN A).
ID1866N METHYL-ACCEPTING CHEMOTAXIS PROTEIN TLPC.
ID1867N FLAGELLAR BIOSYNTHETIC PROTEIN FLIR.
ID1868N FLAGELLAR BIOSYNTHETIC PROTEIN FLIP.
ID1869N ORF starting with ATG of length 1983
ID1870N FLAGELLAR HOOK-BASAL BODY COMPLEX PROTEIN FLHO.
ID1871N COMG OPERON PROTEIN 2.
ID1872N METHYL-ACCEPTING CHEMOTAXIS PROTEIN MCPC.
ID1873N ORF starting with ATG of length 1785
ID1874N ORF starting with ATG of length 1734
ID1875N ORF starting with ATG of length 1725
ID1876N HYPOTHETICAL 28.1 KDA PROTEIN IN PHOD-PCP INTERGENIC REGION
ID1877N FLAGELLAR HOOK-BASAL BODY COMPLEX PROTEIN FLHP.
ID1878N SECDF PROTEIN (PROTEIN-EXPORT MEMBRANE PROTEIN).
ID1879N STAGE III SPORULATION PROTEIN J PRECURSOR.
ID1880N ORF starting with ATG of length 1566
ID1881N HYPOTHETICAL 30.7 KDA LIPOPROTEIN IN GLNQ-ANSR INTERGENIC RE
ID1882N ORF39.
ID1883N PROBABLE FLAGELLAR HOOK-LENGTH CONTROL PROTEIN.
ID1884N Amino acid sequence of a SipW protein of *Bacillus subtilus*.
ID1885N TYPE 4 PREPILIN-LIKE PROTEINS LEADER PEPTIDE PROCESSING ENZY
ID1886N FLAGELLAR FLIJ PROTEIN (CHEMOTAXIS CHEF PROTEIN).
ID1887N SIGNAL PEPTIDASE TYPE I.
ID1888N FLAGELLAR BASAL-BODY ROD PROTEIN FLGG (DISTAL ROD PROTEIN).
ID1889N HYPOTHETICAL 24.6 KDA PROTEIN IN CCPA 3'REGION (ORF2).
ID1890N CHEMOTAXIS PROTEIN CHEW.
ID1891N FLAGELLAR PROTEIN FLIS.
ID1892N HYPOTHETICAL 29.1 KDA PROTEIN IN PHOB-GROES INTERGENIC REGIO
ID1893N YOCH.
ID1894N ORF starting with ATG of length 964
ID1895N ORF starting with ATG of length 954
ID1896N FLAGELLAR FLIL PROTEIN.
ID1897N PREPROTEIN TRANSLOCASE SECA SUBUNIT (FRAGMENT).
ID1898N SIGNAL PEPTIDASE I (EC 3.4.21.89) (SPASE I) (LEADER PEPTIDAS
ID1899N FLAGELLAR BIOSYNTHETIC PROTEIN FLIQ.
ID1900N FLAGELLAR ASSEMBLY PROTEIN.
ID1901N HYPOTHETICAL 9.9 KDA PROTEIN IN SPOVB-TGT INTERGENIC REGION.
ID1902N MOTILITY PROTEIN.
ID1903N COMG OPERON PROTEIN 3 PRECURSOR.
ID1904N ORF starting with ATG of length 620
ID1905N FLAGELLAR BASAL-BODY ROD PROTEIN FLGB.
ID1906N HYPOTHETICAL 13.0 KDA PROTEIN IN HAG-FLID INTERGENIC REGION
ID1907N FLAGELLAR BASAL-BODY ROD PROTEIN FLGC.
ID1908N YRBA PROTEIN.
ID1909N PREPROTEIN TRANSLOCASE SECA SUBUNIT.
ID1910N ORF starting with ATG of length 399
ID1911N ORF starting with ATG of length 336
ID1912N ORF starting with ATG of length 314
ID1913N THA4 PROTEIN PRECURSOR.
ID1914NO HYPOTHETICAL 46.5 KDA PROTEIN IN RPSU-PHOH INTEREGENIC REGIO
ID1915NO PROTEINASE IV.
ID1916NO BH2397 PROTEIN.
ID1917NO PUTATIVE PROTEASE/SCAFFOLD PROTEIN.
ID1918NT FLAGELLAR MOTOR SWITCH PROTEIN FLIY.
ID1919NT PROTEIN-GLUTAMATE METHYL-ESTERASE (EC 3.1.1.61).
ID1920NT CHEMOTAXIS PROTEIN METHYLTRANSFERASE (EC 2.1.1.80).
ID1921NT CHEMOTAXIS PROTEIN CHEC.
ID1922NT CHEMOTAXIS PROTEIN CHED.
ID1923NT CHEMOTAXIS PROTEIN CHEC.
ID1924NT ORF starting with ATG of length 321
ID1925O BACILLOPEPTIDASE F PRECURSOR (EC 3.4.21.-) (ESTERASE) (RP-I
ID1926O NEGATIVE REGULATOR OF GENETIC COMPETENCE CLPC/MECB.
ID1927O TRANSCRIPTIONAL REGULATORY PROTEIN LEVR.
ID1928O *B. subtilis* FtsH protein.
ID1929O ATP-DEPENDENT CLP PROTEASE-LIKE.
ID1930O ATP-DEPENDENT PROTEASE LA HOMOLOG (EC 3.4.21.-).
ID1931O RESB PROTEIN.
ID1932O ATP-DEPENDENT PROTEASE LA 1 (EC 3.4.21.53).

ID1933O MINOR EXTRACELLULAR PROTEASE VPR PRECURSOR (EC 3.4.21.-).
ID1934O ALKALINE SERINE PROTEASE.
ID1935O CELL WALL-ASSOCIATED PROTEASE PRECURSOR (EC 3.4.21.-) [CONTA
ID1936O DNA REPAIR PROTEIN RADA HOMOLOG (DNA REPAIR PROTEIN SMS HOMO
ID1937O THIOREDOXINE REDUCTASE.
ID1938O BACILLOPEPTIDASE F PRECURSOR (EC 3.4.21.-) (ESTERASE) (RP-I
ID1939O ARGININE UTILIZATION REGULATORY PROTEIN ROCR.
ID1940O STAGE V SPORULATION PROTEIN K.
ID1941O RESC PROTEIN.
ID1942O HTRA-LIKE SERINE PROTEASE.
ID1943O YRRO PROTEIN.
ID1944O HYPOTHETICAL PROTEASE IN ROCR-PURA INTERGENIC REGION (EC 3.4
ID1945O HYPOTHETICAL 36.3 KDA PROTEIN IN RECQ-CMK INTERGENIC REGION.
ID1946O ATP-DEPENDENT CLP PROTEASE ATP-BINDING SUBUNIT (CLASSIII HE
ID1947O 60 KDA CHAPERONIN (PROTEIN CPN60) (GROEL PROTEIN) (STRESS PR
ID1948O HEMX PROTEIN.
ID1949O MINOR EXTRACELLULAR PROTEASE EPR PRECURSOR (EC 3.4.21.-).
ID1950O ATP-DEPENDENT CLP PROTEASE (HEAT-SHOCK PROTEIN).
ID1951O CELL DIVISION CYCLE PROTEIN.
ID1952O HEAT SHOCK PROTEIN HTPG.
ID1953O TRIGGER FACTOR (TF) (VEGETATIVE PROTEIN 2) (VEG2).
ID1954O CHAPERONE PROTEIN DNAJ.
ID1955O YKVL PROTEIN.
ID1956O PUTATIVE METALLOPROTEASE YHFN (EC 3.4.24.-) (PSP23).
ID1957O *Bacillus megaterium* HSP (Bmehsp70).
ID1958O ALKYL HYDROPEROXIDE REDUCTASE C22 PROTEIN (EC 1.6.4.-) (GENE
ID1959O ORF starting with ATG of length 1665
ID1960O *Bacillus megaterium* HSP (Bmehsp70).
ID1961O ATP-DEPENDENT PROTEASE HSLV PRECURSOR (EC 3.4.99.-).
ID1962O ALKYL HYDROPEROXIDE REDUCTASE LARGE SUBUNIT (EC 1.6.99.3) (P
ID1963O CYTOCHROME C-TYPE BIOGENESIS PROTEIN CCDA.
ID1964O PUTATIVE SIGMA L-DEPENDENT TRANSCRIPTIONAL REGULATOR IN DFRA
ID1965O YKDA.
ID1966O 33 KDA CHAPERONIN (HEAT SHOCK PROTEIN 33 HOMOLOG) (HSP33).
ID1967O PEPTIDE METHIONINE SULFOXIDE REDUCTASE (EC 1.8.4.6) (PROTEIN
ID1968O YVGV PROTEIN.
ID1969O YVJD.
ID1970O SA2162 PROTEIN.
ID1971O YVGU PROTEIN.
ID1972O HYPOTHETICAL 16.6 KDA PROTEIN IN MSRA 3'REGION.
ID1973O *Bacillus* carlsberg alkaline elastase.
ID1974O PROTEIN EXPORT PROTEIN PRSA PRECURSOR.
ID1975O HYPOTHETICAL 25.2 KDA PROTEIN.
ID1976O GLUTATHIONE PEROXIDASE HOMOLOG BSAA.
ID1977O *Arabidopsis thaliana* protein fragment SEQ ID NO: 56671.
ID1978O CYTOCHROME C-TYPE BIOGENESIS PROTEIN CCDA.
ID1979O GENERAL STRESS PROTEIN 17O (GSP17O).
ID1980O YMAD PROTEIN.
ID1981O YVJD.
ID1982O GRPE PROTEIN (HSP-7O COFACTOR).
ID1983O SUBTILISIN CARLSBERG PRECURSOR (EC 3.4.21.62).
ID1984O THIOL PROTEASE
ID1985O PLASMID PAD1 (FROM ENTEROCOCCUS FAECALIS) CYLLL, CYLLS, CYLM
ID1986O *Staphylococcus aureus* glycoprotease (gcp) protein.
ID1987O Amino acid sequence of a heat shock protein.
ID1988O FORMATE ACETYLTRANSFERASE ACTIVATING ENZYME.
ID1989O YUTI PROTEIN.
ID1990O ATP-DEPENDENT HSL PROTEASE ATP-BINDING SUBUNIT HSLU.
ID1991O ORF starting with ATG of length 750
ID1992O SPORE COAT PROTEIN M.
ID1993O ATP-DEPENDENT CLP PROTEASE ATP-BINDING SUBUNIT (CLASSIII HE
ID1994O 10 KDA CHAPERONIN (PROTEIN CPN10) (PROTEIN GROES).
ID1995O ANAEROBIC RIBONUCLEOSIDE-TRIPHOSPHATE REDUCTASE ACTIVATING P
ID1996O PUTATIVE METALLOPROTEASE YHFN (EC 3.4.24.-) (PSP23).
ID1997O BACTERIOFERRITIN COMIGRATORY PROTEIN HOMOLOG.
ID1998O PYRROLIDONE-CARBOXYLATE PEPTIDASE (EC 3.4.19.3) (5-OXOPROLYL
ID1999O *Bacillus megaterium* HSP (Bmehsp70).
ID2000O CHAPERONE HSLU.
ID2001O ORF starting with ATG of length 498
ID2002O HYPOTHETICAL 16.3 KDA PROTEIN IN PONA-COTD INTERGENIC REGION
ID2003O SMALL PROTEIN B HOMOLOGUE.
ID2004O ALKYL HYDROPEROXIDE REDUCTASE LARGE SUBUNIT (EC 1.6.99.3) (P
ID2005O PYRUVATE FORMATE-LYASE ACTIVATING ENZYME (EC 1.97.1.4) (PFL—
ID2006O ORF starting with ATG of length 276
ID2007O ATP-DEPENDENT PROTEASE LA 1 (EC 3.4.21.53).
ID2008OC RESA PROTEIN.
ID2009OC YKVV PROTEIN.
ID2010OC PUTATIVE THIOREDOXIN.
ID2011OC YDFQ PROTEIN.
ID2012OC YNEN PROTEIN.
ID2013OC YUSE PROTEIN.
ID2014OC Thioredoxin-*Treponema pallidum* 15 kDa antigen fusion protein
ID2015OC ORF starting with ATG of length 219
ID2016P YLOB PROTEIN.
ID2017P POTENTIAL COPPER-TRANSPORTING ATPASE (EC 3.6.3.4).
ID2018P SULFITE REDUCTASE (NADPH).
ID2019P ALKALINE PHOSPHATASE D PRECURSOR (EC 3.1.3.1) (APASED) (RAN1
ID2020P YKVW PROTEIN.
ID2021P HYPOTHETICAL 57.4 KDA PROTEIN.
ID2022P CATALASE HPII.

ID2023P Amino acid sequence of a *Bacillus* P450 monooxygenase protein
ID2024P SULFATE PERMEASE.
ID2025P Alkaline phosphatase.
ID2026P NA+-TRANSPORTING ATP SYNTHASE.
ID2027P NA+/H+ ANTIPORTER.
ID2028P CHROMATE TRANSPORTER.
ID2029P PUTATIVE NITRATE REDUCTASE BETA CHAIN.
ID2030P YJBQ PROTEIN.
ID2031P YFKE PROTEIN.
ID2032P FEOB PROTEIN.
ID2033P CATALASE X (EC 1.11.1.6).
ID2034P NA+-TRANSPORTING ATP SYNTHASE.
ID2035P HOMOLOGUE OF COPPER EXPORT PROTEIN PCOD OF *E. COLI*.
ID2036P YLNA PROTEIN.
ID2037P SULFITE REDUCTASE (NADPH).
ID2038P PROBABLE LOW-AFFINITY INORGANIC PHOSPHATE TRANSPORTER.
ID2039P NITRITE EXTRUSION PROTEIN (NITRITE FACILITATOR).
ID2040P FERRICHROME-BINDING PROTEIN PRECURSOR.
ID2041P YKOK.
ID2042P BH1407 PROTEIN.
ID2043P PROBABLE AMMONIUM TRANSPORTER (MEMBRANE PROTEIN NRGA).
ID2044P IRON-UPTAKE SYSTEM BINDING PROTEIN PRECURSOR.
ID2045P YFJQ PROTEIN.
ID2046P YVGW PROTEIN.
ID2047P MANGANESE-CONTAINING CATALASE.
ID2048P NITRATE TRANSPORTER.
ID2049P HYPOTHETICAL ABC TRANSPORTER ATP-BINDING PROTEIN YQGK.
ID2050P YKOY PROTEIN.
ID2051P YBAF PROTEIN.
ID2052P PROBABLE SUPEROXIDE DISMUTASE [FE] (EC 1.15.1.1).
ID2053P HYPOTHETICAL 57.2 KDA PROTEIN.
ID2054P YTLD.
ID2055P SULFATE ADENYLYLTRANSFERASE (EC 2.7.7.4) (SULFATE ADENYLATET
ID2056P HYPOTHETICAL 33.4 KDA PROTEIN IN DNAJ-RPSU INTEREGENIC REGIO
ID2057P YLMA PROTEIN.
ID2058P HYPOTHETICAL 23.8 KDA PROTEIN IN SPOIISA-HTRA INTERGENIC REG
ID2059P HYPOTHETICAL 31.8 KDA PROTEIN IN GABP-GUAA INTERGENIC REGION
ID2060P HYPOTHETICAL 29.2 KDA PROTEIN IN RAPJ-OPUAA INTERGENIC REGIO
ID2061P FERRIC ANGUIBACTIN-BINDING PROTEIN PRECUSOR FATB OF V. ANGUI
ID2062P HYPOTHETICAL ABC TRANSPORTER ATP-BINDING PROTEIN YBXA.
ID2063P YKRM PROTEIN.
ID2064P HYPOTHETICAL 24.3 KDA PROTEIN IN KINC-ADEC INTERGENIC REGION
ID2065P PROBABLE ABC TRANSPORTER BINDING PROTEIN YQGG PRECURSOR.
ID2066P HYPOTHETICAL 38.6 KDA PROTEIN.
ID2067P HYPOTHETICAL TRANSCRIPTIONAL REGULATOR IN FEUA-SIGW INTERGEN
ID2068P YFIY PROTEIN.
ID2069P COTJC PROTEIN.
ID2070P SA0587 PROTEIN.
ID2071P YLNA PROTEIN.
ID2072P HYPOTHETICAL 37.7 KDA PROTEIN IN SODA-COMGA INTERGENIC REGIO
ID2073P PROBABLE MANGANESE TRANSPORT PROTEIN MNTH.
ID2074P PROBABLE ADENYLYLSULFATE KINASE (EC 2.7.1.25) (APS KINASE)
ID2075P PROBABLE ABC TRANSPORTER PERMEASE PROTEIN YQGI.
ID2076P CYTOCHROME B SUBUNIT OF NITRIC OXIDE REDUCTASE.
ID2077P SUPEROXIDE DISMUTASE (EC 1.15.1.1).
ID2078P YVGL PROTEIN.
ID2079P SULFITE REDUCTASE (NADPH) FLAVOPROTEIN (EC 1.8.1.2).
ID2080P HYPOTHETICAL 21.7 KDA PROTEIN.
ID2081P HYPOTHETICAL PROTEIN YWRB.
ID2082P ORF starting with ATG of length 1458
ID2083P HYPOTHETICAL 49.9 KDA PROTEIN.
ID2084P HYPOTHETICAL 43.2 KDA PROTEIN IN DNAC-RPLI INTERGENIC REGION
ID2085P PEROXIDE OPERON REGULATOR.
ID2086P HYPOTHETICAL 57.2 KDA PROTEIN.
ID2087P YFIY PROTEIN.
ID2088P PUTATIVE ALKALINE PHOSPHATASE.
ID2089P HYPOTHETICAL PROTEIN YWRA.
ID2090P YVGW PROTEIN.
ID2091P PROBABLE ABC TRANSPORTER PERMEASE PROTEIN YQGH.
ID2092P ARSENIC EFFLUX PUMP.
ID2093P YVGQ (FRAGMENT).
ID2094P YJBD PROTEIN.
ID2095P POTASSIUM CHANNEL PROTEIN.
ID2096P A formate transport associated protein, FTAP2.
ID2097P BH0467 PROTEIN.
ID2098P HYPOTHETICAL 14.6 KDA PROTEIN IN GCVT-SPOIIIAA INTERGENIC RE
ID2099P Vancomycin resistant *Enterococcus faecium* expression product
ID2100P PROBABLE ABC TRANSPORTER BINDING PROTEIN YXEB PRECURSOR.
ID2101P YOJM PROTEIN.
ID2102P YUSI PROTEIN.
ID2103P HYDROPHOBIC MEMBRANE PROTEIN ZURM.
ID2104P GENERAL STRESS PROTEIN 80 (GSP80).
ID2105P ORF starting with ATG of length 957
ID2106P ORF starting with ATG of length 954
ID2107P YVGQ (FRAGMENT).
ID2108P MODB PROTEIN.
ID2109P ORF starting with ATG of length 933
ID2110P *S. pneumoniae* phosphate transport ATP-binding protein.
ID2111P *B. subtilis* hydrolase protein YJCH.
ID2112P GENERAL STRESS PROTEIN 80 (GSP80).
ID2113P NA+/H+ ANTIPORTER SUBUNIT.
ID2114P HYPOTHETICAL 12.1 KDA PROTEIN IN SACB-CLPP INTERGENIC REGION
ID2115P HYPOTHETICAL 11.4 KDA PROTEIN IN SACB-CLPP INTERGENIC REGION
ID2116P SA0928 PROTEIN.
ID2117P RPOH (FRAGMENT).
ID2118P ORF starting with ATG of length 799
ID2119P YJBE PROTEIN.
ID2120P HYPOTHETICAL 11.3 KDA PROTEIN IN HMP-PROB INTERGENIC REGION.

ID2121P FEOB PROTEIN.
ID2122P ORF starting with ATG of length 771
ID2123P TRANSPORTER (PH087 FAMILY).
ID2124P PEROXIDE OPERON REGULATOR.
ID2125P PUTATIVE ALKALINE PHOSPHATASE.
ID2126P HYPOTHETICAL 11.9 KDA PROTEIN IN HMP-PROB INTERGENIC REGION.
ID2127P MULTIDRUG RESISTANCE PROTEIN EBRB.
ID2128P PEROXIDE OPERON REGULATOR.
ID2129P ORF starting with ATG of length 1005
ID2130P NA-F/H+ ANTIPORTER SUBUNIT.
ID2131P NA+/H+ ANTIPORTER SUBUNIT.
ID2132P YBCF PROTEIN.
ID2133P NITRATE EXTRUSION PROTEIN (FRAGMENT).
ID2134P ORF starting with ATG of length 624
ID2135P ORF starting with ATG of length 594
ID2136P YDFA PROTEIN.
ID2137P YTWF PROTEIN.
ID2138P NA-F/H+ ANTIPORTER SUBUNIT.
ID2139P CATION-EFFLUX SYSTEM MEMBRANE PROTEIN HOMOLOG.
ID2140P YFLS PROTEIN.
ID2141P B. subtilis hydrolase protein YJCH.
ID2142P HYPOTHETICAL 7.2 KDA PROTEIN.
ID2143P IRON UPTAKE REGULATORY PROTEIN.
ID2144P ABC-TYPE TRANSPORTER, PUTATIVE ATP-BINDING COMPONENT.
ID2145P ORF starting with ATG of length 244
ID2146P PROBABLE MANGANESE TRANSPORT PROTEIN MNTH.
ID2147P HYPOTHETICAL PROTEIN YWRB.
ID2148PH IRON-UPTAKE SYSTEM PERMEASE PROTEIN FEUB.
ID2149PH HOMOLOGUE OF FERRIC ANGUIBACTIN TRANSPORT SYSTEM PERMERASE P
ID2150PH YUSV PROTEIN.
ID2151PH YFHA PROTEIN.
ID2152PH IRON-UPTAKE SYSTEM PERMEASE PROTEIN FEUC.
ID2153PH FERRICHROME TRANSPORT SYSTEM PERMEASE PROTEIN FHUG.
ID2154PH FERRICHROME TRANSPORT ATP-BINDING PROTEIN FHUC.
ID2155PH YVRA PROTEIN.
ID2156PH YFMD PROTEIN.
ID2157PH ENTEROCHELIN UPTAKE PERMEASE.
ID2158PH YFME PROTEIN.
ID2159PH PERMEASE PROTEIN OF ABC TRANSPORTER.
ID2160PH FERRICHROME TRANSPORT PERMEASE.
ID2161PH BIRII, ATR, FBID & FBIC GENES (FRAGMENT).
ID2162PH HOMOLOGUE OF IRON DICITRATE TRANSPORT ATP-BINDING PROTEIN FE
ID2163PH HMUV.
ID2164PH FERRICHROME TRANSPORT SYSTEM PERMEASE PROTEIN FHUB.
ID2165PR ASSIMILATORY NITRITE REDUCTASE [NAD(P)H] SMALL SUBUNIT (EC 1
ID2166Q LCHAB PROTEIN.
ID2167Q LICHENYSIN SYNTHETASE A.
ID2168Q LICHENYSIN SYNTHETASE A.
ID2169Q ORF starting with ATG of length 8268
ID2170Q YERP PROTEIN.
ID2171Q ORF starting with ATG of length 7158
ID2172Q YKNV PROTEIN.
ID2173Q 2,3-DIHYDROXYBENZOATE-AMP LIGASE (EC 6.3.2.-) (DIHYDROXYBENZ
ID2174Q TRANSPORT ATP-BINDING PROTEIN CYDC.
ID2175Q ORF starting with ATG of length 3798
ID2176Q UNIDENTIFIED TRANSPORTER-ATP BINDING.
ID2177Q HYPOTHETICAL 65.1 KDA PROTEIN.
ID2178Q REGULATORY PROTEIN (FRAGMENT).
ID2179Q HYPOTHETICAL 48.5 KDA PROTEIN IN ILVA 3'REGION.
ID2180Q HYPOTHETICAL ABC TRANSPORTER ATP-BINDING PROTEIN IN ACDA 5'R
ID2181Q PUTATIVE CYTOCHROME P450 CYPX (EC 1.14.-.-).
ID2182Q CYTOCHROME P450 109 (EC 1.14.-.-) (ORF405).
ID2183Q ATP-BINDING CASSETTE TRANSPORTER A.
ID2184Q NYSH.
ID2185Q "BIOTIN BIOSYNTHESIS; CYTOCHROME P450-LIKE ENZYME (EC 1.14.-."
ID2186Q BH2620 PROTEIN.
ID2187Q LANTIBIOTIC MERSACIDIN TRANSPORTER SYSTEM.
ID2188Q YKNX PROTEIN.
ID2189Q HYPOTHETICAL 76.3 KDA PROTEIN.
ID2190Q PUTATIVE CYTOCHROME P450 YJIB (EC 1.14.-.-).
ID2191Q LANTIBIOTIC MERSACIDIN TRANSPORTER SYSTEM.
ID2192Q HYPOTHETICAL 33.7 KDA PROTEIN.
ID2193Q ORF starting with ATG of length 3798
ID2194Q ORF starting with ATG of length 1950
ID2195Q TRANSPORT ATP-BINDING PROTEIN CYDD.
ID2196Q PUTATIVE CHALCONE SYNTHASE (EC 2.3.1.74) (NARINGENIN-CHALCON
ID2197Q ALPHA-ACETOLACTATE DECARBOXYLASE (EC 4.1.1.5).
ID2198Q ORF starting with ATG of length 1824
ID2199Q S. xylosus DltA protein.
ID2200Q DNA-DAMAGE-INDUCIBLE PROTEIN.
ID2201Q ORF starting with ATG of length 1677
ID2202Q YLPC PROTEIN.
ID2203Q YUEJ PROTEIN.
ID2204Q ORF starting with ATG of length 1470
ID2205Q ISOCHORISMATASE (EC 3.3.2.1) (2,3 DIHYDRO-2,3 DIHYDROXYBENZO
ID2206Q 4'-PHOSPHOPANTETHEINYL TRANSFERASE (EC 2.-.-.-) (SURFACTIN S
ID2207Q HYPOTHETICAL 20.8 KDA PROTEIN IN SERS-DNAZ INTERGENIC REGION
ID2208Q BACITRACIN SYNTHETASE 3 (BA3) (FRAGMENT).
ID2209Q SURFACTIN SYNTHETASE (FRAGMENT).
ID2210Q TRANSPORT ATP-BINDING PROTEIN CYDD.
ID2211Q ABC TRANSPORTER ECSA HOMOLOG.
ID2212Q PUTATIVE ABC TRANSPORTER SUBUNIT EPIF.
ID2213Q 4-OXALOCROTONATE DECARBOXYLASE-LIKE PROTEIN.
ID2214Q HYPOTHETICAL ABC TRANSPORTER ATP-BINDING PROTEIN 2 IN GLPD-C
ID2215Q YHAQ.
ID2216Q ORF starting with ATG of length 927
ID2217Q ORF starting with ATG of length 927
ID2218Q HYPOTHETICAL 50.0 KDA PROTEIN.
ID2219Q ORF starting with ATG of length 885
ID2220Q LCHA-TE PROTEIN.

ID2221Q YHBJ PROTEIN.
ID2222Q 308AA LONG HYPOTHETICAL ATP-BINDING TRANSPORT PROTEIN.
ID2223Q ORF starting with ATG of length 852
ID2224Q ORF starting with ATG of length 885
ID2225Q ORF starting with ATG of length 834
ID2226Q HYPOTHETICAL 76.3 KDA PROTEIN.
ID2227Q ATP BINDING PROTEIN BVIA.
ID2228Q YOJI PROTEIN.
ID2229Q ORF starting with ATG of length 780
ID2230Q ORF starting with ATG of length 759
ID2231 Q ORF starting with ATG of length 690
ID2232Q CYTOCHROME P450 97B3 (EC 1.14.-.-).
ID2233Q ISOCHORISMATASE (EC 3.3.2.1) (2,3 DIHYDRO-2,3 DIHYDROXYBENZO
ID2234Q ORF starting with ATG of length 636
ID2235Q HYPOTHETICAL 34.4 KDA PROTEIN.
ID2236Q SA1655 PROTEIN.
ID2237Q HYPOTHETICAL 14.8 KDA PROTEIN.
ID2238Q ISOCHORISMATASE (EC 3.3.2.1) (2,3 DIHYDRO-2,3 DIHYDROXYBENZO
ID2239Q ORF starting with ATG of length 489
ID2240Q DNA-DAMAGE-INDUCIBLE PROTEIN.
ID2241Q YHBJ PROTEIN.
ID2242Q PUTATIVE CYTOCHROME P450 YJIB (EC 1.14.-.-).
ID2243Q HYPOTHETICAL 30.2 KDA PROTEIN.
ID2244Q ACETYL XYLAN ESTERASE.
ID2245Q ORF starting with ATG of length 354
ID2246Q ORF starting with ATG of length 353
ID2247Q BH2936 PROTEIN.
ID2248Q Synthetic ferulic acid decarboxylase clone pGS97b1.
ID2249Q ORF starting with ATG of length 204
ID2250QR HYPOTHETICAL OXIDOREDUCTASE IN APRE-COMK INTERGENIC REGION (E
ID2251QR YVAG PROTEIN.
ID2252QR HYPOTHETICAL OXIDOREDUCTASE IN RTP-PELB INTERGENIC REGION (E
ID2253QR D-MANNONATE OXIDOREDUCTASE.
ID2254QR H. ghilianii/B. megaterium fusion protein Tridegin/GlcDH.
ID2255QR 3-KETOACYL-ACP REDUCTASE.
ID2256QR 2,3-DIHYDRO-2,3-DIHYDROXYBENZOATE DEHYDROGENASE (EC 1.3.1.28
ID2257QR YUED PROTEIN.
ID2258QR HYPOTHETICAL 28.3 KDA PROTEIN IN AROD-COMER INTERGENIC REGIO
ID2259QR SORBITOL-6-PHOSPHATE DEHYDROGENASE.
ID2260QR ACETOIN(DIACETYL)REDUCTASE.
ID2261 QR AT1G54870/F14C21__16.
ID2262QR YTQB.
ID2263QR YRRT PROTEIN.
ID2264QR UNIDENTFIED DEHYDROGENASE.
ID2265QR GLUCOSE AND RIBITOL DEHYDROGENASE HOMOLOG (FRAGMENT).
ID2266QR B. subtilis hydrolase protein YODH.
ID2267QR YVAG PROTEIN.
ID2268QR YRRM PROTEIN.
ID2269QR PUTATIVE OXIDOREDUCTASE TM0019 (EC 1.-.-.-).
ID2270QR HYPOTHETICAL 31.5 KDA PROTEIN IN KATB 3'REGION.
ID2271 QR Amino acid sequence of a beta-ketoacyl-ACP reductase protein
ID2272QR HYPOTHETICAL OXIDOREDUCTASE F53C11.3 (EC 1.-.-.-).
ID2273QR YVAG PROTEIN.
ID2274QR SHORT-CHAIN ALCOHOL DEHYDROGENASE.
ID2275QR 282AA LONG HYPOTHETICAL DEHYDROGENASE.
ID2276QR HYPOTHETICAL 28.3 KDA PROTEIN IN XPAC-ABRB INTERGENIC REGION
ID2277QR YMFI PROTEIN.
ID2278QR MLL3372 PROTEIN.
ID2279QR ORF starting with ATG of length 765
ID2280QR 3-OXOACYL-[ACYL-CARRIER-PROTEIN] REDUCTASE.
ID2281 QR PUTATIVE OXIDOREDUCTASE H10048 (EC 1.-.-.-).
ID2282QR ORF starting with ATG of length 597
ID2283QR GRA-ORF6 PROTEIN.
ID2284QR ORF starting with ATG of length 534
ID2285QR HYPOTHETICAL 19.0 KDA PROTEIN IN ILVD-THYB INTERGENIC REGION
ID2286QR ORF starting with ATG of length 432
ID2287QR ORF starting with TTG or GTG of length 468
ID2288R PUTATIVE FORMATE DEHYDROGENASE, ALPHA SUBUNIT (EC 1.2.1.2)
ID2289R HYPOTHETICAL 74.3 KDA PROTEIN IN RPLI-COTF INTERGENIC REGION
ID2290R HYPOTHETICAL 79.2 KDA PROTEIN IN PHOH-DGKA INTERGENIC REGION
ID2291R HYPOTHETICAL 61.5 KDA PROTEIN IN ADEC-PDHA INTERGENIC REGION
ID2292R YTSD.
ID2293R YFMR.
ID2294R HYPOTHETICAL 78.8 KDA PROTEIN IN TETB-EXOA INTERGENIC REGION
ID2295R HYPOTHETICAL 60.2 KDA PROTEIN IN CSPB-GLPP INTERGENIC REGION
ID2296R YFMM PROTEIN.
ID2297R FORMATE DEHYDROGENASE ALPHA SUBUNIT HOMOLOG.
ID2298R YURU PROTEIN.
ID2299R PROBABLE GTP-BINDING PROTEIN ENGA.
ID2300R HYPOTHETICAL 70.5 KDA PROTEIN IN IDH 3'REGION.
ID2301R SPOOB-ASSOCIATED GTP-BINDING PROTEIN.
ID2302R YURX PROTEIN.
ID2303R BH0531PROTEIN.
ID2304R HYPOTHETICAL 56.1 KDA PROTEIN IN MFD-DIVIC INTERGENIC REGION
ID2305R ORF11.
ID2306R COME OPERON PROTEIN 3.
ID2307R HYPOTHETICAL HELICASE IN PONA-COTD INTERGENIC REGION.
ID2308R PBSX PHAGE TERMINASE LARGE SUBUNIT.
ID2309R YKPA PROTEIN.
ID2310R HYPOTHETICAL 51.2 KDA PROTEIN IN RECQ-CMK INTERGENIC REGION
ID2311R YKVU PROTEIN.
ID2312R HYPOTHETICAL 48.9 KDA PROTEIN.
ID2313R MMGE PROTEIN.
ID2314R HYPOTHETICAL 40.1 KDA GTP-BINDING PROTEIN IN RPSF-SPOOJ INTE
ID2315R ORF11.
ID2316R HYPOTHETICAL 50.9 KDA PROTEIN IN SPOIIIC-CWLA INTERGENIC REG ID2317R POSSIBLE THIOPHENE AND FURAN OXIDATION PROTEIN.
ID2318R *Bacillus subtilis* inositol dehydrogenase.
ID2319R ORNITHINE ACETYLTRANSFERASE.
ID2320R HYPOTHETICAL 40.9 KDA PROTEIN IN MECB-GLTX INTERGENIC REGION
ID2321R HYPOTHETICAL 43.6 KDA PROTEIN IN GBSA-TLPB INTERGENIC REGION
ID2322R HYPOTHETICAL 50.0 KDA PROTEIN IN SODA-COMGA INTERGENIC REGIO
ID2323R HYPOTHETICAL 40.7 KDA PROTEIN IN MECB-GLTX INTERGENIC REGION
ID2324R HYPOTHETICAL 48.3 KDA PROTEIN IN QCRA-AROE INTERGENIC REGION
ID2325R YTQA.
ID2326R YESM PROTEIN.
ID2327R HYPOTHETICAL SYMPORTER YHCL.
ID2328R HYPOTHETICAL 41.0 KDA PROTEIN IN NUCB-AROD INTERGENIC REGION
ID2329R YMFA PROTEIN.
ID2330R HYPOTHETICAL 42.1 KDA PROTEIN IN MOAD-FRUR INTERGENIC REGION
ID2331R ORF starting with ATG of length 2879
ID2332R HYPOTHETICAL 51.5 KDA PROTEIN IN CITA-SSPB INTERGENIC REGION
ID2333R HYPOTHETICAL 57.4 KDA PROTEIN IN MFD-DIVIC INTERGENIC REGION
ID2334R BH0889 PROTEIN.
ID2335R GTP-BINDING PROTEIN ERA HOMOLOG (BEX PROTEIN).
ID2336R YTRF.
ID2337R AMINOPEPTIDASE.
ID2338R HYPOTHETICAL 51.0 KDA PROTEIN IN PTA 3'REGION.
ID2339R HYPOTHETICAL 37.1 KDA PROTEIN IN FOLK-LYSSINTERGENIC REGION
ID2340R HYPOTHETICAL OXIDOREDUCTASE IN FHUD-OPUBD INTERGENIC REGION.
ID2341R HYPOTHETICAL 33.6 KDA PROTEIN IN TDK-PRFA INTERGENIC REGION.
ID2342R YDFJ PROTEIN.
ID2343R HYPOTHETICAL 37.5 KDA PROTEIN IN DEGA-NPRB INTERGENIC REGION
ID2344R YHAA PROTEIN.
ID2345R YBFQ PROTEIN.
ID2346R YLOQ PROTEIN.
ID2347R PUTATIVE SODIUM-DEPENDENT INNER MEMBRANE TRANSPORT PROTEIN.
ID2348R HOMOLOGUE OF HYPOTHETICAL PROTEIN IN A RAPAMYCIN SYNTHESIS G
ID2349R BH2362 PROTEIN.
ID2350R HYPOTHETICAL 32.9 KDA PROTEIN IN GCVT-SPOIIIAA INTERGENIC RE
ID2351R HYPOTHETICAL 29.5 KDA PROTEIN.
ID2352R YEBB PROTEIN.
ID2353R 2-NITROPROPANE DIOXYGENASE.
ID2354R ORF starting with ATG of length 2250
ID2355R YKOQ.
ID2356R YTQI.
ID2357R HYPOTHETICAL 30.2 KDA PROTEIN IN IDH-DEOR INTERGENIC REGION.
ID2358R YTNP.
ID2359R SIMILAR TO BACILLUS SUBTILIS YXEH AND YCSE PROTEINS AND TO E
ID2360R PUTATIVE MORPHINE DEHYDROGENASE.
ID2361R HYPOTHETICAL 20.0 KDA PROTEIN IN RRNG-FEUC INTERGENIC REGION
ID2362R ORF starting with ATG of length 2055
ID2363R YHAA PROTEIN.
ID2364R HYPOTHETICAL 34.5 KDA PROTEIN IN GLTP-CWLJ INTERGENIC REGION
ID2365R YTIP.
ID2366R YRRL PROTEIN.
ID2367R BH2393 PROTEIN.
ID2368R NUCLEOTIDE BINDING PROTEIN EXPZ.
ID2369R YTFP (YTFP PROTEIN).
ID2370R HYPOTHETICAL 33.9 KDA PROTEIN IN LIPB-SSPK INTERGENIC REGION
ID2371R HYPOTHETICAL 24.7 KDA PROTEIN.
ID2372R YQZB PROTEIN.
ID2373R HOMOLOGUES TO NITRILE HYDRATASE REGION 3'-HYPOTHETICAL PROTE
ID2374R HOMOLOGUE OF HYPOTHETICAL PROTEIN INA RAPAMYCIN SYNTHESIS G
ID2375R YVGN PROTEIN.
ID2376R HYPOTHETICAL 39.3 KDA PROTEIN.
ID2377R HYPOTHETICAL 32.7 KDA PROTEIN IN FEUA-SIGW INTERGENIC REGION
ID2378R HYPOTHETICAL 24.1 KDA PROTEIN YDIH.
ID2379R PUTATIVE TRANSPORTER.
ID2380R PCRB PROTEIN HOMOLOG.
ID2381R YOJE PROTEIN.
ID2382R HYPOTHETICAL 24.7 KDA PROTEIN IN CSPB-GLPP INTERGENIC REGION
ID2383R YUSB PROTEIN.
ID2384R HYPOTHETICAL ZINC PROTEASE YMXG (EC 3.4.99.-) (ORFP).
ID2385R YCCF PROTEIN.
ID2386R YMFH PROTEIN.
ID2387R YTMQ.
ID2388R HEMOLYSIN III HOMOLOG.
ID2389R TUAB PROTEIN.
ID2390R HYPOTHETICAL 31.5 KDA PROTEIN IN GLVBC 3'REGION.
ID2391R YFNB.
ID2392R YFHG PROTEIN.
ID2393R BH1896 PROTEIN.
ID2394R *Bacillus subtilis* yihA family member polypeptide sequence.
ID2395R DNA FOR 25-36 DEGREE REGION CONTAINING THE AMYE-SRFA REGION,
ID2396R YKVM PROTEIN.
ID2397R HPR(SER-P)PHOSPHATASE (WOE PROTEIN).
ID2398R YFLN PROTEIN.
ID2399R YUNE PROTEIN.
ID2400R HYPOTHETICAL OXIDOREDUCTASE IN ANSR-BMRU INTERGENIC REGION (E
ID2401R HYPOTHETICAL 28.9 KDA PROTEIN.
ID2402R HYPOTHETICAL ABC TRANSPORTER ATP-BINDING PROTEIN IN IDH 3'RE
ID2403R ORF starting with ATG of length 1722
ID2404R ABC TRANSPORTER ATP-BINDING PROTEIN HOMOLOGUE.
ID2405R YKVJ PROTEIN.
ID2406R YOAZ.
ID2407R YCZE PROTEIN.
ID2408R HYPOTHETICAL 23.7 KDA PROTEIN IN CCCA-SODA INTERGENIC REGION
ID2409R *Bacillus subtilis* serine protease SP3 (YITV).
ID2410R HYPOTHETICAL 19.0 KDA PROTEIN IN GLPD-CSPB INTERGENIC REGION
ID2411R UNKNOWN (BH2089 PROTEIN).
ID2412R HYPOTHETICAL 35.9 KDA PROTEIN.
ID2413R YRRB PROTEIN.

ID2414R HYPOTHETICAL 37.5 KDA PROTEIN YDHJ.
ID2415R HYPOTHETICAL 30.6 KDA PROTEIN.
ID2416R ORF starting with ATG of length 1584
ID2417R RECOMBINATION PROTEIN U (PENICILLIN-BINDING PROTEIN-RELATED
ID2418R PUTATIVE ACETYLTRANSFERASE.
ID2419R HYPOTHETICAL 27.6 KDA PROTEIN IN BLTR-SPOIIIC INTERGENIC REG
ID2420R PUTATIVE BETA-PHOSPHOGLUCOMUTASE (EC 5.4.2.6) (BETA-PGM).
ID2421R YTSC PROTEIN.
ID2422R HOMOLOGUE OF UNIDENTIFIED PROTEIN OF E. COLI.
ID2423R HYPOTHETICAL 32.9 KDA PROTEIN IN BLTR-SPOIIIC INTERGENIC REG
ID2424R FUNCTION UNKNOWN.
ID2425R BH1010 PROTEIN.
ID2426R HYPOTHETICAL 33.2 KDA PROTEIN.
ID2427R HYPOTHETICAL 19.7 KDA PROTEIN IN CYSS 3'REGION.
ID2428R HYPOTHETICAL 137.4 KDA PROTEIN IN BCSA-DEGR INTERGENIC REGIO
ID2429R YNGD PROTEIN.
ID2430R HYPOTHETICAL 35.8 KDA PROTEIN IN GLNQ-ANSR INTERGENIC REGION
ID2431R YTDI.
ID2432R YTET.
ID2433R HYPOTHETICAL 24.5 KDA PROTEIN IN NARQ-SPOIID INTERGENIC REGI
ID2434R YKUE PROTEIN.
ID2435R HYPOTHETICAL ABC TRANSPORTER ATP-BINDING PROTEIN YDIF.
ID2436R YDCA PROTEIN.
ID2437R BH1564 PROTEIN.
ID2438R HYPOTHETICAL 20.1 KDA PROTEIN IN NUCB-AROD INTERGENIC REGION
ID2439R YTET.
ID2440R YTOA.
ID2441R HYPOTHETICAL 27.9 KDA PROTEIN.
ID2442R ORF starting with ATG of length 1419
ID2443R HYPOTHETICAL 41.6 KDA PROTEIN IN FMT-SPOVM INTERGENIC REGION
ID2444R ORF starting with ATG of length 1413
ID2445R GENERAL STRESS PROTEIN 18 (GSP18).
ID2446R CINA-LIKE PROTEIN.
ID2447R HYPOTHETICAL 49.5 KDA PROTEIN IN TGL-PGI INTERGENIC REGION.
ID2448R B. subtilis hydrolase protein YUII.
ID2449R SA0421PROTEIN.
ID2450R YLOV PROTEIN.
ID2451R YTNM.
ID2452R HYPOTHETICAL 40.6 KDA PROTEIN IN CITZ-PYKA INTERGENIC REGION
ID2453R MLL7248 PROTEIN.
ID2454R BH3078 PROTEIN.
ID2455R YTPR.
ID2456R YKUL PROTEIN.
ID2457R ACETOIN UTILIZATION ACUB PROTEIN.
ID2458R MALTOSE TRANSACETYLASE (MALTOSE O-ACETYLTRANSFERASE) (EC 2.3
ID2459R JAG PROTEIN (SPOIIIJ ASSOCIATED PROTEIN).
ID2460R HYPOTHETICAL 22.0 KDA PROTEIN IN RECQ-CMK INTERGENIC REGION.
ID2461R HYPOTHETICAL 41.6 KDA PROTEIN IN FMT-SPOVM INTERGENIC REGION
ID2462R BH1956 PROTEIN.
ID2463R BH0846 PROTEIN.
ID2464R COMF OPERON PROTEIN 3.
ID2465R HYPOTHETICAL 56.4 KDA PROTEIN IN SODA-COMGA INTERGENIC REGIO
ID2466R LIPOPOLYSACCHARIDE BIOSYNTHESIS PROTEIN BPLA.
ID2467R YUIG PROTEIN.
ID2468R YKNY PROTEIN.
ID2469R BH3002 PROTEIN.
ID2470R HYPOTHETICAL 23.2 KDA PROTEIN.
ID2471R HYPOTHETICAL 22.5 KDA PROTEIN.
ID2472R ORF starting with ATG of length 1233
ID2473R YFHB PROTEIN.
ID2474R BH2921PROTEIN.
ID2475R UNKNOWN (BH2089 PROTEIN).
ID2476R HYPOTHETICAL 41.0 KDA PROTEIN.
ID2477R B. subtilis hydrolase protein YCGS.
ID2478R SPORE MATURATION PROTEIN A.
ID2479R YOLF.
ID2480R PUTATIVE_PROBABLE ESTERASE.
ID2481R HYPOTHETICAL 39.6 KDA PROTEIN IN ALAS-GLNQ INTERGENIC REGION
ID2482R HYPOTHETICAL 34.9 KDA PROTEIN IN GLPD-CSPB INTERGENIC REGION
ID2483R Human secreted protein sequence encoded by gene 4 SEQ ID NO:
ID2484R GALACTOSYLTRANSFERASE-RELATED PROTEIN.
ID2485R HYPOTHETICAL 18.8 KDA PROTEIN IN ECSC-PBPF INTERGENIC REGION
ID2486R HYPOTHETICAL 24.0 KDA PROTEIN IN NARQ-SPOIID INTERGENIC REGI
ID2487R ORF starting with ATG of length 1146
ID2488R HYPOTHETICAL 41.0 KDA PROTEIN.
ID2489R ORF starting with ATG of length 1134
ID2490R HYPOTHETICAL ABC TRANSPORTER ATP-BINDING PROTEIN YDIF.
ID2491R YDCJ PROTEIN.
ID2492R HYPOTHETICAL 17.4 KDA PROTEIN.
ID2493R YJBI PROTEIN.
ID2494R HYPOTHETICAL 21.1 KDA PROTEIN.
ID2495R HYPOTHETICAL.
ID2496R HYPOTHETICAL 137.4 KDA PROTEIN IN BCSA-DEGR INTERGENIC REGIO
ID2497R COENZYME PQQ SYNTHESIS PROTEIN (PQQE).
ID2498R HYPOTHETICAL 28.6 KDA PROTEIN IN RECQ-CMK INTERGENIC REGION
ID2499R ORF starting with ATG of length 1056
ID2500R HYPOTHETICAL 22.8 KDA PROTEIN.
ID2501R HYPOTHETICAL 19.5 KDA PROTEIN.
ID2502R ORF starting with ATG of length 1053
ID2503R HYPOTHETICAL 14.9 KDA PROTEIN IN CSPB-GLPP INTERGENIC REGION
ID2504R ORF starting with ATG of length 1044
ID2505R BH2278 PROTEIN.
ID2506R HYPOTHETICAL 49.5 KDA PROTEIN IN TGL-PGI INTERGENIC REGION.
ID2507R ORF starting with ATG of length 1020
ID2508R PHOSPHOTRIESTERASE HOMOLOGY PROTEIN.
ID2509R ACYLTRANSFERASE, PUTATIVE.
ID2510R INTRACELLULAR PROTEINASE.
ID2511R ABC TRANSPORTER (ATP-BINDING PROTEIN).
ID2512R YLOV PROTEIN.

ID2513R HYPOTHETICAL ABC TRANSPORTER ATP-BINDING PROTEIN YDIF.
ID2514R VEGETATIVE PROTEIN 296 (VEG296).
ID2515R BH2279 PROTEIN.
ID2516R HYPOTHETICAL 49.0 KDA PROTEIN IN BLTD-TRKA INTERGENIC REGION
ID2517R HYPOTHETICAL 23.1 KDA PROTEIN IN BSAA-ILVD INTERGENIC REGION
ID2518R SA0084 PROTEIN.
ID2519R HYPOTHETICAL 11.3 KDA PROTEIN.
ID2520R HYPOTHETICAL 20.5 KDA PROTEIN.
ID2521R BH1964 PROTEIN.
ID2522R HYPOTHETICAL 21.6 KDA PROTEIN IN ILVA 3'REGION.
ID2523R HYPOTHETICAL PROTEIN NMB0739.
ID2524R HOMOLOGUES TO NITRILE HYDRATASE REGION 3'-HYPOTHETICAL PROTE
ID2525R BH2398 PROTEIN.
ID2526R LYASE (OXO-ACID)
ID2527R PROBABLE MEMBRANE SPANNING PROTEIN.
ID2528R HOMOLOGUE OF HYPOTHETICAL PROTEIN IN A RAPAMYCIN SYNTHESIS G
ID2529R ORF starting with ATG of length 879
ID2530R MDAB PROTEIN HOMOLOG.
ID2531R HYPOTHETICAL 27.7 KDA PROTEIN.
ID2532R HOMOLOGUE OF UNIDENTIFIED PROTEIN OF *E. COLI*.
ID2533R YO BT.
ID2534R HYPOTHETICAL 36.5 KDA PROTEIN IN GBSA-TLPB INTERGENIC REGION
ID2535R HYPOTHETICAL 19.2 KDA PROTEIN IN RPH-ILVB INTERGENIC REGION.
ID2536R BH1151PROTEIN.
ID2537R CHAPERONIN INVOLVED IN PROTEIN SECRETION.
ID2538R YTDI.
ID2539R FORMATE HYDROGENASE.
ID2540R HYPOTHETICAL 30.7 KDA PROTEIN.
ID2541R LACTAM UTILIZATION PROTEIN.
ID2542R ORF starting with ATG of length 783
ID2543R ORF starting with ATG of length 774
ID2544R ABC TRANSPORTER, ATP BINDING PROTEIN.
ID2545R YTGP.
ID2546R *B. subtilis* nitroreductase Bs YrwO.
ID2547R HYPOTHETICAL 13.0 KDA PROTEIN IN GLNQ-ANSR INTERGENIC REGION
ID2548R YDFJ PROTEIN.
ID2549R ORF starting with ATG of length 756
ID2550R YDFE PROTEIN.
ID2551R BH0392 PROTEIN.
ID2552R HYPOTHETICAL 32.6 KDA PROTEIN.
ID2553R SA2112 PROTEIN.
ID2554R HYPOTHETICAL 28.6 KDA PROTEIN IN RECQ-CMK INTERGENIC REGION
ID2555R DLTE PROTEIN.
ID2556R INTRACELLULAR PROTEINASE (EC 3.2.).
ID2557R *Bacillus subtilis* metalloprotease YhaA.
ID2558R HYPOTHETICAL 39.6 KDA PROTEIN IN ALAS-GLNQ INTERGENIC REGION
ID2559R BH2605 PROTEIN.
ID2560R ORF starting with ATG of length 687
ID2561R YBBA PROTEIN.
ID2562R HYPOTHETICAL 13.6 KDA PROTEIN.
ID2563R YDDR PROTEIN.
ID2564R YTKL.
ID2565R ORF starting with ATG of length 648
ID2566R BH2138 PROTEIN.
ID2567R CG1349 PROTEIN.
ID2568R MLL5156 PROTEIN.
ID2569R ORF starting with ATG of length 609
ID2570R ORF starting with ATG of length 735
ID2571R COMPETENCE-DAMAGE INDUCIBLE PROTEIN.
ID2572R YFHB PROTEIN.
ID2573R YVAK PROTEIN.
ID2574R YKVM PROTEIN.
ID2575R HYPOTHETICAL 78.8 KDA PROTEIN IN TETB-EXOA INTERGENIC REGION
ID2576R HYPOTHETICAL 9.1 KDA PROTEIN IN TETB-EXOA INTERGENIC REGION.
ID2577R ORF starting with ATG of length 546
ID2578R YTNM.
ID2579R HYPOTHETICAL HELICASE IN PONA-COTD INTERGENIC REGION.
ID2580R FORMATE HYDROGENASE.
ID2581R HYPOTHETICAL 7.1 KDA PROTEIN.
ID2582R NAD(P)H OXIDOREDUCTASE.
ID2583R ORF starting with ATG of length 2879
ID2584R BH2906 PROTEIN.
ID2585R ORF starting with ATG of length 480
ID2586R ORF starting with ATG of length 447
ID2587R BH2982 PROTEIN.
ID2588R HYPOTHETICAL 23.6 KDA PROTEIN.
ID2589R HYPOTHETICAL PROTEIN VC2101.
ID2590R YFMR.
ID2591R HYPOTHETICAL 27.6 KDA PROTEIN.
ID2592R ORF starting with ATG of length 408
ID2593R ORF starting with ATG of length 409
ID2594R Amino acid sequence of *N. meningitidis* protein ORF77.
ID2595R CMP-BINDING PROTEIN.
ID2596R BH3997 PROTEIN.
ID2597R PUTATIVE MEMBRANE PROTEIN YDGH.
ID2598R COENZYME PQQ SYNTHESIS PROTEIN (PQQE).
ID2599R BH2605 PROTEIN.
ID2600R ORF starting with TTG or GTG of length 726
ID2601R ORF starting with ATG of length 354
ID2602R PUTATIVE BIFUNCTIONAL ENZYME WXCM.
ID2603R ORF starting with ATG of length 348
ID2604R GENERAL STRESS PROTEIN 14 (GSP14) (EC 1.6.99.-).
ID2605R ORF starting with ATG of length 324
ID2606R ORF starting with ATG of length 321
ID2607R HYPOTHETICAL 33.0 KDA PROTEIN IN XPAC-ABRB INTERGENIC REGION
ID2608R PUTATIVE METHIONYL-TRNA SYNTHETASE.
ID2609R F44E7.4 PROTEIN.
ID2610R PUTATIVE TERMINASE LARGE SUBUNIT.
ID2611R ORF starting with ATG of length 270
ID2612R HYPOTHETICAL 30.8 KDA PROTEIN.
ID2613R BH0590 PROTEIN.
ID2614R YTPR.
ID2615R ORF starting with ATG of length 225
ID2616R HYPOTHETICAL 32.8 KDA PROTEIN IN B103-HXT17 INTERGENIC REGIO
ID2617R ORF starting with ATG of length 210
ID2618R BIOTIN SULFOXIDE REDUCTASE.
ID2619R ORF starting with ATG of length 870
ID2620R HYPOTHETICAL 79.2 KDA PROTEIN IN PHOH-DGKA INTERGENIC REGION ID2621R HYPOTHETICAL 74.3 KDA PROTEIN IN RPLI-COTF INTERGENIC REGION
ID2622S ATP-DEPENDENT NUCLEASE SUBUNIT B.
ID2623S YVNB.
ID2624S Enzyme exhibiting activity on arabinan and galactan. Possibl
ID2625S *Bacillus licheniformis* Pectin lyase III.
ID2626S YFHO PROTEIN.
ID2627S YESX PROTEIN.
ID2628S YETA PROTEIN.
ID2629S HYPOTHETICAL 171.0 KDA PROTEIN IN SPOIIIC-CWLA INTERGENIC RE
ID2630S YDAL PROTEIN.
ID2631S YDAN PROTEIN.
ID2632S ORF starting with ATG of length 4557
ID2633S STAGE V SPORULATION PROTEIN R.
ID2634S YFIX.
ID2635S BETA-N-ACETYLGLUCOSAMINIDASE PRECURSOR (EC 3.2.1.-).
ID2636S BH1550 PROTEIN.
ID2637S Patent NN No. 5481 Arabinogalactan endo-1,4-beta-galactosidas
ID2638S *Bacillus licheniformis* endo-beta-1,4-glucanase.
ID2639S HYPOTHETICAL 46.0 KDA PROTEIN (TRANSPOSASE OF TN10).
ID2640S Phytase gene from *Bacillus licheniformis*. Homologous to unkn
ID2641S STAGE IV SPORULATION PROTEIN A.
ID2642S ORF starting with ATG of length 3927
ID2643S SEPTATION RING FORMATION REGULATOR.
ID2644S LEVANSUCRASE PRECURSOR (EC 2.4.1.10) (BETA-D-FRUCTOFURANOSYL
ID2645S PHAGE-LIKE ELEMENT PBSX PROTEIN XKDE.
ID2646S ORF starting with ATG of length 3519
ID2647S YKOR.
ID2648S DNA FOR 25-36 DEGREE REGION CONTAINING THE AMYE-SRFA REGION,
ID2649S STAGE V SPORULATION PROTEIN AF.
ID2650S A *Bacillus* pectate lyase and JP170 alpha-amylase fusion prot
ID2651S HYPOTHETICAL 58.0 KDA PROTEIN IN COTC-LEXA INTERGENIC REGION
ID2652S HYPOTHETICAL ATP:GUANIDO PHOSPHOTRANSFERASE YACI (EC 2.7.3.—
ID2653S YTPB.
ID2654S ORF starting with ATG of length 3222
ID2655S Family 1Pectate lyase.29% identical to BioPrep (SP958).50%
ID2656S YBBR PROTEIN.
ID2657S HYPOTHETICAL 48.8 KDA PROTEIN.
ID2658S HYPOTHETICAL 46.0 KDA PROTEIN IN FEUA-SIGW INTERGENIC REGION
ID2659S YESS PROTEIN.
ID2660S ORF starting with ATG of length 3057
ID2661S YDJI PROTEIN.
ID2662S HYPOTHETICAL 35.6 KDA PROTEIN IN RPSU-PHOH INTEREGENIC REGIO
ID2663S 2-KETO-3-DEOXYGLUCONATE PERMEASE (KDG PERMEASE).
ID2664S HYPOTHETICAL 42.6 KDA PROTEIN.
ID2665S C4-DICARBOXYLATE TRANSPORT SYSTEM (PERMEASE LARGE PROTEIN).
ID2666S HYPOTHETICAL 36.3 KDA PROTEIN.
ID2667S STAGE III SPORULATION PROTEIN AE.
ID2668S Xyloglucanase
ID2669S ORF starting with ATG of length 3519
ID2670S YESR PROTEIN.
ID2671S HYPOTHETICAL 48.6 KDA PROTEIN IN SERS-DNAZ INTERGENIC REGION
ID2672S HYPOTHETICAL 47.4 KDA PROTEIN.
ID2673S PROBABLE HTH_LYSR_FAMILY TRANSCRIPTIONAL REGULATOR.
ID2674S YFHP PROTEIN.
ID2675S YDJG PROTEIN.
ID2676S YNDJ PROTEIN.
ID2677S HYPOTHETICAL 45.3 KDA PROTEIN IN PRKA-CSPB INTERGENIC REGION
ID2678S YDAJ PROTEIN.
ID2679S PHAGE-LIKE ELEMENT PBSX PROTEIN XKDG.
ID2680S YLBC PROTEIN.
ID2681S SPORE GERMINATION PROTEIN KA.
ID2682S YTER.
ID2683S BH2622 PROTEIN.
ID2684S YKRT PROTEIN.
ID2685S DNA, COMPLETE SEQUENCE.
ID2686S HYPOTHETICAL 43.8 KDA PROTEIN IN XPAC-ABRB INTERGENIC REGION
ID2687S HYPOTHETICAL 37.7 KDA PROTEIN IN RPSF-SPOOJ INTERGENIC REGIO
ID2688S HYPOTHETICAL 34.7 KDA PROTEIN IN CRH-TRXB INTERGENIC REGION.
ID2689S PTS SYSTEM, FRUCTOSE-SPECIFIC IID COMPONENT (EIID-FRU) (FRUC
ID2690S PROTEIN ECSB.
ID2691S LANTIBIOTIC MERSACIDIN MODIFYING ENZYME.
ID2692S HYPOTHETICAL 45.0 KDA PROTEIN IN FDRA-ARCC INTERGENIC REGION
ID2693S HYPOTHETICAL 37.0 KDA PROTEIN IN SPOIIIC-CWLA INTERGENIC REG
ID2694S YWSC PROTEIN.
ID2695S HYPOTHETICAL PROTEIN VC1332.
ID2696S YCEH.
ID2697S YLQG PROTEIN.
ID2698S IOLB PROTEIN.
ID2699S HYPOTHETICAL 43.0 KDA PROTEIN (YVFB PROTEIN).
ID2700S YNDE PROTEIN (PUTATIVE SPORE GERMINATION PROTEIN).
ID2701S HYPOTHETICAL 30.3 KDA PROTEIN IN GLYS-DNAG/DNAE INTERGENIC R
ID2702S HYPOTHETICAL 38.5 KDA PROTEIN IN PONA-COTD INTERGENIC REGION
ID2703S HYPOTHETICAL 41.5 KDA PROTEIN.
ID2704S YJBA PROTEIN.
ID2705S PROTEIN DLTD PRECURSOR.
ID2706S PTS SYSTEM, FRUCTOSE-SPECIFIC IIC COMPONENT (EIIC-FRU) (FRUC
ID2707S HYPOTHETICAL 35.0 KDA PROTEIN IN SPOIIIC-CWLA INTERGENIC REG
ID2708S GALACTOSE-1-PHOSPHATE URIDYLTRANSFERASE.
ID2709S HYPOTHETICAL 34.4 KDA PROTEIN IN RRND 5'REGION.
ID2710S YBCD PROTEIN.
ID2711S HYPOTHETICAL 51.4 KDA PROTEIN.
ID2712S HYPOTHETICAL 32.5 KDA PROTEIN IN CCCA-SODA INTERGENIC REGION
ID2713S YVLB.
ID2714S YLAA PROTEIN.
ID2715S HYPOTHETICAL 41.9 KDA PROTEIN.

ID2716S EXO-POLY-ALPHA-D-GALACTURONOSI-DASE, PUTATIVE.
ID2717S SPORULATION SIGMA-E FACTOR PROCESSING PEPTIDASE (EC 3.4.23.—
ID2718S YUBB PROTEIN.
ID2719S SPORE GERMINATION PROTEIN A2.
ID2720S PUTATIVE SUGAR ISOMERASE.
ID2721S TUAE PROTEIN.
ID2722S HYPOTHETICAL 40.6 KDA PROTEIN.
ID2723S LEVANSUCRASE AND SUCRASE SYNTHESIS OPERON ANTITERMINATOR.
ID2724S DIPICOLINATE SYNTHASE, A CHAIN.
ID2725S YKOV PROTEIN.
ID2726S HYPOTHETICAL 36.0 KDA PROTEIN IN GCVT-SPOIIIAA INTERGENIC RE
ID2727S YOAT.
ID2728S HYPOTHETICAL 42.9 KDA PROTEIN.
ID2729S BH2618 PROTEIN.
ID2730S SACPA OPERON ANTITERMINATOR.
ID2731S YFLP PROTEIN.
ID2732S SPORE GERMINATION PROTEIN KB.
ID2733S YFNK.
ID2734S YDCC PROTEIN.
ID2735S YJCL PROTEIN.
ID2736S YVJA.
ID2737S SPORE GERMINATION PROTEIN A1.
ID2738S HYPOTHETICAL 32.2 KDA PROTEIN IN BMRU-ANSR INTERGENIC REGION
ID2739S PUTATIVE SPORE GERMINATION PROTEIN.
ID2740S HYPOTHETICAL 29.6 KDA PROTEIN IN RIBT-DACB INTERGENIC REGION
ID2741S YFKD PROTEIN.
ID2742S HYPOTHETICAL 45.7 KDA PROTEIN IN RPSU-PHOH INTEREGENIC REGIO
ID2743S DEGV PROTEIN.
ID2744S PHAGE-LIKE ELEMENT PBSX PROTEIN XKDK.
ID2745S YVOD.
ID2746S YDAH PROTEIN.
ID2747S HYPOTHETICAL 48.2 KDA PROTEIN IN SODA-COMGA INTERGENIC REGIO
ID2748S YTAP.
ID2749S RESPONSE REGULATOR ASPARTATE PHOSPHATASE.
ID2750S HYPOTHETICAL 37.3 KDA PROTEIN.
ID2751S YJBH PROTEIN.
ID2752S LANTIBIOTIC MERSACIDIN MODIFYING ENZYME.
ID2753S PTS SYSTEM, GLUCITOL/SORBITOL-SPECIFIC IIBC COMPONENT (EIIBC
ID2754S ORF starting with ATG of length 2089
ID2755S YOAJ.
ID2756S YITL PROTEIN.
ID2757S EXOGLUCANASE B PRECURSOR (EC 3.2.1.91) (EXOCELLOBIOHYDROLASE
ID2758S HYPOTHETICAL 28.1 KDA PROTEIN IN SIPU-KIPI INTERGENIC REGION
ID2759S YDEG PROTEIN.
ID2760S YERB PROTEIN.
ID2761S ORF25.
ID2762S HYPOTHETICAL 51.5 KDA PROTEIN.
ID2763S YCEG.
ID2764S HYPOTHETICAL 38.0 KDA PROTEIN IN GIRA-GUAB INTERGENIC REGION
ID2765S ORF starting with ATG of length 1974
ID2766S SAPB PROTEIN.
ID2767S PUTATIVE SIGMA-B REGULATOR.
ID2768S YQFO PROTEIN.
ID2769S ORF40.
ID2770S YLNE PROTEIN.
ID2771S HYPOTHETICAL 31.2 KDA PROTEIN IN XPAC-ABRB INTERGENIC REGION
ID2772S ORF22.
ID2773S ORF starting with ATG of length 1935
ID2774S Amino acid sequence of a mature TasA antibiotic protein.
ID2775S PBSX PHAGE TERMINASE SMALL SUBUNIT.
ID2776S BH3947 PROTEIN.
ID2777S HYPOTHETICAL 38.6 KDA PROTEIN IN CYSG-TRPS INTERGENIC REGION
ID2778S YVBY PROTEIN.
ID2779S ORF starting with ATG of length 1896
ID2780S ORF starting with ATG of length 1860
ID2781S YFLM PROTEIN.
ID2782S ORF starting with ATG of length 1854
ID2783S YBCD PROTEIN.
ID2784S *Bacillus licheniformis* endo-beta-1,4-glucanase.
ID2785S YUTH PROTEIN.
ID2786S DNA FOR 25-36 DEGREE REGION CONTAINING THE AMYE-SRFA REGION,
ID2787S HYPOTHETICAL 33.3 KDA PROTEIN IN DNAI-THRS INTERGENIC REGION
ID2788S INTRACELLULAR ALKALINE PROTEASE.
ID2789S SPAE.
ID2790S YOJO PROTEIN.
ID2791S HYPOTHETICAL 22.2 KDA PROTEIN IN RECQ-CMK INTERGENIC REGION.
ID2792S YUNF PROTEIN.
ID2793S ACETOIN UTILIZATION PROTEIN ACUA (EC 2.3.1.-).
ID2794S SPORE GERMINATION PROTEIN A3 PRECURSOR.
ID2795S HYPOTHETICAL 47.7 KDA PROTEIN IN METS-KSGA INTERGENIC REGION
ID2796S YLBM PROTEIN.
ID2797S HYPOTHETICAL 21.3 KDA PROTEIN.
ID2798S HYPOTHETICAL 25.4 KDA PROTEIN IN DPPE-HMP INTERGENIC REGION.
ID2799S HYPOTHETICAL 28.7 KDA PROTEIN IN GLXK-ALLC INTERGENIC REGION
ID2800S BH226S PROTEIN.
ID2801S ORF starting with ATG of length 1782
ID2802S SPOIISA PROTEIN.
ID2803S NECROSIS AND ETHYLENE INDUCING PROTEIN.
ID2804S YLOP PROTEIN.
ID2805S YLOC PROTEIN.
ID2806S HYPOTHETICAL 40.7 KDA PROTEIN IN FER-RECQ INTERGENIC REGION.
ID2807S HYPOTHETICAL 23.8 KDA PROTEIN.
ID2808S HYPOTHETICAL 25.7 KDA PROTEIN IN BCSA-DEGR INTERGENIC REGION
ID2809S YDEI (BH2088 PROTEIN).
ID2810S ORF38.
ID2811S YJBC PROTEIN.
ID2812S YITD PROTEIN.
ID2813S ORF starting with ATG of length 1725
ID2814S INNER SPORE COAT PROTEIN H.
ID2815S PHAGE-LIKE ELEMENT PBSX PROTEIN XKDF.
ID2816S ORF13.
ID2817S BH1298 PROTEIN.
ID2818S PROTEIN ECSC.
ID2819S YBDO PROTEIN.

ID2820S PROBABLE PROTEIN ASP-PHOSPHATASE.
ID2821S N-ACETYLMURAMOYL-L-ALANINE AMIDASE CWLL PRECURSOR (EC 3.5.1.
ID2822S YDJN PROTEIN.
ID2823S YJBM PROTEIN.
ID2824S HYPOTHETICAL 62.6 KDA PROTEIN IN RPMF-FTSL INTERGENIC REGION
ID2825S YOJO PROTEIN.
ID2826S *Bacillus licheniformis* Pectate lyase I.
ID2827S HYPOTHETICAL 27.7 KDA PROTEIN IN GPSA-SPOIVA INTERGENIC REGI
ID2828S YKR1PROTEIN.
ID2829S STREPTOGRAMIN B LACTONASE.
ID2830S YDBA PROTEIN.
ID2831S YVQF PROTEIN.
ID2832S BH2292 PROTEIN.
ID2833S YKRX PROTEIN.
ID2834S HYPOTHETICAL 19.5 KDA PROTEIN.
ID2835S HYPOTHETICAL 23.3 KDA PROTEIN.
ID2836S HYPOTHETICAL 51.0 KDA PROTEIN IN TRXB-HISI INTERGENIC REGION
ID2837S TRANSCRIPTION ANTITERMINATOR LICT.
ID2838S SIMILAR TO BACILLUS SUBTILIS YXID PROTEIN.
ID2839S HYPOTHETICAL 27.6 KDA PROTEIN IN FNR-NARG INTERGENIC REGION.
ID2840S STAGE III SPORULATION PROTEIN AA.
ID2841S YJAZ PROTEIN.
ID2842S *Bacillus* sp. *transglutaminase*.
ID2843S BH0974 PROTEIN.
ID2844S HYPOTHETICAL 33.3 KDA PROTEIN IN KSGA-VEG INTERGENIC REGION.
ID2845S HYPOTHETICAL 23.4 KDA PROTEIN IN NRDF-CWLC INTERGENIC REGION
ID2846S YVQJ PROTEIN.
ID2847S HYPOTHETICAL 24.8 KDA PROTEIN IN DAPB-PAPS INTERGENIC REGION
ID2848S KINB SIGNALING PATHWAY ACTIVATION PROTEIN.
ID2849S STAGE III SPORULATION PROTEIN AG.
ID2850S YESU PROTEIN.
ID2851S HYPOTHETICAL 22.5 KDA PROTEIN IN RPSF-SPOOJ INTERGENIC REGIO
ID2852S YJAU PROTEIN.
ID2853S YUIC PROTEIN.
ID2854S YDFS PROTEIN.
ID2855S *S. pneumoniae* derived protein #146.
ID2856S ORF27.
ID2857S YVBJ PROTEIN.
ID2858S HYPOTHETICAL 23.3 KDA PROTEIN.
ID2859S YCDA.
ID2860S YVGT PROTEIN.
ID2861S BH3996 PROTEIN.
ID2862S YOBG.
ID2863S YTRC.
ID2864S MINOR SPIKE PROTEIN (H PROTEIN) (PILOT PROTEIN).
ID2865S YTEU.
ID2866S HYPOTHETICAL 21.3 KDA PROTEIN IN QCRC-DAPB INTERGENIC REGION
ID2867S RAP60.
ID2868S PHAGE-LIKE ELEMENT PBSX PROTEIN XKDO.
ID2869S YLXX PROTEIN.
ID2870S ORF starting with ATG of length 1491
ID2871S YKWB PROTEIN.
ID2872S PUTATIVE TRANSCRIPTION REGULATOR.
ID2873S YRVE PROTEIN.
ID2874S SIMILAR TO STAPHYLOCOCCUS AUREUS CAPC PROTEIN.
ID2875S HYPOTHETICAL 30.1 KDA PROTEIN.
ID2876S YUAD PROTEIN.
ID2877S HYPOTHETICAL 21.0 KDA PROTEIN IN LYSS-MECB INTERGENIC REGION
ID2878S ORF starting with ATG of length 1458
ID2879S YTLR.
ID2880S HYPOTHETICAL 26.5 KDA PROTEIN IN RAPH-COTJA INTERGENIC REGIO
ID2881S YWMB PROTEIN.
ID2882S YRRS PROTEIN.
ID2883S ORF starting with ATG of length 1443
ID2884S PROTEIN BMRU.
ID2885S ORF starting with ATG of length 1438
ID2886S YDAE PROTEIN.
ID2887S SPORE GERMINATION PROTEIN GERD PRECURSOR.
ID2888S ORF starting with ATG of length 1434
ID2889S PHAGE-LIKE ELEMENT PBSX PROTEIN XKDM.
ID2890S SPORE GERMINATION PROTEIN A2.
ID2891S ORF starting with ATG of length 1431
ID2892S HYPOTHETICAL 19.4 KDA PROTEIN IN SPOIIR-GLYC INTERGENIC REGI
ID2893S HYPOTHETICAL 21.9 KDA PROTEIN IN XYND-PPSE INTERGENIC REGION
ID2894S HYPOTHETICAL 30.8 KDA PROTEIN IN SINI-GCVT INTERGENIC REGION
ID2895S YNDL PROTEIN.
ID2896S HYPOTHETICAL 19.7 KDA PROTEIN.
ID2897S HYPOTHETICAL 34.5 KDA PROTEIN IN RPLI-COTF INTERGENIC REGION
ID2898S SPORE PROTEASE (EC 3.4.99.-).
ID2899S Family 1Pectate lyase.29% identical to BioPrep (SP958).50%
ID2900S STAGE II SPORULATION PROTEIN P.
ID2901S YFLK PROTEIN.
ID2902S HYPOTHETICAL 16.2 KDA PROTEIN IN BMRU-ANSR INTERGENIC REGION
ID2903S GERMINATION PROTEIN GERM.
ID2904S ORF starting with ATG of length 1392
ID2905S YJBF PROTEIN.
ID2906S HYPOTHETICAL 19.7 KDA PROTEIN IN SPOIIR-GLYC INTERGENIC REGI
ID2907S PUTATIVE TRANSCRIPTIONAL REGULATOR (YVHJ).
ID2908S YYCI PROTEIN.
ID2909S ORF starting with ATG of length 1379
ID2910S YTOQ.
ID2911S ORF starting with ATG of length 1374
ID2912S YTR1.
ID2913S HYPOTHETICAL 17.1 KDA PROTEIN IN SPOIIIC-CWLA INTERGENIC REG
ID2914S YITE PROTEIN.
ID2915S AMINOGLYCOSIDE ADENYLTRANSFERASE.
ID2916S COMPETENCE TRANSCRIPTION FACTOR (CTF) (COMPETENCE PROTEIN K)
ID2917S HYPOTHETICAL 27.3 KDA PROTEIN IN TYRZ-SACY INTERGENIC REGION
ID2918S STAGE VI SPORULATION PROTEIN D.
ID2919S HYPOTHETICAL 16.6 KDA PROTEIN IN RPMF-FTSL INTERGENIC REGION
ID2920S YUID PROTEIN.

ID2921S HYPOTHETICAL 24.8 KDA PROTEIN IN CSPB-GLPP INTERGENIC REGION
ID2922S YKUB PROTEIN.
ID2923S YKOX PROTEIN.
ID2924S PEROXIDASE.
ID2925S SIMILAR TO BACILLUS ANTHRACIS CAPC PROTEIN.
ID2926S YKNT PROTEIN (CSE15 PROTEIN) (CSE15).
ID2927S ORF starting with ATG of length 1344
ID2928S BH2938 PROTEIN.
ID2929S HYPOTHETICAL 17.8 KDA PROTEIN IN BLTR-SPOIIIC INTERGENIC REG
ID2930S ORF starting with ATG of length 1332
ID2931S TRANSCRIPTIONAL REGULATOR CTSR.
ID2932S HYPOTHETICAL 17.6 KDA PROTEIN IN NUSA 5'REGION (P15A) (ORF1)
ID2933S ORF starting with ATG of length 1323
ID2934S YOAS PROTEIN.
ID2935S YISF PROTEIN.
ID2936S STAGE II SPORULATION PROTEIN B.
ID2937S YTWI.
ID2938S HYPOTHETICAL 37.0 KDA PROTEIN IN SPOIIIC-CWLA INTERGENIC REG
ID2939S YETF PROTEIN.
ID2940S SPAG.
ID2941S HYPOTHETICAL 64.3 KDA PROTEIN IN HUTP-BGLP INTERGENIC REGION
ID2942S YDJH PROTEIN.
ID2943S YODP.
ID2944S YKOP.
ID2945S HYPOTHETICAL 26.7 KDA PROTEIN IN CSBX-COXA INTERGENIC REGION
ID2946S YOCC.
ID2947S PUTATIVE_SOME HOMOLOGY WITH H11034.
ID2948S HYPOTHETICAL TRANSCRIPTIONAL REGULATOR IN GSPA-TYRZ INTERGEN
ID2949S HYPOTHETICAL 29.1 KDA PROTEIN.
ID2950S HYPOTHETICAL 23.0 KDA PROTEIN IN CMK-GPSA INTERGENIC REGION.
ID2951S SPORE PROTEASE (EC 3.4.99.-).
ID2952S ORF starting with ATG of length 1257
ID2953S CCDC PROTEIN.
ID2954S HYPOTHETICAL 18.4 KDA PROTEIN.
ID2955S HYPOTHETICAL 25.1 KDA PROTEIN IN MFD-DIVIC INTERGENIC REGION
ID2956S SPORULATION INITIATION PHOSPHOTRANSFERASE B (EC 2.7.-.-) (ST
ID2957S Bacillus subtilis prenyl diphosphate synthetase subunit.
ID2958S DNA FOR 25-36 DEGREE REGION CONTAINING THE AMYE-SRFA REGION,
ID2959S HYPOTHETICAL 24.7 KDA PROTEIN IN RECQ-CMK INTERGENIC REGION.
ID2960S YMCA PROTEIN.
ID2961S PROBABLE PROTEIN ASP-PHOSPHATASE.
ID2962S ORF starting with ATG of length 1239
ID2963S B. subtilis hydrolase protein YQJL.
ID2964S ORF starting with ATG of length 1238
ID2965S ORF starting with ATG of length 1233
ID2966S SIMILAR TO PHOSPHATASES.
ID2967S BH2308 PROTEIN.
ID2968S HYPOTHETICAL 16.0 KDA PROTEIN IN COTF-TETB INTERGENIC REGION
ID2969S YKUO PROTEIN.
ID2970S YTLQ.
ID2971S YFLK PROTEIN.
ID2972S HYPOTHETICAL 15.0 KDA PROTEIN.
ID2973S ORF12.
ID2974S YNDG PROTEIN.
ID2975S REQUIRED FOR REPLICATION INITIATION.
ID2976S DNA FOR 25-36 DEGREE REGION CONTAINING THE AMYE-SRFA REGION,
ID2977S YRBG PROTEIN.
ID2978S YMAC PROTEIN.
ID2979S BH1973 PROTEIN.
ID2980S YNDH PROTEIN.
ID2981S YJBB PROTEIN.
ID2982S GENERAL STRESS PROTEIN 26 (GSP26).
ID2983S ORF starting with ATG of length 1200
ID2984S ORF starting with ATG of length 1200
ID2985S HYPOTHETICAL 16.3 KDA PROTEIN IN TGL-PGI INTERGENIC REGION.
ID2986S HYPOTHETICAL 19.1 KDA PROTEIN IN SPOOF-PYRG INTERGENIC REGIO
ID2987S HYPOTHETICAL 21.1 KDA PROTEIN IN ILVA 3'REGION.
ID2988S HYPOTHETICAL 23.6 KDA PROTEIN IN QCRC-DAPB INTERGENIC REGION
ID2989S STAGE III SPORULATION PROTEIN AD.
ID2990S PHAGE-LIKE ELEMENT PBSX PROTEIN XKDA.
ID2991S YJBK PROTEIN.
ID2992S CODY PROTEIN (VEGETATIVE PROTEIN 286B) (VEG286B).
ID2993S STAGE II SPORULATION PROTEIN M.
ID2994S BH0621PROTEIN.
ID2995S HYPOTHETICAL 17.9 KDA PROTEIN IN SPOIIIC-CWLA INTERGENIC REG
ID2996S YMAC PROTEIN.
ID2997S HYPOTHETICAL 17.0 KDA PROTEIN IN CCDC-CITB INTERGENIC REGION
ID2998S HYPOTHETICAL 17.5 KDA PROTEIN IN SIGV-GREA INTERGENIC REGION
ID2999S ORF starting with ATG of length 1155
ID3000S ORF starting with ATG of length 1155
ID3001S YOQW PROTEIN.
ID3002S DNA, COMPLETE SEQUENCE.
ID3003S YLAJ PROTEIN.
ID3004S YBFI PROTEIN.
ID3005S HYPOTHETICAL 18.1 KDA PROTEIN IN TTK-CCDA INTERGENIC REGION.
ID3006S ORF starting with ATG of length 1137
ID3007S YESV PROTEIN.
ID3008S YKUD PROTEIN.
ID3009S STAGE III SPORULATION PROTEIN AH.
ID3010S YKVT PROTEIN.
ID3011S YTFJ.
ID3012S ORF starting with ATG of length 1119
ID3013S BH3151PROTEIN.
ID3014S HYPOTHETICAL 20.3 KDA PROTEIN IN UNG-ROCA INTERGENIC REGION.
ID3015S ORF starting with ATG of length 1116
ID3016S HYPOTHETICAL 17.9 KDA PROTEIN IN DING-ASPB INTERGENIC REGION
ID3017S YVR1PROTEIN.
ID3018S STAGE V SPORULATION PROTEIN AA.
ID3019S TRANSMEMBRANE PROTEIN.
ID3020S YBBK.
ID3021S FTSL PROTEIN.
ID3022S YLOU PROTEIN.
ID3023S DNA REPLICATION PROTEIN DNAD.
ID3024S YKVI PROTEIN.

ID3025S 4-DEOXY-L-THREO-5-HEXOSULOSE-URONATE KETOL-ISOMERASE (EC 5.3
ID3026S HYPOTHETICAL 32.9 KDA PROTEIN IN CMK-GPSA INTERGENIC REGION.
ID3027S HYPOTHETICAL 59.7 KDA PROTEIN IN CWLA-CISA INTERGENIC REGION
ID3028S YUAE PROTEIN.
ID3029S BH0186 PROTEIN.
ID3030S YEEE.
ID3031S ORF starting with ATG of length 1077
ID3032S TRANSCRIPTION ANTITERMINATOR (BIGG FAMILY).
ID3033S HYPOTHETICAL 13.3 KDA PROTEIN IN AROD-COMER INTERGENIC REGIO
ID3034S BH1562 PROTEIN.
ID3035S HYPOTHETICAL 23.9 KDA PROTEIN IN GLNQ-ANSR INTERGENIC REGION
ID3036S PHAGE-LIKE ELEMENT PBSX PROTEIN XKDI.
ID3037S POSITIVE CONTROL FACTOR.
ID3038S HYPOTHETICAL 16.4 KDA PROTEIN.
ID3039S BH399S PROTEIN.
ID3040S YLBF PROTEIN.
ID3041S ORF starting with ATG of length 1065
ID3042S ORF starting with ATG of length 1059
ID3043S YDAT PROTEIN.
ID3044S STAGE V SPORULATION PROTEIN AB.
ID3045S MLR3962PROTEIN.
ID3046S YOAO.
ID3047S HYPOTHETICAL 14.1 KDA PROTEIN IN XPAC-ABRB INTERGENIC REGION
ID3048S SPORULATION-SPECIFIC EXTRACELLULAR NUCLEASE PRECURSOR (EC 3.
ID3049S YHZB PROTEIN.
ID3050S HYPOTHETICAL 28.8 KDA PROTEIN IN DNAJ-RPSU INTEREGENIC REGIO
ID3051S HYPOTHETICAL 23.3 KDA PROTEIN IN DNAI-THRS INTERGENIC REGION
ID3052S RIBT PROTEIN.
ID3053S STAGE III SPORULATION PROTEIN AB.
ID3054S YTFI.
ID3055S ORF starting with ATG of length 1032
ID3056S METHYLASE HOMOLOG (CSPR).
ID3057S HYPOTHETICAL 23.3 KDA PROTEIN IN DFRA-ILVA INTERGENIC REGION
ID3058S SPORE COAT PROTEIN F.
ID3059S YAZC PROTEIN.
ID3060S GENERAL STRESS PROTEIN 17M (GSP17M).
ID3061S YKUW PROTEIN.
ID3062S YLBD PROTEIN.
ID3063S ORF starting with ATG of length 1005
ID3064S ORF starting with ATG of length 1002
ID3065S HYPOTHETICAL 40.7 KDA PROTEIN.
ID3066S CHORISMATE MUTASE (EC 5.4.99.5) (CM).
ID3067S YUTE PROTEIN.
ID3068S ORF16.
ID3069S HYPOTHETICAL 25.1 KDA PROTEIN IN PRKA 5'REGION (ORF2).
ID3070S HYPOTHETICAL 21.4 KDA PROTEIN IN QCRA-AROE INTERGENIC REGION
ID3071S BH0817 PROTEIN.
ID3072S CHITIN-BINDING PROTEIN.
ID3073S HYPOTHETICAL 16.2 KDA PROTEIN IN COMF-FLGM INTERGENIC REGION
ID3074S ORF starting with ATG of length 984
ID3075S HYPOTHETICAL 64.3 KDA PROTEIN IN HUTP-BGLP INTERGENIC REGION
ID3076S HYPOTHETICAL 13.2 KDA PROTEIN IIN GUTB-COTA INTERGENIC REGIO
ID3077S BH1290 PROTEIN.
ID3078S ORF starting with ATG of length 978
ID3079S HYPOTHETICAL 18.1 KDA PROTEIN IN NARK-NARG INTERGENIC REGION
ID3080S PHAGE-LIKE ELEMENT PBSX PROTEIN XKDJ.
ID3081S HYPOTHETICAL 14.0 KDA PROTEIN IN SIGV-GREA INTERGENIC REGION
ID3082S YTTB.
ID3083S YVQK PROTEIN.
ID3084S YJCS PROTEIN.
ID3085S HYPOTHETICAL 41.5 KDA PROTEIN IN AMHX-AMYE INTERGENIC REGION
ID3086S PUTATIVE PHOSPHO-BETA-GLUCOSIDASE.
ID3087S BH0923 PROTEIN.
ID3088S YVBK PROTEIN.
ID3089S YOAR.
ID3090S BOFC PROTEIN PRECURSOR (BYPASS-OF-FORESPORE PROTEIN C).
ID3091S HYPOTHETICAL 27.7 KDA PROTEIN IN HMP-PROB INTERGENIC REGION
ID3092S HYPOTHETICAL 44.1 KDA PROTEIN.
ID3093S BETA-MANNOSIDASE.
ID3094S YOEB PROTEIN.
ID3095S YDHG PROTEIN.
ID3096S HYPOTHETICAL 20.4 KDA PROTEIN IN RIBT-DACB INTERGENIC REGION
ID3097S HYPOTHETICAL 48.2 KDA PROTEIN IN COTF-TETB INTERGENIC REGION
ID3098S HYPOTHETICAL 30.5 KDA PROTEIN IN GABP-GUAA INTERGENIC REGION
ID3099S A AND A* PROTEINS (GPA).
ID3100S SIMILAR TO STAPHYLOCOCCUS AUREUS CAPA PROTEIN.
ID3101S HYPOTHETICAL 15.7 KDA PROTEIN.
ID3102S YOJF PROTEIN.
ID3103S YVZD PROTEIN.
ID3104S Amino acid sequence of a spore-associated protein called Yqx
ID3105S YNDF PROTEIN.
ID3106S ORF starting with ATG of length 945
ID3107S HYPOTHETICAL 39.0 KDA PROTEIN IN GLNQ-ANSR INTERGENIC REGION
ID3108S FENH.
ID3109S SPORE COAT PROTEIN E.
ID3110S YITI PROTEIN.
ID3111S ORF starting with ATG of length 936
ID3112S ORF starting with ATG of length 936
ID3113S YLMD PROTEIN.
ID3114S YFJM PROTEIN.
ID3115S BACITRACIN RESISTANCE PROTEIN (UNDECAPRENOL KINASE).
ID3116S YMCC PROTEIN.
ID3117S BH2340 PROTEIN.
ID3118S RIBONUCLEASE PRECURSOR (EC 3.1.27.-) (BARNASE) (RNASE BA).
ID3119S HYPOTHETICAL 31.3 KDA PROTEIN IN LYSA-PPIB INTERGENIC REGION
ID3120S HYPOTHETICAL 19.3 KDA PROTEIN IN PONA-NTH INTERGENIC REGION
ID3121S YVLD.
ID3122S HYPOTHETICAL 15.6 KDA PROTEIN.
ID3123S BH3953 PROTEIN.
ID3124S HYPOTHETICAL 22.5 KDA PROTEIN IN GLYS-DNAG/DNAE INTERGENIC R ID3125S PUTATIVE SECRETED PECTINESTERASE.
ID3126S KINASE-ASSOCIATED PROTEIN B.
ID3127S YHBB PROTEIN.
ID3128S ORF starting with ATG of length 906
ID3129S ORF starting with ATG of length 903
ID3130S ORF starting with ATG of length 903
ID3131S HYPOTHETICAL 24.1 KDA PROTEIN IN CSPB-GLPP INTERGENIC REGION
ID3132S ORF22.
ID3133S HYPOTHETICAL 12.0 KDA PROTEIN IN XPAC-ABRB INTERGENIC REGION
ID3134S FENI.
ID3135S DNA REPLICATION PROTEIN DNAD.
ID3136S ORF starting with ATG of length 899
ID3137S YHZA HOMOLOG.
ID3138S ORF starting with ATG of length 897
ID3139S HYPOTHETICAL 25.9 KDA PROTEIN IN CCCA-SODA INTERGENIC REGION
ID3140S HYPOTHETICAL 15.6 KDA PROTEIN IN PURA-DNAC INTERGENIC REGION
ID3141S HYPOTHETICAL 15.7 KDA PROTEIN IN PBPD-COMA INTERGENIC REGION
ID3142S YMDB PROTEIN.
ID3143S HYPOTHETICAL 13.2 KDA PROTEIN IN FTSY-FFH INTERGENIC REGION.
ID3144S GLUCOSE STARVATION-INDUCIBLE PROTEIN B (GENERAL STRESS PROTE
ID3145S YUTD PROTEIN.
ID3146S FLAA LOCUS 22.9 KDA PROTEIN (ORF 6).
ID3147S HYPOTHETICAL 10.1 KDA PROTEIN IN ORF3 5'REGION.
ID3148S BH3627 PROTEIN.
ID3149S HYPOTHETICAL 18.2 KDA PROTEIN IN FLGM-FLGK INTERGENIC REGION
ID3150S YUIB PROTEIN.
ID3151S YCEG.
ID3152S YDFB PROTEIN.
ID3153S YUSN PROTEIN.
ID3154S YDBL PROTEIN.
ID3155S YNGA PROTEIN.
ID3156S ORF starting with ATG of length 864
ID3157S YQZD PROTEIN.
ID3158S YERQ PROTEIN.
ID3159S SMALL BASIC PROTEIN.
ID3160S BH2308 PROTEIN.
ID3161S ORF starting with ATG of length 861
ID3162S HYPOTHETICAL 9.5 KDA PROTEIN IN ORF3 5'REGION.
ID3163S ORF starting with ATG of length 852
ID3164S YDBS PROTEIN.
ID3165S ALKALINE PHOSPHATASE.
ID3166S HYPOTHETICAL 24.8 KDA PROTEIN IN DEGS-TAGO INTERGENIC REGION
ID3167S *Bacillus subtilis* IFO 3336 PGA synthesising enzyme.
ID3168S HYPOTHETICAL 14.1 KDA PROTEIN IN PCP 5'REGION (ORF15).
ID3169S ORF starting with ATG of length 849
ID3170S HYPOTHETICAL 13.1 KDA PROTEIN.
ID3171S ORF starting with ATG of length 843
ID3172S ORF starting with ATG of length 843
ID3173S HYPOTHETICAL PROTEIN TC0114.
ID3174S HYPOTHETICAL PROTEIN VC1285.
ID3175S HYPOTHETICAL 16.5 KDA PROTEIN IN SPOIIR-GLYC INTERGENIC REGI
ID3176S YNER.
ID3177S HYPOTHETICAL 10.8 KDA PROTEIN IN RPSU-PHOH INTEREGENIC REGIO
ID3178S MBL, FLH[O,P], RAPD, YWP[B,C,D,E,F,G,H,I,J] AND YWQA GENES.
ID3179S COMPLETE NUCLEOTIDE SEQUENCE.
ID3180S HYPOTHETICAL 21.7 KDA PROTEIN IN LON-HEMA INTERGENIC REGION
ID3181S YRRD PROTEIN.
ID3182S YUTC PROTEIN.
ID3183S COMPLETE NUCLEOTIDE SEQUENCE.
ID3184S YKRK PROTEIN.
ID3185S YJCA PROTEIN.
ID3186S HYPOTHETICAL 20.2 KDA PROTEIN IN GCVT-SPOIIIAA INTERGENIC RE
ID3187S ORF starting with ATG of length 822
ID3188S HYPOTHETICAL 27.7 KDA PROTEIN IN SPOIIIC-CWLA INTERGENIC REG
ID3189S ORF starting with ATG of length 822
ID3190S BH3473 PROTEIN.
ID3191S GP8 PROTEIN.
ID3192S YUZD PROTEIN.
ID3193S YRZB PROTEIN.
ID3194S GP8 PROTEIN.
ID3195S TUAF PROTEIN.
ID3196S ORF starting with ATG of length 812
ID3197S FIBRONECTIN-BINDING PROTEIN, 25KDA.
ID3198S YVGZ PROTEIN.
ID3199S PROBABLE HTH_LYSR_FAMILY TRANSCRIPTIONAL REGULATOR.
ID3200S YLBA PROTEIN.
ID3201S HYPOTHETICAL 15.6 KDA PROTEIN (ORF2).
ID3202S ORF starting with ATG of length 800
ID3203S YUEI PROTEIN.
ID3204S YODL.
ID3205S YKUK PROTEIN.
ID3206S YLAH PROTEIN.
ID3207S ORF starting with ATG of length 792
ID3208S YDGC PROTEIN.
ID3209S HYPOTHETICAL 22.3 KDA PROTEIN IN WPRA-ASNO INTERGENIC REGION
ID3210S YNDE PROTEIN.
ID3211S ORF starting with ATG of length 783
ID3212S HYPOTHETICAL 21.0 KDA LIPOPROTEIN IN CSPB-GLPP INTERGENIC RE
ID3213S ORF starting with ATG of length 780
ID3214S HYPOTHETICAL 19.3 KDA PROTEIN IN BCSA-DEGR INTERGENIC REGION
ID3215S HYPOTHETICAL 19.2 KDA PROTEIN.
ID3216S HYPOTHETICAL 64.3 KDA PROTEIN IN HUTP-BGLP INTERGENIC REGION
ID3217S SIMILAR TO BACILLUS SUBTILIS YXID PROTEIN.
ID3218S MBL, FLH[O,P], RAPD, YWP[B,C,D,E,F,G,H,I,J] AND YWQA GENES.
ID3219S YJQB PROTEIN.
ID3220S YDZA PROTEIN.
ID3221S HYPOTHETICAL 13.3 KDA PROTEIN.
ID3222S YKUC PROTEIN.
ID3223S MAJOR CAPSID PROTEIN.
ID3224S YUBF PROTEIN.
ID3225S PUTATIVE PBSX REPRESSOR.
ID3226S YTES.
ID3227S ORF starting with ATG of length 765
ID3228S ORF starting with ATG of length 762
ID3229S HYPOTHETICAL PROTEIN VC0429.
ID3230S CHLORAMPHENICOL ACETYLTRANSFERASE (EC 2.3.1.28) (CAT).

ID3231S HYPOTHETICAL 27.6 KDA PROTEIN IN NUCB-AROD INTERGENIC REGION
ID3232S ORF starting with ATG of length 753
ID3233S YWZC PROTEIN.
ID3234S BH0424 PROTEIN.
ID3235S YKOE.
ID3236S HYPOTHETICAL 19.8 KDA PROTEIN.
ID3237S YJCC PROTEIN.
ID3238S YFHH PROTEIN.
ID3239S YUSQ PROTEIN.
ID3240S HYPOTHETICAL 9.4 KDA PROTEIN IN SODA-COMGA INTERGENIC REGION
ID3241S HYPOTHETICAL 9.9 KDA PROTEIN IN GCVT-SPOIIIAA INTERGENIC REG
ID3242S YKZC PROTEIN.
ID3243S HYPOTHETICAL 27.7 KDA PROTEIN IN SPOIIIC-CWLA INTERGENIC REG
ID3244S BH399S PROTEIN.
ID3245S BH1312 PROTEIN.
ID3246S ORF starting with ATG of length 735
ID3247S PHAGE-LIKE ELEMENT PBSX PROTEIN XKDH.
ID3248S HYPOTHETICAL 31.8 KDA PROTEIN IN SODA-COMGA INTERGENIC REGIO
ID3249S YFIT PROTEIN.
ID3250S YKUJ PROTEIN.
ID3251S PHAGE-LIKE ELEMENT PBSX PROTEIN XKDE.
ID3252S ORF starting with ATG of length 731
ID3253S HYPOTHETICAL 10.0 KDA PROTEIN IN QOXD-VPR INTERGENIC REGION
ID3254S ORF starting with ATG of length 729
ID3255S YDFG PROTEIN.
ID3256S YDZE PROTEIN.
ID3257S YMFJ PROTEIN.
ID3258S HYPOTHETICAL 33.3 KDA PROTEIN IN KSGA-VEG INTERGENIC REGION.
ID3259S ORF starting with ATG of length 720
ID3260S STAGE II SPORULATION PROTEIN R.
ID3261S SIMILAR TO B. ANTHRACIS STERNER ELEMENT ORFA.
ID3262S Pectate Lyase Family 3.Putative ORF with homology to this gr
ID3263S SIMILAR TO B. ANTHRACIS STERNER ELEMENT ORFA.
ID3264S SIMILAR TO B. ANTHRACIS STERNER ELEMENT ORFA.
ID3265S DNA-ENTRY NUCLEASE INHIBITOR (COMPETENCE PROTEIN J).
ID3266S BH1921PROTEIN.
ID3267S HYPOTHETICAL 14.8 KDA PROTEIN.
ID3268S ORF starting with ATG of length 717
ID3269S YKUC PROTEIN.
ID3270S HYPOTHETICAL 11.0 KDA PROTEIN IN CWLL 5'REGION.
ID3271S HYPOTHETICAL 12.8 KDA PROTEIN IN PAIA-THRB INTERGENIC REGION
ID3272S MEMBRANE PROTEIN CSK22.
ID3273S ORF starting with ATG of length 714
ID3274S ORF starting with ATG of length 714
ID3275S HYPOTHETICAL 19.7 KDA PROTEIN IN PHEA-NIFS INTERGENIC REGION
ID3276S YJCL PROTEIN.
ID3277S YLMC PROTEIN.
ID3278S ORF (FRAGMENT).
ID3279S YNCE.
ID3280S HYPOTHETICAL 9.7 KDA PROTEIN IN CWLL 5'REGION.
ID3281S HYPOTHETICAL 13.0 KDA PROTEIN IN IDH-DEOR INTERGENIC REGION
ID3282S YNDM PROTEIN.
ID3283S SIMILAR TO B. ANTHRACIS STERNER ELEMENT ORFA.
ID3284S ORF starting with ATG of length 708
ID3285S ORF starting with ATG of length 705
ID3286S HYPOTHETICAL 17.2 KDA PROTEIN.
ID3287S HYPOTHETICAL 21.4 KDA PROTEIN IN IDH-DEOR INTERGENIC REGION.
ID3288S BH0586 PROTEIN.
ID3289S COMPLETE NUCLEOTIDE SEQUENCE.
ID3290S ORF starting with ATG of length 699
ID3291S ORF starting with ATG of length 699
ID3292S ORF starting with ATG of length 699
ID3293S ORF starting with ATG of length 696
ID3294S SPORE COAT PROTEIN X.
ID3295S ORF starting with ATG of length 690
ID3296S PTS SYSTEM, GLUCITOL/SORBITOL-SPECIFIC IIC COMPONENT, ONE OF
ID3297S HYPOTHETICAL 47.7 KDA PROTEIN IN METS-KSGA INTERGENIC REGION
ID3298S ORF starting with ATG of length 687
ID3299S HYPOTHETICAL 14.6 KDA PROTEIN IN GCVT-SPOIIIAA INTERGENIC RE
ID3300S HYPOTHETICAL 12.4 KDA PROTEIN IN MURC-AROA INTERGENIC REGION
ID3301S HYPOTHETICAL 49.4 KDA PROTEIN.
ID3302S TET.BSR.
ID3303S HYPOTHETICAL 17.6 KDA PROTEIN IN CWLD 5'REGION (ORF1).
ID3304S YLBE PROTEIN.
ID3305S ORF starting with ATG of length 681
ID3306S YTZH PROTEIN.
ID3307S SPORE COAT PROTEIN D.
ID3308S ORF42.
ID3309S YDGD PROTEIN.
ID3310S ORF starting with ATG of length 678
ID3311S ORF starting with ATG of length 675
ID3312S NITRIC OXIDE SYNTHASE.
ID3313S STAGE III SPORULATION PROTEIN AC.
ID3314S YETA PROTEIN.
ID3315S HYPOTHETICAL 21.3 KDA PROTEIN.
ID3316S ORF starting with ATG of length 666
ID3317S BH1437 PROTEIN.
ID3318S YTKC.
ID3319S HYPOTHETICAL 11.7 KDA PROTEIN IN EPR-GALK INTERGENIC REGION.
ID3320S YNDB PROTEIN.
ID3321S YISC PROTEIN.
ID3322S HYPOTHETICAL 12.7 KDA PROTEIN.
ID3323S ORF starting with ATG of length 660
ID3324S YJBL PROTEIN.
ID3325S HYPOTHETICAL 16.9 KDA PROTEIN.
ID3326S ORF starting with ATG of length 651
ID3327S YISD PROTEIN.
ID3328S ORF starting with ATG of length 652
ID3329S HYPOTHETICAL 8.6 KDA PROTEIN.
ID3330S ORF starting with ATG of length 648
ID3331S YESL PROTEIN.
ID3332S VEG PROTEIN.
ID3333S ORF29.
ID3334S ORF starting with ATG of length 645
ID3335S YUAJ PROTEIN.
ID3336S ORF starting with ATG of length 642

ID3337S YUNC PROTEIN.
ID3338S DNA-ENTRY NUCLEASE (EC 3.-.-.-) (COMPETENCE-SPECIFIC NUCLEAS
ID3339S ORF starting with ATG of length 639
ID3340S YUZA PROTEIN.
ID3341S SPORE COAT PROTEIN V.
ID3342S YFHJ PROTEIN.
ID3343S HYPOTHETICAL 8.5 KDA PROTEIN.
ID3344S HYPOTHETICAL 9.8 KDA PROTEIN.
ID3345S BH2016 PROTEIN.
ID3346S YUSW PROTEIN.
ID3347S YQZG PROTEIN.
ID3348S HYPOTHETICAL 11.8 KDA PROTEIN IN UNG-ROCA INTERGENIC REGION.
ID3349S YOJC.
ID3350S ORF starting with ATG of length 630
ID3351S CSBA PROTEIN.
ID3352S ORF starting with ATG of length 627
ID3353S YLMG PROTEIN.
ID3354S COMPLETE NUCLEOTIDE SEQUENCE.
ID3355S ORF starting with ATG of length 624
ID3356S ORF starting with ATG of length 624
ID3357S SPORE COAT PROTEIN D.
ID3358S ORF starting with ATG of length 621
ID3359S ORF starting with ATG of length 618
ID3360S YNZC PROTEIN.
ID3361S ORF starting with ATG of length 618
ID3362S YKUO PROTEIN.
ID3363S ORF starting with ATG of length 617
ID3364S ORF starting with ATG of length 615
ID3365S YCZC PROTEIN.
ID3366S SPORE COAT PROTEIN.
ID3367S YRZD PROTEIN.
ID3368S ORF starting with ATG of length 612
ID3369S HYPOTHETICAL 15.0 KDA PROTEIN IN ASNH-GNTR INTERGENIC REGION
ID3370S HYPOTHETICAL 9.9 KDA PROTEIN IN BCSA-DEGR INTERGENIC REGION.
ID3371S YRVD PROTEIN.
ID3372S YUEC PROTEIN.
ID3373S ORF starting with ATG of length 606
ID3374S ORF starting with ATG of length 606
ID3375S HYPOTHETICAL 19.1 KDA PROTEIN IN SIGD-RPSB INTERGENIC REGION
ID3376S ORF starting with ATG of length 606
ID3377S HYPOTHETICAL 9.3 KDA PROTEIN IN PCKA-DPS INTERGENIC REGION.
ID3378S ORF starting with ATG of length 603
ID3379S YUEE PROTEIN.
ID3380S ORF starting with ATG of length 603
ID3381S YOLA.
ID3382S YISH PROTEIN.
ID3383S HYPOTHETICAL 30.6 KDA PROTEIN IN QCRC-DAPB INTERGENIC REGION
ID3384S ORF starting with ATG of length 597
ID3385S ORF starting with ATG of length 597
ID3386S BH3337 PROTEIN.
ID3387S ORF starting with ATG of length 597
ID3388S BH088S PROTEIN.
ID3389S HYPOTHETICAL 17.8 KDA PROTEIN.
ID3390S YKWD PROTEIN.
ID3391S ORF starting with ATG of length 591
ID3392S HYPOTHETICAL 25.1 KDA PROTEIN IN RECQ-CMK INTERGENIC REGION.
ID3393S HYPOTHETICAL 42.3 KDA PROTEIN (YVFT PROTEIN).
ID3394S *Streptomyces* galilaeus putative cyclase encoded by sga10 gen
ID3395S ORF starting with ATG of length 589
ID3396S LYSIS PROTEIN (E PROTEIN) (GPE).
ID3397S HYPOTHETICAL 15.3 KDA PROTEIN IN CSPB-GLPP INTERGENIC REGION
ID3398S ORF starting with ATG of length 588
ID3399S YBYB PROTEIN.
ID3400S YVLA.
ID3401S YUNG PROTEIN.
ID3402S ORF starting with ATG of length 585
ID3403S BH0588 PROTEIN.
ID3404S YJZC PROTEIN.
ID3405S ORF starting with ATG of length 585
ID3406S ORF starting with ATG of length 582
ID3407S BH0589 PROTEIN.
ID3408S STAGE V SPORULATION PROTEIN AC.
ID3409S COMPLETE NUCLEOTIDE SEQUENCE.
ID3410S ORF starting with ATG of length 582
ID3411S ORF starting with ATG of length 579
ID3412S YBFF PROTEIN.
ID3413S ORF starting with ATG of length 579
ID3414S SMALL, ACID-SOLUBLE SPORE PROTEIN 1 (SASP).
ID3415S HYPOTHETICAL 14.7 KDA PROTEIN IN SPOIIIC-CWLA INTERGENIC REG
ID3416S ORF starting with ATG of length 576
ID3417S SIGMA-G-DEPENDENT SPORULATION SPECIFIC SASP PROTEIN.
ID3418S HYPOTHETICAL OXIDOREDUCTASE IN RTP-PELB INTERGENIC REGION (E
ID3419S ORF starting with ATG of length 573
ID3420S BH3170 PROTEIN.
ID3421S ORF starting with ATG of length 570
ID3422S ORF starting with ATG of length 570
ID3423S PRODUCT REQUIRED FOR HEAD MORPHOGENESIS.
ID3424S ORF starting with ATG of length 567
ID3425S HYPOTHETICAL 7.5 KDA PROTEIN IN CSGA 3'REGION (ORF3).
ID3426S YFJT PROTEIN.
ID3427S YUEH PROTEIN.
ID3428S HYPOTHETICAL 14.5 KDA PROTEIN IN PONA-COTD INTERGENIC REGION
ID3429S SPORULATION CORTEX PROTEIN COXA.
ID3430S HYPOTHETICAL 28.3 KDA PROTEIN.
ID3431S HYPOTHETICAL PROTEIN.
ID3432S HYPOTHETICAL 9.8 KDA PROTEIN IN SPOVFA 5'REGION (ORFZ).
ID3433S BH3870 PROTEIN.
ID3434S YERC PROTEIN.
ID3435S ORF starting with ATG of length 558
ID3436S HYPOTHETICAL 12.0 KDA PROTEIN IN UNG-ROCA INTERGENIC REGION.
ID3437S HYPOTHETICAL TRANSCRIPTIONAL REGULATOR YOAU.
ID3438S YNDF PROTEIN.
ID3439S HYPOTHETICAL 21.1 KDA PROTEIN IN COTD-KDUD INTERGENIC REGION
ID3440S mLL7394 PROTEIN.
ID3441S ORF starting with ATG of length 555
ID3442S CTAG PROTEIN.
ID3443S XPAC PROTEIN.
ID3444S YFMB PROTEIN.
ID3445S YTZC PROTEIN.
ID3446S HYPOTHETICAL 16.7 KDA PROTEIN IN XPAC-ABRB INTERGENIC REGION ID3447S YDJO PROTEIN.
ID3448S HYPOTHETICAL 64.3 KDA PROTEIN IN HUTP-BGLP INTERGENIC REGION
ID3449S HYPOTHETICAL 9.2 KDA PROTEIN IN RECR-BOFA INTERGENIC REGION.
ID3450S ORF starting with TTG or GTG of length 1098
ID3451S ORF starting with ATG of length 549
ID3452S RAPA.
ID3453S HYPOTHETICAL 7.3 KDA PROTEIN IN PONA-COTD INTERGENIC REGION.
ID3454S ORF starting with ATG of length 543
ID3455S YUSG PROTEIN.
ID3456S ORF starting with ATG of length 540
ID3457S BH4052 PROTEIN.
ID3458S ORF starting with ATG of length 537
ID3459S SMALL, ACID-SOLUBLE SPORE PROTEIN A (SASP).
ID3460S HYPOTHETICAL 10.8 KDA PROTEIN IN CCCA-SODA INTERGENIC REGION
ID3461S ORF starting with ATG of length 531
ID3462S ORF starting with ATG of length 531
ID3463S HYPOTHETICAL 11.4 KDA PROTEIN IN MFD-DIVIC INTERGENIC REGION
ID3464S STAGE V SPORULATION PROTEIN AC.
ID3465S YOJB PROTEIN.
ID3466S HYPOTHETICAL 8.2 KDA PROTEIN IN NPRE-PYCA INTERGENIC REGION.
ID3467S FLAGELLAR PROTEIN REQUIRED FOR FLAGELLAR FORMATION.
ID3468S YOED PROTEIN.
ID3469S ORF starting with ATG of length 525
ID3470S SINI PROTEIN.
ID3471S YLBG PROTEIN.
ID3472S YEBG PROTEIN.
ID3473S ORF starting with ATG of length 522
ID3474S SORBITOL OPERON ACTIVATOR.
ID3475S SMALL ACID SOLUBLE SPORE PROTEIN SSPD.
ID3476S ORF starting with ATG of length 519
ID3477S BH069S PROTEIN.
ID3478S CSE60.
ID3479S ORF starting with ATG of length 521
ID3480S HYPOTHETICAL 23.2 KDA PROTEIN.
ID3481S YRZE PROTEIN.
ID3482S STAGE 0 SPORULATION PROTEIN A (SPOOA) (FRAGMENT).
ID3483S HYPOTHETICAL 27.3 KDA PROTEIN IN RECQ-CMK INTERGENIC REGION.
ID3484S YFMQ.
ID3485S SSPF PROTEIN.
ID3486S ORF starting with ATG of length 516
ID3487S HYPOTHETICAL 15.7 KDA PROTEIN IN RPSU-PHOH INTEREGENIC REGIO
ID3488S COMPLETE NUCLEOTIDE SEQUENCE.
ID3489S COMG OPERON PROTEIN 4 PRECURSOR.
ID3490S E22 PROTEIN (GENE 43 PROTEIN).
ID3491S HYPOTHETICAL 10.2 KDA PROTEIN IN ILVA 3'REGION.
ID3492S ORF starting with ATG of length 511
ID3493S HYPOTHETICAL 11.1 KDA PROTEIN YITR.
ID3494S ORF starting with ATG of length 513
ID3495S YOZB PROTEIN.
ID3496S HYPOTHETICAL 8.3 KDA PROTEIN IN TTK-CCDA INTERGENIC REGION.
ID3497S YRZG PROTEIN.
ID3498S HYPOTHETICAL 20.3 KDA PROTEIN.
ID3499S YVBJ PROTEIN.
ID3500S BH294S PROTEIN.
ID3501S HYPOTHETICAL 10.3 KDA PROTEIN.
ID3502S COMG OPERON PROTEIN 6.
ID3503S ORF starting with ATG of length 504
ID3504S XPAC PROTEIN.
ID3505S YRZA PROTEIN.
ID3506S ORF starting with ATG of length 504
ID3507S HYPOTHETICAL 10.5 KDA PROTEIN IN ACDA 5'REGION.
ID3508S ORF 36 (FRAGMENT).
ID3509S HYPOTHETICAL 19.9 KDA PROTEIN (FRAGMENT).
ID3510S ORF starting with ATG of length 501
ID3511S YKZF PROTEIN.
ID3512S ORF N001.
ID3513S ORF starting with ATG of length 498
ID3514S ORF starting with ATG of length 495
ID3515S HYPOTHETICAL 17.8 KDA PROTEIN.
ID3516S HYPOTHETICAL 9.8 KDA PROTEIN IN HUTP-BGLP INTERGENIC REGION.
ID3517S YISG PROTEIN.
ID3518S ORF starting with ATG of length 495
ID3519S ORF starting with ATG of length 492
ID3520S YKZI PROTEIN.
ID3521S HYPOTHETICAL 21.4 KDA PROTEIN.
ID3522S SIMILAR TO STAPHYLOCOCCUS AUREUS CAPA PROTEIN.
ID3523S BH2911PROTEIN.
ID3524S ORF starting with ATG of length 488
ID3525S ORF starting with ATG of length 489
ID3526S CSFB PROTEIN.
ID3527S BH2618 PROTEIN.
ID3528S STAGE V SPORULATION PROTEIN AE.
ID3529S YOZD PROTEIN.
ID3530S DNA, COMPLETE SEQUENCE.
ID3531S YWIB PROTEIN.
ID3532S YOQW PROTEIN.
ID3533S YFNK.
ID3534S YLAD PROTEIN.
ID3535S HYPOTHETICAL 6.6 KDA PROTEIN IN DING-ASPB INTERGENIC REGION.
ID3536S ORF starting with ATG of length 480
ID3537S HYPOTHETICAL 62.6 KDA PROTEIN IN RPMF-FTSL INTERGENIC REGION
ID3538S ORF14.
ID3539S BH2266 PROTEIN.
ID3540S ORF14.
ID3541S ORF starting with ATG of length 478
ID3542S SPORE COAT PROTEIN D.
ID3543S ORF starting with ATG of length 477
ID3544S SIMILAR TO BACILLUS SUBTILIS YXIC PROTEIN.
ID3545S ORF starting with ATG of length 474
ID3546S PLASMID PBS2 ORIGIN OF REPLICATION.
ID3547S HYPOTHETICAL 20.1 KDA PROTEIN.
ID3548S ORF starting with ATG of length 468
ID3549S ORF starting with ATG of length 468
ID3550S ORF starting with ATG of length 468
ID3551S GERMINATION PROTEIN.
ID3552S OUTER MEMBRANE PORIN PROTEIN PRECURSOR.
ID3553S PAL-RELATED LIPOPROTEIN PRECURSOR.
ID3554S ORF starting with ATG of length 465
ID3555S ORF starting with ATG of length 462
ID3556S ORF starting with ATG of length 462
ID3557S ORF starting with ATG of length 462
ID3558S YFKK PROTEIN.

ID3559S HYPOTHETICAL 38.5 KDA PROTEIN IN TNRA-SSPD INTERGENIC REGION
ID3560S SPORE COAT PROTEIN L.
ID3561S ORF starting with ATG of length 459
ID3562S DEGRADATION ENZYME REGULATION PROTEIN DEGQ (SACQ REGULATORY
ID3563S BH195S PROTEIN.
ID3564S PHAGE-LIKE ELEMENT PBSX PROTEIN XKDD.
ID3565S BH0893 PROTEIN.
ID3566S ORF starting with ATG of length 456
ID3567S ORF starting with ATG of length 456
ID3568S ORF starting with ATG of length 456
ID3569S ORF starting with ATG of length 456
ID3570S ORF starting with ATG of length 456
ID3571S YUZC PROTEIN.
ID3572S SPORE GERMINATION PROTEIN A1.
ID3573S ORF starting with ATG of length 453
ID3574S ORF starting with ATG of length 452
ID3575S PHAGE-LIKE ELEMENT PBSX PROTEIN XTRA.
ID3576S YOLD PROTEIN.
ID3577S ORF starting with ATG of length 453
ID3578S ORF starting with ATG of length 453
ID3579S ORF starting with ATG of length 450
ID3580S ORF starting with ATG of length 981
ID3581S ORF starting with ATG of length 447
ID3582S HYPOTHETICAL 28.0 KDA PROTEIN.
ID3583S ORF starting with ATG of length 447
ID3584S HYPOTHETICAL 28.2 KDA PROTEIN IN CCCA-SODA INTERGENIC REGION
ID3585S ORF starting with ATG of length 447
ID3586S ORF starting with ATG of length 444
ID3587S YKZG PROTEIN.
ID3588S ORF starting with ATG of length 444
ID3589S ORF starting with ATG of length 444
ID3590S HYPOTHETICAL 8.8 KDA PROTEIN IN SPOVC-MFD INTERGENIC REGION.
ID3591S ORF starting with ATG of length 441
ID3592S ORF starting with ATG of length 441
ID3593S PROBABLE HTH_LYSR_FAMILY TRANSCRIPTIONAL REGULATOR.
ID3594S ORF starting with ATG of length 438
ID3595S ORF starting with ATG of length 438
ID3596S PROBABLE PROTEIN ASP-PHOSPHATASE.
ID3597S ORF starting with ATG of length 438
ID3598S ORF starting with ATG of length 438
ID3599S ORF starting with ATG of length 438
ID3600S ORF starting with ATG of length 435
ID3601S ORF starting with ATG of length 435
ID3602S HYPOTHETICAL 30.6 KDA PROTEIN IN QCRC-DAPB INTERGENIC REGION
ID3603S Thermotoga maritima endoglucanase.
ID3604S ORF starting with ATG of length 432
ID3605S ORF starting with ATG of length 432
ID3606S HYPOTHETICAL 9.8 KDA PROTEIN IN HUTP-BGLP INTERGENIC REGION.
ID3607S SPORE COAT PROTEIN K.
ID3608S BH3113 PROTEIN.
ID3609S Sorangium cellulosum protein Orf 4.
ID3610S YUEG PROTEIN.
ID3611S HYPOTHETICAL 9.1 KDA PROTEIN IN GLNQ-ANSR INTERGENIC REGION.
ID3612S ORF starting with ATG of length 432
ID3613S ORF starting with ATG of length 432
ID3614S SIMILAR TO BACILLUS SUBTILIS YXIC PROTEIN.
ID3615S CAPSID PROTEIN (F PROTEIN) (GPF).
ID3616S ORF starting with ATG of length 426
ID3617S ORF starting with ATG of length 423
ID3618S ORF starting with ATG of length 423
ID3619S ORF starting with ATG of length 423
ID3620S ORF starting with ATG of length 423
ID3621S ORF starting with ATG of length 423
ID3622S HYPOTHETICAL 58.5 KDA PROTEIN IN SPOIIIC-CWLA INTERGENIC REG
ID3623S ORF starting with TTG or GTG of length 843
ID3624S ORF starting with ATG of length 420
ID3625S ORF starting with ATG of length 421
ID3626S ORF starting with ATG of length 420
ID3627S YDAS PROTEIN.
ID3628S HYPOTHETICAL 15.7 KDA PROTEIN IN MURC-AROA INTERGENIC REGION
ID3629S HYPOTHETICAL 25.3 KDA PROTEIN PH0221.
ID3630S ORF16.
ID3631S ORF starting with ATG of length 417
ID3632S Chlamydia pneumoniae lipoprotein sequence.
ID3633S ORF starting with ATG of length 417
ID3634S COMG OPERON PROTEIN 7.
ID3635S ORF starting with ATG of length 414
ID3636S BH126S PROTEIN.
ID3637S ORF starting with ATG of length 414
ID3638S BH2053 PROTEIN.
ID3639S ORF starting with ATG of length 411
ID3640S ORF starting with ATG of length 411
ID3641S HYPOTHETICAL 21.0 KDA PROTEIN IN RIBT-DACB INTERGENIC REGION
ID3642S YUEE PROTEIN.
ID3643S HYPOTHETICAL 30.8 KDA PROTEIN IN SINI-GCVT INTERGENIC REGION
ID3644S DNA FOR 25-36 DEGREE REGION CONTAINING THE AMYE-SRFA REGION,
ID3645S ORF starting with ATG of length 409
ID3646S ORF starting with ATG of length 409
ID3647S HYPOTHETICAL 7.6 KDA PROTEIN IN SPOIIIC-CWLA INTERGENIC REGI
ID3648S ORF starting with ATG of length 405
ID3649S ORF starting with ATG of length 405
ID3650S ORF starting with ATG of length 405
ID3651S ORF starting with ATG of length 405
ID3652S Porphyromonas gingivalis protein PG22.
ID3653S SMALL CORE PROTEIN (J PROTEIN).
ID3654S ORF starting with ATG of length 402
ID3655S ORF starting with ATG of length 402
ID3656S ORF starting with ATG of length 399
ID3657S ORF starting with ATG of length 399
ID3658S ORF starting with ATG of length 399
ID3659S ORF starting with ATG of length 399
ID3660S YFHD PROTEIN.
ID3661S ORF starting with ATG of length 395
ID3662S HYPOTHETICAL 7.3 KDA PROTEIN IN PONA-COTD INTERGENIC REGION.
ID3663S HYPOTHETICAL 9.5 KDA PROTEIN IN ORF3 5'REGION.
ID3664S MRSM PROTEIN.
ID3665S HYPOTHETICAL 16.7 KDA PROTEIN.
ID3666S ORF starting with ATG of length 393
ID3667S ORF starting with ATG of length 393
ID3668S ORF starting with ATG of length 393
ID3669S ORF starting with ATG of length 393
ID3670S HYPOTHETICAL 31.3 KDA PROTEIN.
ID3671S HYPOTHETICAL PROTEIN HI1600.
ID3672S ORF starting with ATG of length 393
ID3673S ORF starting with ATG of length 390

ID3674S ORF starting with ATG of length 389
ID3675S ORF starting with ATG of length 387
ID3676S ORF starting with ATG of length 389
ID3677S ORF starting with ATG of length 387
ID3678S BH2118 PROTEIN.
ID3679S HYPOTHETICAL 9.2 KDA PROTEIN.
ID3680S PXO1-135.
ID3681S ORF starting with ATG of length 384
ID3682S HYPOTHETICAL 20.5 KDA PROTEIN IN HMP-PROB INTERGENIC REGION.
ID3683S ORF starting with ATG of length 384
ID3684S PHI PVL ORF 63 HOMOLOGUE.
ID3685S SIMILAR TO B. ANTHRACIS WEYAR ELEMENT ORFB.
ID3686S ORF starting with ATG of length 381
ID3687S ORF starting with ATG of length 381
ID3688S ORF starting with ATG of length 381
ID3689S ORF starting with ATG of length 381
ID3690S ORF starting with ATG of length 381
ID3691S ORF starting with ATG of length 381
ID3692S ORF starting with ATG of length 381
ID3693S ORF starting with ATG of length 381
ID3694S ORF starting with ATG of length 381
ID3695S ORF starting with ATG of length 380
ID3696S YVLB.
ID3697S YODN.
ID3698S YTEJ.
ID3699S ORF starting with ATG of length 378
ID3700S ORF starting with ATG of length 378
ID3701S ORF starting with ATG of length 375
ID3702S ORF starting with ATG of length 375
ID3703S HYPOTHETICAL 7.5 KDA PROTEIN IN DNAC-RPLI INTERGENIC REGION.
ID3704S ORF starting with ATG of length 377
ID3705S ORF starting with ATG of length 375
ID3706S ORF starting with ATG of length 375
ID3707S YQZE PROTEIN.
ID3708S YFHS PROTEIN.
ID3709S ORF starting with ATG of length 372
ID3710S HYPOTHETICAL 12.8 KDA PROTEIN IN COMJ 5'REGION PRECURSOR (OR
ID3711S ORF starting with ATG of length 371
ID3712S ORF starting with ATG of length 372
ID3713S HYPOTHETICAL 24.6 KDA PROTEIN IN DAE-TYRZ INTERGENIC REGION.
ID3714S HYPOTHETICAL 9.8 KDA PROTEIN.
ID3715S ORF starting with ATG of length 369
ID3716S ORF starting with ATG of length 369
ID3717S YJCF PROTEIN.
ID3718S BH0973 PROTEIN.
ID3719S HYPOTHETICAL 14.9 KDA PROTEIN.
ID3720S ORF starting with ATG of length 368
ID3721S ORF starting with ATG of length 369
ID3722S ORF starting with ATG of length 366
ID3723S ORF starting with ATG of length 366
ID3724S ORF starting with ATG of length 366
ID3725S ORF starting with ATG of length 366
ID3726S ORF starting with ATG of length 363
ID3727S ORF starting with ATG of length 363
ID3728S ORF starting with ATG of length 363
ID3729S ORF starting with ATG of length 363
ID3730S ORF starting with ATG of length 365
ID3731S ORF starting with ATG of length 364
ID3732S (CLONE LAMBDA-BS1) CELL DIVISION AND SPORULATION PROTEIN (DD
ID3733S ORF starting with ATG of length 363
ID3734S ORF starting with ATG of length 363
ID3735S ORF starting with ATG of length 363
ID3736S ORF starting with ATG of length 363
ID3737S HYPOTHETICAL 7.1 KDA PROTEIN IN RECQ-CMK INTERGENIC REGION.
ID3738S NADP-SPECIFIC GLUTAMATE DEHYDROGENASE (EC 1.4.1.4) (GLUTAMAT
ID3739S POSITIVE TRANSCRIPTIONAL ACTIVATOR.
ID3740S YOLD PROTEIN.
ID3741S ORF starting with ATG of length 360
ID3742S ORF starting with ATG of length 360
ID3743S DIVISION INITIATION PROTEIN (DIVIB) (FRAGMENT).
ID3744S POTENTIAL ABC TRANSPORTER.
ID3745S ORF starting with TTG or GTG of length 711
ID3746S ORF starting with ATG of length 357
ID3747S ORF starting with ATG of length 357
ID3748S ORF starting with ATG of length 357
ID3749S GENOMIC DNA, CHROMOSOME 3, BAC CLONE:F1D9.
ID3750S ORF starting with ATG of length 357
ID3751S ORF starting with ATG of length 357
ID3752S ORF starting with TTG or GTG of length 708
ID3753S ORF starting with ATG of length 354
ID3754S VCO28.
ID3755S ORF starting with ATG of length 354
ID3756S ORF starting with ATG of length 351
ID3757S ORF starting with ATG of length 353
ID3758S ORF starting with ATG of length 351
ID3759S ORF starting with ATG of length 351
ID3760S ORF starting with ATG of length 351
ID3761S *Bacillus licheniformis* (BLC) $R^P$-II protease.
ID3762S HYPOTHETICAL 29.5 KDA PROTEIN IN ROCC-PTA INTERGENIC REGION.
ID3763S ORF starting with ATG of length 348
ID3764S YOMP PROTEIN.
ID3765S PROBABLE HTH_ARAC_FAMILY OF TRANSCRIPTIONAL REGULATOR.
ID3766S SPORE COAT PROTEIN.
ID3767S ORF starting with ATG of length 345
ID3768S ORF starting with ATG of length 345
ID3769S HYPOTHETICAL 6.9 KDA PROTEIN IN SODA-COMGA INTERGENIC REGION
ID3770S ORF starting with ATG of length 345
ID3771S PUTATIVE PERMEASE.
ID3772S YKZB PROTEIN.
ID3773S ORF starting with ATG of length 345
ID3774S YKZE PROTEIN.
ID3775S ORF starting with ATG of length 342
ID3776S ORF starting with ATG of length 342
ID3777S ORF starting with ATG of length 342
ID3778S ORF starting with ATG of length 339
ID3779S ORF starting with ATG of length 339
ID3780S ORF starting with ATG of length 339
ID3781S ORF starting with ATG of length 339
ID3782S BH0644 PROTEIN.
ID3783S ORF starting with ATG of length 339
ID3784S ORF starting with ATG of length 339
ID3785S YDCC PROTEIN.
ID3786S ORF starting with ATG of length 339
ID3787S ORF starting with ATG of length 339
ID3788S ORF starting with ATG of length 339
ID3789S ORF starting with ATG of length 339
ID3790S ORF starting with ATG of length 339
ID3791S ORF starting with ATG of length 341
ID3792S YFLB PROTEIN.
ID3793S ORF starting with ATG of length 335
ID3794S BH031S PROTEIN.

ID3795S ORF starting with ATG of length 336
ID3796S YOAF PROTEIN.
ID3797S SIMILAR TO B. ANTHRACIS WEYAR ELEMENT ORFB.
ID3798S HYPOTHETICAL TRANSCRIPTIONAL REGULATOR YYBE.
ID3799S ORF starting with ATG of length 333
ID3800S ORF starting with ATG of length 333
ID3801S HYPOTHETICAL 7.5 KDA PROTEIN IN GPSA-SPOIVA INTERGENIC REGIO
ID3802S ORF starting with ATG of length 333
ID3803S HYPOTHETICAL 21.0 KDA PROTEIN IN RIBT-DACB INTERGENIC REGION
ID3804S ORF starting with ATG of length 333
ID3805S ORF starting with ATG of length 333
ID3806S ORF starting with ATG of length 333
ID3807S ORF starting with ATG of length 333
ID3808S HYPOTHETICAL 18.8 KDA PROTEIN PH0220.
ID3809S ORF starting with ATG of length 330
ID3810S ORF starting with TTG or GTG of length 660
ID3811S REPRESSOR.
ID3812S ORF starting with ATG of length 327
ID3813S ORF starting with ATG of length 327
ID3814S ORF starting with TTG or GTG of length 651
ID3815S HYPOTHETICAL 4.5 KDA PROTEIN.
ID3816S ORF starting with ATG of length 324
ID3817S YNZD PROTEIN.
ID3818S EATRO 164 KINETOPLAST (CR4).
ID3819S HYPOTHETICAL 18.8 KDA PROTEIN PH0220.
ID3820S GAMMA-GLUTAMYL PHOSPHATE REDUCTASE (GPR) (EC 1.2.1.41) (GLUT
ID3821S ORF starting with ATG of length 324
ID3822S ORF starting with ATG of length 324
ID3823S ORF starting with ATG of length 1059
ID3824S PHAGE-LIKE ELEMENT PBSX PROTEIN XKDW.
ID3825S 403AA LONG HYPOTHETICAL COENZYME PQQ SYNTHESIS PROTEIN.
ID3826S ORF starting with ATG of length 321
ID3827S ORF starting with ATG of length 319
ID3828S ORF starting with ATG of length 321
ID3829S ORF starting with ATG of length 321
ID3830S YKZH PROTEIN.
ID3831S ORF starting with ATG of length 318
ID3832S ORF starting with ATG of length 318
ID3833S BH1226 PROTEIN.
ID3834S ORF starting with ATG of length 318
ID3835S FLAGELLAR PROTEIN FLIT.
ID3836S YFLJ PROTEIN.
ID3837S ORF starting with ATG of length 318
ID3838S ORF starting with TTG or GTG of length 633
ID3839S ORF starting with ATG of length 315
ID3840S ORF starting with ATG of length 315
ID3841S ORF starting with ATG of length 315
ID3842S HYPOTHETICAL 6.3 KDA PROTEIN IN SODA-COMGA INTERGENIC REGION
ID3843S ORF21.
ID3844S LACA.
ID3845S ORF starting with ATG of length 315
ID3846S ORF starting with ATG of length 315
ID3847S CYTOCHROME AA3 CONTROLLING PROTEIN.
ID3848S YVKN.
ID3849S ORF starting with ATG of length 312
ID3850S ORF starting with ATG of length 313
ID3851S ORF starting with ATG of length 312
ID3852S HYPOTHETICAL 19.5 KDA PROTEIN IN DEGA-NPRB INTERGENIC REGION
ID3853S ORF starting with ATG of length 311
ID3854S ORF starting with ATG of length 312
ID3855S QUINOLONE RESISTANCE PROTEIN.
ID3856S YEEF PROTEIN.
ID3857S HYPOTHETICAL 18.8 KDA PROTEIN PH0220.
ID3858S ORF starting with ATG of length 313
ID3859S ORF starting with ATG of length 312
ID3860S ORF starting with ATG of length 312
ID3861S ORF starting with TTG or GTG of length 621
ID3862S ORF starting with ATG of length 309
ID3863S YUIA PROTEIN.
ID3864S YRZK PROTEIN.
ID3865S IOLB PROTEIN.
ID3866S BH1709 PROTEIN.
ID3867S BH0952 PROTEIN.
ID3868S PHOSPHATIDYLSERINE SYNTHASE.
ID3869S HYPOTHETICAL 17.9 KDA PROTEIN IN RECQ-CMK INTERGENIC REGION.
ID3870S ORF starting with ATG of length 306
ID3871S REPRESSOR
ID3872S ORF starting with ATG of length 353
ID3873S ORF starting with ATG of length 306
ID3874S ORF starting with ATG of length 306
ID3875S ORF starting with ATG of length 303
ID3876S ORF starting with ATG of length 303
ID3877S ORF starting with ATG of length 303
ID3878S ORF starting with ATG of length 303
ID3879S CYTOCHROME C-550.
ID3880S YOSA PROTEIN.
ID3881S Thymidylate kinase-2.
ID3882S HYPOTHETICAL 13.7 KDA PROTEIN.
ID3883S ORF starting with ATG of length 300
ID3884S ORF starting with ATG of length 301
ID3885S ORF starting with ATG of length 300
ID3886S ORF starting with ATG of length 300
ID3887S YUNB PROTEIN.
ID3888S BH3172 PROTEIN.
ID3889S ORF starting with ATG of length 300
ID3890S ORF starting with ATG of length 300
ID3891S HYPOTHETICAL 10.9 KDA PROTEIN.
ID3892S ORF starting with ATG of length 333
ID3893S ORF starting with ATG of length 298
ID3894S YOMM PROTEIN.
ID3895S ORF starting with ATG of length 297
ID3896S PLASMID PAM-BETA1 ADENINE METHYLASE GENE (FRAGMENT).
ID3897S HYPOTHETICAL 42.0 KDA PROTEIN IN DAPB-PAPS INTERGENIC REGION
ID3898S YVQI PROTEIN.
ID3899S ORF starting with ATG of length 297
ID3900S ORF starting with ATG of length 297
ID3901S GLYCINE-RICH_PROTEIN PRECURSOR.
ID3902S ORF starting with ATG of length 294
ID3903S ORF starting with ATG of length 294
ID3904S YOZM PROTEIN.
ID3905S ORF starting with ATG of length 294
ID3906S ORF starting with ATG of length 291
ID3907S ORF starting with ATG of length 291
ID3908S ORF starting with ATG of length 291
ID3909S HYPOTHETICAL 23.2 KDA PROTEIN.
ID3910S HYPOTHETICAL 16.5 KDA PROTEIN.
ID3911S ORF starting with ATG of length 291
ID3912S ORF starting with ATG of length 288
ID3913S ORF starting with ATG of length 288
ID3914S ORF starting with ATG of length 288

ID3915S ORF starting with ATG of length 288
ID3916S CDP-DIACYLGLYCEROL-SERINE O-PHOSPHATIDYLTRANSFERASE (EC 2.7
ID3917S ORF starting with ATG of length 288
ID3918S HPR(SER) KINASE/PHOSPHATASE (EC 2.7.1.-) (EC 3.1.3.-).
ID3919S MLR7758PROTEIN.
ID3920S L-ASPARTATE OXIDASE (EC 1.4.3.16) (QUINOLINATE SYNTHETASE B)
ID3921S HYPOTHETICAL 23.3 KDA PROTEIN IN ROCC-PTA INTERGENIC REGION.
ID3922S BH0606 PROTEIN.
ID3923S ORF starting with ATG of length 285
ID3924S ORF starting with TTG or GTG of length 569
ID3925S LANTIBIOTIC MERSACIDIN PRECURSOR.
ID3926S ORF starting with ATG of length 285
ID3927S ORF starting with ATG of length 285
ID3928S ORF starting with ATG of length 285
ID3929S ORF starting with ATG of length 285
ID3930S ORF starting with ATG of length 285
ID3931S ORF starting with ATG of length 282
ID3932S ORF starting with ATG of length 282
ID3933S ORF starting with ATG of length 282
ID3934S ORF starting with ATG of length 282
ID3935S PROLINE PERMEASE.
ID3936S ORF starting with ATG of length 282
ID3937S STRESS RESPONSE HOMOLOG HSP.
ID3938S ORF starting with ATG of length 279
ID3939S ORF starting with ATG of length 279
ID3940S ORF starting with ATG of length 279
ID3941S HYPOTHETICAL 4.0 KDA PROTEIN.
ID3942S ORF starting with ATG of length 279
ID3943S YJBI PROTEIN.
ID3944S ORF starting with ATG of length 276
ID3945S ORF42.
ID3946S ORF starting with ATG of length 276
ID3947S TRNA PSEUDOURIDINE SYNTHASE B (EC 4.2.1.70) (TRNA PSEUDOURID
ID3948S HYPOTHETICAL 73.6 KDA PROTEIN.
ID3949S Human protein sequence SEQ ID NO:11751.
ID3950S ORF starting with ATG of length 273
ID3951S HYPOTHETICAL 22.4 KDA PROTEIN IN RPMF-FTSL INTERGENIC REGION
ID3952S BH2341PROTEIN.
ID3953S Right origin-binding protein.
ID3954S ORF starting with ATG of length 273
ID3955S ORF starting with ATG of length 273
ID3956S ORF starting with ATG of length 273
ID3957S ORF starting with ATG of length 270
ID3958S ORF starting with ATG of length 270
ID3959S ORF starting with ATG of length 270
ID3960S YDBN PROTEIN.
ID3961S DAUNORUBICIN RESISTANCE ATP-BINDING PROTEIN (DRRA-1).
ID3962S ORF starting with ATG of length 270
ID3963S ORF starting with ATG of length 267
ID3964S ORF starting with ATG of length 267
ID3965S ORF starting with ATG of length 267
ID3966S ORF starting with ATG of length 267
ID3967S BH2327 PROTEIN.
ID3968S HYPOTHETICAL 30.7 KDA LIPOPROTEIN IN GLNQ-ANSR INTERGENIC RE
ID3969S HYPOTHETICAL 17.1 KDA PROTEIN IN RAPH-COTJA INTERGENIC REGIO
ID3970S YLBB PROTEIN.
ID3971S ORF starting with TTG or GTG of length 530
ID3972S METHYLTRANSFERASE/UROPORPHYRINOGEN-III SYNTHASE.
ID3973S HYPOTHETICAL OXIDOREDUCTASE IN ANSR-BMRU INTERGENIC REGION.
ID3974S ORF starting with ATG of length 264
ID3975S ORF starting with ATG of length 264
ID3976S ORF starting with ATG of length 264
ID3977S ORF starting with ATG of length 264
ID3978S YOBG.
ID3979S ORF starting with ATG of length 261
ID3980S ORF starting with ATG of length 261
ID3981S ORF starting with ATG of length 261
ID3982S ORF starting with ATG of length 261
ID3983S ORF starting with ATG of length 261
ID3984S ORF starting with TTG or GTG of length 522
ID3985S ORF starting with ATG of length 259
ID3986S BH1397 PROTEIN.
ID3987S YFIQ PROTEIN.
ID3988S ORF starting with ATG of length 259
ID3989S YYZB PROTEIN.
ID3990S HYPOTHETICAL 6.0 KDA PROTEIN.
ID3991S ORF starting with ATG of length 261
ID3992S 50S RIBOSOMAL PROTEIN L2 (BL2).
ID3993S YQZH PROTEIN.
ID3994S ORF starting with ATG of length 258
ID3995S HYPOTHETICAL 12.8 KDA PROTEIN.
ID3996S IMMUNOGENIC PROTEIN.
ID3997S ORF starting with ATG of length 258
ID3998S BH1336 PROTEIN.
ID3999S BH2912 PROTEIN.
ID4000S ORF starting with ATG of length 258
ID4001S ORF starting with ATG of length 258
ID4002S HYPOTHETICAL 8.7 KDA PROTEIN.
ID4003S YDBT PROTEIN.
ID4004S ORF starting with ATG of length 255
ID4005S ORF starting with ATG of length 255
ID4006S BH0426 PROTEIN.
ID4007S BH0636 PROTEIN.
ID4008S HYPOTHETICAL 6.3 KDA PROTEIN.
ID4009S ORF starting with ATG of length 255
ID4010S ORF starting with ATG of length 255
ID4011S YFLI PROTEIN.
ID4012S EBV tethering protein EBNA1.
ID4013S BH1502 PROTEIN.
ID4014S HYPOTHETICAL 8.5 KDA PROTEIN (FRAGMENT).
ID4015S OCTAPEPTIDE-REPEAT PROTEIN T2.
ID4016S ORF starting with ATG of length 252
ID4017S SIGNAL PEPTIDASE I P (EC 3.4.21.89) (SPASE I) (LEADER PEPTID
ID4018S ORF starting with ATG of length 252
ID4019S ORF starting with ATG of length 252
ID4020S PUTATIVE_SOME HOMOLOGY WITH METH2.
ID4021S SITE-SPECIFIC RECOMBINASE XERC.
ID4022S *Arabidopsis thaliana* protein fragment SEQ ID NO: 48115.
ID4023S ORF starting with ATG of length 252
ID4024S ORF starting with ATG of length 252
ID4025S ORF starting with ATG of length 252
ID4026S HYPOTHETICAL 42.6 KDA PROTEIN IN BSAA-ILVD INTERGENIC REGION
ID4027S SAl216 PROTEIN.
ID4028S REGULATORY PROTEIN GLNR.
ID4029S ORF starting with ATG of length 249
ID4030S ORF starting with ATG of length 248
ID4031S ORF starting with ATG of length 249

ID4032S ORF starting with ATG of length 249
ID4033S ORF starting with ATG of length 249
ID4034S ORF starting with ATG of length 249
ID4035S 30S RIBOSOMAL PROTEIN S21.
ID4036S YFMJ PROTEIN.
ID4037S STAGE V SPORULATION PROTEIN M.
ID4038S ORF starting with ATG of length 249
ID4039S ORF starting with ATG of length 249
ID4040S ORF starting with ATG of length 249
ID4041S ORF starting with ATG of length 249
ID4042S ORF starting with ATG of length 249
ID4043S ORF starting with ATG of length 246
ID4044S VMP3 PROTEIN.
ID4045S ORF starting with ATG of length 246
ID4046S ORF starting with ATG of length 246
ID4047S ORF starting with ATG of length 246
ID4048S ORF starting with ATG of length 246
ID4049S ORF starting with ATG of length 243
ID4050S PUTATIVE TRANSPOSASE.
ID4051S Human protein sequence SEQ ID NO:17122.
ID4052S ORF starting with ATG of length 243
ID4053S ORF starting with ATG of length 243
ID4054S HYDROXYPROLINE-RICH PROTEIN.
ID4055S HYPOTHETICAL 34.8 KDA PROTEIN.
ID4056S T08D2.8 PROTEIN.
ID4057S PBSX PHAGE TERMINASE LARGE SUBUNIT.
ID4058S ORF starting with ATG of length 240
ID4059S ORF starting with ATG of length 240
ID4060S ORF starting with ATG of length 240
ID4061S HYPOTHETICAL 40.9 KDA PROTEIN IN MECB-GLTX INTERGENIC REGION
ID4062S YWIB PROTEIN.
ID4063S PROLINE-RICH PROTEIN.
ID4064S CG2839 PROTEIN (FRAGMENT).
ID4065S NADH DEHYDROGENASE (EC 1.6.99.3) (ALKYL HYDROPEROXIDE REDUCT
ID4066S HSDS.
ID4067S SP62-HUMAN.
ID4068S HYPOTHETICAL 7.7 KDA PROTEIN IN ILVA 3'REGION.
ID4069S ORF starting with ATG of length 237
ID4070S YCZF PROTEIN.
ID4071S ALANYL-TRNA SYNTHETASE (EC 6.1.1.7) (ALANINE-TRNA LIGASE)
ID4072S TRANSPOSON TN10 TETD PROTEIN (ORFR).
ID4073S ORF starting with ATG of length 237
ID4074S ORF starting with ATG of length 234
ID4075S ORF starting with ATG of length 234
ID4076S ORF starting with ATG of length 234
ID4077S HYPOTHETICAL 18.5 KDA PROTEIN IN SODA-COMGA INTERGENIC REGIO
ID4078S ORF starting with ATG of length 234
ID4079S DNA BINDING PROTEIN.
ID4080S ORF starting with ATG of length 234
ID4081S ORF starting with ATG of length 234
ID4082S ORF starting with ATG of length 234
ID4083S ORF starting with ATG of length 234
ID4084S ORF starting with ATG of length 234
ID4085S ORF starting with ATG of length 234
ID4086S ORF starting with ATG of length 234
ID4087S ORF starting with ATG of length 231
ID4088S ORF starting with ATG of length 231
ID4089S ORF starting with ATG of length 231
ID4090S TRNA LIGASE (EC 6.5.1.3).
ID4091S ORF starting with ATG of length 375
ID4092S HYPOTHETICAL 48.6 KDA PROTEIN IN SERS-DNAZ INTERGENIC REGION
ID4093S ORF starting with ATG of length 231
ID4094S ORF starting with ATG of length 231
ID4095S ORF starting with ATG of length 231
ID4096S ORF starting with ATG of length 231
ID4097S CELL DEATH REGULATOR AVEN.
ID4098S ORF starting with TTG or GTG of length 460
ID4099S BH0850 PROTEIN.
ID4100S HYPOTHETICAL 21.0 KDA PROTEIN IN TLP-GRLB INTERGENIC REGION.
ID4101S BH1321PROTEIN.
ID4102S ORF starting with ATG of length 228
ID4103S ORF starting with ATG of length 228
ID4104S ORF starting with ATG of length 228
ID4105S KIAA1297 PROTEIN (FRAGMENT).
ID4106S HYPOTHETICAL 15.9 KDA PROTEIN.
ID4107S HYPOTHETICAL 24.5 KDA PROTEIN.
ID4108S ACETYL-COA ACETYLTRANSFERASE (EC 2.3.1.9).
ID4109S ORF starting with ATG of length 228
ID4110S ORF starting with ATG of length 228
ID4111S PTS SYSTEM, GLUCITOL/SORBITOL-SPECIFIC ENZYME IIA COMPONENT.
ID4112S ORF33.
ID4113S YNZH PROTEIN.
ID4114S ODHA (EC 1.2.4.2) (OXOGLUTARATE DEHYDROGENASE (LIPOAMIDE)) (O
ID4115S YOST PROTEIN.
ID4116S ORF starting with ATG of length 225
ID4117S ORF starting with ATG of length 225
ID4118S ORF starting with ATG of length 225
ID4119S ORF starting with ATG of length 225
ID4120S ORF starting with ATG of length 225
ID4121S ORF starting with ATG of length 225
ID4122S BH1397 PROTEIN.
ID4123S P-HYDROXYBENZOATE HYDROXYLASE (EC 1.14.13.2) (4-HYDROXYBENZO
ID4124S ORF starting with ATG of length 225
ID4125S ORF starting with ATG of length 225
ID4126S ORF starting with TTG or GTG of length 447
ID4127S ORF starting with ATG of length 225
ID4128S ORF starting with ATG of length 225
ID4129S ORF starting with ATG of length 222
ID4130S ORF starting with ATG of length 222
ID4131S YFKG.
ID4132S ORF starting with ATG of length 222
ID4133S ORF starting with ATG of length 222
ID4134S UNIDENTIFIED TRANSPORTER-ATP BINDING.
ID4135S HYPOTHETICAL 11.5 KDA PROTEIN PH0217.
ID4136S HYPOTHETICAL 7.3 KDA PROTEIN.
ID4137S ORF starting with ATG of length 222
ID4138S YUTJ PROTEIN.
ID4139S ORF starting with ATG of length 222
ID4140S ORF starting with ATG of length 222
ID4141S ORF starting with ATG of length 219
ID4142S ORF starting with ATG of length 219
ID4143S ORF starting with ATG of length 219
ID4144S ORF starting with ATG of length 219
ID4145S ORF starting with ATG of length 219
ID4146S ORF starting with ATG of length 219
ID4147S ORF starting with ATG of length 220
ID4148S ORF starting with ATG of length 219
ID4149S ORF starting with ATG of length 219
ID4150S ORF starting with ATG of length 219
ID4151S ORF starting with ATG of length 218
ID4152S COMX.
ID4153S ORF starting with ATG of length 216

ID4154S ORF starting with ATG of length 215
ID4155S ORF starting with ATG of length 216
ID4156S ORF starting with ATG of length 216
ID4157S ORF starting with ATG of length 216
ID4158S ORF starting with ATG of length 216
ID4159S ORF starting with ATG of length 216
ID4160S Deduced protein sequence of p170-2 comprising T4.
ID4161S REGULATOR OF THE ACTIVITY OF PHOSPHATASE RAPK.
ID4162S *M. tuberculosis* SYNEC protein.
ID4163S ORF starting with ATG of length 216
ID4164S ORF starting with ATG of length 216
ID4165S ORF starting with ATG of length 216
ID4166S ORF starting with ATG of length 216
ID4167S ORF starting with ATG of length 216
ID4168S *Streptococcus pneumoniae* encoded polypeptide.
ID4169S ORF starting with ATG of length 216
ID4170S ORF starting with ATG of length 214
ID4171S Nucleic acid transporter system peptide ligand SEQ ID NO 60.
ID4172S ORF starting with ATG of length 213
ID4173S ORF starting with TTG or GTG of length 426
ID4174S ORF starting with ATG of length 212
ID4175S ORF starting with ATG of length 213
ID4176S ORF starting with ATG of length 213
ID4177S ORF starting with ATG of length 213
ID4178S ORF starting with ATG of length 213
ID4179S ORF starting with ATG of length 213
ID4180S ORF starting with ATG of length 213
ID4181S 90K-PROTEASE (BACILLOPEPTIDASE F) PRECURSOR (BACILLOPEPTIDAS
ID4182S HYPOTHETICAL PROTEIN HI1600.
ID4183S ORF starting with ATG of length 213
ID4184S ORF starting with ATG of length 213
ID4185S ORF starting with ATG of length 213
ID4186S ORF starting with ATG of length 210
ID4187S ORF starting with ATG of length 210
ID4188S ORF starting with ATG of length 210
ID4189S ORF starting with ATG of length 210
ID4190S ORF starting with ATG of length 210
ID4191S ORF starting with ATG of length 210
ID4192S ORF starting with ATG of length 210
ID4193S BH3511PROTEIN.
ID4194S YISL PROTEIN.
ID4195S PROTEIN-TYROSINE PHOSPHATASE, RECEPTOR-TYPE, F POLYPEPTIDE P
ID4196S ORF starting with ATG of length 207
ID4197S ORF starting with ATG of length 207
ID4198S ORF starting with ATG of length 207
ID4199S ORF starting with ATG of length 207
ID4200S ORF starting with TTG or GTG of length 414
ID4201S ORF starting with ATG of length 207
ID4202S ORF starting with ATG of length 207
ID4203S HYPOTHETICAL TRANSCRIPTIONAL REGULATOR IN GNTR-HTPG INTERGEN
ID4204S PROBABLE AMINO-ACID ABC TRANSPORTER PERMEASE PROTEIN YQIY.
ID4205S PHOSPHOTRANSACETYLASE.
ID4206S D-ISOMER SPECIFIC 2-HYDROXYACID DEHYDROGENASE FAMILY.
ID4207S ORF starting with ATG of length 204
ID4208S ORF starting with ATG of length 204
ID4209S ORF starting with ATG of length 204
ID4210S BH3131PROTEIN.
ID4211S *Arabidopsis thaliana* protein fragment SEQ ID NO: 22242.
ID4212S ORF starting with ATG of length 203
ID4213S ORF starting with ATG of length 204
ID4214S ORF starting with ATG of length 204
ID4215S ORF starting with ATG of length 204
ID4216S ORF starting with ATG of length 204
ID4217S ORF starting with ATG of length 205
ID4218S RESPONSE REGULATOR PROTEIN (FRAGMENT).
ID4219S ORF starting with ATG of length 201
ID4220S ORF starting with ATG of length 201
ID4221S ORF starting with ATG of length 201
ID4222S ORF starting with ATG of length 201
ID4223S ORF starting with ATG of length 201
ID4224S ORF starting with ATG of length 201
ID4225S ORF starting with ATG of length 201
ID4226S ORF starting with ATG of length 201
ID4227S ORF starting with ATG of length 201
ID4228S ORF starting with TTG or GTG of length 402
ID4229S ORF starting with ATG of length 201
ID4230S ORF starting with ATG of length 201
ID4231S SPOIISA PROTEIN.
ID4232S YFIX.
ID4233S INTRACELLULAR ALKALINE PROTEASE.
ID4234S STAGE V SPORULATION PROTEIN AA.
ID4235S YJZC PROTEIN.
ID4236S YFHO PROTEIN.
ID4237T PRKA PROTEIN.
ID4238T PUTATIVE SIGMA L-DEPENDENT TRANSCRIPTIONAL REGULATOR IN MMGE
ID4239T HOMOLOGOUS TO SP:PHOR_BACSU.
ID4240T CARBON STARVATION PROTEIN A HOMOLOG.
ID4241T SPORULATION KINASE A (EC 2.7.3.-) (STAGE II SPORULATION PROT
ID4242T YKRQ PROTEIN.
ID4243T POBABLE SENSORY TRANSDUCTION HISTIDINE KINASE.
ID4244T YVRG PROTEIN.
ID4245T YLAK PROTEIN.
ID4246T YKUI PROTEIN.
ID4247T ALKALINE PHOSPHATASE SYNTHESIS SENSOR PROTEIN PHOR (EC 2.7.3
ID4248T SENSOR PROTEIN RESE (EC 2.7.3.-).
ID4249T YVQB PROTEIN.
ID4250T HOMOLOGUE OF ALKALINE PHOSPHATASE SYNTHESIS SENSOR PROTEIN P
ID4251T YKVD PROTEIN.
ID4252T AUTOLYSIN SENSOR KINASE.
ID4253⁻1SUBTILIN BIOSYNTHESIS SENSOR PROTEIN SPAK (EC 2.7.3.-).
ID4254T HYPOTHETICAL 47.9 KDA PROTEIN IN DEGQ 5'REGION.
ID4255T HYPOTHETICAL 58.9 KDA PROTEIN.
ID4256T YTRP.
ID4257T YVQE PROTEIN.
ID4258T PUTATIVE SIGMA-B REGULATOR.
ID4259T YLOP PROTEIN.
ID4260T SIGNAL TRANSDUCTION PROTEIN KINASE.
ID4261T FNR PROTEIN.
ID4262T HYPOTHETICAL SENSOR-LIKE HISTIDINE KINASE (EC 2.7.3.-) (ORFH
ID4263⁻1 CRP/FNR FAMILY PROTEIN.
ID4264T CITS (TWO-COMPONENT SENSOR HISTIDINE KINASE).
ID4265T YLBL PROTEIN.
ID4266T PROBABLE SERINE/THREONINE-PROTEIN KINASE IN SPOIIE-HPT INTER ID4267T HYPOTHETICAL 35.7 KDA SENSORY TRANSDUCTION PROTEIN (ORFJ) (0
ID4268T HYPOTHETICAL 42.3 KDA PROTEIN (YVFT PROTEIN).
ID4269T HYPOTHETICAL SENSOR-LIKE HISTIDINE KINASE IN IDH 3'REGION (EC
ID4270T SENSOR PROTEIN DEGS (EC 2.7.3.-).
ID4271T ORF4 PROTEIN.
ID4272T GENERAL STRESS PROTEIN 16U (GSP16U).
ID4273~1STRESS RESPONSE PROTEIN SCP2.
ID4274T HYPOTHETICAL 27.7 KDA PROTEIN (ORFQ).
ID4275T CITS (TWO-COMPONENT SENSOR HISTIDINE KINASE).
ID4276T ORF starting with ATG of length 1569
ID4277T ORF starting with ATG of length 1545
ID4278T SIGNAL SENSOR PROTEIN HISTIDINE KINASE.
ID4279T BH2505 PROTEIN.
ID4280T PUTATIVE SIGMA-B REGULATOR.
ID4281T HYPOTHETICAL SENSOR-LIKE HISTIDINE KINASE IN IDH 3'REGION (EC
ID4282T SENSOR PROTEIN.
ID4283~1ORF starting with ATG of length 1233
ID4284T ORF starting with ATG of length 1182
ID4285T ORF starting with ATG of length 1170
ID4286T SPORULATION INITIATION PHOSPHOTRANSFERASE F (EC 2.7.-.-) (ST
ID4287T ORF starting with ATG of length 1164
ID4288T ANTI-SIGMA F FACTOR ANTAGONIST (STAGE II SPORULATION PROTEIN
ID4289T SPORULATION KINASE C (EC 2.7.3.-).
ID4290T ORF starting with ATG of length 1119
ID4291T CHEMOTAXIS PROTEIN CHEY HOMOLOG.
ID4292T ORF starting with ATG of length 1083
ID4293~1 ANTI-SIGMA B FACTOR ANTAGONIST.
ID4294T YDCE PROTEIN.
ID4295T ANTI-SIGMA B FACTOR ANTAGONIST.
ID4296T TWO-COMPONENT SENSOR HISTIDINE KINASE HOMOLOG.
ID4297T ARSENATE REDUCTASE (ARSENICAL PUMP MODIFIER).
ID4298T YTAB PROTEIN.
ID4299T PUTATIVE LOW MOLECULAR WEIGHT PROTEIN-TYROSINE-PHOSPHATASE Y
ID4300T SPORULATION KINASE C (EC 2.7.3.-).
ID4301T ORF starting with ATG of length 936
ID4302T YJBP PROTEIN.
ID4303T HYPOTHETICAL 20.1 KDA PROTEIN.
ID4304T YBDM PROTEIN.
ID4305T YKOW PROTEIN.
ID4306T HYPOTHETICAL 20.3 KDA PROTEIN.
ID4307T BH0415 PROTEIN.
ID4308T ORF starting with ATG of length 699
ID4309T HYPOTHETICAL 40.7 KDA PROTEIN IN CSPB-GLPP INTERGENIC REGION
ID4310T ORF starting with ATG of length 1389
ID4311T YFKJ PROTEIN.
ID4312T ANTI-SIGMA F FACTOR (STAGE II SPORULATION PROTEIN AB).
ID4313T HYPOTHETICAL 31.8 KDA PROTEIN IN SODA-COMGA INTERGENIC REGIO
ID4314T RECEPTOR-LIKE HISTIDINE KINASE BPDS.
ID4315T AUTOLYSIN SENSOR KINASE.
ID4316T YKOW PROTEIN.
ID4317T LYTS AND LYTR GENES, COMPLETE CDS.
ID4318T BH2016 PROTEIN.
ID4319T ANTI-SIGMA F FACTOR (STAGE II SPORULATION PROTEIN AB).
ID4320T RESPONSE REGULATOR ACTA.
ID4321T ORF starting with ATG of length 1170
ID4322T ORF starting with ATG of length 780
ID4323T ORF starting with ATG of length 255
ID4324T ORF starting with ATG of length 249
ID4325T ORF starting with ATG of length 239
ID4326T CITS (TWO-COMPONENT SENSOR HISTIDINE KINASE).
ID4327T YLAK PROTEIN.
ID4328TK STAGE II SPORULATION PROTEIN E (EC 3.1.3.16).
ID4329TK GTP PYROPHOSPHOKINASE (EC 2.7.6.5) (ATP:GTP 3'-PYROPHOSPHOTR
ID4330TK PUTATIVE SIGMA-B REGULATOR.
ID4331TK Peptide which promotes form of B. subtilis extracellular p
ID4332TK SIGNAL TRANSDUCTION REGULATOR.
ID4333TK *Streptococcus pneumoniae* spo/rel protein sequence.
ID4334TK YVQA PROTEIN.
ID4335TK YVQC PROTEIN.
ID4336TK YVRH PROTEIN (RECEIVER MODULE OF PUTATIVE RESPONSE REGULATOR
ID4337TK *Staphylococcus aureus* response regulator protein.
ID4338TK HYPOTHETICAL 27.5 KDA PROTEIN.
ID4339TK HYPOTHETICAL 27.2 KDA SENSORY TRANSDUCTION PROTEIN IN ROCR-P
ID4340TK MTRA PROTEIN.
ID4341TK CITT (TWO-COMPONENT RESPONSE REGULATOR).
ID4342TK HYPOTHETICAL 22.8 KDA PROTEIN.
ID4343TK PHOSPHATE REGULATORY PROTEIN PHOB.
ID4344TK HYPOTHETICAL 22.8 KDA PROTEIN.
ID4345TK YVRH PROTEIN (RECEIVER MODULE OF PUTATIVE RESPONSE REGULATOR
ID4346TK PUTATIVE TWO COMPONENT RESPONSE REGULATOR.
ID4347TK SCNR PROTEIN.
ID4348TK ORF starting with ATG of length 615
ID4349TK TWO-COMPONENT RESPONSE REGULATOR HOMOLOG.
ID4350TK ORF starting with ATG of length 506
ID4351TK ORF starting with ATG of length 240
ID4352TK ORF starting with ATG of length 228
ID4353TQ YUNI PROTEIN.
ID4354TQ HYPOTHETICAL 47.8 KDA PROTEIN IN CAH-NASF INTERGENIC REGION.
ID4355TQ ACETOIN UTILIZATION ACUC PROTEIN.
ID4356TQ ORF starting with ATG of length 1614
ID4357TQ ORF starting with ATG of length 1239
ID4358TQ HYPOTHETICAL 47.8 KDA PROTEIN IN CAH-NASF INTERGENIC REGION.
ID4359TQ ORF starting with ATG of length 942
ID4360TQ ORF starting with ATG of length 864
ID4361Z transfer RNA-Ala
ID4362Z transfer RNA-Ile
ID4363Z transfer RNA-Ala
ID4364Z transfer RNA-Arg
ID4365Z transfer RNA-Asn
ID4366Z transfer RNA-Asp
ID4367Z transfer RNA-Glu
ID4368Z transfer RNA-Gly
ID4369Z transfer RNA-Gly ID4370Z transfer RNA-His
ID4371Z transfer RNA-Ile
ID4372Z transfer RNA-Leu
ID4373Z transfer RNA-Leu
ID4374Z transfer RNA-Lys
ID4375Z transfer RNA-Met
ID4376Z transfer RNA-Met
ID4377Z transfer RNA-Met
ID4378Z transfer RNA-Phe
ID4379Z transfer RNA-Pro
ID4380Z transfer RNA-Ser
ID4381Z transfer RNA-Ser
ID4382Z transfer RNA-Thr
ID4383Z transfer RNA-Val
ID4384Z transfer RNA-Asn
ID4385Z transfer RNA-Asp
ID4386Z transfer RNA-Gln
ID4387Z transfer RNA-Glu
ID4388Z transfer RNA-Gly
ID4389Z transfer RNA-His
ID4390Z transfer RNA-Leu
ID4391Z transfer RNA-Leu
ID4392Z transfer RNA-Met
ID4393Z transfer RNA-Phe
ID4394Z transfer RNA-Ser
ID4395Z transfer RNA-Thr
ID4396Z transfer RNA-Trp
ID4397Z transfer RNA-Tyr
ID4398Z transfer RNA-Val
ID4399Z transfer RNA-Arg
ID4400Z transfer RNA-Asp
ID4401Z transfer RNA-Gly
ID4402Z transfer RNA-Met
ID4403Z transfer RNA-Ala
ID4404Z transfer RNA-Arg
ID4405Z transfer RNA-Asn
ID4406Z transfer RNA-Gly
ID4407Z transfer RNA-Pro
ID4408Z transfer RNA-Thr
ID4409Z transfer RNA-Ala
ID4410Z transfer RNA-Arg
ID4411Z transfer RNA-Gly
ID4412Z transfer RNA-Leu
ID4413Z transfer RNA-Leu
ID4414Z transfer RNA-Lys
ID4415Z transfer RNA-Pro
ID4416Z transfer RNA-Thr
ID4417Z transfer RNA-Val
ID4418Z transfer RNA-Ala
ID4419Z transfer RNA-Ile
ID4420Z transfer RNA-Arg
ID4421 Z transfer RNA-Asn
ID4422 Z transfer RNA-Gln
ID4423Z transfer RNA-Glu
ID4424 Z transfer RNA-Leu
ID4425Z transfer RNA-Leu
ID4426Z transfer RNA-Lys
ID4427Z transfer RNA-Ser
ID4428Z transfer RNA-Ala
ID4429Z transfer RNA-Arg
ID4430Z transfer RNA-Arg
ID4431Z transfer RNA-Gln
ID4432Z transfer RNA-Gln
ID4433Z transfer RNA-Glu
ID4434Z transfer RNA-Glu
ID4435Z transfer RNA-Gly
ID4436Z transfer RNA-Met
ID4437Z transfer RNA-Ser
ID4438Z transfer RNA-Thr
ID4439Z transfer RNA-Tyr
ID4440Z transfer RNA-Val
ID4441Z transfer RNA-Val
ID4442 Z transfer RNA-Asp
ID4443Z transfer RNA-Glu
ID4444 Z transfer RNA-Lys
ID4445Z transfer RNA-Phe
ID4446Z ribosomal RNA-16S
ID4447Z ribosomal RNA-23S
ID4448Z ribosomal RNA-5S

APPENDIX 2

*Bacillus clausii* Annotation and Divisions into Functional Categories

Information Storage and Processing
J 1135-1295 Translation, ribosomal structure and biogenesis
K 1296-1472 Transcription
L 1473-1634 DNA replication, recombination and repair
Cellular Orocesses
D 185-232 Cell division and chromosome partitioning
O 1816-1894 Posttranslational modification, protein turnover, chaperones
M 1635-1754 Cell envelope biogenesis, outer membrane
N 1755-1815 Cell motility and secretion
P 1895-2025 Inorganic ion transport and metabolism
T 3852-3947 Signal transduction mechanisms
Metabolism
C 1-184 Energy production and conversion
G 640-968 Carbohydrate transport and metabolism
E 233-544 Amino acid transport and metabolism
F 545-639 Nucleotide transport and metabolism
H 969-1067 Coenzyme metabolism
I 1068-1134 Lipid metabolism
Q 2026-2111 Secondary metabolites biosynthesis, transport and catabolism
Structural RNA
Z 3948-4033 tRNA and rRNA
Functional Category not Assigned
R 2212-2381 Functional category not assigned
S 2382-3851 Functional category not assigned
ID0001C NADH DEHYDROGENASE.
ID0002C ACONITATE HYDRATASE (EC 4.2.1.3) (CITRATE HYDRO-LYASE) (ACON
ID0003C L-LACTATE DEHYDROGENASE (EC 1.1.1.27).
ID0004C CYTOCHROME AA3 QUINOL OXIDASE SUBUNIT III (EC 1.10.3.).
ID0005C CYTOCHROME AA3 QUINOL OXIDASE SUBUNIT I (EC 1.10.3.).
ID0006C QOXA (CYTOCHROME AA3 QUINOL OXIDASE SUBUNIT II) (EC 1.10.3.)
ID0007C MALATE SYNTHASE.
ID0008C ACETATE KINASE (EC 2.7.2.1) (ACETOKINASE).
ID0009C ALCOHOL DEHYDROGENASE.
ID0010C L-lactic acid dehydrogenase.
ID0011C HYPOTHETICAL 35.0 KDA PROTEIN IN RAPJ-OPUAA INTERGENIC REGIO
ID0012C HYPOTHETICAL 49.3 KDA PROTEIN IN IDH-DEOR INTERGENIC REGION.
ID0013C PYRUVATE DEHYDROGENASE E2 (DIHYDROLIPOAMIDE ACETYLTRANSFERAS
ID0014C HYPOTHETICAL OXIDOREDUCTASE IN ANSR-BMRU INTERGENIC REGION.

ID0015C ACONITATE HYDRATASE (EC 4.2.1.3) (CITRATE HYDRO-LYASE) (ACON
ID0016C HYPOTHETICAL 49.3 KDA PROTEIN IN IDHDEOR INTERGENIC REGION.
ID0017C ORF starting with ATG of length 558
ID0018C DIHYDROLIPOAMIDE DEHYDROGENASE (EC 1.8.1.4) (E3 COMPONENT OF
ID0019C 68% IDENTITY PROTEIN TO 1-PYRROLINE-5-CARBOXYLATE DEHYDROGEN
ID0020C GLYCEROL KINASE.
ID0021C ELECTRON TRANSFER FLAVOPROTEIN (BETA SUBUNIT).
ID0022C ALDEHYDE DEHYDROGENASE, THERMOSTABLE (EC 1.2.1.3).
ID0023C NADH DEHYDROGENASE.
ID0024C NADH DEHYDROGENASE-LIKE PROTEIN.
ID0025C Heat resistant aldehyde dehydrogenase.
ID0026C GLYCOLATE OXIDASE SUBUNIT.
ID0027C ORF starting with ATG of length 351
ID0028C MAGNESIUM CITRATE SECONDARY TRANSPORTER.
ID0029C Heat resistant aldehyde dehydrogenase.
ID0030C NITRITE REDUCTASE [NAD(P)H] (EC 1.6.6.4).
ID0031C H(+)/SODIUM-GLUTAMATE SYMPORTER.
ID0032C PHOSPHOTRANSACETYLASE (EC 2.3.1.8).
ID0033C ORF starting with ATG of length 708
ID0034C CITRATE SYNTHASE (EC 4.1.3.7).
ID0035C DIHYDROLIPOAMIDE DEHYDROGENASE (EC 1.8.1.4) (E3 COMPONENT OF
ID0036C BRANCHED-CHAIN ALPHA-KETO ACID DEHYDROGENASE E1.
ID0037C OXIDOREDUCTASE.
ID0038C GLYCEROL KINASE (EC 2.7.1.30) (ATP:GLYCEROL 3-PHOSPHOTRANSFE
ID0039C ATP SYNTHASE ALPHA SUBUNIT (EC 3.6.1.34).
ID0040C ISOCITRATE LYASE.
ID0041C Amino acid sequence of respiratory Nitrate Reductase 1 alpha
ID0042C *Staphylococcus aureus* respiratory nitrate reductase alpha su
ID0043C PTS SYSTEM, MANNITOL-SPECIFIC ENZYME II, BC COMPONENT.
ID0044C *Staphylococcus carnosus* nitrate reductase biogenesis protein
ID0045C PUTATIVE PROTON-TRANSLOCATING ATPASE, BETA SUBUNIT (EC 3.6.1
ID0046C PUTATIVE NITRATE REDUCTASE ALPHA CHAIN.
ID0047C ATP SYNTHASE BETA SUBUNIT (EC 3.6.1.34).
ID0048C ASSIMILATORY NITRATE REDUCTASE CATALYTIC SUBUNIT (EC 1.7.99.
ID0049C ORF starting with ATG of length 918
ID0050C ASSIMILATORY NITRATE REDUCTASE CATALYTIC SUBUNIT (EC 1.7.99.
ID0051C GLYCOLATE OXIDASE SUBUNIT.
ID0052C L-lactic acid dehyrogenase.
ID0053C GLYCOLATE OXIDASE SUBUNIT.
ID0054C HYPOTHETICAL 49.2 KDA PROTEIN.
ID0055C PROBABLE METHYLMALONATE-SEMIALDEHYDE DEHYDROGENASE [ACYLATI N
ID0056C GLYCOLATE OXIDASE IRON-SULFUR SUBUNIT.
ID0057C ALDO/KETO REDUCTASE.
ID0058C NA(+)/H(+) ANTIPORTER (SODIUM/PROTON ANTIPORTER).
ID0059C MALIC ENZYME (MALATE DEHYDROGENASE) (EC 1.1.1.38).
ID0060C HYPOTHETICAL 48.5 KDA PROTEIN.
ID0061C PROBABLE D-LACTATE DEHYDROGENASE.
ID0062C PROBABLE METHYLMALONATE-SEMIALDEHYDE DEHYDROGENASE [ACYLATI N
ID0063C GLYCEROL-3-PHOSPHATE DEHYDROGENASE (EC 1.1.99.5).
ID0064C GLYCEROL-3-PHOSPHATE DEHYDROGENASE.
ID0065C ALKANESULFONATE MONOOXYGENASE.
ID0066C GLYCEROL-3-PHOSPHATE DEHYDROGENASE.
ID0067C GLYCOLATE OXIDASE IRON-SULFUR SUBUNIT.
ID0068C MALATE SYNTHASE.
ID0069C CITRATE SYNTHASE III (EC 4.1.3.7).
ID0070C BH1020 PROTEIN.
ID0071C METHYLMALONATE-SEMIALDEHYDE DEHYDROGENASE.
ID0072C METHYLMALONATE-SEMIALDEHYDE DEHYDROGENASE.
ID0073C OMEGA-CRYSTALLIN.
ID0074C L-LACTATE PERMEASE.
ID0075C GLYCOLATE OXIDASE.
ID0076C BH1833 PROTEIN.
ID0077C HYPOTHETICAL 49.2 KDA PROTEIN.
ID0078C GLYCEROL KINASE.
ID0079C ATP SYNTHASE B SUBUNIT (EC 3.6.1.34).
ID0080C SUCCINATE DEHYDROGENASE FLAVOPROTEIN SUBUNIT.
ID0081C NADH DEHYDROGENASE.
ID0082C HYPOTHETICAL 47.8 KDA PROTEIN.
ID0083C PYRUVATE DEHYDROGENASE E2 (DIHYDROLIPOAMIDE ACETYLTRANSFERAS
ID0084C DIHYDROLIPOAMIDE DEHYDROGENASE (EC 1.8.1.4) (E3 COMPONENT OF
ID0085C PROBABLE ALDEHYDE DEHYDROGENASE YCBD (EC 1.2.1.3).
ID0086C PROBABLE FLAVODOXIN 1.
ID0087C HYPOTHETICAL 79.2 KDA PROTEIN IN ACDA 5'REGION.
ID0088C ORF starting with ATG of length 969
ID0089C TPP-DEPENDENT ACETOIN DEHYDROGENASE, E1 ALPHA-SUBUNIT.
ID0090C GLYCEROPHOSPHODIESTER PHOSPHODIESTERASE.
ID0091C ATP SYNTHASE ALPHA SUBUNIT (EC 3.6.1.34).
ID0092C *Staphylococcus aureus* respiratory nitrate reductase alpha su
ID0093C MANGANESE-DEPENDENT INORGANIC PYROPHOSPHATASE (EC 3.6.1.1) (P
ID0094C PROBABLE NADH-DEPENDENT BUTANOL DEHYDROGENASE 1 (EC 1.1.1.-)
ID0095C MALATE DEHYDROGENASE (EC 1.1.1.37).
ID0096C ASSIMILATORY NITRITE REDUCTASE (SUBUNIT).
ID0097C ISOCITRATE DEHYDROGENASE (EC 1.1.1.42).
ID0098C NITRATE REDUCTASE (FRAGMENT).
ID0099C ASSIMILATORY NITRITE REDUCTASE (SUBUNIT).
ID0100C ALDEHYDE DEHYDROGENASE, THERMOSTABLE (EC 1.2.1.3).
ID0101C BH0875 PROTEIN.
ID0102C ALDEHYDE DEHYDROGENASE.

ID0103C SUCCINATE-SEMIALDEHYDE DEHYDROGENASE.
ID0104C HYDA (FRAGMENT).
ID0105C PROBABLE ALDEHYDE DEHYDROGENASE YCBD (EC 1.2.1.3).
ID0106C PTS SYSTEM, MANNITOL-SPECIFIC ENZYME II, BC COMPONENT.
ID0107C PROBABLE ALDEHYDE DEHYDROGENASE YWDH (EC 1.2.1.3).
ID0108C ATP SYNTHASE SUBUNIT C (EC 3.6.1.34).
ID0109C ATP SYNTHASE A SUBUNIT (EC 3.6.1.34).
ID0110C NADP-DEPENDENT ALDEHYDE DEHYDROGENASE (EC 1.2.1.3).
ID0111C L-ARABINOSE UTILIZATION PROTEIN.
ID0112C PROBABLE ALDEHYDE DEHYDROGENASE YCBD (EC 1.2.1.3).
ID0113C L-RIBULOKINASE.
ID0114C L-ARABINOSE UTILIZATION PROTEIN.
ID0115C ALDEHYDE DEHYDROGENASE, THERMOSTABLE (EC 1.2.1.3).
ID0116C CYTOCHROME CAA3 OXIDASE (SUBUNIT I).
ID0117C GLYCEROL-3-PHOSPHATE DEHYDROGENASE.
ID0118C GLYCEROL-3-PHOSPHATE DEHYDROGENASE (EC 1.1.99.5).
ID0119C OXOGLUTARATE DEHYDROGENASE.
ID0120C PHOSPHOENOLPYRUVATE CARBOXYLASE (EC 4.1.1.31) (PEPCASE) (PEP
ID0121C PHOSPHOENOLPYRUVATE CARBOXYLASE (EC 4.1.1.31) (PEPCASE) (PEP
ID0122C NADPH-FLAVIN OXIDOREDUCTASE.
ID0123C Protein encoded by *C. trachomatis* LGV II clone 4C9-18 #2.
ID0124C *Staphylococcus carnosus* nitrate reductase NarJ subunit.
ID0125C HYPOTHETICAL OXIDOREDUCTASE IN CSTA-AHPC INTERGENIC REGION.
ID0126C PROBABLE NADH-DEPENDENT BUTANOL DEHYDROGENASE 1 (EC 1.1.1.-)
ID0127C MG++/CITRATE COMPLEX TRANSPORTER.
ID0128C MALATE SYNTHASE.
ID0129C SUCCINATE DEHYDROGENASE FLAVOPROTEIN (EC 1.3.99.1).
ID0130C MALIC ENZYME (MALATE DEHYDROGENASE) (EC 1.1.1.38).
ID0131C SUCCINATE DEHYDROGENASE IRON-SULFUR PROTEIN (EC 1.3.99.1).
ID0132C MALATE OXIDOREDUCTASE (NAD) (MALIC ENZYME) (EC 1.1.1.38).
ID0133C FUMARATE HYDRATASE.
ID0134C NAD-DEPENDENT METHANOL DEHYDROGENASE.
ID0135C SUCCINYL-COA SYNTHETASE (ALPHA SUBUNIT).
ID0136C NADH-DEPENDENT FLAVIN OXIDOREDUCTASE, PUTATIVE.
ID0137C CYTOCHROME CAA3 OXIDASE (SUBUNIT III).
ID0138C CYTOCHROME CAA3 OXIDASE (SUBUNIT IV).
ID0139C GLYCEROL DEHYDROGENASE (EC 1.1.1.6) (GLDH).
ID0140C ALDEHYDE DEHYDROGENASE.
ID0141C ORF starting with ATG of length 942
ID0142C CYTOCHROME AA3 QUINOL OXIDASE SUBUNIT I (EC 1.10.3.).
ID0143C CYTOCHROME AA3 QUINOL OXIDASE SUBUNIT II (EC 1.10.3.).
ID0144C ASSIMILATORY NITRATE REDUCTASE CATALYTIC SUBUNIT (EC 1.7.99.
ID0145C RIESKE.
ID0146C PYRUVATE DEHYDROGENASE E1 COMPONENT, BETA SUBUNIT (EC 1.2.4.
ID0147C SUCCINYL-COA SYNTHETASE (BETA SUBUNIT).
ID0148C BH1718 PROTEIN.
ID0149C ACETOIN DEHYDROGENASE E1 COMPONENT (TPP-DEPENDENT BETA SUBUN
ID0150C HYPOTHETICAL 47.8 KDA PROTEIN.
ID0151C CITRATE PERMEASE/TRANSPORTER.
ID0152C PUTATIVE MALATE OXIDOREDUCTASE.
ID0153C ALDEHYDE DEHYDROGENASE, THERMOSTABLE (EC 1.2.1.3).
ID0154C MAGNESIUM CITRATE SECONDARY TRANSPORTER.
ID0155C DIHYDROLIPOAMIDE SUCCINYLTRANSFERASE COMPONENT OF 2-OXOGLUTA
ID0156C FERREDOXIN.
ID0157C ACETOIN DEHYDROGENASE E2 COMPONENT (DIHYDROLIPOAMIDEACETYLTR
ID0158C OXIDOREDUCTASE, N5,N10-METHYLENETETRAHYDROMETHANOPTERIN REDU
ID0159C PROBABLE ALDEHYDE DEHYDROGENASE YCBD (EC 1.2.1.3).
ID0160C CITRATE TRANSPORTER.
ID0161C GLYCOLATE OXIDASE SUBUNIT.
ID0162C BH3449 PROTEIN.
ID0163C PYRUVATE CARBOXYLASE.
ID0164C SULFONATE MONOOXYGENASE.
ID0165C ORF starting with ATG of length 702
ID0166C ATP SYNTHASE GAMMA SUBUNIT (EC 3.6.1.34).
ID0167C ATP SYNTHASE ALPHA SUBUNIT (EC 3.6.1.34).
ID0168C ATP SYNTHASE DELTA SUBUNIT (EC 3.6.1.34).
ID0169C ATP SYNTHASE B SUBUNIT (EC 3.6.1.34).
ID0170C GLYCEROPHOSPHODIESTER PHOSPHODIESTERASE.
ID0171C GLYCOLATE OXIDASE IRON-SULFUR SUBUNIT.
ID0172C METHYLMALONATE-SEMIALDEHYDE DEHYDROGENASE.
ID0173C BH0303 PROTEIN.
ID0174C ASSIMILATORY NITRITE REDUCTASE (SUBUNIT).
ID0175C ALDEHYDE DEHYDROGENASE, THERMOSTABLE (EC 1.2.1.3).
ID0176C PYRUVATE DEHYDROGENASE E1 COMPONENT, BETA SUBUNIT (EC 1.2.4.
ID0177CHR YVCT PROTEIN.
ID0178CP ORF1 (NA+/H+ ANTIPORTER).
ID0179CP MULTIPLE RESISTANCE AND PH REGULATION RELATED PROTEIN A.
ID0180CP NADH DEHYDROGENASE, PUTATIVE.
ID0181CP ORF1 (NA+/H+ ANTIPORTER).
ID0182CP YUFT PROTEIN.
ID0183CP NA+/H+ ANTIPORTER.
ID0184CR ORF starting with ATG of length 626
ID0185D SEPTUM SITE-DETERMINING PROTEIN.
ID0186D CELL-SHAPE DETERMINING PROTEIN.
ID0187D BH0975 PROTEIN.

ID0188D HYPOTHETICAL 53.5 KDA PROTEIN IN SPOIIE-HPT INTERGENIC REGIO
ID0189D YUKA PROTEIN.
ID0190D CENTROMERE-LIKE FUNCTION INVOLVED IN FORESPORE CHROMOSOME PA
ID0191 D CELL SHAPE DETERMINING PROTEIN (MREB-LIKE PROTEIN).
ID0192D CELL-CYCLE PROTEIN.
ID0193D STAGE V SPORULATION PROTEIN E.
ID0194D SPOIIIE PROTEIN.
ID0195D SPORULATION PROTEIN SPOIIIE.
ID0196D STAGE V SPORULATION PROTEIN E.
ID0197D GLUCOSE INHIBITED DIVISION PROTEIN A.
ID0198D BH0975 PROTEIN.
ID0199D SCDA.
ID0200D STAGE V SPORULATION PROTEIN E.
ID0201 D CELL-SHAPE DETERMINING PROTEIN.
ID0202D CELL-SHAPE DETERMINING PROTEIN.
ID0203D CAPSULAR POLYSACCHARIDE BIOSYNTHESIS.
ID0204D SPOIIIE PROTEIN.
ID0205D SA0276 PROTEIN.
ID0206D BH0975 PROTEIN.
ID0207D DIARRHEAL TOXIN.
ID0208D ORF starting with ATG of length 351
ID0209D ORF starting with ATG of length 1014
ID0210D CHROMOSOME PARTITION PROTEIN SMC.
ID0211D GLUCOSE-INHIBITED DIVISION PROTEIN.
ID0212D STAGE V SPORULATION PROTEIN E.
ID0213D CELL-SHAPE DETERMINING PROTEIN.
ID0214D LATENT NUCLEAR ANTIGEN.
ID0215D CELL-DIVISION INITIATION PROTEIN (SEPTUM PLACEMENT).
ID0216D CELL-DIVISION INITIATION PROTEIN (SEPTUM FORMATION).
ID0217D CELL-DIVISION PROTEIN (SEPTUM FORMATION).
ID0218D CELL-DIVISION PROTEIN (SEPTUM FORMATION).
ID0219D CHROMOSOME SEGREGATION SMC PROTEIN.
ID0220D STAGE II SPORULATION PROTEIN D.
ID0221 D CELL SHAPE DETERMINING PROTEIN (MREB-LIKE PROTEIN).
ID0222D GLUCOSE INHIBITED DIVISION PROTEIN A.
ID0223D ATP-BINDING MRP PROTEIN (MRP/NBP35 FAMILY).
ID0224D STAGE V SPORULATION PROTEIN E (REQUIRED FOR SPORE CORTEX SYN
ID0225D DNA TRANSLOCASE (STAGE III SPORULATION PROTEIN SPOIIIE).
ID0226D GLUCOSE-INHIBITED DIVISION PROTEIN.
ID0227D CENTROMERE-LIKE FUNCTION INVOLVED IN FORESPORE CHROMOSOME PA
ID0228D GLUCOSE-INHIBITED DIVISION PROTEIN.
ID0229D SPOIIIE PROTEIN.
ID0230D Amino acid sequence of a *Chlamydia trachomatis* protein.
ID0231 D STAGE V SPORULATION PROTEIN E.
ID0232D 186AA LONG HYPOTHETICAL MAF PROTEIN.
ID0233E CYSTATHIONINE GAMMA-SYNTHASE (O-SUCCINYLHOMOSERINE (THIOL)-L
ID0234E SA1216 PROTEIN.
ID0235E RIESKE.
ID0236E CEPHALOSPORIN ACYLASE.
ID0237E DIAMINOPIMELATE DECARBOXYLASE.
ID0238E 5-METHYLTETRAHYDROFOLATE S-HOMOCYSTEINE METHYLTRANSFERASE (EC
ID0239E TRYPTOPHAN SYNTHASE (ALPHA SUBUNIT).
ID0240E HOMOSYSTEIN METHYL TRANSFERASE.
ID0241E GLUTAMATE SYNTHASE (LARGE SUBUNIT).
ID0242E TRYPTOPHAN SYNTHASE (BETA SUBUNIT).
ID0243E PHOSPHORIBOSYL ANTHRANILATE ISOMERASE.
ID0244E HOMOCITRATE SYNTHASE.
ID0245E HOMOSYSTEIN METHYL TRANSFERASE.
ID0246E ORF starting with ATG of length 417
ID0247E PROLINE OXIDASE (PROLINE DEHYDROHENASE).
ID0248E ASPARAGINE SYNTHETASE.
ID0249E GAMMA-GLUTAMYL KINASE.
ID0250E L-CYSTEINE SULFURTRANSFERASE (IRON-SULFUR COFACTOR SYNTHESIS
ID0251E AMINOTRANSFERASE REQUIRED FOR NAD BIOSYNTHESIS (NIFS PROTEIN
ID0252E HYPOTHETICAL 38.3 KDA PROTEIN IN PEPT-KATB INTERGENIC REGION
ID0253E ORF starting with ATG of length 357
ID0254E AROMATIC AMINO ACID TRANSPORTER.
ID0255E FE-S CLUSTER FORMATION PROTEIN.
ID0256E GLUTAMINE TRANSPORT ATP-BINDING PROTEIN GLNQ.
ID0257E UROCANATE HYDRATASE.
ID0258E PROBABLE AMINOTRANSFERASE IN KATA 3'REGION (EC 2.6.-.-) (ORF
ID0259E DPPA.
ID0260E TETRAHYDRODIPICOLINATE SUCCINYLASE.
ID0261E ARGININOSUCCINATE SYNTHASE (CITRULLINE-ASPARATE LIGASE) (EC
ID0262E INDOLE-3-GLYCEROL PHOSPHATE SYNTHASE (EC 4.1.1.48) (IGPS).
ID0263E SA0678 PROTEIN.
ID0264E HOMOSERINE DEHYDROGENASE (EC 1.1.1.3).
ID0265E LYSINE-SPECIFIC PERMEASE.
ID0266E BH0591PROTEIN.
ID0267E PREPHENATE DEHYDROGENASE.
ID0268E HISTIDINOL-PHOSPHATE AMINOTRANSFERASE (EC 2.6.1.9) (IMIDAZOL
ID0269E HYPOTHETICAL 34.8 KDA PROTEIN PH1048.
ID0270E O-ACETYLHOMOSERINE SULFHYDRYLASE.
ID0271E *Arabidopsis thaliana* protein fragment SEQ ID NO: 8020.
ID0272E PROLINE OXIDASE (PROLINE DEHYDROHENASE).
ID0273E FOSFOMYCIN RESISTANCE PROTEIN.
ID0274E *Corynebacterium glutamicum* MP protein sequence SEQ ID NO:338
ID0275E ARGININOSUCCINATE LYASE (EC 4.3.2.1).
ID0276E HOMOSERINE KINASE (EC 2.7.1.39).
ID0277E ASPARTATE AMINOTRANSFERASE.
ID0278E PROBABLE CYSTEINE SYNTHASE (EC 4.2.99.8) (O-ACETYLSERINESULF
ID0279E GLYCINE DEHYDROGENASE SUBUNIT 1.
ID0280E PROLINE DEHYDROGENASE.
ID0281E SERINE ACETYLTRANSFERASE (EC 2.3.1.30) (SAT).
ID0282E LYSINE DECARBOXYLASE.
ID0283E YLMB PROTEIN.

ID0284E GLYCINE DEHYDROGENASE SUBUNIT 2.
ID0285E PROBABLE GLYCINE DEHYDROGENASE [DECARBOXYLATING] SUBUNIT 1(E
ID0286E BH3148 PROTEIN.
ID0287E ORNITHINE AMINOTRANSFERASE (EC 2.6.1.13) (ORNITHINE-OXO-ACI
ID0288E HYPOTHETICAL CYCLODEAMINASE Y4TK (EC 4.3.1.-).
ID0289E PEPTIDASE T (EC 3.4.11.-) (AMINOTRIPEPTIDASE) (TRIPEPTIDASE)
ID0290E ORF starting with ATG of length 1224
ID0291E YURW PROTEIN.
ID0292E HYDANTOINASE.
ID0293E 3-DEHYDROQUINATE SYNTHASE.
ID0294E S. pneumoniae phospho-2-dehydro-3-deoxyheptonate aldolase.
ID0295E CHORISMATE SYNTHASE (EC 4.6.1.4) (5-ENOLPYRUVYLSHIKIMATE-3-P
ID0296E BH1779 PROTEIN.
ID0297E UROCANATE HYDRATASE.
ID0298E TRANSCRIPTIONAL REGULATOR OF ARGININE METABOLISM EXPRESSION.
ID0299E HYPOTHETICAL 63.8 KDA PROTEIN IN SIPU-PBPC INTERGENIC REGION
ID0300E AMINOMETHYLTRANSFERASE.
ID0301E PUTATIVE THREONINE DEHYDRATASE (EC 4.2.1.16) (THREONINE DEAM
ID0302E BH2170 PROTEIN.
ID0303E AROMATIC AMINO ACID TRANSPORTER.
ID0304E GLUTAMATE SYNTHASE (LARGE SUBUNIT).
ID0305E AROMATIC AMINO ACID TRANSPORTER.
ID0306E AMINOTRANSFERASE.
ID0307E 0 DAY NEONATE SKIN cDNA, RIKEN FULL-LENGTH ENRICHED LIBRARY,
ID0308E DIAMINOBUTYRIC ACID AMINOTRANSFERASE.
ID0309E L-SERINE DEHYDRATASE BETA SUBUNIT.
ID0310E L-SERINE DEHYDRATASE ALPHA SUBUNIT.
ID0311E BH0606 PROTEIN.
ID0312E TRYPTOPHAN 2,3-DIOXYGENASE, PUTATIVE.
ID0313E XAA-PRO DIPEPTIDASE.
ID0314E CYSTEINE SYNTHASE A (EC 4.2.99.8).
ID0315E PROBABLE PERMEASE OF ABC TRANSPORTER.
ID0316E SA1675 PROTEIN.
ID0317E HIGH-AFFINITY PERIPLASMIC GLUTAMINE BINDING PROTEIN.
ID0318E ORF starting with ATG of length 1137
ID0319E GLYCINE BETAINE TRANSPORT SYSTEM PERMEASE PROTEIN.
ID0320E ORF starting with ATG of length 499
ID0321E SHIKIMATE 5-DEHYDROGENASE.
ID0322E ARGININOSUCCINATE LYASE (EC 4.3.2.1) (ARGINOSUCCINASE) (ASAL
ID0323E PROLIDASE (PROLINE DIPEPTIDASE) (EC 3.4.13.9).
ID0324E LEUCINE DEHYDROGENASE (EC 1.4.1.9) (LEUDH).
ID0325E ATPASE HOMOLOG GBUA.
ID0326E CYSTEINE SYNTHASE.
ID0327E BH3306 PROTEIN.
ID0328E OLIGOENDOPEPTIDASE F.
ID0329E BH1629 PROTEIN.
ID0330E 5-METHYLTETRAHYDROFOLATE S-HOMOCYSTEINE METHYLTRANSFERASE (EC
ID0331E BH1629 PROTEIN.
ID0332E BH0654 PROTEIN.
ID0333E LYSINE DECARBOXYLASE.
ID0334E GLYCINE BETAINE-BINDING PROTEIN PRECURSOR.
ID0335E BH1629 PROTEIN.
ID0336E ORF starting with ATG of length 525
ID0337E GLUTAMINE ABC TRANSPORTER (GLUTAMINE-BINDING PROTEIN).
ID0338E LYSINE DECARBOXYLASE.
ID0339E GLUTAMINE ABC TRANSPORTER (INTEGRAL MEMBRANE PROTEIN).
ID0340E GLUTAMINE ABC TRANSPORTER (INTEGRAL MEMBRANE PROTEIN).
ID0341E ORF starting with ATG of length 492
ID0342E GLUTAMINE SYNTHETASE.
ID0343E CYSS.
ID0344E CYSTEINE SYNTHASE.
ID0345E ORF starting with ATG of length 240
ID0346E CYSTATHIONINE GAMMA-LYASE.
ID0347E HYPOTHETICAL 39.7 KDA PROTEIN IN GLNQ-ANSR INTERGENIC REGION
ID0348E ASPARTATE AMMONIA-LYASE.
ID0349E 5-METHYLTETRAHYDROFOLATE S-HOMOCYSTEINE METHYLTRANSFERASE (EC
ID0350E ALANINE DEHYDROGENASE (STAGE V SPORULATION PROTEIN N) (EC 1.
ID0351E GLUTAMINE SYNTHETASE.
ID0352E GLUTAMINE SYNTHETASE (GLUTAMATE-AMMONIA LIGASE) (EC 6.3.1.2
ID0353E T. vaginalis homocysteinase #2.
ID0354E BH0774 PROTEIN.
ID0355E XAA-PRO DIPEPTIDASE.
ID0356E CYSTATHIONINE GAMMA-LYASE.
ID0357E NON-ESSENTIAL GENE FOR COMPETENCE (PYRROLINE-5-CARBOXYLATE R
ID0358E MLR3804PROTEIN.
ID0359E THERMOSTABLE DIPEPTIDASE BDP.
ID0360E N-CARBAMOYL-L-AMINO ACID AMIDOHYDROLASE (AMAB) (EC 3.5.1.).
ID0361E THREONINE DEHYDRATASE.
ID0362E MLR3804PROTEIN.
ID0363E NAD BIOSYNTHESIS.
ID0364E 3-PHOSPHOSHIKIMATE 1-CARBOXYVINYL-TRANSFERASE.
ID0365E GLUTAMATE DEHYDROGENASE.
ID0366E PREPHENATE DEHYDRATASE.
ID0367E N-CARBAMOYL-L-AMINO ACID AMIDOHYDROLASE (EC 3.5.1.-) (L-CARB
ID0368E 3-PHOSPHOSHIKIMATE 1-CARBOXYVINYL-TRANSFERASE.
ID0369E HYPOTHETICAL 39.4 KDA OXIDOREDUCTASE IN HOM-MRGA INTERGENIC
ID0370E PROBABLE D-SERINE DEHYDRATASE (EC 4.2.1.14) (D-SERINE DEAMIN
ID0371E SERINE DEAMINASE (FRAGMENT).
ID0372E ANTHRANILATE PHOSPHORIBOSYLTRANSFERASE (EC 2.4.2.18).
ID0373E HISTIDINOL DEHYDROGENASE (EC 1.1.1.23).
ID0374E ATP PHOSPHORIBOSYLTRANSFERASE (EC 2.4.2.17).
ID0375E N-ACETYLORNITHINE AMINOTRANSFERASE (EC 2.6.1.11).
ID0376E GLYCINE BETAINE/CARNITINE/CHOLINE ABC TRANSPORTER (ATP-BINDI ID0377E ACETYLORNITHINE DEACETYLASE (EC 3.5.1.16) (ACETYLORNITHINASE
ID0378E ORF starting with ATG of length 778
ID0379E GLYCINE DEHYDROGENASE SUBUNIT 2.
ID0380E SA0677 PROTEIN.
ID0381E CHOLINE ABC TRANSPORTER ATP BINDING PROTEIN.
ID0382E ARGININOSUCCINATE LYASE.
ID0383E PUTATIVE GLYCINE-BETAINE BINDING PERMEASE PROTEIN.
ID0384E ORF starting with ATG of length 564
ID0385E 3-ISOPROPYLMALATE DEHYDROGENASE (EC 1.1.1.85).
ID0386E DEF-6 PROTEIN.
ID0387E YUSX PROTEIN.
ID0388E 3-ISOPROPYLMALATE DEHYDRATASE SMALL SUBUNIT (EC 4.2.1.33).
ID0389E 3-ISOPROPYLMALATE DEHYDRATASE LARGE SUBUNIT (EC 4.2.1.33).
ID0390E PROBABLE PEPTIDASE YUXL (EC 3.4.21.-).
ID0391E ORF starting with ATG of length 612
ID0392E PHOSPHORIBOSYLFORMIMINO-5-AMINOIMIDAZOLE CARBOXAMIDE RIBOTID
ID0393E ABC TRANSPORTER (ATP-BINDING PROTEIN).
ID0394E PROBABLE AMINO-ACID ABC TRANSPORTER PERMEASE PROTEIN YCKA.
ID0395E PROBABLE ABC TRANSPORTER EXTRACELLULAR BINDING PROTEIN YCKB
ID0396E HOMOSERINE DEHYDROGENASE.
ID0397E ORF starting with ATG of length 492
ID0398E AMINO ACID CARRIER PROTEIN (SODIUM/ALANINE SYMPORTER).
ID0399E 3-HYDROXY-3-METHYLGLUTARATE-COA LYASE.
ID0400E XAA-PRO DIPEPTIDASE.
ID0401E AMIDOTRANSFERASE HISH (EC 2.4.2.-).
ID0402E PHOSPHORIBOSYLFORMIMINO-5-AMINOIMIDAZOLE CARBOXAMIDE RIBOTID
ID0403E SHIKIMATE KINASE.
ID0404E ASPARAGINE SYNTHETASE [GLUTAMINE-HYDROLYZING] 3 (EC 6.3.5.4)
ID0405E HYDANTOINASE.
ID0406E HYPOTHETICAL 39.5 KDA PROTEIN.
ID0407E ORF starting with ATG of length 465
ID0408E CYSTEINE SYNTHASE.
ID0409E PEPTIDASE, M20/M25/M40 FAMILY.
ID0410E ILVA.
ID0411E HYPOTHETICAL 33.1 KDA PROTEIN IN MTLD-SIPU INTERGENIC REGION
ID0412E GAMMA-GLUTAMYL PHOSPHATE REDUCTASE (GPR) (EC 1.2.1.41) (GLUT
ID0413E CYCLASE.
ID0414E HISTIDINE BIOSYNTHESIS BIFUNCTIONAL PROTEIN HISIE [INCLUDES:
ID0415E SA0010 PROTEIN.
ID0416E DIAMINOPIMELATE DECARBOXYLASE.
ID0417E BH3875 PROTEIN.
ID0418E PROBABLE PEPTIDASE YUXL (EC 3.4.21.-).
ID0419E ASPARTATE AMMONIA-LYASE (EC 4.3.1.1) (ASPARTASE).
ID0420E PROBABLE AMINO-ACID ABC TRANSPORTER ATP-BINDING PROTEIN Y4TH
ID0421E ACETYLORNITHINE AMINOTRANSFERASE (EC 2.6.1.11) (ACOAT).
ID0422E ORNITHINE AMINOTRANSFERASE.
ID0423E BH3875 PROTEIN.
ID0424E DIAMINOPIMELATE EPIMERASE.
ID0425E MEMBRANE PERMEASE OPUCD.
ID0426E AMINOTRANSFERASE REQUIRED FOR NAD BIOSYNTHESIS (NIFS PROTEIN
ID0427E GLYCINE DEHYDROGENASE SUBUNIT 2.
ID0428E GLYCINE DEHYDROGENASE SUBUNIT 1.
ID0429E ORNITHINE AMINOTRANSFERASE (EC 2.6.1.13) (ORNITHINE-OXO-ACI
ID0430E 3-DEHYDROQUINATE SYNTHASE.
ID0431E HISTIDASE (HISTIDINE AMMONIA-LYASE) (EC 4.3.1.3).
ID0432E 3-PHOSPHOSHIKIMATE 1-CARBOXYVINYL-TRANSFERASE.
ID0433E BH0606 PROTEIN.
ID0434E SHIKIMATE KINASE.
ID0435E ORF starting with ATG of length 327
ID0436EF CARBAMOYL-PHOSPHATE SYNTHETASE (CATALYTIC SUBUNIT).
ID0437EF CARBAMOYL-PHOSPHATE SYNTHETASE (CATALYTIC SUBUNIT).
ID0438EF CARBAMOYL-PHOSPHATE SYNTHASE, PYRIMIDINE-SPECIFIC, SMALL CHA
ID0439EF CARBAMOYL-PHOSPHATE SYNTHETASE (CATALYTIC SUBUNIT).
ID0440EF ARGININE SPECIFIC CARBAMOYL-PHOSPHATE SYNTHASE SUBUNIT A (EC
ID0441EF CARBAMOYL-PHOSPHATE SYNTHETASE (CATALYTIC SUBUNIT).
ID0442EF CARBAMOYL-PHOSPHATE SYNTHETASE (CATALYTIC SUBUNIT).
ID0443EF ORF starting with ATG of length 462
ID0444EF CARBAMOYL-PHOSPHATE SYNTHASE LARGE SUBUNIT.
ID0445EF ARGININE SPECIFIC CARBAMOYL-PHOSPHATE SYNTHASE SUBUNIT B (EC
ID0446EF *H. pylori* cytoplasmic protein 04ge10816orf2.
ID0447EF ARGININE SPECIFIC CARBAMOYL-PHOSPHATE SYNTHASE SUBUNIT B (EC
ID0448EG HYPOTHETICAL 69.4 KDA PROTEIN IN PERR-ARGF INTERGENIC REGION
ID0449EG HYPOTHETICAL 69.4 KDA PROTEIN IN PERR-ARGF INTERGENIC REGION
ID0450EH KETOL-ACID REDUCTOISOMERASE (EC 1.1.1.86).
ID0451EH ACETOLACTATE SYNTHASE LARGE SUBUNIT.
ID0452EH KETOL-ACID REDUCTOISOMERASE (EC 1.1.1.86).
ID0453EH ACETOLACTATE SYNTHASE LARGE SUBUNIT (EC 4.1.3.18) (AHAS) (ACE
ID0454EH ANTHRANILATE SYNTHASE.
ID0455EH MYO-INOSITOL CATABOLISM.
ID0456EH ANTHRANILATE SYNTHASE BETA SUBUNIT.
ID0457EH PARA-AMINOBENZOATE/ANTHRANILATE SYNTHASE GLUTAMINE AMIDOTRAN
ID0458EH 4-AMINO-4-DEOXYCHORISMATE LYASE (EC 4.).
ID0459EH PARA-AMINOBENZOATE SYNTHASE COMPONENT I (EC 4.1.3.).
ID0460EH ANTHRANILATE SYNTHASE COMPONENT I (EC 4.1.3.27).
ID0461EH ORF starting with ATG of length 1008
ID0462EH MYO-INOSITOL CATABOLISM.
ID0463EH PARA-AMINOBENZOATE/ANTHRANILATE SYNTHASE GLUTAMINE AMIDOTRAN ID0464EH 4-AMINO-4-DEOXYCHORISMATE LYASE (EC 4.-.-.-) (ADC LYASE) (AD
ID0465EH ORF starting with ATG of length 840
ID0466EH ORF starting with TTG or GTG of length 546
ID0467EHR NA+/MYO-INOSITOL COTRANSPORTER.
ID0468EHR HYPOTHETICAL 55.0 KDA PROTEIN IN EPR-GALK INTERGENIC REGION.
ID0469EHR HYPOTHETICAL PROTEIN HI1728.
ID0470EHR OSMOREGULATED PROLINE TRANSPORTER (SODIUM/PROLINE SYMPORTER)
ID0471EHR NA+/MYO-INOSITOL COTRANSPORTER.
ID0472EHR ORF starting with ATG of length 1269
ID0473EHR BH1820 PROTEIN.
ID0474EJ L-ASPARAGINASE (EC 3.5.1.1) (L-ASPARAGINE AMIDOHYDROLASE).
ID0475EM PROBABLE 5-DEHYDRO-4-DEOXYGLUCARATE DEHYDRATASE (EC 4.2.1.41
ID0476EM PROBABLE 5-DEHYDRO-4-DEOXYGLUCARATE DEHYDRATASE (EC 4.2.1.41
ID0477EM HYPOTHETICAL 33.3 KDA PROTEIN IN PERR-ARGF INTERGENIC REGION
ID0478EP OLIGOPEPTIDE ABC TRANSPORTER (OLIGOPEPTIDE-BINDING PROTEIN).
ID0479EP ORF starting with ATG of length 408
ID0480EP DIPEPTIDE TRANSPORT SYSTEM PERMEASE PROTEIN DPPB.
ID0481EP BH1159 PROTEIN.
ID0482EP DIPEPTIDE TRANSPORT SYSTEM PERMEASE PROTEIN DPPC.
ID0483EP OLIGOPEPTIDE ABC TRANSPORTER (OLIGOPEPTIDE-BINDING PROTEIN).
ID0484EP OLIGOPEPTIDE ABC TRANSPORTER (OLIGOPEPTIDE-BINDING PROTEIN).
ID0485EP OLIGOPEPTIDE ABC TRANSPORTER (ATP-BINDING PROTEIN).
ID0486EP 420AA LONG HYPOTHETICAL OLIGOPEPTIDE TRANSPORT ATP-BINDING P
ID0487EP OLIGOPEPTIDE ABC TRANSPORTER (PERMEASE).
ID0488EP OLIGOPEPTIDE ABC TRANSPOTER (OLIGOPEPTIDE-BINDING PROTEIN).
ID0489EP OPPB PROTEIN.
ID0490EP OLIGOPEPTIDE ABC TRANSPORTER (ATP-BINDING PROTEIN).
ID0491EP OLIGOPEPTIDE ABC TRANSPOTER (OLIGOPEPTIDE-BINDING PROTEIN).
ID0492EP OLIGOPEPTIDE TRANSPORT ATP-BINDING PROTEIN APPF.
ID0493EP *B. subtilis* oppC membrane protein.
ID0494EP ORF starting with ATG of length 768
ID0495EP OLIGOPEPTIDE ABC TRANSPORTER, PERMEASE PROTEIN.
ID0496EP OLIGOPEPTIDE-BINDING PROTEIN APPA PRECURSOR.
ID0497EP OLIGOPEPTIDE ABC TRANSPORTER ATP-BINDING PROTEIN.
ID0498EP DIPEPTIDE-BINDING PROTEIN DPPE PRECURSOR.
ID0499EP OLIGOPEPTIDE ABC TRANSPORTER ATP-BINDING PROTEIN HOMOLOG.
ID0500EP PROBABLE OLIGOPEPTIDE TRANSPORT ATP-BINDING PROTEIN APPF (FR
ID0501EP OLIGOPEPTIDE ABC TRANSPORTER ATP-BINDING PROTEIN.
ID0502EP OLIGOPEPTIDE ABC TRANSPORTER (PERMEASE).
ID0503EP OLIGOPEPTIDE ABC TRANSPORTER (ATP-BINDING PROTEIN).
ID0504EP OLIGOPEPTIDE ABC TRANSPORTER (ATP-BINDING PROTEIN).
ID0505EP DIPEPTIDE TRANSPORT ATP-BINDING PROTEIN DPPD.
ID0506EP *Enterococcus faecalis* antigenic polypeptide fragment EF045.
ID0507EP OLIGOPEPTIDE ABC TRANSPORTER (PERMEASE).
ID0508EP ORF starting with ATG of length 711
ID0509EP DIPEPTIDE ABC TRANSPORTER (DIPEPTIDE-BINDING PROTEIN).
ID0510EP OLIGOPEPTIDE ABC TRANSPORTER (PERMEASE).
ID0511EP OLIGOPEPTIDE ABC TRANSPORTER (PERMEASE).
ID0512EP DPPD PROTEIN.
ID0513EP OLIGOPEPTIDE ABC TRANSPORTER (OLIGOPEPTIDE-BINDING PROTEIN).
ID0514EP OLIGOPEPTIDE ABC TRANSPORTER (OLIGOPEPTIDE-BINDING PROTEIN).
ID0515EP DIPEPTIDE ABC TRANSPORTER (PERMEASE).
ID0516EP DPPB PROTEIN.
ID0517EP DIPEPTIDE TRANSPORTER PROTEIN DPPA (FRAGMENT).
ID0518EP DIPEPTIDE TRANSPORT SYSTEM PERMEASE PROTEIN DPPB.
ID0519EP ORF starting with ATG of length 1161
ID0520EP OLIGOPEPTIDE ABC TRANSPORTER (PERMEASE).
ID0521EP OLIGOPEPTIDE TRANSPORT SYSTEM INTEGRAL MEMBRANE PROTEIN.
ID0522EP DIPEPTIDE ABC TRANSPORTER (PERMEASE).
ID0523EP OLIGOPEPTIDE ABC TRANSPORTER (PERMEASE).
ID0524EP OLIGOPEPTIDE ABC TRANSPORTER (OLIGOPEPTIDE-BINDING PROTEIN).
ID0525EP OLIGOPEPTIDE ABC TRANSPORTER (PERMEASE).
ID0526EP OLIGOPEPTIDE ABC TRANSPORTER (ATP-BINDING PROTEIN).
ID0527EP OLIGO/DIPEPTIDE TRANSPORT, ATP BINDING PROTEIN. CARBOXY-END
ID0528EP OPPF PROTEIN.
ID0529EP SA0851PROTEIN.
ID0530EP OLIGOPEPTIDE ABC TRANSPORTER, ATP-BINDING PROTEIN.
ID0531EP ORF starting with ATG of length 708
ID0532EPGR *Corynebacterium glutamicum* MCT protein SEQ ID NO:522.
ID0533ER GLUTAMATE SYNTHASE SMALL CHAIN.
ID0534ER ZINC-CONTAINING ALCOHOL DEHYDROGENASE.
ID0535ER GLUTAMATE SYNTHASE, BETA SUBUNIT.
ID0536ER DEHYDROGENASE.
ID0537ER *Arabidopsis thaliana* protein fragment SEQ ID NO: 1993.
ID0538ER SORBITOL DEHYDROGENASE (EC 1.1.1.14).
ID0539ER SORBITOL DEHYDROGENASE (EC 1.1.1.14).
ID0540ER SORBITOL DEHYDROGENASE (EC 1.1.1.14).
ID0541ER YTVP.

ID0542ER GLUTAMATE SYNTHASE (SMALL SUBUNIT).
ID0543ER GLUTAMATE SYNTHASE (SMALL SUBUNIT).
ID0544ER FISSION YEAST (FRAGMENT).
ID0545FE PHOSPHORIBOSYL PYROPHOSPHATE SYNTHETASE (EC 2.7.6.1).
ID0546FE PHOSPHORIBOSYL PYROPHOSPHATE SYNTHETASE (EC 2.7.6.1).
ID0547FE PHOSPHORIBOSYL PYROPHOSPHATE SYNTHETASE (EC 2.7.6.1).
ID0548F PHOSPHORIBOSYLGLYCINAMIDE SYNTHETASE.
ID0549F ORF starting with ATG of length 531
ID0550F PHOSPHORIBOSYLAMINOIMIDAZOLE SYNTHETASE.
ID0551F PHOSPHORIBOSYLGLYCINAMIDE FORMYLTRANSFERASE.
ID0552F GUANYLATE KINASE (EC 2.7.4.8).
ID0553F CYTOSINE PERMEASE.
ID0554F PHOSPHORIBOSYLFORMYLGLYCINAMIDE SYNTHETASE I.
ID0555F DIHYDROOROTASE.
ID0556F URACIL TRANSPORTER (PERMEASE).
ID0557F PHOSPHORIBOSYLAMINOIMIDAZOLE-CARBOXAMIDE FORMYLTRANSFERASE/IM
ID0558F THIAMIN BIOSYNTHESIS.
ID0559F TGLUTAMINE AMIDOTRANSFERASE
ID0560F PHOSPHORIBOSYLAMINOIMIDAZOLE SYNTHETASE.
ID0561F PHOSPHORIBOSYLGLYCINAMIDE FORMYLTRANSFERASE.
ID0562F INOSINE-URIDINE NUCLEOSIDE HYDROLASE.
ID0563F DEOXYCYTIDINE TRIPHOSPHATE DEAMINASE.
ID0564F MTA/SAH NUCLEOSIDASE (P46).
ID0565F ASPARTATE CARBAMOYLTRANSFERASE.
ID0566F DIHYDROOROTASE (EC 3.5.2.3) (DHOASE).
ID0567F ADENYLOSUCCINATE LYASE (EC 4.3.2.2) (ADENYLOSUCCINASE) (ASL)
ID0568F METHYLPHOSPHOTRIESTER-DNA ALKYLTRANSFERASE.
ID0569F THYMIDYLATE KINASE (EC 2.7.4.9).
ID0570F URACIL PHOSPHORIBOSYLTRANSFERASE (EC 2.4.2.9) (UMP PYROPHOSP
ID0571F PUR OPERON REPRESSOR.
ID0572F CYTOSINE PERMEASE.
ID0573F TRANSCRIPTIONAL REPRESSOR OF THE PURINE OPERON.
ID0574F THYMIDYLATE SYNTHASE B (EC 2.1.1.45).
ID0575F ORF starting with ATG of length 528
ID0576F PHOSPHORIBOSYLAMINOIMIDAZOLE-CARBOXAMIDE FORMYLTRANSFERASE/IM
ID0577F FORMYLTETRAHYDROFOLATE DEFORMYLASE.
ID0578F ORF starting with ATG of length 1554
ID0579F THYMIDYLATE SYNTHASE B (EC 2.1.1.45).
ID0580F BH3453 PROTEIN.
ID0581F OROTIDINE 5'-PHOSPHATE DECARBOXYLASE.
ID0582F OROTATE PHOSPHORIBOSYLTRANSFERASE.
ID0583F DIHYDROOROTATE DEHYDROGENASE, CATALYTIC SUBUNIT (EC 1.3.3.1)
ID0584F PHOSPHORIBOSYLFORMYLGLYCINAMIDE SYNTHETASE I.
ID0585F PHOSPHORIBOSYLFORMYLGLYCINAMIDE SYNTHETASE II.
ID0586F D-HYDANTOINASE (EC 3.5.2.2) (DIHYDROPYRIMIDINASE) (DHPASE).
ID0587F PROBABLE OXIDOREDUCTASE.
ID0588F XANTHINE PHOSPHORIBOSYLTRANSFERASE.
ID0589F PUTATIVE INOSINE-URIDINE PREFERRING NUCLEOSIDE HYDROLASE.
ID0590F NUCLEOSIDE TRANSPORTER.
ID0591F BH1014 PROTEIN.
ID0592F ADENINE DEAMINASE (EC 3.5.4.2) (ADENASE) (ADENINE AMINASE).
ID0593F ADENINE DEAMINASE.
ID0594F PYRIMIDINE-NUCLEOSIDE PHOSPHORYLASE (EC 2.4.2.2).
ID0595F ADENYLATE KINASE (EC 2.7.4.3) (ATP-AMP TRANSPHOSPHORYLASE).
ID0596F ADENINE DEAMINASE.
ID0597F LATE COMPETENCE OPERON REQUIRED FOR DNA BINDING AND UPTAKE.
ID0598F THYMIDINE KINASE (EC 2.7.1.21).
ID0599F CYTOSINE PERMEASE/TRANSPORT.
ID0600F S. pneumoniae adenylosuccinate lyase.
ID0601F ADENYLOSUCCINATE SYNTHETASE.
ID0602F GMP SYNTHASE [GLUTAMINE-HYDROLYZING] (EC 6.3.5.2) (GLUTAMINE
ID0603F ADENINE PHOSPHORIBOSYLTRANSFERASE.
ID0604F NUCLEOTIDASE PRECURSOR.
ID0605F ORF starting with ATG of length 247
ID0606F GMP SYNTHETASE.
ID0607F CYTIDYLATE KINASE (EC 2.7.4.14) (CK) (CYTIDINE MONOPHOSPHATE
ID0608F RIBONUCLEOSIDE-DIPHOSPHATE REDUCTASE BETA CHAIN (EC 1.17.4.1
ID0609F RIBONUCLEOSIDE-DIPHOSPHATE REDUCTASE ALPHA CHAIN (EC 1.17.4.
ID0610F BH1015 PROTEIN.
ID0611F BH1015 PROTEIN.
ID0612F MTA/SAH NUCLEOSIDASE (P46).
ID0613F TRANSCRIPTIONAL ATTENUATION OF THE PYRIMIDINE OPERON/URACILP
ID0614F URACIL TRANSPORTER (PERMEASE).
ID0615F PHOSPHORIBOSYLAMINOIMIDAZOLE SUCCINOCARBOXAMIDE SYNTHETASE.
ID0616F ORF starting with ATG of length 1377
ID0617F ADENYLOSUCCINATE LYASE.
ID0618F PHOSPHORIBOSYLAMINOIMIDAZOLE SUCCINOCARBOXAMIDE SYNTHETASE.
ID0619F BH0627 PROTEIN.
ID0620F PHOSPHORIBOSYLFORMYLGLYCINAMIDE SYNTHASE I (EC 6.3.5.3) (F
ID0621F FGAM SYNTHETASE (FRAGMENT).
ID0622F PHOSPHORIBOSYLFORMYLGLYCINAMIDE SYNTHETASE I.
ID0623F PHOSPHORIBOSYLFORMYLGLYCINAMIDE SYNTHETASE I.
ID0624F URACIL TRANSPORTER (PERMEASE).
ID0625F PHOSPHORIBOSYLAMINOIMIDAZOLE SUCCINOCARBOXAMIDE SYNTHETASE.
ID0626F BH0627 PROTEIN.
ID0627F PHOSPHORIBOSYLFORMYLGLYCINAMIDE SYNTHETASE II.
ID0628F BH1014 PROTEIN.
ID0629F DNA TOPOLOGY MODULATION PROTEIN FLAR-RELATED PROTEIN.

ID0630F HYPOTHETICAL 43.5 KDA PROTEIN.
ID0631F ADENINE PHOSPHORIBOSYLTRANSFERASE.
ID0632FGR HIT-LIKE PROTEIN INVOLVED IN CELL-CYCLE REGULATION.
ID0633FGR ORF starting with ATG of length 333
ID0634FGR CELL-CYCLE REGULATION HISTIDINE TRIAD (HIT FAMILY).
ID0635FJ HYPOTHETICAL 17.8 KDA PROTEIN IN SERS-DNAH INTERGENIC REGION
ID0636FJ YKOA.
ID0637FR BH1692 PROTEIN.
ID0638FR HYPOTHETICAL PROTEIN MTH1505.
ID0639FR *E. coli* cytosine-deaminase.
ID0640GC HYPOTHETICAL GLYCOSYL TRANSFERASE.
ID0641GE GLUCONATE PERMEASE.
ID0642GE BH3897 PROTEIN.
ID0643GE LOW-AFFINITY GLUCONATE TRANSPORTER (GLUCONATE PERMEASE) (GNT
ID0644GE BH3897 PROTEIN.
ID0645GE GLUCONATE PERMEASE.
ID0646GE PUTATIVE GLUCONATE PERMEASE (FRAGMENT).
ID0647GE GNTP (GLUCONATE PERMEASE).
ID0648GE PUTATIVE GLUCONATE PERMEASE (FRAGMENT).
ID0649GE GLUCONATE PERMEASE.
ID0650GE GNTP (GLUCONATE PERMEASE).
ID0651GE BH3897 PROTEIN.
ID0652GEPR BH1161PROTEIN.
ID0653GEPR MULTIDRUG RESISTANCE EFFLUX PUMP.
ID0654GEPR BH1161PROTEIN.
ID0655GEPR PUTATIVE SUGAR EFFLUX TRANSPORTER DR1322.
ID0656GEPR ORF starting with ATG of length 432
ID0657GEPR ORF starting with ATG of length 534
ID0658GEPR ORF starting with ATG of length 1077
ID0659GEPR ORF starting with ATG of length 735
ID0660GEPR ORF starting with ATG of length 1092
ID0661GEPR MULTIDRUG RESISTANCE PROTEIN 2 (MULTIDRUG-EFFLUX TRANSPORTER
ID0662GEPR MULTIDRUG RESISTANCE PROTEIN 2 (MULTIDRUG-EFFLUX TRANSPORTER
ID0663GEPR ORF starting with ATG of length 885
ID0664GEPR HYPOTHETICAL 44.9 KDA PROTEIN.
ID0665GEPR TRANSPORTER.
ID0666GEPR HOMOLOGUE OF MULTIDRUG RESISTANCE PROTEIN B, EMRB, OF E. COL
ID0667GER BH0725 PROTEIN.
ID0668GER ORF starting with ATG of length 522
ID0669GER HYPOTHETICAL 33.6 KDA PROTEIN IN CSPC-NAP INTERGENIC REGION.
ID0670GER BH1931PROTEIN.
ID0671G LACTOSE TRANSPORT SYSTEM PERMEASE PROTEIN LACG.
ID0672G PROBABLE ABC-TRANSPORT PROTEIN, INNER MEMBRANE COMPONENT.
ID0673G PUTATIVE TRANSPORT SYSTEM INNER MEMBRANE PROTEIN.
ID0674G CONSERVED HYPOTHETICAL PROTEIN.
ID0675G PUTATIVE PTS ENZYME III.
ID0676G PHOSPHOENOLPYRUVATE MUTASE.
ID0677G GALACTOKINASE.
ID0678G L-ARABINOSE ABC TRANSPORTER (ATP-BINDING PROTEIN).
ID0679G L-ARABINOSE MEMBRANE PERMEASE.
ID0680G PUTATIVE TRANSKETOLASE N-TERMINAL SECTION (EC 2.2.1.1) (TK).
ID0681G HYPOTHETICAL 37.6 KDA PROTEIN.
ID0682G *Arabidopsis thaliana* protein fragment SEQ ID NO: 43508.
ID0683G Lung cancer associated polypeptide sequence SEQ ID 769.
ID0684G *Paenibacillus* pabuli 2,6-beta-D-fructan hydrolase.
ID0685G *Streptococcus pneumoniae* photomutase yhxB.
ID0686G SUGAR ABC TRANSPORTER (PERMEASE).
ID0687G BETA-GLUCOSIDASE (EC 3.2.1.21).
ID0688G XYLOSIDASE/ARABINOSIDASE [INCLUDES: BETA-XYLOSIDASE (EC 3.2.
ID0689G ALPHA-GLUCURONIDASE.
ID0690G RHAMNULOKINASE.
ID0691G SA0233 PROTEIN.
ID0692G SUGAR HYDROLASE.
ID0693G ORF starting with ATG of length 348
ID0694G ALGM1.
ID0695G TRANSMEMBRANE LIPOPROTEIN.
ID0696G *S. pneumoniae* derived protein #253.
ID0697G PHOSPHOENOLPYRUVATE-PROTEIN PHOSPHOTRANSFERASE (EC 2.7.3.9)
ID0698G ALTRONATE HYDROLASE.
ID0699G GLUCONOKINASE (EC 2.7.1.12) (GLUCONATE KINASE).
ID0700G ALPHA-GLUCOSIDASE.
ID0701G PHOSPHO-CELLOBIASE (EC 3.2.1.-).
ID0702G ORF starting with ATG of length 906
ID0703G YBCL PROTEIN.
ID0704G ABC TRANSPORTER SUGAR PERMEASE.
ID0705G ABC TRANSPORTER SUGAR PERMEASE.
ID0706G BETA-GALACTOSIDASE.
ID0707G PUTATIVE N-ACETYLMANNOSAMINE-6-P EPIMERASE.
ID0708G GLUCONATE-6-PHOSPHATE DEHYDROGENASE, DECARBOXYLATING.
ID0709G BH1117 PROTEIN.
ID0710G PUTATIVE GLUTAMYL-AMINOPEPTIDASE (FRAGMENT).
ID0711G ENDO-1,4-BETA-GLUCANASE.
ID0712G Non-maltogenic exoamylase amino acid sequence.
ID0713G Non-maltogenic exoamylase amino acid sequence.
ID0714G ENOLASE (EC 4.2.1.11) (2-PHOSPHOGLYCERATE DEHYDRATASE) (2-PH
ID0715G ENOLASE (2-PHOSPHOGLYCERATE DEHYDRATASE) (EC 4.2.1.11).
ID0716G *Enterococcus faecalis* protein EF048.
ID0717G XYLQ.
ID0718G PROBABLE SUGAR TRANSPORT PROTEIN (PERMEASE).
ID0719G BH1905 PROTEIN.
ID0720G PROBABLE FRUCTOSE-BISPHOSPHATE ALDOLASE 2 (EC 4.1.2.13).
ID0721G SPERMIDINE/PUTRESCINE TRANSPORT ATP-BINDING PROTEIN POTA.
ID0722G 6-PHOSPHO-BETA-GLUCOSIDASE.
ID0723G SUGAR TRANSPORT SYSTEM (PERMEASE) (BINDING PROTEIN DEPENDENT
ID0724G HYPOTHETICAL 38.4 KDA PROTEIN IN DPPE-HMP INTERGENIC REGION.
ID0725G PROBABLE ABC-TRANSPORT PROTEIN, INNER MEMBRANE COMPONENT.
ID0726G BETA-GLUCOSIDASE.
ID0727G HYPOTHETICAL 48.4 KDA PROTEIN.

ID0728G MALTOSE TRANSPORTOR ATP-BINDING PROTEIN.
ID0729G SUGAR ABC TRANSPORTER (PERMEASE).
ID0730G PUTATIVE CARBOXYVINYL-CARBOXYPHOSPHONATE PHOSPHORYLMUTASE (EC
ID0731G PTS SYSTEM, FRUCTOSE-SPECIFIC IIABC COMPONENT (FRUA-1).
ID0732G PTS SYSTEM, MANNITOL-1-PHOSPHATE DEHYDROGENASE (ENZYME III).
ID0733G SUCROSE-6-P HYDROLASE.
ID0734G PUTATIVE SUCROSE-SPECIFIC PTS PERMEASE, ENZYME II.
ID0735G DEOXYPHOSPHOGLUCONATE ALDOLASE.
ID0736G TRANSMEMBRANE LIPOPROTEIN.
ID0737G SUGAR ABC TRANSPORTER (PERMEASE).
ID0738G ENDO-1,4-BETA-XYLANASE.
ID0739G SUGAR TRANSPORT SYSTEM (PERMEASE) (BINDING PROTEIN DEPENDENT
ID0740G *S. pneumoniae* derived protein #302.
ID0741G FRUCTOSE BISPHOSPHATE ALDOLASE.
ID0742G BH1074 PROTEIN.
ID0743G SA0233 PROTEIN.
ID0744G ALPHA-GALACTOSIDASE.
ID0745G URONATE ISOMERASE (EC 5.3.1.12) (GLUCURONATE ISOMERASE) (URO
ID0746G ORF starting with ATG of length 633
ID0747G endo 1,5 alpha-L-arabinase
ID0748G BETA-XYLOSIDASE/ALPHA-L-ARABINOSIDASE.
ID0749G FBAA.
ID0750G ORF starting with ATG of length 558
ID0751G ALPHA-GALACTOSIDASE (EC 3.2.1.22) (MELIBIASE).
ID0752G ALPHA-GALACTOSIDASE (EC 3.2.1.22) (MELIBIASE).
ID0753G 6-PHOSPHO-BETA-GLUCOSIDASE.
ID0754G L-ARABINOSE MEMBRANE PERMEASE.
ID0755G PTS SYSTEM, CELLOBIOSE-SPECIFIC IIA COMPONENT (EIIA-CEL) (CE
ID0756G *Streptococcus pneumoniae* type 4 protein sequence #56.
ID0757G ALPHA-GALACTOSIDASE (EC 3.2.1.22) (MELIBIASE).
ID0758G XYLOSE ISOMERASE (EC 5.3.1.5).
ID0759G BH1878 PROTEIN.
ID0760G LIPOPROTEIN.
ID0761G TRANSMEMBRANE LIPOPROTEIN.
ID0762G ABC TRANSPORTER (PERMIASE).
ID0763G ENDO-1,4-BETA-GLUCANASE.
ID0764G 362AA LONG HYPOTHETICAL MALTOSE/MALTODEXTRIN TRANSPORT ATP-B
ID0765G FRUCTOKINASE.
ID0766G BH1117 PROTEIN.
ID0767G LACTOSE TRANSPORT SYSTEM (PERMEASE).
ID0768G ORF starting with ATG of length 666
ID0769G GLUCOSIDASE.
ID0770G SUGAR TRANSPORT SYSTEM (PERMEASE) (BINDING PROTEIN DEPENDENT
ID0771G SULFATE ABC TRANSPORTER, ATP-BINDING PROTEIN.
ID0772G 2,3-BISPHOSPHOGLYCERATE-INDEPENDENT PHOSPHOGLYCERATE MUTASE.
ID0773G LIPOPROTEIN.
ID0774G PTS SYSTEM, FRUCTOSE-SPECIFIC IIBC COMPONENT (EIIBC-FRU) (FR
ID0775G PHOSPHOTRANSFERASE SYSTEM (PTS) FRUCTOSE-SPECIFIC ENZYME IIB
ID0776G PHOSPHOGLYCERATE KINASE (EC 2.7.2.3).
ID0777G TRIOSEPHOSPHATE ISOMERASE (EC 5.3.1.1) (TIM).
ID0778G ORF starting with ATG of length 774
ID0779G PHOSPHOMANNOMUTASE.
ID0780G Recombinant glucose-6-phosphate dehydrogenase.
ID0781G MELIBIASE (ALPHA-GALACTOSIDASE) (EC 3.2.1.22).
ID0782G 6-PHOSPHOGLUCONATE DEHYDROGENASE, DECARBOXYLATING (EC 1.1.1.
ID0783G HYPOTHETICAL 24.5 KDA PROTEIN.
ID0784G ORF starting with ATG of length 642
ID0785G PUTATIVE SUGAR HYDROLASE.
ID0786G PTS SYSTEM, CELLOBIOSE-SPECIFIC ENZYME II, B COMPONENT (EIIA
ID0787G ORF starting with ATG of length 375
ID0788G PTS SYSTEM, CELLOBIOSE-SPECIFIC ENZYME II, C COMPONENT (EIIA
ID0789G HYPOTHETICAL 38.7 KDA PROTEIN.
ID0790G PUTATIVE SUGAR TRANSPORT SYSTEM PERMEASE PROTEIN.
ID0791G ORF starting with ATG of length 615
ID0792G HYPOTHETICAL 54.3 KDA PROTEIN.
ID0793G PUTATIVE SUGAR ABC TRANSPORTER (ATP-BINDING PROTEIN).
ID0794G PUTATIVE CARBOXYVINYL-CARBOXYPHOSPHONATE PHOSPHORYLMUTASE (EC
ID0795G PTS SYSTEM, FRUCTOSE-SPECIFIC ENZYME II, BC COMPONENT.
ID0796G 1-PHOSPHOFRUCTOKINASE (EC 2.7.1.56) (FRUCTOSE 1-PHOSPHATE KI
ID0797G PTS SYSTEM, BETA-GLUCOSIDE-SPECIFIC ENZYME II, ABC COMPONENT
ID0798G PUTATIVE TRANSKETOLASE C-TERMINAL SECTION (EC 2.2.1.1) (TK).
ID0799G EXO-INULINASE.
ID0800G SUCROSE-6-PHOSPHATE HYDROLASE (EC 3.2.1.26) (SUCRASE) (INVER
ID0801G SURFACE PROTEIN PLS.
ID0802G YBCL PROTEIN.
ID0803G SUCROSE-6-PHOSPHATE HYDROLASE.
ID0804G PYRUVATE KINASE (EC 2.7.1.40) (PK).
ID0805G PHOSPHOCARRIER PROTEIN HPR (CATABOLITE REPRESSION).
ID0806G BH0789 PROTEIN.
ID0807G PUTATIVE SUCROSE-SPECIFIC PTS PERMEASE, ENZYME II.
ID0808G SCRB.
ID0809G L-FUCULOSE PHOSPHATE ALDOLASE (EC 4.1.2.17) (L-FUCULOSE-1-PH
ID0810G FRUCTOSE-SPECIFIC PTS SYSTEM ENZYME IIBC COMPONENT (EC 2.7.1
ID0811G 6-PHOSPHOFRUCTOKINASE (EC 2.7.1.11) (PHOSPHOFRUCTOKINASE) (PH
ID0812G HYPOTHETICAL 40.2 KDA PROTEIN.
ID0813G ORF starting with ATG of length 975
ID0814G PUTATIVE SUCROSE-SPECIFIC PTS PERMEASE, ENZYME II.
ID0815G HYPOTHETICAL PROTEIN H11028 PRECURSOR.
ID0816G LACTOSE TRANSPORT SYSTEM (PERMEASE).
ID0817G BH1117 PROTEIN.

ID0818G CHLORAMPHENICOL RESISTANCE PROTEIN.
ID0819G PROTEIN H10146 PRECURSOR.
ID0820G *Streptococcus pneumoniae* type 4 protein sequence #18.
ID0821G HYPOTHETICAL 43.3 KDA PROTEIN.
ID0822G HYPOTHETICAL ABC TRANSPORTER PERMEASE PROTEIN YURN.
ID0823G ORF starting with ATG of length 454
ID0824G MYO-INOSITOL CATABOLISM.
ID0825G *B. subtilis* hexylose phosphate synthase.
ID0826G MALTOSE/MALTODEXTRIN TRANSPORT SYSTEM (PERMEASE).
ID0827G SA2241PROTEIN.
ID0828G YBCL PROTEIN.
ID0829G ORF starting with ATG of length 861
ID0830G SA0233 PROTEIN.
ID0831G ZY044582 signal trapped geneweak similarity to yeso type gen
ID0832G TRANSMEMBRANE LIPOPROTEIN.
ID0833G ABC TRANSPORTER (PERMIASE).
ID0834G 2-KETO-3-DEOXY-GLUCONATE KINASE.
ID0835G D-MANNONATE HYDROLASE.
ID0836G ORF starting with ATG of length 385
ID0837G ORF starting with ATG of length 680
ID0838G XYLOSE ISOMERASE (EC 5.3.1.5).
ID0839G XYLULOSE KINASE (EC 2.7.1.17) (XYLULOKINASE).
ID0840G SUCROSE-SPECIFIC PTS PERMEASE.
ID0841G XYLOSIDASE/ARABINOSIDASE [INCLUDES: BETA-XYLOSIDASE (EC 3.2.
ID0842G MYO-INOSITOL CATABOLISM.
ID0843G SUGAR TRANSPORT SYSTEM (PERMEASE).
ID0844G CHITOOLIGOSACCHARIDE DEACETYLASE (EC 3.5.1.).
ID0845G ARAD.
ID0846G SUGAR ABC TRANSPORTER (PERMEASE).
ID0847G ORF starting with ATG of length 534
ID0848G SUGAR FERMENTATION STIMULATION PROTEIN.
ID0849G PHOSPHOMANNOMUTASE.
ID0850G PHOSPHOGLUCOSAMINE MUTASE.
ID0851G BH0285 PROTEIN.
ID0852G BH1066 PROTEIN.
ID0853G INTEGRAL MEMBRANE PROTEIN.
ID0854G LIPOPROTEIN.
ID0855G N-ACETYLGLUCOSAMINE-SPECIFIC IIABC COMPONENT.
ID0856G GLUCOSIDASE.
ID0857G SUGAR ABC TRANSPORTER (PERMEASE).
ID0858G PTS SYSTEM FRUCTOSE-LIKE IIB COMPONENT 1.
ID0859G N-ACETYLGLUCOSAMINE-6-PHOSPHATE ISOMERASE (EC 5.3.1.10).
ID0860G GLUCOSAMINE-6-ISOMERASE.
ID0861G PROTEIN YCGS.
ID0862G ORF starting with ATG of length 435
ID0863G SUGAR TRANSPORT SYSTEM (PERMEASE).
ID0864G ORF starting with ATG of length 520
ID0865G PTS SYSTEM, SUCROSE-SPECIFIC IIBC COMPONENT (EIIBC-SCR) (SUC
ID0866G RHAMNULOKINASE.
ID0867G L-ARABINOSE ISOMERASE.
ID0868G SA1198 PROTEIN.
ID0869G LPLB PROTEIN.
ID0870G *S. pneumoniae* derived protein #253.
ID0871G TRANSKETOLASE (EC 2.2.1.1).
ID0872G PROBABLE ABC-TRANSPORT PROTEIN, INNER MEMBRANE COMPONENT.
ID0873G GLUCOSE-6-PHOSPHATE ISOMERASE A (GPI A) (EC 5.3.1.9) (PHOSPH
ID0874G PHOSPHOGLUCOSAMINE MUTASE.
ID0875G BH0222 PROTEIN.
ID0876G PUTATIVE TRANSPORT SYSTEM INNER MEMBRANE PROTEIN.
ID0877G LACTOSE TRANSPORT SYSTEM (PERMEASE).
ID0878G ORF starting with ATG of length 672
ID0879G SUGAR TRANSPORT SYSTEM (PERMEASE) (BINDING PROTEIN DEPENDENT
ID0880G ORF starting with ATG of length 375
ID0881G SUGAR ABC TRANSPORTER (ATP-BINDING PROTEIN).
ID0882G SUGAR TRANSPORT SYSTEM (SUGAR-BINDING PROTEIN).
ID0883G GLYCEROL-3-PHOSPHATE ABC TRANSPORTER (PERMEASE).
ID0884G GLYCEROL-3-PHOSPHATE ABC TRANSPORTER (PERMEASE).
ID0885G TEICHOIC ACID TRANSLOCATION ATP-BINDING PROTEIN TAGH.
ID0886G ABC-TRANSPORTER ATP-BINDING PROTEIN.
ID0887G ALTRONATE HYDROLASE.
ID0888G *Streptococcus pneumoniae* SP0014 protein.
ID0889G SUGAR BINDING PROTEIN
ID0890G 6-PHOSPHO-BETA-GLUCOSIDASE.
ID0891G FRUCTOSE 1-PHOSPHATE KINASE.
ID0892G BETA-GLUCOSIDASE.
ID0893G GLCA PROTEIN.
ID0894G HYPOTHETICAL 24.3 KDA PROTEIN.
ID0895G ABC TRANSPORTER SUGAR PERMEASE.
ID0896G ORF starting with ATG of length 369
ID0897G METHYLGLYOXAL SYNTHASE (EC 4.2.99.11).
ID0898G BH0592 PROTEIN.
ID0899G SUGAR TRANSPORT SYSTEM (PERMEASE).
ID0900G MYO-INOSITOL CATABOLISM.
ID0901G ORF starting with ATG of length 714
ID0902G SUCROSE-6-PHOSPHATE HYDROLASE.
ID0903G D-MANNONATE HYDROLASE.
ID0904G SA2244 PROTEIN.
ID0905G MULTIPLE SUGAR TRANSPORT SYSTEM (MULTIPLE SUGAR-BINDING PROT
ID0906G ALTRONATE OXIDOREDUCTASE.
ID0907G DIHYDROXYACETONE KINASE.
ID0908G PTS SYSTEM, GLUCOSE-SPECIFIC IIABC COMPONENT (EIIABC-GLC) (G
ID0909G PTS SYSTEM, CELLOBIOSE-SPECIFIC ENZYME II, B COMPONENT (EIIA
ID0910G DECARBOXYLATING 6-PHOSPHOGLUCONATE DEHYDROGENASE (EC 1.1.1.4
ID0911G ALTRONATE OXIDOREDUCTASE.
ID0912G HYPOTHETICAL 54.3 KDA PROTEIN.
ID0913G PTS SYSTEM, CELLOBIOSE-SPECIFIC IIA COMPONENT (EIIA-CEL) (CE
ID0914G PTS SYSTEM, CELLOBIOSE-SPECIFIC ENZYME II, C COMPONENT.
ID0915G PTS SYSTEM, CELLOBIOSE-SPECIFIC IIB COMPONENT (EIIB-CEL) (CE
ID0916G PTS SYSTEM, CELLOBIOSE-SPECIFIC ENZYME II, C COMPONENT.
ID0917G PTS SYSTEM, CELLOBIOSE-SPECIFIC IIA COMPONENT (EIIA-CEL) (CE ID0918G HYPOTHETICAL 54.3 KDA PROTEIN.
ID0919G ALTRONATE HYDROLASE.
ID0920G MALTOSE TRANSPORTOR ATP-BINDING PROTEIN.
ID0921G 6-PHOSPHO-BETA-GLUCOSIDASE.
ID0922G MALTOGENIC AMYLASE.
ID0923G BH1066 PROTEIN.
ID0924G INTEGRAL MEMBRANE PROTEIN.
ID0925G ORF starting with ATG of length 529
ID0926G ALPHA,ALPHA-PHOSPHOTREHALASE (EC 3.2.1.93).
ID0927G PHOSPHOCARRIER PROTEIN HPR (CATABOLITE REPRESSION).
ID0928G KBAY.
ID0929G LACTOSE TRANSPORT SYSTEM (PERMEASE).
ID0930G Streptococcus pneumoniae type 4 protein sequence #55.
ID0931G 6-PHOSPHO-BETA-GLUCOSIDASE A, CRYPTIC.
ID0932G PTS SYSTEM, CELLOBIOSE-SPECIFIC IIA COMPONENT (EIIA-CEL) (CE
ID0933G ORF starting with ATG of length 552
ID0934G 6-PHOSPHOGLUCONATE DEHYDROGENASE (EC 1.1.1.44).
ID0935G Recombinant glucose-6-phosphate dehydrogenase.
ID0936G Recombinant glucose-6-phosphate dehydrogenase.
ID0937G ORF starting with ATG of length 924
ID0938G HYPOTHETICAL PROTEIN.
ID0939G CONSERVED HYPOTHETICAL PROTEIN.
ID0940G BETA-GLUCOSIDE SPECIFIC TRANSPORT PROTEIN.
ID0941G PROBABLE HEXULOSE-6-PHOSPHATE SYNTHASE (EC 4.1.2.-) (HUMPS)
ID0942G 2-KETO-3-DEOXYGLUCONATE KINASE (EC 2.7.1.45).
ID0943G HYPOTHETICAL 38.7 KDA PROTEIN.
ID0944G YTCQ.
ID0945G PUTATIVE SUGAR HYDROLASE.
ID0946G PTS SYSTEM, CELLOBIOSE-SPECIFIC ENZYME II, C COMPONENT (EIIA
ID0947G TRANSKETOLASE, C-TERMINAL SECTION (TKT-2) (EC 2.2.1.1).
ID0948G FRUCTOSE-SPECIFIC PTS SYSTEM ENZYME IIBC COMPONENT (EC 2.7.1
ID0949G ORF starting with ATG of length 2064
ID0950G MYO-INOSITOL CATABOLISM.
ID0951G TRIOSEPHOSPHATE ISOMERASE.
ID0952G P-NITROPHENYL PHOSPHATASE.
ID0953G CHITOOLIGOSACCHARIDE DEACETYLASE (EC 3.5.1.).
ID0954G ORF starting with ATG of length 612
ID0955G ORF starting with ATG of length 222
ID0956G ORF starting with ATG of length 552
ID0957GR YOAN.
ID0958GR YOAN.
ID0959GR YOAN.
ID0960GR ORF starting with ATG of length 330
ID0961GT PHOSPHOTRANSFERASE SYSTEM (PTS) FRUCTOSE-SPECIFIC ENZYME IIB
ID0962GT PTS SYSTEM MANNITOL-SPECIFIC COMPONENT IIA (EIIA-MTL).
ID0963GT MANNITOL ENZYME IIA.
ID0964GT PTS SYSTEM, FRUCTOSE-SPECIFIC ENZYME II, BC COMPONENT.
ID0965GT MANNITOL ENZYME IIA.
ID0966GT PTS SYSTEM, FRUCTOSE-SPECIFIC ENZYME II, BC COMPONENT.
ID0967GT HYPOTHETICAL 16.1 KDA PROTEIN.
ID0968GT ORF starting with ATG of length 410
ID0969HC DIHYDROOROTATE DEHYDROGENASE (ELECTRON TRANSFER SUBUNIT).
ID0970HC DIHYDROOROTATE DEHYDROGENASE (ELECTRON TRANSFER SUBUNIT).
ID0971HE PHOSPHOSERINE AMINOTRANSFERASE (EC 2.6.1.52).
ID0972HE PHOSPHOSERINE AMINOTRANSFERASE.
ID0973H THID.
ID0974H FOLYL-POLYGLUTAMATE SYNTHETASE (EC 6.3.2.17).
ID0975H ORF starting with ATG of length 483
ID0976H ABC TRANSPORT SYSTEM PERMEASE PROTEIN.
ID0977H GLUTAMATE-1-SEMIALDEHYDE AMINOTRANSFERASE.
ID0978H FLAVOPROTEIN.
ID0979H MOLYBDOPTERIN BIOSYNTHESIS PROTEIN.
ID0980H ORF starting with ATG of length 552
ID0981H MOLYBDOPTERIN CONVERTING FACTOR (SUBUNIT 2).
ID0982H ORF starting with ATG of length 823
ID0983H BH1752 PROTEIN.
ID0984H RIBOFLAVIN KINASE/FAD SYNTHASE.
ID0985H RIBOFLAVIN BIOSYNTHESIS PROTEIN RIBA [INCLUDES: GTP CYCLOHYD
ID0986H DGOA PROTEIN [INCLUDES: 2-DEHYDRO-3-DEOXYPHOSPHOGALACTONATE
ID0987H 2-HEPTAPRENYL-1,4-NAPHTHOQUINONE METHYLTRANSFERASE (SPORE GE
ID0988H YQHM PROTEIN.
ID0989H SA1729 PROTEIN.
ID0990H GERANYLTRANSTRANSFERASE (EC 2.5.1.10) (FARNESYL-DIPHOSPHATE
ID0991H GLUTAMATE-1-SEMIALDEHYDE AMINOTRANSFERASE.
ID0992H PROBABLE AROMATIC ACID DECARBOXYLASE (EC 4.1.1.-).
ID0993H NH$_3$-DEPENDENT NAD SYNTHETASE (EC 6.3.1.5).
ID0994H BH1752 PROTEIN.
ID0995H TRANSCRIPTIONAL REPRESSOR OF THE BIOTIN OPERON.
ID0996H HEPTAPRENYL DIPHOSPHATE SYNTHASE COMPONENT II (EC 2.5.1.30)
ID0997H SPORE GERMINATION PROTEIN C3 (FRAGMENT).
ID0998H 4-HYDROXYBENZOATE OCTAPRENYLTRANSFERASE.
ID0999H PUTATIVE OCTAPRENYLTRANSFERASE.
ID1000H PANTOTHENATE METABOLISM FLAVOPROTEIN HOMOLOG.
ID1001H DIHYDROFOLATE REDUCTASE (EC 1.5.1.3).
ID1002H GLUTAMATE-1-SEMIALDEHYDE 2,1-AMINOMUTASE 2 (EC 5.4.3.8) (GSA
ID1003H BH1752 PROTEIN.
ID1004H BH1752 PROTEIN.
ID1005H GERANYLTRANSTRANSFERASE (EC 2.5.1.10) (FARNESYL-DIPHOSPHATE
ID1006H CYSG.
ID1007H DELTA-AMINOLEVULINIC ACID DEHYDRATASE (EC 4.2.1.24).

ID1008H PORPHOBILINOGEN DEAMINASE (EC 4.3.1.8).
ID1009H S. carnosus nitrate reductase molybdenum cofactor MoeB.
ID1010H MOLYBDOPTERIN BIOSYNTHESIS.
ID1011H ABC TRANSPORT SYSTEM PERMEASE PROTEIN.
ID1012H ASPARTATE 1-DECARBOXYLASE.
ID1013H PANTOATE BETA-ALANINE LIGASE.
ID1014H Cis-epoxysuccinate hydrolase alpha subunit amino acid sequen
ID1015H TRANSCRIPTIONAL REGULATOR.
ID1016H DIHYDROFOLATE REDUCTASE (EC 1.5.1.3).
ID1017H UNKNOWN (PYRIDOXAL PHOSPHATE BIOSYNTHETIC PROTEIN).
ID1018H HYPOTHETICAL PROTEIN VC0880.
ID1019H PYRIDOXAL PHOSPHATE BIOSYNTHETIC PROTEIN PDXA.
ID1020H Cis-epoxysuccinate hydrolase alpha subunit amino acid sequen
ID1021H UROPORPHYRINOGEN III DECARBOXYLASE.
ID1022H BH3930 PROTEIN.
ID1023H IRON (III) TRANSPORT SYSTEM (PERMEASE).
ID1024H PROBABLE AROMATIC ACID DECARBOXYLASE (EC 4.1.1.-).
ID1025H BH0072 PROTEIN.
ID1026H DGOA PROTEIN [INCLUDES: 2-DEHYDRO-3-DEOXYPHOSPHOGALACTONATE
ID1027H THIAMINE PHOSPHATE PYROPHOSPHORYLASE.
ID1028H CONSERVED HYPOTHETICAL PROTEIN.
ID1029H FERROCHELATASE (EC 4.99.1.1) (PROTOHEME FERRO-LYASE) (HEMESY
ID1030H PROTOPORPHYRINOGEN 1xAND COPROPORPHYRINOGEN III OXIDASE.
ID1031H ORF starting with ATG of length 990
ID1032H MOLYBDENUM COFACTOR BIOSYNTHESIS PROTEIN C.
ID1033H PROBABLE AMINOTRANSFERASE YHXA (EC 2.6.-.-).
ID1034H ORF starting with ATG of length 624
ID1035H FERROCHELATASE (EC 4.99.1.1) (PROTOHEME FERRO-LYASE) (HEMESY
ID1036H DIHYDRONEOPTERIN ALDOLASE (EC 4.1.2.25) (DHNA).
ID1037H FOLATE SYNTHESIS BIFUNCTIONAL PROTEIN [INCLUDES: 2-AMINO-4-H
ID1038H DIHYDROPTEROATE SYNTHASE (DIHYDROPTEROATE PYROPHOSPHORYLASE)
ID1039H SUPEROXIDE-INDUCIBLE PROTEIN.
ID1040H AMIDOTRANSFERASE.
ID1041H ORF starting with ATG of length 267
ID1042H PANTOATE BETA-ALANINE LIGASE.
ID1043H QUINOLINATE SYNTHETASE.
ID1044H CONSERVED HYPOTHETICAL PROTEIN.
ID1045H GLUTAMATE-1-SEMIALDEHYDE 2,1-AMINOTRANSFERASE (EC 5.4.3.8).
ID1046H PHOSPHOMETHYLPYRIMIDINE KINASE (EC 2.7.4.7) (HMP-PHOSPHATE K
ID1047H L-ASPARTATE OXIDASE.
ID1048H FOLYL-POLYGLUTAMATE SYNTHETASE (EC 6.3.2.17).
ID1049H CYTOCHROME CAA3 OXIDASE ASSEMBLY FACTOR.
ID1050H 6,7-DIMETHYL-8-RIBITYLLUMAZINE SYNTHASE (EC 2.5.1.9).
ID1051H PROBABLE 2-DEHYDROPANTOATE 2-REDUCTASE (EC 1.1.1.169) (KETOP
ID1052H PORPHOBILINOGEN DEAMINASE (EC 4.3.1.8).
ID1053H GLUTAMYL-TRNA REDUCTASE (EC 1.2.1.).
ID1054H BS PROMOTER (FRAGMENT).
ID1055H GLUTAMATE-1-SEMIALDEHYDE AMINOTRANSFERASE.
ID1056H UNKNOWN (PYRIDOXAL PHOSPHATE BIOSYNTHETIC PROTEIN).
ID1057H S-ADENOSYLMETHIONINE SYNTHETASE (EC 2.5.1.6) (METHIONINEADEN
ID1058H DIHYDROPTEROATE SYNTHASE (DIHYDROPTEROATE PYROPHOSPHORYLASE)
ID1059H DIHYDRONEOPTERIN ALDOLASE (EC 4.1.2.25).
ID1060H ORF starting with ATG of length 216
ID1061H ORF starting with ATG of length 387
ID1062HI 1-DEOXYXYLULOSE-5-PHOSPHATE SYNTHASE.
ID1063HI Corn 1-deoxy-D-xylulose 5-phosphate synthase putative protei
ID1064HR BH3411 PROTEIN.
ID1065HR BH3143 PROTEIN.
ID1066HR BH3143 PROTEIN.
ID1067HR BH3411PROTEIN.
ID1068I PYRUVATE CARBOXYLASE.
ID1069I PROTEIN LOW TEMPERATURE REQUIREMENT C.
ID1070I 3-HYDROXYACYL-COA DEHYDROGENASE.
ID1071I SHORT-CHAIN-SPECIFIC ACYL-COA DEHYDROGENASE.
ID1072I E. coli proliferation associated protein sequence SEQ ID NO:
ID1073I ENOYL-[ACYL-CARRIER PROTEIN] REDUCTASE.
ID1074I ACETYL-COA SYNTHETASE (EC 6.2.1.1).
ID1075I PUTATIVE ACYL CARRIER PROTEIN PHOSPHODIESTERASE (EC 3.1.4.14
ID1076I ORF starting with ATG of length 341
ID1077I HYPOTHETICAL 24.9 KDA PROTEIN IN CYTOCHROME P450MEG GENE 3'R
ID1078I FATTY ACID DESATURASE (EC 1.14.99.).
ID1079I FATTY ACID DESATURASE.
ID1080I METHYLMALONYL-COA DECARBOXYLASE, SUBUNIT A LPHA (MMDA).
ID1081I PROBABLE CARDIOLIPIN SYNTHETASE 2 (EC 2.7.8.-) (CARDIOLIPIN
ID1082I BUTYRYL-COA DEHYDROGENASE.
ID1083I ACETYL-COA CARBOXYLASE TRANSFERASE BETA SUBUNIT (EC 6.4.1.2)
ID1084I PROPIONYL-COA CARBOXYLASE.
ID1085I ORF starting with ATG of length 549
ID1086I ACETYL-COA SYNTHETASE (EC 6.2.1.1).
ID1087I YVAB PROTEIN.
ID1088I PHOSPHATIDYLGLYCEROPHOSPHATE SYNTHASE.
ID1089I 3-HYDROXYISOBUTYRATE DEHYDROGENASE.
ID1090I ORF starting with ATG of length 561
ID1091I HYPOTHETICAL 38.4 KDA PROTEIN.
ID1092I LIPASE (ESTERASE).
ID1093I BACITRACIN TRANSPORT PERMEASE PROTEIN BCRC.
ID1094I YWJE PROTEIN.

ID1095I 3-HYDROXYISOBUTYRATE DEHYDROGENASE.
ID1096I ACETYL-COA SYNTHETASE (EC 6.2.1.1).
ID1097I ACETYL-COA ACETYLTRANSFERASE (EC 2.3.1.9).
ID1098I ACYL-COA DEHYDROGENASE (EC 1.3.99.).
ID1099I ORF starting with ATG of length 600
ID1100I PROBABLE SUCCINYL-COA:3-KETOACID-COENZYME A TRANSFERASE SUBU
ID1101I 1-DEOXY-D-XYLULOSE 5-PHOSPHATE REDUCTOISOMERASE (EC 1.1.1.-)
ID1102I ACETYL-COA CARBOXYLASE BIOTIN CARBOXYLASE SUBUNIT (EC 6.4.1.
ID1103I ACETATE-COA LIGASE.
ID1104I MALONYL COA-ACYL CARRIER PROTEIN TRANSACYLASE (EC 2.3.1.39).
ID1105I BH1635 PROTEIN.
ID1106I PHOSPHATIDATE CYTIDYLYLTRANSFERASE.
ID1107I UNDECAPRENYL PYROPHOSPHATE SYNTHETASE (EC 2.5.1.31).
ID1108I HYPOTHETICAL 48.2 KDA PROTEIN (FRAGMENT).
ID1109I PROBABLE SUCCINYL-COA:3-KETOACID-COENZYME A TRANSFERASE SUBU
ID1110I ORF starting with ATG of length 597
ID1111I PROBABLE CARDIOLIPIN SYNTHETASE 2 (EC 2.7.8.-) (CARDIOLIPIN
ID1112I HYPOTHETICAL 25.2 KDA PROTEIN.
ID1113I ACETATE-COA LIGASE (EC 6.2.1.1).
ID1114I ACETATE-COA LIGASE.
ID1115I PHOSPHATIDYLGLYCEROPHOSPHATE SYNTHASE.
ID1116I BIOTIN CARBOXYLASE.
ID1117I BUTYRYL-COA DEHYDROGENASE.
ID1118I BACITRACIN TRANSPORT PERMEASE PROTEIN BCRC.
ID1119I 3-HYDROXYACYL-COA DEHYDROGENASE.
ID1120I INVOLVED IN FATTY ACID/PHOSPHOLIPID SYNTHESIS.
ID1121I SHORT-CHAIN FATTY ACIDS TRANSPORTER.
ID1122I 3-HYDROXYACYL-COA DEHYDROGENASE.
ID1123I BUTYRYL-COA DEHYDROGENASE.
ID1124I SIMILAR TO PROPIONYL COENZYME A CARBOXYLASE, ALPHA POLYPEPTI
ID1125I PROTEIN LOW TEMPERATURE REQUIREMENT C.
ID1126I ACETYL-COA ACETYLTRANSFERASE (EC 2.3.1.9).
ID1127I NAD-DEPENDENT BETA-HYDROXYBUTYRYL COENZYME A DEHYDROGENASE
ID1128I HYPOTHETICAL 18.7 KDA PROTEIN IN HOMMRGA INTERGENIC REGION.
ID1129IQ LONG-CHAIN-FATTY-ACID-COA LIGASE (EC 6.2.1.3) (LONG-CHAIN A
ID1130IQ LONG-CHAIN FATTY-ACID-COA LIGASE.
ID1131IQ MEDIUM-CHAIN FATTY ACID-COA LIGASE.
ID1132IQ ACID-COA LIGASE.
ID1133IQ ACID-COA LIGASE.
ID1134IQ LONG CHAIN FATTY ACID ACYL-COA LIGASE.
ID1135J BH1439 PROTEIN.
ID1136J VALYL-TRNA SYNTHETASE (EC 6.1.1.9) (VALINE-TRNA LIGASE) (VA
ID1137J BH1243 PROTEIN.
ID1138J RIBOSOMAL PROTEIN L6 (BL8).
ID1139J RIBOSOMAL PROTEIN L18.
ID1140J RIBOSOMAL PROTEIN S5.
ID1141J *Streptococcus pneumoniae* prfC protein sequence.
ID1142J METHIONYL-TRNA FORMYLTRANSFERASE (EC 2.1.2.9).
ID1143J GLYCYL-TRNA SYNTHETASE (ALPHA SUBUNIT).
ID1144J LYSYL-TRNA SYNTHETASE (EC 6.1.1.6).
ID1145J RIBOSOMAL PROTEIN N-ACETYLTRANSFERASE, PUTATIVE.
ID1146J ISOLEUCYL-TRNA SYNTHETASE.
ID1147J BH2847 PROTEIN.
ID1148J ASPARAGINYL-TRNA SYNTHETASE (EC 6.1.1.22) (ASPARAGINE-TRNA
ID1149J Leucyl-tRNA synthetase from *Staph. aureus*.
ID1150J ASPARAGINYL-TRNA SYNTHETASE.
ID1151J TRNA PSEUDOURIDINE 5S SYNTHASE.
ID1152J METHIONYL-TRNA FORMYLTRANSFERASE (EC 2.1.2.9).
ID1153J SA1060 PROTEIN.
ID1154J GLYCYL-TRNA SYNTHETASE BETA CHAIN (EC 6.1.1.14) (GLYCINE-TR
ID1155J METHIONINE AMINOPEPTIDASE A.
ID1156J RIBOSOMAL PROTEIN S30AE FAMILY.
ID1157J GLYCYL-TRNA SYNTHETASE (BETA SUBUNIT).
ID1158J RRNA METHYLASE.
ID1159J TRYPTOPHANYL-TRNA SYNTHETASE.
ID1160J 16S PSEUDOURIDYLATE SYNTHASE.
ID1161J PUTATIVE TRNA SYNTHETASE.
ID1162J LEUCYL-TRNA SYNTHETASE (EC 6.1.1.4).
ID1163J TRNA/RRNA METHYLTRANSFERASE.
ID1164J HYPOTHETICAL 35.7 KDA PROTEIN IN MALA 3'REGION (ORF3).
ID1165J PROTOPORPHYRINOGEN OXIDASE.
ID1166J CYSTEINYL-TRNA SYNTHETASE (EC 6.1.1.16) (CYSTEINE-TRNA LIGA
ID1167J ISOLEUCYL-TRNA SYNTHETASE, MUPIROCIN RESISTANT (EC 6.1.1.5)
ID1168J TRANSLATION INITIATION INHIBITOR.
ID1169J CYTOSOLIC AXIAL FILAMENT PROTEIN.
ID1170J *H. pylori* GHPO 728 protein.
ID1171J ORF starting with ATG of length 609
ID1172J ORF starting with ATG of length 966
ID1173J THREONYL-TRNA SYNTHETASE 1 (EC 6.1.1.3) (THREONINE-TRNA LIG
ID1174J POLY(A) POLYMERASE.
ID1175J ORF starting with ATG of length 543
ID1176J ASPARTYL-TRNA SYNTHETASE.
ID1177J TRANSLATION INITIATION FACTOR IF-2.
ID1178J ASPARTYL-TRNA SYNTHETASE (EC 6.1.1.12) (ASPARTATE-TRNA LIGA
ID1179J HISTIDYL-TRNA SYNTHETASE (EC 6.1.1.21).
ID1180J ORF starting with ATG of length 321
ID1181J TRANSLATION INITIATION FACTOR IF-2.
ID1182J ORF starting with ATG of length 2301
ID1183J RIBOSOME-BINDING FACTOR A.
ID1184J BH3010 PROTEIN.
ID1185J RIBOSOMAL PROTEIN L27.
ID1186J BH1351PROTEIN.
ID1187J PROBABLE METHYLTRANSFERASE (EC 2.1.1.-).
ID1188J RIBOSOMAL PROTEIN L27.
ID1189J BH3010 PROTEIN.
ID1190J METHYLTRANSFERASE.
ID1191J LEUCYL-TRNA SYNTHETASE (EC 6.1.1.4).
ID1192J PHENYLALANYL-TRNA SYNTHETASE BETA CHAIN (EC 6.1.1.20) (PHENY

[1193J] PSEUDOURIDYLATE SYNTHASE (EC 4.2.1.70).
[1194J] POLY(A) POLYMERASE.
[1195J] POLY(A) POLYMERASE.
[1196J] YFJO PROTEIN.
[1197J] ISOLEUCYL-TRNA SYNTHETASE (EC 6.1.1.5) (ISOLEUCINE-TRNA LIG
[1198J] BH0299 PROTEIN.
[1199J] TRANSLATION ELONGATION FACTOR G (EF-G).
[1200J] YBXF PROTEIN (RIBOSOMAL PROTEIN L7AE FAMILY).
[1201J] RIBOSOMAL PROTEIN S12.
[1202J] RIBOSOMAL PROTEIN S7 (BS7).
[1203J] ELONGATION FACTOR G (EF-G) (FRAGMENT).
[1204J] TRANSLATION ELONGATION FACTOR G (EF-G).
[1205J] SERYL-TRNA SYNTHETASE (EC 6.1.1.11) (SERINE-TRNA LIGASE) (S
[1206J] ARGINYL-TRNA SYNTHETASE (EC 6.1.1.19) (ARGININE-TRNA LIGASE
[1207J] RNA METHYLTRANSFERASE.
[1208J] GLUTAMYL-TRNA (GLN) AMIDOTRANSFERASE SUBUNIT A (EC 6.3.5.-)
[1209J] Arabidopsis thaliana protein fragment SEQ ID NO: 29871.
[1210J] PROBABLE GLUTAMYL-TRNA (GLN) AMIDOTRANSFERASE SUBUNIT B, MITO
[1211J] GLUTAMYL-TRNAGLN AMIDOTRANSFERASE SUBUNIT B.
[1212J] SERYL-TRNA SYNTHETASE (EC 6.1.1.11).
[1213J] DIMETHYLADENOSINE TRANSFERASE (EC 2.1.1.-) (S-ADENOSYLMETHIO
[1214J] RIBONUCLEASE PH (EC 2.7.7.56).
[1215J] HYPOTHETICAL 9.7 KDA PROTEIN IN MFD-DIVIC INTERGENIC REGION.
[1216J] HISTIDYL-TRNA SYNTHETASE (EC 6.1.1.21) (HISTIDINE-TRNA LIGA
[1217J] YFLG PROTEIN.
[1218J] YFLG PROTEIN.
[1219J] PUTATIVE METHYLTRANSFERASE (EC 2.1.1.).
[1220J] Enantioselective amidase of Rhodococcus.
[1221J] 50S RIBOSOMAL PROTEIN L30.
[1222J] 50S RIBOSOMAL PROTEIN L15.
[1223J] 50S RIBOSOMAL PROTEIN L15.
[1224J] HISTIDYL-TRNA SYNTHETASE (EC 6.1.1.21) (HISTIDINE-TRNA LIGA
[1225J] 30S RIBOSOMAL PROTEIN S19.
[1226J] 50S RIBOSOMAL PROTEIN L22.
[1227J] 30S RIBOSOMAL PROTEIN S17.
[1228J] 50S RIBOSOMAL PROTEIN L14.
[1229J] 50S RIBOSOMAL PROTEIN L24.
[1230J] 50S RIBOSOMAL PROTEIN L5.
[1231J] ASPARTYL-TRNA SYNTHETASE.
[1232J] 30S RIBOSOMAL PROTEIN S3.
[1233J] 50S RIBOSOMAL PROTEIN L16.
[1234J] CHLOROPLAST 50S RIBOSOMAL PROTEIN L16 (FRAGMENT).
[1235J] 50S RIBOSOMAL PROTEIN L29.
[1236J] PLASMID PMD101 DNA.
[1237J] ORF starting with ATG of length 756
[1238J] METHIONYL-TRNA SYNTHETASE (EC 6.1.1.10).
[1239J] 30S RIBOSOMAL PROTEIN S17.
[1240J] 50S RIBOSOMAL PROTEIN L14.
[1241J] ARGS.
[1242J] ARGINYL-TRNA SYNTHETASE (EC 6.1.1.19).
[1243J] GLUTAMYL-TRNA SYNTHETASE 1 (EC 6.1.1.17) (GLUTAMATE-TRNA L1
[1244J] RIBOSOME-BINDING FACTOR A.
[1245J] TRANSLATION INITIATION FACTOR IF-2.
[1246J] HISTIDYL-TRNA SYNTHETASE (EC 6.1.1.21).
[1247J] THREONYL-TRNA SYNTHETASE 1 (EC 6.1.1.3).
[1248J] BH2542 PROTEIN.
[1249J] METHIONYL-TRNA SYNTHETASE (EC 6.1.1.10).
[1250J] GLUTAMYL-TRNA (GLN) AMIDOTRANSFERASE SUBUNIT A.
[1251J] TRYPTOPHANYL-TRNA SYNTHETASE.
[1252J] BH1636 PROTEIN.
[1253J] RIBOSOME RECYCLING FACTOR.
[1254J] GLUTAMYL-TRNA SYNTHETASE (EC 6.1.1.17).
[1255J] 30S RIBOSOMAL PROTEIN S14 HOMOLOG.
[1256J] RIBOSOMAL PROTEIN L17.
[1257J] LEUCYL-TRNA SYNTHETASE (EC 6.1.1.4).
[1258J] RIBOSOMAL PROTEIN S11 (BS11).
[1259J] GLUTAMYL-TRNA (GLN) AMIDOTRANSFERASE SUBUNIT A (EC 6.3.5.-)
[1260J] GLUTAMYL-TRNA (GLN) AMIDOTRANSFERASE SUBUNIT B.
[1261J] TRYPTOPHANYL-TRNA SYNTHETASE.
[1262J] RIBOSOMAL PROTEIN L28.
[1263J] BH2507 PROTEIN.
[1264J] ARGINYL-TRNA SYNTHETASE (EC 6.1.1.19) (ARGININE-TRNA LIGASE
[1265J] 50S RIBOSOMAL PROTEIN L19.
[1266J] RIBONUCLEASE P PROTEIN COMPONENT (EC 3.1.26.5) (PROTEIN C5)
[1267J] RIBOSOMAL PROTEIN S9 (BS10).
[1268J] GENERAL STRESS PROTEIN.
[1269J] PEPTIDYL-TRNA HYDROLASE.
[1270J] 50S RIBOSOMAL PROTEIN L10.
[1271J] RIBOSOMAL PROTEIN L7/L12.
[1272J] BH0124 PROTEIN.
[1273J] PEPTIDE CHAIN RELEASE FACTOR 2 IN TRANSLATION.
[1274J] RIBOSOMAL PROTEIN L11 (BL11).
[1275J] BH3771PROTEIN.
[1276J] ORF starting with ATG of length 544
[1277J] ISOLEUCYL-TRNA SYNTHETASE, MUPIROCIN RESISTANT (EC 6.1.1.5)
[1278J] THREONYL-TRNA SYNTHETASE 2 (EC 6.1.1.3) (THREONINE-TRNA LIG
[1279J] PHENYLALANYL-TRNA SYNTHETASE ALPHA CHAIN (EC 6.1.1.20) (PHEN
[1280J] T9A4.4 PROTEIN.
[1281J] ISOLEUCYL-TRNA SYNTHETASE, MUPIROCIN RESISTANT (EC 6.1.1.5)
[1282J] ILE-TRNA SYNTHETASE.
[1283J] RNA METHYLTRANSFERASE.
[1284J] BH3085 PROTEIN.
[1285J] ISOLEUCYL-TRNA SYNTHETASE, MUPIROCIN RESISTANT (EC 6.1.1.5)
[1286J] PUTATIVE SERYL-TRNA SYNTHETASE (EC 6.1.1.11).
[1287J] BH0299 PROTEIN.
[1288J] RIBONUCLEASE PH (FRAGMENT).
[1289J] HISTIDYL-TRNA SYNTHETASE (EC 6.1.1.21).
[1290J] ARGINYL-TRNA SYNTHETASE (EC 6.1.1.19).

ID1291J PUTATIVE ARGINYL-TRNA SYNTHASE (FRAGMENT).
ID1292J TRNA/RRNA METHYLTRANSFERASE.
ID1293J TRANSLATION ELONGATION FACTOR EF-P.
ID1294J PROLYL-TRNA SYNTHETASE.
ID1295J ORF starting with ATG of length 264
ID1296KE Brevibacterium lactofermentum aspC protein.
ID1297KE HYPOTHETICAL 46.8 KDA PROTEIN.
ID1298KE YDFD PROTEIN.
ID1299KE Staphylococcus aureus regulator protein.
ID1300KE YDFD PROTEIN.
ID1301KE ORF starting with ATG of length 542
ID1302KE AMINOTRANSFERASE.
ID1303K TRANSCRIPTIONAL REGULATOR (LACI FAMILY).
ID1304K TRANSCRIPTIONAL REGULATOR.
ID1305K TRANSCRIPTIONAL REPRESSOR OF THE TREHALOSE OPERON.
ID1306K ORF starting with ATG of length 565
ID1307K SUGAR KINASE.
ID1308K BH2511PROTEIN.
ID1309K STAGE 0 SPORULATION PROTEIN J.
ID1310K RIBONUCLEASE R (EC 3.1.-.-) (RNASE R) (VACB PROTEIN HOMOLOG)
ID1311K TRANSCRIPTIONAL REGULATOR INVOLVED IN CARBON CATABOLITE CONT
ID1312K RNA POLYMERASE SIGMA-F FACTOR (STAGE II SPORULATION PROTEIN
ID1313K HYPOTHETICAL PROTEIN TM0326.
ID1314K DNA-DIRECTED RNA POLYMERASE BETA CHAIN (EC 2.7.7.6) (TRANSCR
ID1315K TRANSCRIPTIONAL ANTITERMINATOR OF GLYCEROL UPTAKE OPERON.
ID1316K BH0406 PROTEIN.
ID1317K TRANSCRIPTIONAL REGULATOR (LRP/ASNC FAMILY).
ID1318K STAGE 0 SPORULATION PROTEIN J.
ID1319K VIRULENCE-ASSOCIATED PROTEIN.
ID1320K TRANSCRIPTIONAL REGULATOR (GNTR FAMILY).
ID1321K TRANSCRIPTIONAL REPRESSOR OF THE TREHALOSE OPERON.
ID1322K XYLOSE OPERON REGULATORY PROTEIN (XYLR-2).
ID1323K TRANSCRIPTIONAL REGULATOR (GNTR FAMILY).
ID1324K BH1706 PROTEIN.
ID1325K PUTATIVE FIBRONECTIN-BINDING PROTEIN (YLOA PROTEIN).
ID1326K PUTATIVE FIBRONECTIN-BINDING PROTEIN (YLOA PROTEIN).
ID1327K TRANSCRIPTIONAL REGULATOR.
ID1328K BH0677 PROTEIN.
ID1329K ORF starting with ATG of length 462
ID1330K TRANSCRIPTIONAL REGULATOR (MERR FAMILY).
ID1331K TRANSCRIPTIONAL TERMINATOR.
ID1332K ORF starting with ATG of length 585
ID1333K TRANSCRIPTIONAL REGULATOR (MERR FAMILY).
ID1334K ORF starting with ATG of length 675
ID1335K TRANSCRIPTIONAL REPRESSOR OF THE XYLOSE OPERON.
ID1336K BH3429 PROTEIN.
ID1337K BH3146 PROTEIN.
ID1338K BH0391PROTEIN.
ID1339K TRANSCRIPTIONAL REGULATOR (GNTR FAMILY).
ID1340K ORF starting with ATG of length 573
ID1341K GLUCOSE KINASE.
ID1342K TRANSCRIPTIONAL REGULATOR.
ID1343K TRANSCRIPTIONAL REGULATOR (LYSR FAMILY).
ID1344K COLD SHOCK PROTEIN CSPC.
ID1345K ORF starting with ATG of length 624
ID1346K TWO-COMPONENT RESPONSE REGULATOR.
ID1347K ORF starting with ATG of length 540
ID1348K TRANSCRIPTIONAL PLEIOTROPIC REGULATOR OF TRANSITION STATE GE
ID1349K YBGA PROTEIN.
ID1350K TRANSCRIPTIONAL PLEIOTROPIC REGULATOR OF TRANSITION STATE GE
ID1351K STAGE V SPORULATION PROTEIN T.
ID1352K HYPOTHETICAL 29.9 KDA PROTEIN.
ID1353K ORF starting with ATG of length 504
ID1354K HYPOTHETICAL 26.2 KDA PROTEIN IN FTSH-CYSK INTERGENIC REGION
ID1355K TRANSCRIPTIONAL REGULATOR (ARAC/XYLS FAMILY).
ID1356K VIRULENCE-ASSOCIATED PROTEIN.
ID1357K VIRULENCE-ASSOCIATED PROTEIN.
ID1358K TRANSCRIPTIONAL REGULATOR (TETR/ACRR FAMILY).
ID1359K BH0655 PROTEIN.
ID1360K TRANSCRIPTIONAL REGULATOR INVOLVED IN CARBON CATABOLITE CONT
ID1361K TRANSCRIPTIONAL REGULATOR (HEX REGULON REPRESSOR).
ID1362K TRANSCRIPTIONAL REGULATOR (MERR FAMILY).
ID1363K TRANSCRIPTIONAL REGULATOR.
ID1364K HYPOTHETICAL 13.3 KDA PROTEIN.
ID1365K MLL3592 PROTEIN.
ID1366K TRANSCRIPTIONAL REGULATOR (LYSR FAMILY).
ID1367K MLL3592 PROTEIN.
ID1368K RNA POLYMERASE SIGMA-54 FACTOR.
ID1369K TRANSCRIPTIONAL REGULATOR.
ID1370K TRANSCRIPTIONAL REGULATOR (LACI FAMILY).
ID1371K TRANSCRIPTIONAL REGULATOR (GNTR FAMILY).
ID1372K ORF starting with ATG of length 375
ID1373K ORF starting with ATG of length 225
ID1374K RNA POLYMERASE GENERAL STRESS SIGMA FACTOR (SIGMA B).
ID1375K HYPOTHETICAL TRANSCRIPTIONAL REGULATOR IN COTF-TETB INTERGEN
ID1376K PUTATIVE GNTR-FAMILY TRANSCRIPTIONAL REGULATOR.
ID1377K TRANSCRIPTIONAL REGULATOR.
ID1378K RNA POLYMERASE SIGMA FACTOR (SIGMA54).
ID1379K RNA POLYMERASE SIGMA-D FACTOR.
ID1380K TRANSCRIPTIONAL FACTOR.
ID1381K TRANSCRIPTION REGULATOR.
ID1382K PROBABLE HTH_ARAC_FAMILY OF TRANSCRIPTIONAL REGULATOR.
ID1383K HYPOTHETICAL TRANSCRIPTIONAL REGULATOR YRAN.
ID1384K BH0317 PROTEIN.

ID1385K DNA-DIRECTED RNA POLYMERASE BETA SUBUNIT (EC 2.7.7.6).
ID1386K RNA POLYMERASE BETA SUBUNIT.
ID1387K ORF starting with ATG of length 603
ID1388K TRANSCRIPTIONAL REGULATOR (GNTR FAMILY).
ID1389K TRANSCRIPTIONAL REGULATOR.
ID1390K PUTATIVE TRANSCRIPTIONAL REGULATOR (TRANSCRIPTIONAL REGULATO
ID1391K ORF starting with ATG of length 312
ID1392K TRANSCRIPTIONAL TERMINATOR.
ID1393K RNA POLYMERASE SIGMA FACTOR (SIGMA K) PRECURSOR.
ID1394K TWO-COMPONENT RESPONSE REGULATOR.
ID1395K TRANSCRIPTIONAL REGULATOR (GNTR FAMILY).
ID1396K TRANSCRIPTIONAL REGULATOR.
ID1397K STAGE V SPORULATION PROTEIN T.
ID1398K TRANSCRIPTIONAL REGULATOR, LACI FAMILY.
ID1399K TRANSCRIPTIONAL REGULATOR INVOLVED IN CARBON CATABOLITE CONT
ID1400K PURR.
ID1401K DNA-DIRECTED RNA POLYMERASE BETA CHAIN (EC 2.7.7.6) (TRANSCR
ID1402K PROTEASE PRODUCTION REGULATORY PROTEIN HPR.
ID1403K DNA-DIRECTED RNA POLYMERASE DELTA SUBUNIT (EC 2.7.7.6).
ID1404K PUTATIVE SUCROSE OPERON REPRESSOR.
ID1405K ORF starting with ATG of length 513
ID1406K SIMILAR TO B.SUBTILIS YWGB GENE (BH0656 PROTEIN).
ID1407K FIBRONECTIN/FIBRINOGEN-BINDING PROTEIN.
ID1408K DNA-DIRECTED RNA POLYMERASE ALPHA SUBUNIT (EC 2.7.7.6).
ID1409K DNA-DIRECTED RNA POLYMERASE ALPHA SUBUNIT (EC 2.7.7.6).
ID1410K RNA POLYMERASE GENERAL STRESS SIGMA FACTOR (SIGMA B).
ID1411K RIBONUCLEASE III.
ID1412K BH3951PROTEIN.
ID1413K YOZA PROTEIN.
ID1414K TRANSCRIPTIONAL ACTIVATOR OF THE GLUTAMATE SYNTHASE OPERON
ID1415K TRANSCRIPTIONAL REGULATOR.
ID1416K TRANSCRIPTIONAL ELONGATION FACTOR.
ID1417K ORF starting with ATG of length 599
ID1418K ORF starting with ATG of length 600
ID1419K CATABOLITE CONTROL PROTEIN A.
ID1420K ORF starting with ATG of length 461
ID1421K METHICILLIN RESISTANCE PROTEIN MECI.
ID1422K HIPOTHETICAL PROTEIN.
ID1423K DNA-DIRECTED RNA POLYMERASE BETA CHAIN (EC 2.7.7.6) (TRANSCR
ID1424K BH0406 PROTEIN.
ID1425K TRANSCRIPTIONAL REGULATOR.
ID1426K COLD SHOCK PROTEIN CSPC.
ID1427K YDEB PROTEIN (ORFC).
ID1428K ORF starting with ATG of length 663
ID1429K TRANSCRIPTIONAL REGULATOR (LRP/ASNC FAMILY).
ID1430K HYPOTHETICAL 21.8 KDA PROTEIN YVBF (ORF1).
ID1431K HYPOTHETICAL 31.6 KDA PROTEIN.
ID1432K ORF starting with ATG of length 582
ID1433K YVNA.
ID1434K TRANSCRIPTIONAL REGULATOR (ARAC/XYLS FAMILY).
ID1435K TRANSCRIPTIONAL REGULATOR INVOLVED IN CARBON CATABOLITE CONT
ID1436K TRANSCRIPTIONAL REGULATOR OF EXTRACELLULAR ENZYME GENES.
ID1437K TRANSCRIPTIONAL REGULATOR (GNTR FAMILY).
ID1438K DNA-DIRECTED RNA POLYMERASE BETA' CHAIN (EC 2.7.7.6) (TRANSC
ID1439K DNA-DIRECTED RNA POLYMERASE BETA' CHAIN (EC 2.7.7.6) (TRANSC
ID1440K TRANSCRIPTIONAL REGULATOR (GNTR FAMILY).
ID1441K TRANSCRIPTIONAL REPRESSOR OF THE TREHALOSE OPERON.
ID1442K STAGE 0 SPORULATION PROTEIN J.
ID1443K DNA-BINDING PROTEIN SPOOJ-LIKE HOMOLOG.
ID1444K TRANSCRIPTIONAL REGULATOR (GNTR FAMILY).
ID1445K ORF starting with ATG of length 642
ID1446K HYPOTHETICAL TRANSCRIPTIONAL REGULATOR YKUM.
ID1447K RNA POLYMERASE SIGMA FACTOR (SIGMA54).
ID1448K TRANSCRIPTIONAL REGULATOR (LACI FAMILY).
ID1449K TRANSCRIPTIONAL REGULATOR (MARR FAMILY).
ID1450K ORF starting with ATG of length 603
ID1451K TRANSCRIPTIONAL REGULATOR.
ID1452KG PUTATIVE LACTOSE PHOSPHOTRANSFERASE SYSTEM REPRESSOR PROTEIN
ID1453KG YTZE PROTEIN.
ID1454KG ORF starting with ATG of length 792
ID1455KG TRANSCRIPTIONAL REGULATOR (DEOR FAMILY).
ID1456KG DNA-BINDING PROTEIN IOLR.
ID1457KL SNF2 HELICASE.
ID1458KL SNF2 HELICASE.
ID1459KL ORF starting with ATG of length 489
ID1460KL HELICASE (SNF2/RAD54 FAMILY).
ID1461KL HELICASE (SNF2/RAD54 FAMILY).
ID1462KL SNF2 HELICASE.
ID1463KL SNF2 HELICASE.
ID1464KR BH1438 PROTEIN.
ID1465KR BH0466 PROTEIN.
ID1466KR BH2157 PROTEIN.
ID1467KR BH2157 PROTEIN.
ID1468KR Protease gene expression protein.
ID1469KR ACETYLTRANSFERASE, PUTATIVE.
ID1470KR BH0478 PROTEIN.
ID1471KT TRANSCRIPTIONAL REPRESSOR OF THE SOS REGULON.
ID1472KT TRANSCRIPTIONAL REPRESSOR OF THE SOS REGULON.
ID1473L DNA GYRASE SUBUNIT A (EC 5.99.1.3).
ID1474L RECF PROTEIN (DNA REPAIR AND GENETIC RECOMBINATION).
ID1475L ORF starting with TTG or GTG of length 557
ID1476L PRIMOSOMAL REPLICATION FACTORY.
ID1477L PRIMOSOMAL REPLICATION FACTORY.
ID1478L TRANSPOSASE (09).
ID1479L YOQV PROTEIN.

ID1480L TRANSPOSASE (08).
ID1481L EXCINUCLEASE ABC (SUBUNIT C).
ID1482L DNA POLYMERASE III ALPHA SUBUNIT (EC 2.7.7.7).
ID1483L PUTATIVE TRANSPOSASE.
ID1484L DNA TOPOISOMERASE IV SUBUNIT A.
ID1485L ORF starting with ATG of length 426
ID1486L PRIMOSOMAL REPLICATION FACTORY.
ID1487L DNA-DEPENDENT DNA POLYMERASE BETA CHAIN.
ID1488L TANSPOSASE.
ID1489L HYPOTHETICAL 60.7 KDA PROTEIN.
ID1490L TRANSPOSASE (10).
ID1491L BH2209 PROTEIN.
ID1492L PUTATIVE 3-METHYLADENINE DNA GLYCOSYLASE (EC 3.2.2.-).
ID1493L HYPOTHETICAL 45.9 KDA PROTEIN IN GLNQ-ANSR INTERGENIC REGION
ID1494L ATP/GTP-BINDING PROTEIN (IMPB/MUCB/SAMB FAMILY).
ID1495L DNA PRIMASE.
ID1496L DNA TOPOISOMERASE IV SUBUNIT B.
ID1497L DNA MISMATCH REPAIR PROTEIN (MISMATCH RECOGNITION STEP).
ID1498L DNA MISMATCH REPAIR PROTEIN.
ID1499L EXODEOXYRIBONUCLEASE VII (SMALL SUBUNIT).
ID1500L PUTATIVE TRANSPOSASE.
ID1501L ORF starting with ATG of length 615
ID1502L BH4041PROTEIN.
ID1503L YKFC PROTEIN.
ID1504L EXODEOXYRIBONUCLEASE VII (LARGE SUBUNIT).
ID1505L TRANSPOSASE (09).
ID1506L METHYLATED-DNA-PROTEIN-CYSTEINE METHYLTRANSFERASE (EC 2.1.1
ID1507L EXCINUCLEASE ABC (SUBUNIT B).
ID1508L ENDONUCLEASE-LIKE PROTEIN.
ID1509L PUTATIVE TRANSPOSASE.
ID1510L DNAX, YAAK, RECR, YAAL, BOFA, RRNB-165, RRNB-235, RRNB-5S, O
ID1511L PRIMOSOME COMPONENT (HELICASE LOADER).
ID1512L TYPE I RESTRICTION ENZYME STYSPI M PROTEIN (EC 2.1.1.72) (M.
ID1513L TYPE I RESTRICTION ENZYME ECOKI R PROTEIN (EC 3.1.21.3) (R.E
ID1514L ORF starting with ATG of length 693
ID1515L TRANSPOSASE (08).
ID1516L EXCINUCLEASE ABC (SUBUNIT A).
ID1517L DNA MISMATCH REPAIR PROTEIN MUTL.
ID1518L YRRC PROTEIN.
ID1519L DNA GYRASE SUBUNIT B (EC 5.99.1.3).
ID1520L DNA GYRASE SUBUNIT A (EC 5.99.1.3).
ID1521L PROBABLE ENDONUCLEASE IV (FRAGMENT).
ID1522L FORMAMIDOPYRIMIDINE-DNA GLYCOSIDASE (EC 3.2.2.23).
ID1523L STRESS-AND STARVATION-INDUCED GENE CONTROLLED BY SIGMA-B.
ID1524L HOLLIDAY JUNCTION DNA HELICASE.
ID1525L YLBH PROTEIN.
ID1526L EXCINUCLEASE ABC (SUBUNIT A).
ID1527L PROBABLE DNA TOPOISOMERASE III (EC 5.99.1.2) (RELAXING ENZYM
ID1528L PROBABLE DNA TOPOISOMERASE III (EC 5.99.1.2) (RELAXING ENZYM
ID1529L YVGS PROTEIN.
ID1530L BH4041PROTEIN.
ID1531L INTEGRASE/RECOMBINASE.
ID1532L TRANSPOSASE (09).
ID1533L DNA POLYMERASE III ALPHA SUBUNIT (EC 2.7.7.7).
ID1534L DNA POLYMERASE III ALPHA SUBUNIT (EC 2.7.7.7).
ID1535L PUTATIVE DNA POLYMERASE III, ALPHA SUBUNIT (DNA POLYMERASE
ID1536L HYPOTHETICAL 17.0 KDA PROTEIN.
ID1537L DNA GYRASE SUBUNIT A (EC 5.99.1.3).
ID1538L HYPOTHETICAL PROTEIN IN TETL 3'REGION (FRAGMENT).
ID1539L RESTRICTION MODIFICATION ENZYME.
ID1540L TRANSPOSASE (23).
ID1541L TRANSPOSASE.
ID1542L Potential M. capsulatus transposase.
ID1543L PXO1-18.
ID1544L TRANSPOSASE.
ID1545L DNA MISMATCH REPAIR PROTEIN.
ID1546L ORF starting with ATG of length 366
ID1547L HYPOTHETICAL 20.7 KDA PROTEIN IN METS-KSGA INTERGENIC REGION
ID1548L ATP-DEPENDENT DNA HELICASE.
ID1549L ORF starting with ATG of length 629
ID1550L RIBONUCLEASE HII (EC 3.1.26.4) (RNASE HII).
ID1551L DNA POLYMERASE III SUBUNIT GAMMA/TAU (EC 2.7.7.7).
ID1552L COME OPERON PROTEIN 1.
ID1553L DNA POLYMERASE III GAMMA AND TAU SUBUNITS (EC 2.7.7.7).
ID1554L DNA REPAIR PROTEIN UVRA.
ID1555L EXCINUCLEASE ABC (SUBUNIT B).
ID1556L EXCINUCLEASE ABC (SUBUNIT A).
ID1557L BH3832 PROTEIN.
ID1558L ATP-DEPENDENT DNA HELICASE.
ID1559L Streptomyces globisporus C-1027 gene cluster ORF-1.
ID1560L ATP-DEPENDENT DNA HELICASE.
ID1561L YVGS PROTEIN.
ID1562L EXODEOXYRIBONUCLEASE (EC 3.1.11.2).
ID1563L INT459.
ID1564L DNA REPAIR AND GENETIC RECOMBINATION.
ID1565L BH2382 PROTEIN.
ID1566L DNA REPAIR AND GENETIC RECOMBINATION.
ID1567L RESTRICTION ENDONUCLEASE.
ID1568L SINGLE-STRAND DNA-SPECIFIC EXONUCLEASE.
ID1569L DNA POLYMERASE III, DELTA' SUBUNIT (EC 2.7.7.7).
ID1570L 5'-3' EXONUCLEASE.
ID1571L 5'-3' EXONUCLEASE.
ID1572L ATP-DEPENDENT DNA HELICASE.
ID1573L TYPE I RESTRICTION-MODIFICATION SYSTEM SPECIFICITY DETERMINA
ID1574L DNA POLYMERASE I (EC 2.7.7.7).
ID1575L FORMAMIDOPYRIMIDINE-DNA GLYCOSIDASE (EC 3.2.2.23).
ID1576L DNA POLYMERASE I (EC 2.7.7.7).
ID1577L BH1765 PROTEIN.
ID1578L SPORE PHOTOPRODUCT LYASE (EC 4.1.99.-).
ID1579L ATP-DEPENDENT DNA HELICASE.
ID1580L DNA GYRASE SUBUNIT A (EC 5.99.1.3).

ID1581L ORF starting with ATG of length 426
ID1582L TRANSPOSASE-IS1562.
ID1583L TYPE I RESTRICTION ENZYME ECOKI R PROTEIN (EC 3.1.21.3) (R.E
ID1584L 5'-3' EXONUCLEASE.
ID1585L DNA-3-METHYLADENINE GLYCOSYLASE (EC 3.2.2.21) (3-METHYLADENI
ID1586L DNA POLYMERASE III (ALPHA SUBUNIT).
ID1587L HELICASE IV (EC 3.6.1.-) (75 KDA HELICASE).
ID1588L DNA POLYMERASE III (ALPHA SUBUNIT).
ID1589L TYPE I RESTRICTION ENZYME ECOKI R PROTEIN (EC 3.1.21.3) (R.E
ID1590L METHYLTRANSFERASE.
ID1591L BH1269 PROTEIN.
ID1592L EXCINUCLEASE ABC (SUBUNIT B).
ID1593L DNAH PROTEIN (DNA POLYMERASE III) (BETA SUBUNIT).
ID1594L RECF PROTEIN (DNA REPAIR AND GENETIC RECOMBINATION).
ID1595L DNA GYRASE SUBUNIT B (EC 5.99.1.3).
ID1596L A gyrase protein sequence.
ID1597L TRANSPOSASE (27).
ID1598L DNA MISMATCH REPAIR PROTEIN.
ID1599L TRANSPOSASE (09).
ID1600L CASSETTE CHROMOSOME RECOMBINASE B1.
ID1601L TOPOISOMERASE IV SUBUNIT A (EC 5.99.1.-).
ID1602L ATP-DEPENDENT DNA HELICASE RECQ (EC 3.6.1.-).
ID1603L ATP-DEPENDENT DNA HELICASE RECQ.
ID1604L TRANSPOSASE (10).
ID1605L HYPOTHETICAL 17.0 KDA PROTEIN.
ID1606L DNA MISMATCH REPAIR PROTEIN (MISMATCH RECOGNITION STEP).
ID1607L DNA MISMATCH REPAIR PROTEIN.
ID1608L DNA MISMATCH REPAIR PROTEIN (MISMATCH RECOGNITION STEP).
ID1609L ORF starting with ATG of length 468
ID1610L TRANSPOSASE.
ID1611L TRANSPOSASE (08).
ID1612L STRESS-AND STARVATION-INDUCED GENE CONTROLLED BY SIGMA-B.
ID1613L HYPOTHETICAL 17.0 KDA PROTEIN.
ID1614L PUTATIVE TRANSPOSASE.
ID1615L PXO1-120.
ID1616L ORF starting with ATG of length 1380
ID1617L RIBONUCLEASE HII (EC 3.1.26.4) (RNASE HI1).
ID1618L YVGS PROTEIN.
ID1619L CASSETTE CHROMOSOME RECOMBINASE B1.
ID1620L BH3609 PROTEIN.
ID1621L DNA-3-METHYLADENINE GLYCOSYLASE (EC 3.2.2.21) (3-METHYLADENI
ID1622L DNA REPAIR PROTEIN.
ID1623LK TRANSCRIPTION-REPAIR COUPLING FACTOR (TRCF).
ID1624LK ATP-DEPENDENT DNA HELICASE (EC 3.6.1.).
ID1625LK ATP-DEPENDENT DNA HELICASE (EC 3.6.1.).
ID1626LK TRANSCRIPTION-REPAIR COUPLING FACTOR.
ID1627LKJ ATP-DEPENDENT RNA HELICASE.
ID1628LKJ ATP-DEPENDENT RNA HELICASE.
ID1629LKJ ATP-DEPENDENT RNA HELICASE.
ID1630LKJ LATE COMPETENCE PROTEIN.
ID1631LR MUTATOR MUTT PROTEIN.
ID1632LR BH0986 PROTEIN.
ID1633LR ORF10291-1 (FRAGMENT).
ID1634LR BH1281PROTEIN.
ID1635M HYPOTHETICAL 73.2 KDA PROTEIN IN SODA-COMGA INTERGENIC REGIO
ID1636M S. fradiae tylosin biosynthetic pathway D-alanine carboxypep
ID1637M PENICILLIN-BINDING PROTEIN DACF PRECURSOR (D-ALANYL-D-ALANIN
ID1638M UDP-N-ACETYLGLUCOSAMINE 1-CARBOXYVINYLTRANSFERASE (EC 2.5.1.
ID1639M ORF starting with ATG of length 882
ID1640M CELL-SHAPE DETERMINING PROTEIN.
ID1641M GLYCINE BETAINE TRANSPORTER.
ID1642M CELL-SHAPE DETERMINING PROTEIN.
ID1643M Sequence translated from reading frame b of plasmid pASK46.
ID1644M autolysin useful in degrading bacterial cell walls such as i
ID1645M N-ACETYLMURAMOYL-L-ALANINE AMIDASE.
ID1646M ORF starting with ATG of length 360
ID1647M PENICILLIN-BINDING PROTEINS1A/1 B.
ID1648M ORF starting with ATG of length 537
ID1649M PENICILLIN-BINDING PROTEIN 2A (SPORE OUTGROWTH).
ID1650M S. aureus MurB protein #1.
ID1651M DNAG, RPOD, CPOA GENES AND ORF3 AND ORF5 (FRAGMENT).
ID1652M UDP-GLUCOSE 4-EPIMERASE (EC 5.1.3.2) (GALACTOWALDENASE) (UDP
ID1653M UDP-N-ACETYLGLUCOSAMINE PYROPHOSPHORYLASE (EC 2.7.7.23).
ID1654M GCPE PROTEIN HOMOLOG.
ID1655M BETA-LACTAMASE III PRECURSOR (EC 3.5.2.6).
ID1656M PENICILLIN-BINDING PROTEIN 3 (PBP 3) (PSPB20).
ID1657M B. subtilis hexylose phosphate synthase.
ID1658M PENICILLIN-BINDING PROTEIN 5* PRECURSOR (D-ALANYL-D-ALANINEC
ID1659M YKFC.
ID1660M S. aureus gidB protein sequence.
ID1661M B. stearothermophilus alanine racemase.
ID1662M HYPOTHETICAL 20.0 KDA PROTEIN IN TLPC-SRFAA INTERGENIC REGIO
ID1663M BH1683 PROTEIN.
ID1664M UDP-N-ACETYLGLUCOSAMINE PYROPHOSPHORYLASE (EC 2.7.7.23).
ID1665M YRVJ PROTEIN.
ID1666M SUBSTRATE BINDING PROTEIN OPUCC.
ID1667M UDP-GLUCOSE 4-EPIMERASE (EC 5.1.3.2) (GALACTOWALDENASE) (UDP
ID1668M PENICILLIN-BINDING PROTEIN 4* (PBP 4*) (PBP 4A).
ID1669M OUTER MEMBRANE LIPOPROTEIN GNA1946.
ID1670M BH1683 PROTEIN.
ID1671M autolysin useful in degrading bacterial cell walls such as i
ID1672M PENICILLIN-BINDING PROTEIN 1A (GERMINATION).
ID1673M ORF starting with ATG of length 453

ID1674M PENICILLIN-BINDING PROTEIN 1A (GERMINATION).
ID1675M PENICILLIN-BINDING PROTEINS1A/1B.
ID1676M CELL WALL-BINDING PROTEIN.
ID1677M PENICILLIN-BINDING PROTEIN 1A.
ID1678M HYPOTHETICAL 20.0 KDA PROTEIN IN TLPC-SRFAA INTERGENIC REGIO
ID1679M PENICILLIN-BINDING PROTEIN 1A.
ID1680M D-ALANINE-D-ALANINE LIGASE A.
ID1681M PUTATIVE D-ALANINE:D-ALANINE LIGASE (DDL) (FRAGMENT).
ID1682M HYPOTHETICAL 42.0 KDA PROTEIN IN DAPB-PAPS INTERGENIC REGION
ID1683M PENICILLIN-BINDING PROTEIN.
ID1684M CSBB PROTEIN.
ID1685M UDP-N-ACETYLMURAMATE-ALANINE LIGASE (EC 6.3.2.8).
ID1686M PUTATIVE GLYCOSYLTRANSFERASE (FRAGMENT).
ID1687M PENICILLIN-BINDING PROTEIN 2B (CELL-DIVISION SEPTUM).
ID1688M D-ALANINE-D-ALANINE LIGASE A (EC 6.3.2.4) (D-ALANYLALANINES
ID1689M STAGE V SPORULATION PROTEIN (SOPRULATION SPECIFIC PENICILLIN
ID1690M SIMILAR TO PSEUDOMONAS AERUGINOSA GDP-MANNOSE 6-DEHYDROGENAS
ID1691M TUAG PROTEIN.
ID1692M UDP-GLUCOSE 6-DEHYDROGENASE.
ID1693M BH2420 PROTEIN.
ID1694M YFNI.
ID1695M TUAG PROTEIN.
ID1696M DNAG, RPOD, CPOA GENES AND ORF3 AND ORFS.
ID1697M SPORE CORTEX-LYTIC ENZYME.
ID1698M BH1391PROTEIN.
ID1699M PROLIPOPROTEIN DIACYLGLYCERYL TRANSFERASE (EC 2.4.99.).
ID1700M PUTATIVE PENICILLIN BINDING PROTEIN PRECURSOR.
ID1701M PROLIPOPROTEIN DIACYLGLYCERYL TRANSFERASE (EC 2.4.99.).
ID1702M STAGE V SPORULATION PROTEIN (SOPRULATION SPECIFIC PENICILLIN
ID1703M UDP-N-ACETYLMURAMOYLALANYL-D-GLUTAMYL-2,6-DIAMINOPIMELATE L
ID1704M STAGE II SPORULATION PROTEIN.
ID1705M D-ALANINE-D-ALANINE LIGASE A.
ID1706M UDP-N-ACETYLGLUCOSAMINE-LIKE PROTEIN.
ID1707M UDP-N-ACETYLGLUCOSAMINE 1-CARBOXYVINYLTRANSFERASE (EC 2.5.1.
ID1708M BH3436 PROTEIN.
ID1709M TEICHOIC ACID BIOSYNTHESIS PROTEIN.
ID1710M TEICHOIC ACID TRANSLOCATION PERMEASE PROTEIN TAGG.
ID1711M TEICHOIC ACID TRANSLOCATION PERMEASE PROTEIN TAGG.
ID1712M UTP-GLUCOSE-1-PHOSPHATE URIDYLYL-TRANSFERASE (EC 2.7.7.9) (U
ID1713M N-ACETYLMURAMOYL-L-ALANINE AMIDASE (MAJOR AUTOLYSIN).
ID1714M LIPOPOLYSACCHARIDE BIOSYNTHESIS PROTEIN.
ID1715M INTERCOMPARTMENTAL SIGNALLING OF PRO-SIGMA-K PROCESSING/ACTI
ID1716M UTP-GLUCOSE-1-PHOSPHATE URIDYLYL-TRANSFERASE (EC 2.7.7.9) (U
ID1717M GLYCINE BETAINE TRANSPORTER BETL.
ID1718M Racillus subtilis teichoic acid polymerase.
ID1719M HYPOTHETICAL 73.2 KDA PROTEIN IN SODA-COMGA INTERGENIC REGIO
ID1720M LYTIC TRANSGLYCOSYLASE.
ID1721M ORF starting with ATG of length 894
ID1722M PENICILLIN-BINDING PROTEIN 4 PRECURSOR (PBP 4).
ID1723M PENICILLIN-BINDING PROTEIN 4 PRECURSOR (PBP 4).
ID1724M BH3268 PROTEIN.
ID1725M UDP-N-ACETYLMURAMOYLALANINE-D-GLUTAMATE LIGASE (EC 6.3.2.9)
ID1726M Racillus subtilis teichoic acid polymerase.
ID1727M MRAW PROTEIN (YLLC PROTEIN).
ID1728M ORF starting with ATG of length 459
ID1729M PENICILLIN-BINDING PROTEIN 2B (CELL-DIVISION SEPTUM).
ID1730M S. pneumoniae derived protein #264.
ID1731M PUTATIVE GLYCOSYLTRANSFERASE.
ID1732M BH3436 PROTEIN.
ID1733M ORF starting with ATG of length 888
ID1734M BH2666 PROTEIN.
ID1735M Staphylococcus aureus protein SEQ ID #5196.
ID1736M L-GLUTAMINE-D-FRUCTOSE-6-PHOSPHATE AMIDOTRANSFERASE (EC 2.6.
ID1737M CELL-SHAPE DETERMINING PROTEIN.
ID1738M ORF starting with ATG of length 438
ID1739M S. aureus gidB protein sequence.
ID1740M S. aureus MurB protein SEQ ID 1.
ID1741M GLYCINE BETAINE/CARNITINE/CHOLINE ABC TRANSPORTER (OSMOPROTE
ID1742M TEICHOIC ACID BIOSYNTHESIS PROTEIN F.
ID1743M PENICILLIN-BINDING PROTEIN 2B (CELL-DIVISION SEPTUM).
ID1744M PROTEOPHOSPHOGLYCAN PRECURSOR (FRAGMENT).
ID1745M STAGE V SPORULATION PROTEIN (SOPRULATION SPECIFIC PENICILLIN
ID1746M PUTATIVE UNDECAPRENYL-PHOSPHATE N-ACETYLGLUCOSAMINYLTRANSFER
ID1747M CELL-DIVISION INITIATION PROTEIN (SEPTUM FORMATION).
ID1748M DNAG, RPOD, CPOA GENES AND ORF3 AND ORF5 (FRAGMENT).
ID1749MG GDP-D-MANNOSE DEHYDRATASE.
ID1750MG PROBABLE EPIMERASE.
ID1751 MG HYPOTHETICAL 22.8 KDA PROTEIN.
ID1752M1GCT.
ID1753MJ GLUCOSE-1-PHOSPHATE THYMIDYLYL-TRANSFERASE.
ID1754MJ GLUCOSE-1-PHOSPHATE THYMIDYLYL-TRANSFERASE.
ID1755N METHYL-ACCEPTING CHEMOTAXIS PROTEIN TLPA.
ID1756N HYPOTHETICAL LIPOPROTEIN YUFN PRECURSOR.
ID1757N BH0721PROTEIN.
ID1758N SIGNAL PEPTIDASE I (EC 3.4.21.89) (SPASE I) (LEADER PEPTIDAS
ID1759N ORF starting with ATG of length 819
ID1760N METHYL-ACCEPTING CHEMOTAXIS PROTEIN.
ID1761N PREPROTEIN TRANSLOCASE SUBUNIT.
ID1762N ORF starting with ATG of length 693

ID1763N PREPROTEIN TRANSLOCASE, SECA.
ID1764N METHYL-ACCEPTING CHEMOTAXIS PROTEIN TLPB.
ID1765N DNA TRANSPORT MACHINERY.
ID1766N ORF starting with ATG of length 771
ID1767N HYPOTHETICAL PROTEIN BH0553.
ID1768N FLAGELLAR HOOK-ASSOCIATED PROTEIN 3 (HAP3).
ID1769N ORF starting with ATG of length 762
ID1770N FLAGELLAR HOOK-ASSOCIATED PROTEIN 1 (FLGK).
ID1771N METHYL-ACCEPTING CHEMOTAXIS PROTEIN TLPA.
ID1772N FLAGELLAR BIOSYNTHESIS PROTEIN FLHF (FLAGELLA ASSOCIATED GTP
ID1773N CHEMOTAXIS MOTB PROTEIN (MOTILITY PROTEIN B).
ID1774N FLAGELLAR MOTOR SWITCH PROTEIN.
ID1775N PROTEIN-EXPORT MEMBRANE PROTEIN.
ID1776N PROTEIN-EXPORT MEMBRANE PROTEIN.
ID1777N ORF starting with ATG of length 522
ID1778N PREPROTEIN TRANSLOCASE SUBUNIT.
ID1779N FLAGELLAR-SPECIFIC ATP SYNTHASE.
ID1780N FLAGELLAR MOTOR SWITCH PROTEIN.
ID1781N ORF starting with ATG of length 763
ID1782N BH0721PROTEIN.
ID1783N PREPROTEIN TRANSLOCASE SECY SUBUNIT.
ID1784N ORF starting with ATG of length 2031
ID1785N SIGNAL PEPTIDASE (TYPE I).
ID1786N PREPROTEIN TRANSLOCASE SECY SUBUNIT.
ID1787N FLAGELLAR BASAL-BODY M-RING PROTEIN.
ID1788N ORF starting with ATG of length 669
ID1789N CHEMOTAXIS PROTEIN CHEW.
ID1790N YDII (BH0552 PROTEIN).
ID1791N PREPROTEIN TRANSLOCASE SECA SUBUNIT (FRAGMENT).
ID1792N FLAGELLAR BIOSYNTHETIC PROTEIN FLIP.
ID1793N GTP-BINDING PROTEIN (ELONGATION FACTOR FAMILY).
ID1794N FLAGELLAR HOOK-BASAL BODY PROTEIN.
ID1795N GTP-BINDING PROTEIN TYPA/BIPA (TYROSINE PHOSPHORYLATED PROTE
ID1796N HYPOTHETICAL 24.1 KDA PROTEIN IN SULA-HELD INTERGENIC REGION
ID1797N SPOIIIJ PROTEIN (ESSENTIAL FOR SIGMA-G ACTIVITY AT STAGE III
ID1798N FLAGELLAR HOOK-BASAL BODY PROTEIN.
ID1799N FLAGELLAR HOOK-BASAL BODY COMPLEX PROTEIN FLHO.
ID1800N FLAGELLAR PROTEIN REQUIRED FOR FLAGELLAR FORMATION.
ID1801N FLAGELLAR PROTEIN REQUIRED FOR FLAGELLAR FORMATION.
ID1802N FLAGELLA-ASSOCIATED PROTEIN.
ID1803N FLAGELLAR BIOSYNTHESIS PROTEIN FLHA.
ID1804N METHYL-ACCEPTING CHEMOTAXIS PROTEIN.
ID1805N FLAGELLAR HOOK-ASSOCIATED PROTEIN 1 (HAP1).
ID1806N TYPE 4 PREPILIN-LIKE PROTEINS LEADER PEPTIDE PROCESSING ENZY
ID1807N SIGNAL PEPTIDASE I (EC 3.4.21.89) (SPASE I) (LEADER PEPTIDAS
ID1808N ORF starting with ATG of length 402
ID1809N ORF starting with ATG of length 288
ID1810NO PUTATIVE PROTEASE.
ID1811NO ATP-DEPENDENT CLP PROTEASE PROTEOLYTIC SUBUNIT.
ID1812NO ATP-DEPENDENT CLP PROTEASE PROTEOLYTIC SUBUNIT (EC 3.4.21.).
ID1813NT FLAGELLAR MOTOR SWITCH PROTEIN.
ID1814NT FLAGELLAR MOTOR SWITCH PROTEIN FLIY.
ID1815NT CHEMOTAXIS PROTEIN CHED.
ID1816OC BH1942 PROTEIN.
ID1817OC BH2664 PROTEIN.
ID1818O MINOR EXTRACELLULAR SERINE PROTEASE.
ID1819O PROTEIN-DISULFIDE OXIDOREDUCTASE.
ID1820O TRANSCRIPTIONAL REGULATOR.
ID1821O LEMB (FRAGMENT).
ID1822O PUTATIVE TRANSCRIPTIONAL REGULATOR.
ID1823O YMAD PROTEIN.
ID1824O PYRROLIDONE-CARBOXYLATE PEPTIDASE (EC 3.4.19.3).
ID1825O GLUTATHIONE PEROXIDASE.
ID1826O NITROGEN FIXATION PROTEIN (NIFU PROTEIN).
ID1827O MINOR EXTRACELLULAR SERINE PROTEASE (EC 3.4.21.).
ID1828O ATP-DEPENDENT CLP PROTEASE (HEAT-SHOCK PROTEIN).
ID1829O Subtilisin protein sequence.
ID1830O CLASSIII STRESS RESPONSE-RELATED ATPASE.
ID1831O DNA REPAIR PROTEIN.
ID1832O BH3598 PROTEIN.
ID1833O PEPTIDE METHIONINE SULFOXIDE REDUCTASE.
ID1834O BH1447 PROTEIN.
ID1835O CELL-DIVISION PROTEIN (ATP-DEPENDENT ZN METALLOPEPTIDASE) (EC
ID1836O ARGININE UTILIZATION REGULATORY PROTEIN ROCR.
ID1837O THIOREDOXIN REDUCTASE (NADPH) (EC 1.6.4.5).
ID1838O THIOREDOXIN REDUCTASE (EC 1.6.4.5) (TRXR) (GENERAL STRESS PR
ID1839O HEAT-SHOCK PROTEIN (ACTIVATION OF DNAK).
ID1840O HEAT SHOCK PROTEIN HTPG (HIGH TEMPERATURE PROTEIN G).
ID1841O ATP-DEPENDENT CLP PROTEASE ATP-BINDING SUBUNIT (CLASSIII HE
ID1842O TRIGGER FACTOR (PROLYL ISOMERASE).
ID1843O ORF starting with ATG of length 612
ID1844O NEGATIVE EFFECTOR OF THE CONCENTRATION OF HEMA.
ID1845O ARGININE UTILIZATION REGULATORY PROTEIN ROCR.
ID1846O PUTATIVE SIGMA L-DEPENDENT TRANSCRIPTIONAL REGULATOR IN MMGE
ID1847O TRANSCRIPTIONAL REGULATOR (H-T-H).
ID1848O ORF starting with ATG of length 1242
ID1849O ORF starting with ATG of length 1145
ID1850O THIOREDOXINE REDUCTASE.
ID1851O ORF starting with ATG of length 429
ID1852O 10 KDA CHAPERONIN (PROTEIN CPN10) (PROTEIN GROES).

ID1853O CLASSI HEAT-SHOCK PROTEIN (CHAPERONIN).
ID1854O STAGE V SPORULATION PROTEIN K.
ID1855O CLASSI HEAT-SHOCK PROTEIN (CHAPERONIN).
ID1856O DNA REPAIR PROTEIN.
ID1857O STAGE V SPORULATION PROTEIN K.
ID1858O CLASSI HEAT-SHOCK PROTEIN (CHAPERONIN).
ID1859O BH1623 PROTEIN.
ID1860O PROBABLE O-SIALOGLYCOPROTEIN ENDOPEPTIDASE (EC 3.4.24.57) (GL
ID1861O SERINE PROTEASE DO.
ID1862O SERINE PROTEASE DO.
ID1863O GENERAL STRESS PROTEIN 17O (GSP17O).
ID1864O HEAT-SHOCK PROTEIN (ACTIVATION OF DNAK).
ID1865O CLASSI HEAT-SHOCK PROTEIN (CHAPERONIN).
ID1866O GRPE PROTEIN.
ID1867O CLASSIII STRESS RESPONSE-RELATED ATPASE.
ID1868O CYTOCHROME C BIOGENESIS.
ID1869O C5A PEPTIDASE PRECURSOR (EC 3.4.21.-) (SCP).
ID1870O ORF starting with ATG of length 1056
ID1871O PROTEASE.
ID1872O CLASSIII STRESS RESPONSE-RELATED ATPASE.
ID1873O BH2189 PROTEIN.
ID1874O CLASSI HEAT-SHOCK PROTEIN (CHAPERONIN).
ID1875O CELL DIVISION CYCLE CDC48 HOMOLOG (YJOB PROTEIN).
ID1876O CELL DIVISION PROTEIN FTSH HOMOLOG (EC 3.4.24.-).
ID1877O THIOREDOXIN REDUCTASE.
ID1878O PEPTIDYL-PROLYL CIS-TRANS ISOMERASE B.
ID1879O BH3598 PROTEIN.
ID1880O PROTEIN SECRETION (POST-TRANSLOCATION CHAPERONIN).
ID1881O YKVL PROTEIN.
ID1882O ATP-DEPENDENT PROTEASE LA (EC 3.4.21.53).
ID1883O ATP-DEPENDENT PROTEINASE LA (EC 3.4.21.).
ID1884O ATP-DEPENDENT PROTEINASE LA 1 (LON) (CLASSIII HEAT-SHOCK PR
ID1885O ATP-DEPENDENT PROTEINASE LA (EC 3.4.21.).
ID1886O NEGATIVE EFFECTOR OF THE CONCENTRATION OF HEMA.
ID1887O Subtilisin protein sequence.
ID1888O GLUTATHIONE PEROXIDASE HOMOLOG BSAA.
ID1889O BH3598 PROTEIN.
ID1890O STAGE V SPORULATION PROTEIN K.
ID1891O CLASSIII STRESS RESPONSE-RELATED ATPASE.
ID1892O DNA REPAIR PROTEIN.
ID1893O 10 KDA CHAPERONIN (PROTEIN CPN10) (PROTEIN GROES).
ID1894O CLASSI HEAT-SHOCK PROTEIN (CHAPERONIN).
ID1895P SODIUM-DEPENDENT PHOSPHATE TRANSPORTER.
ID1896P SULFATE ADENYLYLTRANSFERASE.
ID1897P BH1407 PROTEIN.
ID1898P BH1407 PROTEIN.
ID1899P SUPEROXIDE DISMUTASE.
ID1900P Partial sequemce of human manganese superoxide dismutase (hM
ID1901P YDFA PROTEIN.
ID1902P HYPOTHETICAL PROTEIN YWRB.
ID1903P YBXA PROTEIN (ABC TRANSPORTER) (ATP-BINDING PROTEIN).
ID1904P ORF2 (NA+/H+ ANTIPORTER).
ID1905P MULTIPLE RESISTANCE AND PH REGULATION RELATED PROTEIN C.
ID1906P YTGA.
ID1907P FIMA.
ID1908P BH2760 PROTEIN.
ID1909P TRANSCRIPTIONAL REGULATOR (FUR FAMILY).
ID1910P HYPOTHETICAL 31.8 KDA PROTEIN IN GABP-GUAA INTERGENIC REGION
ID1911P MULTIPLE RESISTANCE AND PH REGULATION RELATED PROTEIN F.
ID1912P MULTIPLE RESISTANCE AND PH REGULATION RELATED PROTEIN E.
ID1913P HYPOTHETICAL 43.2 KDA PROTEIN IN DNAC-RPLI INTERGENIC REGION
ID1914P YVRC PROTEIN.
ID1915P TRANSCRIPTIONAL REGULATOR (FUR FAMILY) (YGAG).
ID1916P YTGD.
ID1917P HYPOTHETICAL 11.3 KDA PROTEIN IN HMP-PROB INTERGENIC REGION.
ID1918P THIOSULFATE SULFURTRANSFERASE.
ID1919P CATALASE X (EC 1.11.1.6).
ID1920P CATION-TRANSPORTING ATPASE (EC 3.6.1.).
ID1921P YVGQ (FRAGMENT).
ID1922P PROBABLE PERMEASE OF ABC TRANSPORTER.
ID1923P PROBABLE CADMIUM-TRANSPORTING ATPASE (EC 3.6.1.-) (CADMIUM E
ID1924P ABC TRANSPORTER (ATP-BINDING PROTEIN).
ID1925P MGTE.
ID1926P Bacilus megaterium YkoY protein.
ID1927P SA0168 PROTEIN.
ID1928P HYPOTHETICAL 12.2 KDA PROTEIN.
ID1929P SA0579 PROTEIN.
ID1930P HYPOTHETICAL 17.1 KDA PROTEIN IN PHOB-GROES INTERGENIC REGIO
ID1931P SULFATE TRANSPORT ATP-BINDING PROTEIN CYSA.
ID1932P *Staphylococcus carnosus* nitrate reductase NarH subunit.
ID1933P PROBABLE CATION-TRANSPORTING ATPASE F (EC 3.6.1.-).
ID1934P YVGQ PROTEIN.
ID1935P SA0167 PROTEIN.
ID1936P CATION-TRANSPORTING ATPASE PMA1 (EC 3.6.1.-).
ID1937P HYPOTHETICAL 38.5 KDA PROTEIN (FRAGMENT).
ID1938P HYPOTHETICAL 38.5 KDA PROTEIN (FRAGMENT).
ID1939P ARSENICAL PUMP MEMBRANE PROTEIN.
ID1940P YVGP PROTEIN.
ID1941P PUTATIVE ALIPHATIC SULFONATES TRANSPORT ATP-BINDING PROTEIN ID1942P CADMIUM-TRANSPORTING ATPASE.
ID1943P CONSERVED HYPOTHETICAL PROTEIN.
ID1944P PROBABLE ABC TRANSPORTER PERMEASE PROTEIN YQGI.
ID1945P ORF starting with ATG of length 822
ID1946P PUTATIVE TRANSCRIPTION REGULATOR.
ID1947P YTLB.
ID1948P PUTATIVE TRANSPORTER.
ID1949P CATALASE X (EC 1.11.1.6).
ID1950P BH2760 PROTEIN.
ID1951P CATALASE.
ID1952P BH1028 PROTEIN.
ID1953P SA1709 PROTEIN.
ID1954P AMMONIUM TRANSPORTER.
ID1955P ALKALINE PHOSPHATASE.
ID1956P PUTATIVE MONOOXYGENASE CY21B4.10C (EC 1.14.13.-).
ID1957P NOVC.
ID1958P STEROID MONOOXYGENASE.
ID1959P PUTATIVE TRANSPORTER.
ID1960P YTLD.
ID1961P ABC TRANSPORTER (PERMEASE).
ID1962P ABC TRANSPORTER (SUBSTRATE-BINDING PROTEIN).
ID1963P HYPOTHETICAL 43.2 KDA PROTEIN IN DNAC-RPLI INTERGENIC REGION
ID1964P ZINC ABC TRANSPORTER PERMEASE PROTEIN.
ID1965P YCEA.
ID1966P ZINC ABC TRANSPORTER ATP BINDING PROTEIN.
ID1967P HYPOTHETICAL ABC TRANSPORTER ATP-BINDING PROTEIN YQGK.
ID1968P YVGP PROTEIN.
ID1969P STEROID MONOOXYGENASE.
ID1970P COPPER-TRANSPORTING ATPASE.
ID1971P SULFATE ABC TRANSPORTER, PERMEASE PROTEIN.
ID1972P POTASSIUM UPTAKE PROTEIN.
ID1973P ORF starting with ATG of length 1164
ID1974P PROBABLE CADMIUM-TRANSPORTING ATPASE (EC 3.6.1.-) (CADMIUM E
ID1975P COPPER-TRANSPORTING ATPASE.
ID1976P SULFATE ABC TRANSPORTER (PERMEASE).
ID1977P PROBABLE CADMIUM-TRANSPORTING ATPASE (EC 3.6.1.-) (CADMIUM E
ID1978P BH1440 PROTEIN.
ID1979P CHROMATE TRANSPORTER.
ID1980P SULFATE ADENYLYLTRANSFERASE (EC 2.7.7.4) (SULFATE ADENYLATET
ID1981P CHROMATE TRANSPORTER.
ID1982P NA+/H+ ANTIPORTER.
ID1983P HYPOTHETICAL 28.4 KDA PROTEIN IN SACT-SACP INTERGENIC REGION
ID1984P SA0582 PROTEIN.
ID1985P PROBABLE CATION-TRANSPORTING ATPASE F (EC 3.6.1.-).
ID1986P CATION-TRANSPORTING P-ATPASE PACL.
ID1987P CATALASE (EC 1.11.1.6).
ID1988P CATALASE (EC 1.11.1.6).
ID1989P YTGC.
ID1990P ORF starting with ATG of length 470
ID1991P SUPEROXIDE DISMUTASE.
ID1992P ABC TRANSPORTER ATP-BINDING SUBUNIT.
ID1993P CHAPERONIN.
ID1994P HYPOTHETICAL 57.2 KDA PROTEIN.
ID1995P BH2861PROTEIN.
ID1996P PUTATIVE ABC-TRANSPORTER (FRAGMENT).
ID1997P NITRITE EXTRUSION PROTEIN (NITRITE FACILITATOR).
ID1998P PROBABLE ABC TRANSPORTER PERMEASE PROTEIN YQGH.
ID1999P NA+-TRANSPORTING ATP SYNTHASE.
ID2000P YVGR PROTEIN.
ID2001P CARBONIC ANHYDRASE.
ID2002P PHOSPHONATES TRANSPORT SYSTEM (PERMEASE).
ID2003P NA+-TRANSPORTING ATP SYNTHASE.
ID2004P SUPEROXIDE DISMUTASE.
ID2005P YVGR PROTEIN.
ID2006P ABC TRANSPORTER ATP-BINDING SUBUNIT.
ID2007P CADMIUM-TRANSPORTING ATPASE.
ID2008P NITRITE EXTRUSION PROTEIN (NITRITE FACILITATOR).
ID2009P FERRITIN.
ID2010P STEROID MONOOXYGENASE.
ID2011P ORF starting with ATG of length 723
ID2012P YCEA.
ID2013PH *Corynebacterium glutamicum* MCT protein SEQ ID NO:566.
ID2014PH YVRB PROTEIN.
ID2015PH ORF starting with ATG of length 567
ID2016PH HOMOLOGUE OF FERRIC ANGUIBACTIN TRANSPORT SYSTEM PERMERASE P
ID2017PH ORF starting with ATG of length 954
ID2018PH HOMOLOGUE OF FERRIC ANGUIBACTIN TRANSPORT SYSTEM PERMERASE P
ID2019PH HOMOLOGUE OF IRON DICITRATE TRANSPORT ATP-BINDING PROTEIN FE
ID2020PH FERRICHROME ABC TRANSPORTER (PERMEASE).
ID2021PH FERRICHROME TRANSPORT ATP-BINDING PROTEIN FHUC.
ID2022PH FERRICHROME TRANSPORT SYSTEM PERMEASE PROTEIN FHUG.
ID2023PR ASSIMILATORY NITRITE REDUCTASE (SUBUNIT).
ID2024PR ASSIMILATORY NITRITE REDUCTASE (SUBUNIT).
ID2025PR ASSIMILATORY NITRITE REDUCTASE (SUBUNIT).
ID2026Q YERP PROTEIN.
ID2027Q ORF starting with ATG of length 929
ID2028Q BH2163 PROTEIN.
ID2029Q ABC TRANSPORTER (ATP-BINDING PROTEIN).
ID2030Q ABC TRANSPORTER (ATP-BINDING PROTEIN).
ID2031Q SPORE COAT PROTEIN A.
ID2032Q NATA.
ID2033Q ABC TRANSPORTER (ATP-BINDING PROTEIN).
ID2034Q ABC TRANSPORTER (ATP-BINDING PROTEIN).
ID2035Q ABC TRANSPORTER (ATP-BINDING PROTEIN).
ID2036Q BH3008 PROTEIN.
ID2037Q IMIDAZOLONEPROPIONASE (EC 3.5.2.7) (IMIDAZOLONE-5-PROPIONATE
ID2038Q ABC TRANSPORTER (ATP-BINDING PROTEIN).

ID2039Q HYPOTHETICAL ABC TRANSPORTER ATP-BINDING PROTEIN IN ACDA 5'R
ID2040Q BH1071PROTEIN.
ID2041Q SPAF.
ID2042Q ABC TRANSPORTER (ATP-BINDING PROTEIN).
ID2043Q NARINGENIN-CHALCONE SYNTHASE.
ID2044Q ABC TRANSPORTER (ATP-BINDING PROTEIN).
ID2045Q HYPOTHETICAL 20.8 KDA PROTEIN IN SERS-DNAZ INTERGENIC REGION
ID2046Q SA0829 PROTEIN.
ID2047Q BH3008 PROTEIN.
ID2048Q Amino acid sequence of picromycin/methymycin cytochrome P450
ID2049Q BH3008 PROTEIN.
ID2050Q DIHYDROPYRIMIDINASE RELATED PROTEIN-3 (DRP-3) (NEURAL SPECIF
ID2051Q ORF starting with ATG of length 669
ID2052Q ABC TRANSPORTER ATP-BINDING PROTEIN.
ID2053Q ACETYLXYLAN ESTERASE (CEPHALOSPORIN-C DEACETYLASE) (EC 3.1.1
ID2054Q YERP PROTEIN.
ID2055Q PUTATIVE TRANSMEMBRANE PROTEIN (FRAGMENT).
ID2056Q HYPOTHETICAL 28.2 KDA PROTEIN.
ID2057Q HYPOTHETICAL ABC TRANSPORTER ATP-BINDING PROTEIN 2 IN GLVBC
ID2058Q HYPOTHETICAL ABC TRANSPORTER ATP-BINDING PROTEIN 1 IN GLVBC
ID2059Q HYPOTHETICAL 64.5 KDA PROTEIN.
ID2060Q ABC TRANSPORTER (ATP-BINDING PROTEIN).
ID2061Q ABC TRANSPORTER ATP-BINDING PROTEIN.
ID2062Q YERP PROTEIN.
ID2063Q ABC TRANSPORTER (ATP-BINDING PROTEIN).
ID2064Q ORF starting with ATG of length 639
ID2065Q ABC TRANSPORTER (ATP-BINDING PROTEIN).
ID2066Q ORF starting with ATG of length 951
ID2067Q ABC TRANSPORTER (ATP-BINDING PROTEIN).
ID2068Q Group B *Streptococcus* protein sequence SEQ ID NO:4.
ID2069Q ABC TRANSPORTER (ATP-BINDING PROTEIN).
ID2070Q 4-HYDROXYPHENYLACETATE-3-HYDROXYLASE.
ID2071Q FATTY ACID ALPHA HYDROXYLASE.
ID2072Q SA1734 PROTEIN.
ID2073Q BH2620 PROTEIN.
ID2074Q MRSF PROTEIN.
ID2075Q ABC TRANSPORTER (ATP-BINDING PROTEIN).
ID2076Q ABC TRANSPORTER (ATP-BINDING PROTEIN).
ID2077Q YERP PROTEIN.
ID2078Q ABC TRANSPORTER (ATP-BINDING PROTEIN).
ID2079Q ABC TRANSPORTER (ATP-BINDING PROTEIN).
ID2080Q ABC TRANSPORTER (ATP-BINDING PROTEIN).
ID2081Q ABC TRANSPORTER (ATP-BINDING PROTEIN).
ID2082Q BH2163 PROTEIN.
ID2083Q ABC TRANSPORTER (ATP-BINDING PROTEIN).
ID2084Q ABC TRANSPORTER (ATP-BINDING PROTEIN).
ID2085Q ABC TRANSPORTER (ATP-BINDING PROTEIN).
ID2086Q ORF starting with ATG of length 461
ID2087Q ABC TRANSPORTER (ATP-BINDING PROTEIN).
ID2088QR BH3955 PROTEIN.
ID2089QR Amino acid sequence of a beta-ketoacyl-ACP reductase protein
ID2090QR 3-OXOACYL-[ACYL-CARRIER PROTEIN] REDUCTASE (EC 1.1.1.100) (3
ID2091 QR 2,5-DICHLORO-2,5-CYCLOHEXADIENE-1,4-DIOL DEHYDROGENASE.
ID2092QR D-MANNONATE OXIDOREDUCTASE.
ID2093QR BH2367 PROTEIN.
ID2094QR YVAG PROTEIN.
ID2095QR SORBITOL-6-PHOSPHATE DEHYDROGENASE.
ID2096QR ORF starting with ATG of length 810
ID2097QR 3-OXOACYL-[ACYL-CARRIER PROTEIN] REDUCTASE.
ID2098QR ORF starting with ATG of length 885
ID2099QR DEHYDROGENASE/REDUCTASE FAMILY.
ID2100QR 2-DEOXY-D-GLUCONATE 3-DEHYDROGENASE (EC 1.1.1.125).
ID2101QR HYPOTHETICAL OXIDOREDUCTASE IN RTP-PELB INTERGENIC REGION (E
ID2102QR BH1330 PROTEIN.
ID2103QR BH0410 PROTEIN.
ID2104QR 3-OXOACYL-[ACYL CARRIER PROTEIN] REDUCTASE.
ID2105QR SHORT CHAIN ALCOHOL DEHYDROGENASE.
ID2106QR HYPOTHETICAL 28.3 KDA PROTEIN IN XPAC-ABRB INTERGENIC REGION
ID2107QR HYPOTHETICAL OXIDOREDUCTASE IN CHEV-MOBA INTERGENIC REGION (E
ID2108QR ORF starting with ATG of length 504
ID2109QR D-MANNONATE OXIDOREDUCTASE.
ID2110QR 3-OXOACYL-(ACYL-CARRIER PROTEIN) REDUCTASE (EC 1.1.1.100).
ID2111QR 3-OXOACYL-[ACYL CARRIER PROTEIN] REDUCTASE.
ID2112R INDOLE-3-ACETYL-ASPARTIC ACID HYDROLASE.
ID2113R BH3467 PROTEIN.
ID2114R HYPOTHETICAL 13.6 KDA PROTEIN.
ID2115R HMRA.
ID2116R HYPOTHETICAL 30.2 KDA PROTEIN IN IDH-DEOR INTERGENIC REGION.
ID2117R HYPOTHETICAL 38.3 KDA PROTEIN.
ID2118R METHANOL DEHYDROGENASE REGULATORY PROTEIN.
ID2119R PUTATIVE ABC TRANSPORTER, INTEGRAL MEMBRANE SUBUNIT.
ID2120R HYPOTHETICAL PROTEIN.
ID2121R IMMUNOGENIC PROTEIN.
ID2122R YBFQ PROTEIN.
ID2123R BH2689 PROTEIN.
ID2124R PUTATIVE ESTERASE/LIPASE.
ID2125R BH1482 PROTEIN.

ID2126R BH1746 PROTEIN.
ID2127R YKPA PROTEIN.
ID2128R SPORE CORTEX PROTEIN.
ID2129R ABC TRANSPORTER (ATP-BINDING PROTEIN).
ID2130R CARBOXYLESTERASE.
ID2131R GUAB (FRAGMENT).
ID2132R YLQF (BH2476 PROTEIN).
ID2133R BH1362 PROTEIN.
ID2134R SODIUM-DEPENDENT TRANSPORTER.
ID2135R SEQUENCE 1 FROM PATENT WO9934002.
ID2136R ABC TRANSPORTER (ATP-BINDING PROTEIN).
ID2137R CONSERVED HYPOTHETICAL PROTEIN.
ID2138R BH3108 PROTEIN.
ID2139R HMRA.
ID2140R LATE COMPETENCE OPERON REQUIRED FOR DNA BINDING AND UPTAKE.
ID2141R BH2099 PROTEIN.
ID2142R ORF starting with ATG of length 734
ID2143R PHENOL 2-HYDROXYLASE COMPONENT B.
ID2144R BH2155 PROTEIN.
ID2145R ATP-BINDING PROTEIN.
ID2146R HYPOTHETICAL PROTEIN PA4923.
ID2147R BH1122 PROTEIN.
ID2148R BH1372 PROTEIN.
ID2149R BH3923 PROTEIN.
ID2150R ORF starting with ATG of length 599
ID2151R BH3254 PROTEIN.
ID2152R *B. subtilis* hydrolase protein YFHM.
ID2153R BH0079 PROTEIN.
ID2154R CONSERVED HYPOTHETICAL PROTEIN.
ID2155R BH1308 PROTEIN.
ID2156R YKOQ.
ID2157R YISU PROTEIN.
ID2158R BH3866 PROTEIN.
ID2159R HYPOTHETICAL 37.5 KDA PROTEIN IN DEGA-NPRB INTERGENIC REGION
ID2160R ORF starting with ATG of length 570
ID2161R RIBOSOMAL-PROTEIN (S18)-ALANINE ACETYLTRANSFERASE.
ID2162R BH1956 PROTEIN.
ID2163R HYPOTHETICAL 32.8 KDA PROTEIN.
ID2164R HYPOTHETICAL 17.9 KDA PROTEIN IN PHOB-GROES INTERGENIC REGIO
ID2165R CONSERVED HYPOTHETICAL PROTEIN.
ID2166R BH3279 PROTEIN.
ID2167R PHT4-RELATED PROTEIN.
ID2168R BH0392 PROTEIN.
ID2169R BH1700 PROTEIN.
ID2170R ORF starting with ATG of length 933
ID2171R NADH OXIDASE (EC 1.6.99.3) (NOXASE).
ID2172R *Neisseria meningitidis* strain A antigen encoded by ORF6.
ID2173R MMGE PROTEIN.
ID2174R HYPOTHETICAL 23.3 KDA PROTEIN.
ID2175R PENICILLIN G ACYLASE.
ID2176R PROTEASE (PROCESSING OF PRO-SIGMA-K TO ACTIVE SIGMA-K).
ID2177R BH3470 PROTEIN.
ID2178R BH2835 PROTEIN.
ID2179R HYPOTHETICAL ABC TRANSPORTER ATP-BINDING PROTEIN TM0352.
ID2180R SODIUM-DEPENDENT TRANSPORTER.
ID2181R HYPOTHETICAL 37.8 KDA PROTEIN.
ID2182R BH2854 PROTEIN.
ID2183R MLL8760 PROTEIN.
ID2184R HYPOTHETICAL 28.1 KDA PROTEIN IN SIPU 3'REGION.
ID2185R ORF starting with ATG of length 600
ID2186R HYPOTHETICAL 32.2 KDA PROTEIN.
ID2187R PUTATIVE OXIDOREDUCTASE.
ID2188R ABC TRANSPORTER (ATP-BINDING PROTEIN).
ID2189R BH3572 PROTEIN.
ID2190R ABC TRANSPORTER.
ID2191R ABC TRANSPORTER.
ID2192R BH3569 PROTEIN.
ID2193R YUSC PROTEIN.
ID2194R ORF starting with ATG of length 621
ID2195R BH1266 PROTEIN.
ID2196R BH1896 PROTEIN.
ID2197R SA0211PROTEIN.
ID2198R BH1421PROTEIN.
ID2199R ABC TRANSPORTER, PERMEASE PROTEIN.
ID2200R BH2013 PROTEIN.
ID2201R ORF starting with ATG of length 701
ID2202R BH2498 PROTEIN.
ID2203R ORF starting with ATG of length 474
ID2204R THERMOSTABLE CARBOXYPEPTIDASE (CPSA-2) (EC 3.4.17.).
ID2205R ORF starting with ATG of length 972
ID2206R ORF starting with ATG of length 396
ID2207R CARBOXYLESTERASE.
ID2208R ORF starting with ATG of length 431
ID2209R METHANOL DEHYDROGENASE REGULATORY PROTEIN.
ID2210R BH0720 PROTEIN.
ID2211R COMPETENCE-DAMAGE INDUCIBLE PROTEIN CINA.
ID2212R HYPOTHETICAL 36.8 KDA PROTEIN.
ID2213R BH3279 PROTEIN.
ID2214R *Bacillus subtilis* metalloprotease YhaA.
ID2215R SPORE CORTEX PROTEIN.
ID2216R BH0287 PROTEIN.
ID2217R BH0287 PROTEIN.
ID2218R HYPOTHETICAL 43.5 KDA PROTEIN.
ID2219R WZX.
ID2220R AMINOBENZOYL-GLUTAMATE UTILIZATION PROTEIN A HOMOLOG.
ID2221R BH2392 PROTEIN.
ID2222R HYPOTHETICAL 49.4 KDA PROTEIN.
ID2223R BH2703 PROTEIN.
ID2224R FLORFENICOL RESISTANCE PROTEIN.
ID2225R BH0105 PROTEIN.
ID2226R BH2921PROTEIN.
ID2227R HYPOTHETICAL.
ID2228R BH2279 PROTEIN.
ID2229R ORF starting with ATG of length 552
ID2230R BH4031PROTEIN.
ID2231R HYPOTHETICAL PROTEIN.
ID2232R BH3883 PROTEIN.
ID2233R BH1700 PROTEIN.
ID2234R BH0531PROTEIN.
ID2235R ABC TRANSPORTER (ATP-BINDING PROTEIN).
ID2236R ABC TRANSPORTER (ATP-BINDING PROTEIN).
ID2237R ORF starting with ATG of length 626
ID2238R BH0822 PROTEIN.
ID2239R HYPOTHETICAL ABC TRANSPORTER ATP-BINDING PROTEIN YDIF.
ID2240R BH0560 PROTEIN.
ID2241R NADH OXIDASE (NOX).

ID2242R YLQF (BH2476 PROTEIN).
ID2243R HYPOTHETICAL PROTEIN YWRF.
ID2244R BH2835 PROTEIN.
ID2245R ORF starting with ATG of length 489
ID2246R SA0780 PROTEIN.
ID2247R HYPOTHETICAL 19.2 KDA PROTEIN IN RPH-ILVB INTERGENIC REGION.
ID2248R BH2805 PROTEIN.
ID2249R ORF starting with ATG of length 906
ID2250R NADH-DEPENDENT DEHYDROGENASE HOMOLOG.
ID2251R LATE COMPETENCE OPERON REQUIRED FOR DNA BINDING AND UPTAKE.
ID2252R HYPOTHETICAL PROTEIN.
ID2253R ABC TRANSPORTER ATP BINDING PROTEIN.
ID2254R ORFL1.
ID2255R HYPOTHETICAL 73.4 KDA PROTEIN.
ID2256R HYPOTHETICAL 44.4 KDA PROTEIN IN EPR-GALK INTERGENIC REGION.
ID2257R CONSERVED HYPOTHETICAL PROTEIN.
ID2258R ORF starting with ATG of length 663
ID2259R BH1362 PROTEIN.
ID2260R PUTATIVE TRANSPORTER.
ID2261R RIBONUCLEASE H-RELATED PROTEIN.
ID2262R BH2393 PROTEIN.
ID2263R INVOLVED IN SPORE CORTEX SYNTHESIS.
ID2264R BH1363 PROTEIN.
ID2265R BH1362 PROTEIN.
ID2266R GTP-BINDING PROTEIN INVOLVED IN INITIATION OF SPORULATION.
ID2267R BH0106 PROTEIN.
ID2268R YTPR.
ID2269R BH0052 PROTEIN.
ID2270R TWO-COMPONENT SENSOR HISTIDINE KINASE.
ID2271R BH1746 PROTEIN.
ID2272R BH1089 PROTEIN.
ID2273R Bacillus subtilis metalloprotease YmfH.
ID2274R THDF PROTEIN (THIOPHEN AND FURAN OXIDATION).
ID2275R BH0487 PROTEIN.
ID2276R BH2820 PROTEIN.
ID2277R BH3178 PROTEIN.
ID2278R TRANSCRIPTIONAL REGULATOR INVOLVED IN NITROGEN REGULATION (N
ID2279R YFIN (BH1056 PROTEIN).
ID2280R BH3470 PROTEIN.
ID2281R ABC TRANSPORTER (ATP-BINDING PROTEIN).
ID2282R HYPOTHETICAL ABC TRANSPORTER ATP-BINDING PROTEIN YLIA.
ID2283R HYPOTHETICAL 89.7 KDA PROTEIN.
ID2284R HYPOTHETICAL 8.1 KDA PROTEIN IN KDGK 5'REGION (K2 ORF).
ID2285R BH3359 PROTEIN.
ID2286R BH2393 PROTEIN.
ID2287R HYPOTHETICAL 33.7 KDA PROTEIN.
ID2288R BH1669 PROTEIN.
ID2289R PHOSPHOGLYCOLATE PHOSPHATASE.
ID2290R ORF starting with ATG of length 397
ID2291R BH3054 PROTEIN.
ID2292R HYPOTHETICAL 24.1 KDA PROTEIN YDIH.
ID2293R BH1266 PROTEIN.
ID2294R BH1266 PROTEIN.
ID2295R BH0608 PROTEIN.
ID2296R HYPOTHETICAL 73.4 KDA PROTEIN.
ID2297R HYPOTHETICAL 43.4 KDA PROTEIN IN CTAF 3'REGION (ORF2).
ID2298R BH3254 PROTEIN.
ID2299R ABC TRANSPORTER (ATP-BINDING PROTEIN).
ID2300R BH2587 PROTEIN.
ID2301R CG3609 PROTEIN.
ID2302R ORF starting with ATG of length 431
ID2303R BH2165 PROTEIN.
ID2304R Staphylococcal ABC transporter protein.
ID2305R ORF starting with ATG of length 574
ID2306R GTP-BINDING PROTEIN INVOLVED IN INITIATION OF SPORULATION.
ID2307R BH2503 PROTEIN.
ID2308R HYPOTHETICAL 41.6 KDA PROTEIN IN FMT-SPOVM INTERGENIC REGION
ID2309R UNKNOWN.
ID2310R COMF OPERON PROTEIN 3.
ID2311R ORF starting with ATG of length 347
ID2312R BH3121PROTEIN.
ID2313R BH2498 PROTEIN.
ID2314R BH0720 PROTEIN.
ID2315R COMPETENCE-DAMAGE INDUCIBLE PROTEIN.
ID2316R ORF starting with ATG of length 465
ID2317R HYPOTHETICAL ABC TRANSPORTER ATP-BINDING PROTEIN IN IDH 3'RE
ID2318R ORF11.
ID2319R IMMUNOGENIC PROTEIN.
ID2320R BH1271PROTEIN.
ID2321R GTP-BINDING PROTEIN (ERA/THDF FAMILY).
ID2322R JAG PROTEIN (SPOIIIJ-ASSOCIATED PROTEIN).
ID2323R BH2906 PROTEIN.
ID2324R BH3090 PROTEIN.
ID2325R BH3467 PROTEIN.
ID2326R BH3359 PROTEIN.
ID2327R ORF starting with ATG of length 452
ID2328R BH3090 PROTEIN.
ID2329R BH2378 PROTEIN.
ID2330R ORFA1.
ID2331R PUTATIVE VIRULENCE FACTOR.
ID2332R BH1811PROTEIN.
ID2333R YKVM PROTEIN.
ID2334R BH0590 PROTEIN.
ID2335R HYPOTHETICAL 32.8 KDA PROTEIN.
ID2336R HOMOLOGUES TO NITRILE HYDRATASE REGION 3'-HYPOTHETICAL PROTE
ID2337R HYPOTHETICAL 35.7 KDA PROTEIN.
ID2338R ATP-BINDING PROTEIN ABC.
ID2339R ORF starting with ATG of length 549
ID2340R BH1679 PROTEIN.
ID2341R ORF starting with ATG of length 1227
ID2342R UNKNOWN (BH3837 PROTEIN).
ID2343R BH2972 PROTEIN.
ID2344R SODIUM-DEPENDENT TRANSPORTER.
ID2345R HYPOTHETICAL 28.1 KDA PROTEIN IN SIPU 3'REGION.
ID2346R BH2030 PROTEIN.
ID2347R MYO-INOSITOL 2-DEHYDROGENASE.
ID2348R BH3289 PROTEIN.
ID2349R Ammonifex degensii KC4 alkaline phosphatase (3A1A=3A2A).
ID2350R ORF starting with ATG of length 756
ID2351R ALUMINUM RESISTANCE PROTEIN (FRAGMENT).

ID2352R BH1047 PROTEIN.
ID2353R ORF starting with ATG of length 749
ID2354R FORMATE DEHYDROGENASE ALPHA SUBUNIT HOMOLOG.
ID2355R BH1746 PROTEIN.
ID2356R ORF starting with ATG of length 750
ID2357R HYPOTHETICAL PROTEIN YWRF.
ID2358R BH1362 PROTEIN.
ID2359R WZX.
ID2360R YMFF PROTEIN.
ID2361R BH2393 PROTEIN.
ID2362R BH2392 PROTEIN.
ID2363R ORF starting with ATG of length 933
ID2364R ORF starting with ATG of length 1126
ID2365R BH1421PROTEIN.
ID2366R HYPOTHETICAL 26.3 KDA PROTEIN.
ID2367R HYPOTHETICAL 36.8 KDA PROTEIN.
ID2368R HYPOTHETICAL 33.7 KDA PROTEIN.
ID2369R BH0105 PROTEIN.
ID2370R BH0106 PROTEIN.
ID2371R BH2921PROTEIN.
ID2372R CONSERVED HYPOTHETICAL PROTEIN.
ID2373R YLQF (BH2476 PROTEIN).
ID2374R HYPOTHETICAL 19.2 KDA PROTEIN IN RPH-ILVB INTERGENIC REGION.
ID2375R PUTATIVE TRANSPORTER.
ID2376R CMP-BINDING PROTEIN.
ID2377R ORF starting with ATG of length 559
ID2378R ORF starting with ATG of length 216
ID2379R ORF starting with ATG of length 202
ID2380R ORF starting with ATG of length 339
ID2381R ORF starting with ATG of length 386
ID2382S GALACTOSE-1-PHOSPHATE URIDYLTRANSFERASE.
ID2383S BH2588 PROTEIN.
ID2384S BH1442 PROTEIN.
ID2385S BH1440 PROTEIN.
ID2386S BH1437 PROTEIN.
ID2387S BH1436 PROTEIN.
ID2388S CITS (TWO-COMPONENT SENSOR HISTIDINE KINASE).
ID2389S ORF starting with ATG of length 324
ID2390S HYPOTHETICAL 16.2 KDA PROTEIN IN COMF-FLGM INTERGENIC REGION
ID2391S PUTATIVE TWO-COMPONENT SYSTEM SENSOR KINASE.
ID2392S DNA, COMPLETE SEQUENCE.
ID2393S GTP-BINDING PROTEIN.
ID2394S BH4052 PROTEIN.
ID2395S BH1263 PROTEIN.
ID2396S BH2161PROTEIN.
ID2397S ORF starting with ATG of length 315
ID2398S BH1789 PROTEIN.
ID2399S ORF starting with ATG of length 302
ID2400S YDHG PROTEIN.
ID2401S MULTIDRUG RESISTANCE PROTEIN.
ID2402S BH1496 PROTEIN.
ID2403S ORF starting with ATG of length 510
ID2404S DIAMINOPIMELATE EPIMERASE (EC 5.1.1.7) (DAP EPIMERASE).
ID2405S BH3939 PROTEIN.
ID2406S ORF starting with ATG of length 330
ID2407S HYPOTHETICAL 11.7 KDA PROTEIN.
ID2408S Staphylococcus aureus protein homologous to hypothetical pro
ID2409S ORF starting with ATG of length 390
ID2410S BH1410 PROTEIN.
ID2411S ORF starting with ATG of length 450
ID2412S ORF starting with ATG of length 499
ID2413S ORF starting with ATG of length 498
ID2414S STAGE V SPORULATION PROTEIN AF.
ID2415S STAGE V SPORULATION PROTEIN AE.
ID2416S SPORE GERMINATION PROTEIN A3 PRECURSOR.
ID2417S BH2169 PROTEIN.
ID2418S GCPE PROTEIN HOMOLOG.
ID2419S ORF starting with ATG of length 390
ID2420S HYPOTHETICAL 19.7 KDA PROTEIN.
ID2421S BH1740 PROTEIN.
ID2422S ORF starting with ATG of length 234
ID2423S HYPOTHETICAL 18.9 KDA PROTEIN IN CYPA-AADK INTERGENIC REGION
ID2424S ORF starting with ATG of length 237
ID2425S BH060S PROTEIN.
ID2426S DAUNORUBICIN RESISTANCE ATP-BINDING PROTEIN DRRA.
ID2427S GLUCOSIDASE
ID2428S ORF starting with ATG of length 351
ID2429S ORF starting with ATG of length 747
ID2430S ORF starting with ATG of length 336
ID2431S HYPOTHETICAL 7.1 KDA PROTEIN.
ID2432S ORF starting with ATG of length 363
ID2433S YFHO PROTEIN.
ID2434S ORF starting with ATG of length 258
ID2435S HYPOTHETICAL 22.4 KDA PROTEIN IN RPMF-FTSL INTERGENIC REGION
ID2436S ORF starting with ATG of length 336
ID2437S BH2332 PROTEIN.
ID2438S HYPOTHETICAL 93.5 KDA PROTEIN.
ID2439S ORF starting with ATG of length 314
ID2440S MANGANESE ABC TRANSPORTER ATP BINDING PROTEIN.
ID2441S TRANSPOSASE FOR TRANSPOSON TN554.
ID2442S HYPOTHETICAL 23.7 KDA PROTEIN.
ID2443S E. coli proliferation associated protein sequence SEQ ID NO:
ID2444S ORF starting with ATG of length 348
ID2445S ALDOSE 1-EPIMERASE.
ID2446S BH3567 PROTEIN.
ID2447S SCRT.
ID2448S BH0789 PROTEIN.
ID2449S YFHO PROTEIN.
ID2450S Streptococcus pneumoniae polypeptide.
ID2451S BH1373 PROTEIN.
ID2452S NAD-DEPENDENT METHANOL DEHYDROGENASE.
ID2453S BH1064 PROTEIN.
ID2454S SMALL ACID-SOLUBLE SPORE PROTEIN.
ID2455S ORF starting with ATG of length 621
ID2456S STREPTOCOCCAL HEMAGGLUTININ.
ID2457S ORF starting with ATG of length 1032
ID2458S M. tuberculosis polypeptide sequence comprising Mtb-81 antig
ID2459S ORF starting with ATG of length 885
ID2460S pJH10 gene product-bacterial endotoxin with insecticidal a
ID2461S Sequence attached to hepatitis B virus (HBV) pre-S(1) sequen
ID2462S CHLORAMPHENICOL ACETYLTRANSFERASE (EC 2.3.1.28).
ID2463S ORF starting with ATG of length 332
ID2464S ORF starting with ATG of length 422
ID2465S GALACTOSE-1-PHOSPHATE URIDYLTRANSFERASE.

ID2466S BH1694 PROTEIN.
ID2467S ORF, HYPOTHETICAL PROTEIN.
ID2468S IOLB PROTEIN.
ID2469S ORF starting with ATG of length 322
ID2470S INVOLVED IN SPORE CORTEX SYNTHESIS.
ID2471S BH1398 PROTEIN.
ID2472S Staphylococcus aureus protein homologous to subunit fmdE.
ID2473S Staphylococcus aureus protein homologous to hypothetical pro
ID2474S SURFACE PROTEIN PLS.
ID2475S BH2296 PROTEIN.
ID2476S BH229S PROTEIN.
ID2477S HYPOTHETICAL 25.5 KDA PROTEIN.
ID2478S ACETOIN DEHYDROGENASE.
ID2479S YFLM PROTEIN.
ID2480S BH3472 PROTEIN.
ID2481S BH3473 PROTEIN.
ID2482S HYPOTHETICAL 25.7 KDA PROTEIN IN BCSA-DEGR INTERGENIC REGION
ID2483S HYPOTHETICAL 15.7 KDA PROTEIN IN SPOIIIC-CWLA INTERGENIC REG
ID2484S RELATED TO DIMERIC DIHYDRODIOL DEHYDROGENASE.
ID2485S BH0220 PROTEIN.
ID2486S ORF starting with ATG of length 402
ID2487S DNA TOPOISOMERASE III-LIKE PROTEIN.
ID2488S L-ASPARAGINASE (EC 3.5.1.1) (L-ASPARAGINE AMIDOHYDROLASE).
ID2489S Amino acid sequence of a partial holB polypeptide.
ID2490S CYTOCHROME P450 107B1 (EC 1.14.-.-) (P450CVIIB1).
ID2491S PUTATIVE ISOCHORISMATASE.
ID2492S HYPOTHETICAL 17.8 KDA PROTEIN.
ID2493S ORF starting with ATG of length 693
ID2494S SPORE PROTEASE (DEGRADATION OF SASPS).
ID2495S BH4053 PROTEIN.
ID2496S ORF starting with ATG of length 324
ID2497S BIOTIN SYNTHASE, PUTATIVE.
ID2498S INITIATION OF CHROMOSOME REPLICATION.
ID2499S PROBABLE GLUTAMINASE YLAM (EC 3.5.1.2).
ID2500S PHOH-LIKE PROTEIN.
ID2501S BH1399 PROTEIN.
ID2502S PROBABLE ABC TRANSPORTER PERMEASE PROTEIN IN OPUD-BIOI INTER
ID2503S ORF starting with ATG of length 933
ID2504S YOBO.
ID2505S PHAGE-LIKE ELEMENT PBSX PROTEIN XKDV.
ID2506S ORF starting with ATG of length 2268
ID2507S ORF starting with ATG of length 375
ID2508S SA2422 PROTEIN.
ID2509S YURZ PROTEIN.
ID2510S BH0817 PROTEIN.
ID2511S BH2983 PROTEIN.
ID2512S ORF starting with ATG of length 564
ID2513S BH1703 PROTEIN.
ID2514S PROPIONYL-COA CARBOXYLASE, ALPHA SUBUNIT, PUTATIVE.
ID2515S ORF starting with ATG of length 503
ID2516S HYPOTHETICAL PROTEIN.
ID2517S PROLIDASE (XAA-PRO DIPEPTIDASE) (PEPQ-LIKE2) (EC 3.4.13.9).
ID2518S ORF starting with ATG of length 463
ID2519S ORF starting with ATG of length 347
ID2520S ORF starting with ATG of length 279
ID2521S ORF10.
ID2522S FERRICHROME ABC TRANSPORTER (PERMEASE).
ID2523S GLYCINE BETAINE TRANSPORTER BETL.
ID2524S ORF starting with ATG of length 363
ID2525S BH3219 PROTEIN.
ID2526S SMALL PROTEIN B.
ID2527S ORF starting with ATG of length 373
ID2528S BH0893 PROTEIN.
ID2529S YTJA.
ID2530S BH0407 PROTEIN.
ID2531S ORF starting with ATG of length 234
ID2532S C4-DICARBOXYLATE TRANSPORT SYSTEM (PERMEASE LARGE PROTEIN).
ID2533S CHROMOSOME PARTITION PROTEIN SMC.
ID2534S ORF starting with ATG of length 249
ID2535S TRANSCRIPTIONAL REGULATOR.
ID2536S TRANSPOSASE (07).
ID2537S PTS SYSTEM, GALACTITOL-SPECIFIC ENZYME II, B COMPONENT (EC 2
ID2538S ORF starting with ATG of length 547
ID2539S UNSATURATED GLUCURONYL HYDROLASE.
ID2540S THID.
ID2541S HYPOTHETICAL 56.4 KDA PROTEIN IN SODA-COMGA INTERGENIC REGIO
ID2542S Streptococcus pneumoniae encoded polypeptide.
ID2543S HYPOTHETICAL 14.9 KDA PROTEIN.
ID2544S Amino acid sequence of a Chlamydia pneumoniaeprotein.
ID2545S HYPOTHETICAL PROTEIN TC0114.
ID2546S PTS SYSTEM, BETA-GLUCOSIDE-SPECIFIC ENZYME II, ABC COMPONENT
ID2547S HYPOTHETICAL 57.5 KDA PROTEIN IN VMA7-RPS25A INTERGENIC REGI
ID2548S BH0193 PROTEIN.
ID2549S SUGAR TRANSPORT SYSTEM (PERMEASE) (BINDING PROTEIN DEPENDENT
ID2550S GLUCOSE 1-DEHYDROGENASE.
ID2551S SMALL ACID-SOLUBLE SPORE PROTEIN (MAJOR GAMMA-TYPE SASP).
ID2552S TRANSCRIPTIONAL REPRESSOR.
ID2553S BH1432 PROTEIN.
ID2554S BH1770 PROTEIN.
ID2555S ORF13.
ID2556S PROBABLE AMINO ACID PERMEASE.
ID2557S 228AA LONG HYPOTHETICAL HYDANTOIN RACEMASE.
ID2558S HYPOTHETICAL 30.7 KDA PROTEIN.
ID2559S FUMARATE REDUCTASE FLAVOPROTEIN SUBUNIT PRECURSOR (EC 1.3.99
ID2560S BH2577 PROTEIN.
ID2561S BH2576 PROTEIN.
ID2562S BH2208 PROTEIN.
ID2563S ORF starting with ATG of length 433
ID2564S ORF starting with ATG of length 567
ID2565S ORF starting with ATG of length 340
ID2566S ORF starting with ATG of length 230
ID2567S ORF starting with ATG of length 340
ID2568S CONSERVED HYPOTHETICAL PROTEIN.
ID2569S BH1373 PROTEIN.
ID2570S STAGE III SPORULATION PROTEIN D.
ID2571S ORF starting with ATG of length 924
ID2572S BH2734 PROTEIN.
ID2573S BH3113 PROTEIN.

ID2574S BH3134 PROTEIN.
ID2575S ORF starting with ATG of length 569
ID2576S ORF starting with ATG of length 280
ID2577S CELL WALL HYDROLASE (SPORULATION).
ID2578S HYPOTHETICAL 20.3 KDA PROTEIN IN UNG-ROCA INTERGENIC REGION.
ID2579S BH3828 PROTEIN.
ID2580S BH3829 PROTEIN.
ID2581S BH0790 PROTEIN.
ID2582S BH3416 PROTEIN.
ID2583S BH2326 PROTEIN.
ID2584S ORF starting with ATG of length 381
ID2585S BH1357 PROTEIN.
ID2586S BH1704 PROTEIN.
ID2587S BH3063 PROTEIN.
ID2588S BH2916 PROTEIN.
ID2589S SUCROSE-6-PHOSPHATE HYDROLASE.
ID2590S YFLK PROTEIN.
ID2591S HYPOTHETICAL 41.2 KDA PROTEIN.
ID2592S 3-OXOACYL-(ACYL-CARRIER PROTEIN) REDUCTASE.
ID2593S HYPOTHETICAL 33.7 KDA PROTEIN.
ID2594S ORF starting with ATG of length 300
ID2595S CONSERVED HYPOTHETICAL PROTEIN.
ID2596S ORF starting with ATG of length 324
ID2597S PTS SYSTEM, GLUCOSE-SPECIFIC IIBC COMPONENT (EIIBC-GLC) (GLU
ID2598S YFHO PROTEIN.
ID2599S BH1692 PROTEIN.
ID2600S DEDA FAMILY PROTEIN.
ID2601S ORF starting with ATG of length 258
ID2602S BH1610 PROTEIN.
ID2603S CONSERVED HYPOTEHT1CAL PROTEIN.
ID2604S ORF starting with ATG of length 351
ID2605S SPORE GERMINATION PROTEIN A2.
ID2606S SPORE GERMINATION PROTEIN A3 PRECURSOR.
ID2607S HYPOTHETICAL 27.6 KDA PROTEIN IN FNR-NARG INTERGENIC REGION.
ID2608S BH1148 PROTEIN.
ID2609S BH2691 PROTEIN.
ID2610S YVNB.
ID2611S PUTATIVE INNER MEMBRANE PROTEIN.
ID2612S UNDECAPRENOL KINASE (BACITRACIN RESISTANCE PROTEIN).
ID2613S C4-DICARBOXYLATE TRANSPORT SYSTEM (PERMEASE LARGE PROTEIN).
ID2614S THREONINE SYNTHASE (EC 4.2.99.2).
ID2615S SPORE GERMINATION PROTEIN.
ID2616S HYPOTHETICAL 41.2 KDA PROTEIN IN GAPA-RND INTERGENIC REGION.
ID2617S PUTATIVE DNA BINDING PROTEIN.
ID2618S ADENINE DEAMINASE.
ID2619S BH1400 PROTEIN.
ID2620S BH1399 PROTEIN.
ID2621S HYPOTHETICAL 13.3 KDA PROTEIN IN AROD-COMER INTERGENIC REGIO
ID2622S TRANSCRIPTIONAL PLEIOTROPIC REPRESSOR.
ID2623S TRYPTOPHANYL-TRNA SYNTHETASE.
ID2624S BH2871 PROTEIN.
ID2625S BH2872 PROTEIN.
ID2626S HYPOTHETICAL 21.0 KDA LIPOPROTEIN IN CSPB-GLPP INTERGENIC RE
ID2627S ORF starting with ATG of length 549
ID2628S BH1162 PROTEIN.
ID2629S SA2180 PROTEIN.
ID2630S YLNF PROTEIN.
ID2631S BH1789 PROTEIN.
ID2632S TRANSCRIPTIONAL REGULATOR (GNTR FAMILY).
ID2633S RNA POLYMERASE SIGMA FACTOR (SIGMA54).
ID2634S BH3562 PROTEIN.
ID2635S PRE-NECK APPENDAGE PROTEIN (LATE PROTEIN GP12).
ID2636S BH1560 PROTEIN.
ID2637S LACTOSE TRANSPORT SYSTEM (PERMEASE).
ID2638S CYSTEINYL-TRNA SYNTHETASE (EC 6.1.1.16) (CYSTEINE-TRNA LIGA
ID2639S SPORE GERMINATION PROTEIN.
ID2640S TRANSCRIPTIONAL REGULATOR.
ID2641S SPAE.
ID2642S ORF starting with ATG of length 396
ID2643S ENDO-BETA-1,3-GLUCANASE PRECURSOR.
ID2644S SPORE MATURATION PROTEIN.
ID2645S SPORE MATURATION PROTEIN.
ID2646S YOBO.
ID2647S BH0709 PROTEIN.
ID2648S ORF starting with ATG of length 459
ID2649S SENSOR KINASE.
ID2650S SENSOR REGULATOR.
ID2651S ORF starting with ATG of length 553
ID2652S BH2838 PROTEIN.
ID2653S PROBABLE ABC TRANSPORTER PERMEASE PROTEIN YQGI.
ID2654S BH0618 PROTEIN.
ID2655S BH162S PROTEIN.
ID2656S YFHO PROTEIN.
ID2657S YFHO PROTEIN.
ID2658S ACETOHYDROXY ACID SYNTHASE (EC 4.1.3.18) (ACETOLACTATE SYNTH
ID2659S ORF starting with ATG of length 588
ID2660S TRANSPOSASE (22).
ID2661S ORF starting with ATG of length 488
ID2662S ORF starting with ATG of length 327
ID2663S ORF starting with ATG of length 354
ID2664S ORF starting with ATG of length 354
ID2665S CONSERVED HYPOTHETICAL PROTEIN.
ID2666S ORF starting with ATG of length 474
ID2667S WZX.
ID2668S TRANSCRIPTIONAL ANTITERMINATOR.
ID2669S PTS SYSTEM, GLUCITOL/SORBITOL-SPECIFIC ENZYME IIA COMPONENT.
ID2670S SORBITOL OPERON ACTIVATOR.
ID2671S BH156S PROTEIN.
ID2672S BH3147 PROTEIN.
ID2673S STAGE V SPORULATION PROTEIN AF.
ID2674S ORF starting with ATG of length 564
ID2675S PXβ1-40.
ID2676S ORF starting with ATG of length 378
ID2677S Human ORFX ORF873 polypeptide sequence SEQ ID NO:1746.
ID2678S BH1913 PROTEIN.
ID2679S ORF starting with ATG of length 567
ID2680S ORF starting with ATG of length 237
ID2681S ORF starting with ATG of length 567
ID2682S YDAS PROTEIN.
ID2683S YFMR.
ID2684S CHORISMATE MUTASE (ISOZYMES1 AND 2).
ID2685S HYPOTHETICAL 42.4 KDA PROTEIN.
ID2686S BH3142 PROTEIN.
ID2687S HYPOTHETICAL 32.8 KDA PROTEIN PH1052.

ID2688S BH0392 PROTEIN.
ID2689S ORF starting with ATG of length 435
ID2690S mLL6980 PROTEIN.
ID2691S 217AA LONG HYPOTHETICAL AROM PROTEIN.
ID2692S HYPOTHETICAL 34.0 KDA PROTEIN PH1050.
ID2693S Amino acid sequence of threonyl-tRNA synthetase I.
ID2694S BH3142 PROTEIN.
ID2695S Endo-beta-N-acetylglucosaminidase A.
ID2696S BH0854 PROTEIN.
ID2697S SPORULATION PROTEIN.
ID2698S ORF starting with ATG of length 425
ID2699S HYPOTHETICAL (PUTATIVE.
ID2700S BH1883 PROTEIN.
ID2701S MULTIDRUG RESISTANCE PROTEIN.
ID2702S STAGE V SPORULATION PROTEIN AF.
ID2703S YUEI PROTEIN.
ID2704S ORF starting with ATG of length 510
ID2705S ORF1PROTEIN.
ID2706S YUNF PROTEIN.
ID2707S BH285S PROTEIN.
ID2708S YJBK PROTEIN.
ID2709S ORF 13.
ID2710S OLIGOPEPTIDE ABC TRANSPORTER (ATP-BINDING PROTEIN).
ID2711S BH0971PROTEIN.
ID2712S BH0971PROTEIN.
ID2713S UNKNOWN PROTEIN.
ID2714S ORF starting with ATG of length 360
ID2715S HYPOTHETICAL 30.7 KDA PROTEIN.
ID2716S BH2709 PROTEIN.
ID2717S SPORE GERMINATION PROTEIN GERYA.
ID2718S SPORE GERMINATION PROTEIN.
ID2719S SPORE GERMINATION PROTEIN.
ID2720S *S. pneumoniae* derived protein #199.
ID2721S GLYCEROPHOSPHODIESTER PHOSPHODIESTERASE.
ID2722S YUNB PROTEIN.
ID2723S YUNB PROTEIN.
ID2724S 5-KETO-4-DEOXYURONATE ISOMERASE.
ID2725S BH1876 PROTEIN.
ID2726S BH2417 PROTEIN.
ID2727S Nitrate reductase alpha chain protein.
ID2728S BH0697 PROTEIN.
ID2729S ORF starting with ATG of length 347
ID2730S ORF starting with ATG of length 524
ID2731S TRANSCRIPTIONAL REGULATOR (ARAC/XYLS FAMILY).
ID2732S BH1350 PROTEIN.
ID2733S *Staphylococcus aureus* histidine kinase polypeptide sequence.
ID2734S DNA POLYMERASE, BACTERIOPHAGE-TYPE.
ID2735S STAGE V SPORULATION PROTEIN AD.
ID2736S STAGE V SPORULATION PROTEIN AC.
ID2737S BH1418 PROTEIN.
ID2738S MOLYBDOPTERIN BIOSYNTHESIS.
ID2739S NADH-DEPENDENT FMN REDUCTASE (EC 1.6.8.1).
ID2740S SA2369 PROTEIN.
ID2741S BH1387 PROTEIN.
ID2742S BETA-GLUCOSIDASE.
ID2743S ORF starting with ATG of length 540
ID2744S ASSIMILATORY NITRATE REDUCTASE ELECTRON TRANSFER SUBUNIT.
ID2745S BH1114 PROTEIN.
ID2746S ORF starting with ATG of length 404
ID2747S ORF starting with ATG of length 696
ID2748S BH3142 PROTEIN.
ID2749S ORF starting with ATG of length 316
ID2750S BH2938 PROTEIN.
ID2751S TRANSCRIPTION-REPAIR COUPLING FACTOR (TRCF).
ID2752S BH0354 PROTEIN.
ID2753S BH3134 PROTEIN.
ID2754S ORF starting with ATG of length 420
ID2755S ORF starting with ATG of length 678
ID2756S PTS SYSTEM, GLUCITOL/SORBITOL-SPECIFIC IIC2 COMPONENT (EIIC2
ID2757S ORF starting with ATG of length 369
ID2758S ORF starting with ATG of length 334
ID2759S *Staphylococcus aureus* protein of unknown function.
ID2760S PROBABLE METHYLTRANSFERASE.
ID2761S ORF starting with ATG of length 1317
ID2762S HYPOTHETICAL 15.9 KDA PROTEIN IN ILVD-THYB INTERGENIC REGION
ID2763S THIOREDOXIN.
ID2764S OXIDOREDUCTASE (SHORT CHAIN DEHYDROGENASE/REDUCTASE FAMILY).
ID2765S VIOMYCIN PHOSPHOTRANSFERASE (EC 2.7.1.103) (VIOMYCIN KINASE)
ID2766S ORF starting with ATG of length 534
ID2767S BH3881PROTEIN.
ID2768S RNA POLYMERASE ECF-TYPE SIGMA FACTOR.
ID2769S NA+/H+ ANTIPORTER.
ID2770S HYPOTHETICAL 51.3 KDA PROTEIN.
ID2771S BH2161PROTEIN.
ID2772S ORF starting with ATG of length 240
ID2773S HYPOTHETICAL 32.5 KDA PROTEIN IN CCCA-SODA INTERGENIC REGION
ID2774S CHEMOTAXIS MOTA PROTEIN (MOTILITY PROTEIN A).
ID2775S UROPORPHYRINOGEN III SYNTHASE/METHYLTRANSFERASE (EC 4.2.1.75
ID2776S BH3888 PROTEIN.
ID2777S ORF starting with ATG of length 483
ID2778S ORF starting with ATG of length 228
ID2779S HYPOTHETICAL 43.6 KDA PROTEIN IN GBSA-TLPB INTERGENIC REGION
ID2780S YOKH PROTEIN.
ID2781S ORF starting with ATG of length 455
ID2782S *Streptococcus pneumoniae* encoded polypeptide.
ID2783S HYPOTHETICAL 14.9 KDA PROTEIN.
ID2784S Amino acid sequence of a *Chlamydia* pneumoniaeprotein.
ID2785S HYPOTHETICAL PROTEIN TC0114.
ID2786S C4-DICARBOXYLATE TRANSPORT SYSTEM (PERMEASE LARGE PROTEIN).
ID2787S BH3131PROTEIN.
ID2788S ORF starting with ATG of length 373
ID2789S MULTIDRUG RESISTANCE PROTEIN.
ID2790S SIGMA-54-DEPENDENT TRANSCRIPTIONAL ACTIVATOR.
ID2791S ORF starting with ATG of length 753
ID2792S HYPOTHETICAL PROTEIN VC1334.
ID2793S CITS (TWO-COMPONENT SENSOR HISTIDINE KINASE).
ID2794S ASPARAGINE SYNTHETASE.
ID2795S YJDC PROTEIN.
ID2796S HYPOTHETICAL 48.5 KDA PROTEIN.
ID2797S BH3666 PROTEIN.

ID2798S ORF starting with ATG of length 684
ID2799S BH1222 PROTEIN.
ID2800S PROBABLE POLY(A) POLYMERASE (EC 2.7.7.19) (PAP).
ID2801S TRANSCRIPTIONAL REGULATOR (GNTR FAMILY).
ID2802S ORF starting with ATG of length 324
ID2803S ORF starting with ATG of length 273
ID2804S ORF starting with ATG of length 1043
ID2805S BH0896 PROTEIN.
ID2806S ALKALINE PHOSPHATASE LIKE PROTEIN.
ID2807S YFID (BH3304 PROTEIN).
ID2808S ORF starting with ATG of length 537
ID2809S BH3040 PROTEIN.
ID2810S ORF starting with ATG of length 711
ID2811S BH3040 PROTEIN.
ID2812S HYPOTHETICAL 34.3 KDA PROTEIN.
ID2813S BH123S PROTEIN.
ID2814S INVOLVED IN SPORE CORTEX SYNTHESIS.
ID2815S PTS SYSTEM, GLUCITOL/SORBITOL-SPECIFIC ENZYME II, BC COMPONE
ID2816S ORF starting with ATG of length 602
ID2817S ORF starting with ATG of length 822
ID2818S BH2596 PROTEIN.
ID2819S TRANSCRIPTIONAL REGULATOR (ICLR FAMILY).
ID2820S TRANSCRIPTIONAL ANTITERMINATOR.
ID2821S BH2622 PROTEIN.
ID2822S ORF starting with ATG of length 465
ID2823S ORF starting with ATG of length 390
ID2824S ORF starting with ATG of length 226
ID2825S ALPHA-MANNOSIDASE.
ID2826S ORF starting with ATG of length 365
ID2827S ORF starting with ATG of length 406
ID2828S ORF starting with ATG of length 549
ID2829S ORF starting with ATG of length 372
ID2830S ORF starting with ATG of length 510
ID2831S ORF starting with ATG of length 1235
ID2832S ORF starting with ATG of length 1418
ID2833S ORF starting with ATG of length 825
ID2834S PUTATIVE TRANSCRIPTION REGULATOR.
ID2835S ORF starting with ATG of length 593
ID2836S HYPOTHETICAL 16.3 KDA PROTEIN IN TGL-PGI INTERGENIC REGION.
ID2837S BH0852 PROTEIN.
ID2838S HYPOTHETICAL 15.0 KDA PROTEIN.
ID2839S TWO-COMPONENT RESPONSE REGULATOR.
ID2840S YVRD PROTEIN.
ID2841S ORF starting with ATG of length 387
ID2842S SERINE PROTEASE DO.
ID2843S BH4024 PROTEIN.
ID2844S STAGE V SPORULATION PROTEIN AD.
ID2845S SIMILAR TO STAPHYLOCOCCUS AUREUS CAPA PROTEIN.
ID2846S YVBK PROTEIN.
ID2847S ORF starting with ATG of length 510
ID2848S BH0988 PROTEIN.
ID2849S HYPOTHETICAL 9.7 KDA PROTEIN IN PURC-PURL INTERGENIC REGION.
ID2850S ORF starting with ATG of length 890
ID2851S ORF starting with ATG of length 381
ID2852S HYPOTHETICAL OXIDOREDUCTASE IN GBSA-TLPB INTERGENIC REGION (E
ID2853S ORF starting with ATG of length 468
ID2854S ORF starting with ATG of length 283
ID2855S ORF starting with ATG of length 601
ID2856S ORF starting with ATG of length 930
ID2857S HYPOTHETICAL 25.4 KDA PROTEIN IN DPPE-HMP INTERGENIC REGION.
ID2858S HYPOTHETICAL.
ID2859S ORF starting with ATG of length 564
ID2860S HOMOLOG OF PECTIN DEGRADING ENZYME 5-KETO 4-DEOXYURONATE ISO
ID2861S ORF26.
ID2862S ORF starting with ATG of length 237
ID2863S BH0236 PROTEIN.
ID2864S HYPOTHETICAL 33.9 KDA PROTEIN IN CRH-TRXB INTERGENIC REGION.
ID2865S BH3568 PROTEIN.
ID2866S BH2633 PROTEIN.
ID2867S BH2637 PROTEIN.
ID2868S ORF starting with ATG of length 882
ID2869S BH2252 PROTEIN.
ID2870S HYPOTHETICAL 45.4 KDA PROTEIN IN THIAMINASE 15'REGION.
ID2871S TRANSPOSASE (22).
ID2872S ABC TRANSPORTER (PERMEASE).
ID2873S PTS SYSTEM, FRUCTOSE-SPECIFIC IIABC COMPONENT.
ID2874S PHOSPHOTRANSFERASE ENZYME II (EC 2.7.1.69) (PROTEIN-N(PI)-PHO
ID2875S BH3567 PROTEIN.
ID2876S ORF starting with ATG of length 306
ID2877S BH285S PROTEIN.
ID2878S BH2638 PROTEIN.
ID2879S BH2637 PROTEIN.
ID2880S BH2284 PROTEIN.
ID2881S HYPOTHETICAL 100.1 KDA PROTEIN.
ID2882S BH2857 PROTEIN.
ID2883S Endo-beta-N-acetylglucosaminidase A.
ID2884S BH0676 PROTEIN.
ID2885S BH1374 PROTEIN.
ID2886S C4-DICARBOXYLATE TRANSPORT SYSTEM (PERMEASE LARGE PROTEIN).
ID2887S C4-DICARBOXYLATE TRANSPORT SYSTEM (PERMEASE LARGE PROTEIN).
ID2888S PUTATIVE METHYLTRANSFERASE.
ID2889S BH146S PROTEIN.
ID2890S ORF starting with ATG of length 693
ID2891S BH1921PROTEIN.
ID2892S E22 PROTEIN (GENE 43 PROTEIN).
ID2893S ORFZ (FRAGMENT).
ID2894S HYPOTHETICAL PROTEIN.
ID2895S ORF starting with ATG of length 791
ID2896S BH0586 PROTEIN.
ID2897S BH0587 PROTEIN.
ID2898S ORF starting with ATG of length 504
ID2899S ORF starting with ATG of length 282
ID2900S S. pneumoniae 30S ribosomal protein S2.
ID2901S ORF starting with ATG of length 486
ID2902S HYPOTHETICAL 39.5 KDA PROTEIN IN SIGZ-CSN INTERGENIC REGION.
ID2903S INDIRECT NEGATIVE REGULATOR OF SIGMA-B ACTIVITY (SERINE PHOS
ID2904S DIHYDROLIPOAMIDE DEHYDROGENASE.
ID2905S ORF starting with ATG of length 399
ID2906S MULTIDRUG RESISTANCE PROTEIN.
ID2907S BH2837 PROTEIN.
ID2908S ORF starting with ATG of length 387
ID2909S ORF starting with ATG of length 362
ID2910S GERMINATION (CORTEX HYDROLYSIS) AND SPORULATION (STAGE II, M ID2911S HYPOTHETICAL TRANSCRIPTIONAL REGULATOR IN FEUA-SIGW INTERGEN
ID2912S YNGK PROTEIN.
ID2913S TWO-COMPONENT SENSOR HISTIDINE KINASE.
ID2914S BH1943 PROTEIN.
ID2915S PENICILLIN-BINDING PROTEIN 1A (GERMINATION).
ID2916S BH2802 PROTEIN.
ID2917S BH1071PROTEIN.
ID2918S *Corynebacterium glutamicum* SMP protein sequence SEQ ID NO:50
ID2919S TRIOSEPHOSPHATE ISOMERASE (EC 5.3.1.1) (TIM).
ID2920S ORF starting with ATG of length 492
ID2921S BH3562 PROTEIN.
ID2922S MODIFICATION METHYLASE CEQI (EC 2.1.1.72) (ADENINE-SPECIFICM
ID2923S BH4007 PROTEIN.
ID2924S BH4008 PROTEIN.
ID2925S BH0058 PROTEIN.
ID2926S BH0589 PROTEIN.
ID2927S ORF starting with ATG of length 297
ID2928S BH3197 PROTEIN.
ID2929S PUTATIVE HOST CELL SURFACE-EXPOSED LIPOPROTEIN.
ID2930S BH0962 PROTEIN.
ID2931S ORF starting with ATG of length 294
ID2932S TWO-COMPONENT SENSOR HISTIDINE KINASE.
ID2933S BH2007 PROTEIN.
ID2934S PENICILLIN TOLERANCE PROTEIN.
ID2935S BH3341PROTEIN.
ID2936S ORF starting with ATG of length 357
ID2937S BH3829 PROTEIN.
ID2938S PUTATIVE SUGAR TRANSPORTER SUGAR BINDING PROTEIN.
ID2939S Nitrate reductase alpha chain protein.
ID2940S YETF PROTEIN.
ID2941S SMALL, ACID-SOLUBLE SPORE PROTEIN D (SASP).
ID2942S BH4008 PROTEIN.
ID2943S YYDA PROTEIN.
ID2944S PUTATIVE REPLICATION FACTOR.
ID2945S ORF starting with ATG of length 570
ID2946S ORF starting with ATG of length 389
ID2947S SPORULATION INITIATION PHOSPHOPROTEIN.
ID2948S ORF starting with ATG of length 388
ID2949S XYLOSIDASE/ARABINOSIDASE.
ID2950S HYPOTHETICAL 56.0 KDA PROTEIN IN GLGB-GBSB INTERGENIC REGION
ID2951S ALKALINE PHOSPHATASE.
ID2952S ORF starting with ATG of length 231
ID2953S BH3404 PROTEIN.
ID2954S BH3402 PROTEIN.
ID2955S ORF starting with ATG of length 420
ID2956S PTS SYSTEM, GLUCITOL/SORBITOL-SPECIFIC ENZYME II, C2 COMPONE
ID2957S PTS SYSTEM, GLUCITOL/SORBITOL-SPECIFIC ENZYME II, BC COMPONE
ID2958S ORF starting with ATG of length 469
ID2959S ORF, HYPOTHETICAL PROTEIN.
ID2960S YFHO PROTEIN.
ID2961S HYPOTHETICAL 13.1 KDA PROTEIN C29B12.12 IN CHROMOSOME I.
ID2962S BH1053 PROTEIN.
ID2963S ENOYL-[ACYL-CARRIER PROTEIN] REDUCTASE.
ID2964S BH2840 PROTEIN.
ID2965S X-LINKED RETINOPATHY PROTEIN (FRAGMENT).
ID2966S TRANSPORTER.
ID2967S *Staphylococcus aureus* protein of unknown function.
ID2968S CYTIDINE DEAMINASE (EC 3.5.4.5).
ID2969S BH031S PROTEIN.
ID2970S SMALL CORE PROTEIN (J PROTEIN).
ID2971S SCAFFOLDING PROTEIN D (GPD).
ID2972S CAPSID PROTEIN (F PROTEIN) (GPF).
ID2973S BH1682 PROTEIN.
ID2974S 50S RIBOSOMAL PROTEIN L30.
ID2975S ORF starting with ATG of length 519
ID2976S BH2274 PROTEIN.
ID2977S ORF starting with ATG of length 336
ID2978S ORF starting with ATG of length 588
ID2979S BH2981PROTEIN.
ID2980S BH1804 PROTEIN.
ID2981S HYPOTHETICAL PROTEIN VC1332.
ID2982S ORF starting with ATG of length 333
ID2983S BH3423 PROTEIN.
ID2984S BH3430 PROTEIN.
ID2985S ORF starting with ATG of length 600
ID2986S BH1089 PROTEIN.
ID2987S BH1707 PROTEIN.
ID2988S ORF starting with ATG of length 360
ID2989S YUBB PROTEIN.
ID2990S YNGK PROTEIN.
ID2991S YTER.
ID2992S TRANSCRIPTION ANTITERMINATOR.
ID2993S BH1883 PROTEIN.
ID2994S EXTENSIN PRECURSOR (CELL WALL HYDROXYPROLINE-RICH GLYCOPROTE
ID2995S ORF starting with ATG of length 389
ID2996S BH1336 PROTEIN.
ID2997S TWO-COMPONENT SENSOR HISTIDINE KINASE.
ID2998S ORF starting with ATG of length 498
ID2999S THYMIDINE KINASE (EC 2.7.1.21).
ID3000S YVR1PROTEIN.
ID3001S ORF starting with ATG of length 270
ID3002S ORF starting with ATG of length 486
ID3003S HYPOTHETICAL 11.0 KDA PROTEIN IN HSP18 3'REGION (ORFA1).
ID3004S BH0973 PROTEIN.
ID3005S BH0974 PROTEIN.
ID3006S Cyclohexanone monooxygenase sequence.
ID3007S HYPOTHETICAL 76.9 KDA PROTEIN.
ID3008S MN CATALASE.
ID3009S SA0330 PROTEIN.
ID3010S ORNITHINE CARBAMOYLTRANSFERASE.
ID3011S ACETOIN DEHYDROGENASE.
ID3012S ORF starting with ATG of length 258
ID3013S HYPOTHETICAL 6.4 KDA PROTEIN.
ID3014S HYPOTHETICAL 48.6 KDA PROTEIN IN SERS-DNAZ INTERGENIC REGION
ID3015S MINOR TEICHOIC ACIDS BIOSYNTHESIS PROTEIN GGAA.
ID3016S HYPOTHETICAL PROTEIN XF1280.
ID3017S ORF starting with ATG of length 472
ID3018S BH3318 PROTEIN.
ID3019S ORF starting with ATG of length 618
ID3020S *Bacillus* clausii $NNO_{4909}S$ BXM20 beta-1,4-mannanase precursor ID3021S ORF starting with ATG of length 474
ID3022S HYPOTHETICAL 4.8 KDA PROTEIN.
ID3023S HYPOTHETICAL 8.0 KDA PROTEIN.
ID3024S SPORE COAT PROTEIN X (INSOLUBLE FRACTION).
ID3025S TRANSCRIPTIONAL REGULATOR.
ID3026S ORF starting with ATG of length 771
ID3027S DAUNORUBICIN RESISTANCE PROTEIN.
ID3028S mLL2253 PROTEIN.
ID3029S ORF starting with ATG of length 495
ID3030S ORF starting with ATG of length 402
ID3031S SPAG.
ID3032S YO LA.
ID3033S *S. pneumoniae* diacylglycerol kinase.
ID3034S CHORISMATE MUTASE.
ID3035S TRANSCRIPTIONAL ANTITERMINATOR.
ID3036S TRANSCRIPTIONAL REGULATOR (LYSR FAMILY).
ID3037S HYPOTHETICAL 37.5 KDA PROTEIN (FRAGMENT).
ID3038S BH010S PROTEIN.
ID3039S GLYCEROL-3-PHOSPHATE CYTIDYLTRANSFERASE.
ID3040S BH1230 PROTEIN.
ID3041S ORF starting with ATG of length 456
ID3042S *Streptococcus pneumoniae* encoded polypeptide.
ID3043S HYPOTHETICAL 14.9 KDA PROTEIN.
ID3044S Amino acid sequence of a *Chlamydia* pneumoniaeprotein.
ID3045S HYPOTHETICAL PROTEIN TC0114.
ID3046S CATION TRANSPORT ATPASE, E1-E2 FAMILY.
ID3047S mLL1121PROTEIN.
ID3048S BH1620 PROTEIN.
ID3049S ORF starting with ATG of length 386
ID3050S BH2390 PROTEIN.
ID3051S ORF starting with ATG of length 294
ID3052S ID867.
ID3053S VALYL-TRNA SYNTHETASE (EC 6.1.1.9).
ID3054S BH0488 PROTEIN.
ID3055S ORF starting with ATG of length 844
ID3056S BH1492 PROTEIN.
ID3057S ORF starting with ATG of length 366
ID3058S BH2821PROTEIN.
ID3059S CONSERVED HYPOTHETICAL PROTEIN.
ID3060S BH1550 PROTEIN.
ID3061S BH2938 PROTEIN.
ID3062S PXβ1-37.
ID3063S BH3176 PROTEIN.
ID3064S HYPOTHETICAL 50.9 KDA PROTEIN IN KATA 3'REGION (ORF A).
ID3065S ORF starting with ATG of length 534
ID3066S BH3627 PROTEIN.
ID3067S ORF starting with ATG of length 558
ID3068S ORF starting with ATG of length 632
ID3069S ORF starting with ATG of length 650
ID3070S L-RHAMNOSE ISOMERASE.
ID3071S BH2412 PROTEIN.
ID3072S DNA TRANSPORT MACHINERY.
ID3073S BH0051PROTEIN.
ID3074S OLIGOPEPTIDE ABC TRANSPORTER (PERMEASE).
ID3075S PXβ1-37.
ID3076S ORF starting with ATG of length 588
ID3077S IMMUNOGENIC PROTEIN.
ID3078S ORF starting with ATG of length 518
ID3079S BH1232 PROTEIN.
ID3080S SENSOR HISTIDINE KINASE CHEA.
ID3081S REPRESSOR.
ID3082S BH2052 PROTEIN.
ID3083S SSPF PROTEIN.
ID3084S ORF starting with ATG of length 279
ID3085S ORF starting with ATG of length 569
ID3086S ANTHRANILATE SYNTHASE COMPONENT I (EC 4.1.3.27).
ID3087S SPORE GERMINATION PROTEIN A1.
ID3088S MUTANTS BLOCK SPORULATION AFTER ENGULFMENT.
ID3089S MUTANTS BLOCK SPORULATION AFTER ENGULFMENT.
ID3090S ORF starting with ATG of length 272
ID3091S SPORE GERMINATION PROTEIN KC.
ID3092S YBFO PROTEIN.
ID3093S PEPTIDASE.
ID3094S ORF starting with TTG or GTG of length 573
ID3095S SODIUM-DEPENDENT PHOSPHATE TRANSPORTER.
ID3096S HYPOTHETICAL 41.4 KDA PROTEIN IN IADA-MCRD INTERGENIC REGION
ID3097S STAGE III SPORULATION PROTEIN AE.
ID3098S STAGE III SPORULATION PROTEIN AF.
ID3099S BH0266 PROTEIN.
ID3100S BH2381PROTEIN.
ID3101S ORF starting with ATG of length 312
ID3102S BH031S PROTEIN.
ID3103S PUTATIVE RNA POLYMERASE SIGMA FACTOR.
ID3104S BH3310 PROTEIN.
ID3105S HYPOTHETICAL 18.1 KDA PROTEIN.
ID3106S HYPOTHETICAL 44.9 KDA PROTEIN.
ID3107S GLYCEROL UPTAKE OPERON ANTITERMINATOR REGULATORY PROTEIN.
ID3108S cDNA FLJ20489 FIS, CLONE KAT08285.
ID3109S CREATINE KINASE.
ID3110S YVRH PROTEIN (RECEIVER MODULE OF PUTATIVE RESPONSE REGULATOR
ID3111S YFIT PROTEIN.
ID3112S BH3588 PROTEIN.
ID3113S YFIT PROTEIN.
ID3114S YRVE PROTEIN.
ID3115S BH1239 PROTEIN.
ID3116S ORF starting with ATG of length 379
ID3117S BH2912 PROTEIN.
ID3118S BH0043 PROTEIN.
ID3119S BH3320 PROTEIN.
ID3120S BH3319 PROTEIN.
ID3121S BH1498 PROTEIN.
ID3122S DNA POLYMERASE III DELTA' SUBUNIT (EC 2.7.7.7).
ID3123S SIGNAL PEPTIDASE-LIKE PROTEIN.
ID3124S ORF starting with ATG of length 435
ID3125S Human secreted protein sequence encoded by gene 4S SEQ ID NO
ID3126S Human secreted protein, SEQ ID NO: 7174.
ID3127S ORFII.
ID3128S BH126S PROTEIN.
ID3129S BH1264 PROTEIN.
ID3130S FLAGELLAR BIOSYNTHETIC PROTEIN FLIZ PRECURSOR.
ID3131S ORF starting with ATG of length 498
ID3132S MOLYBDOPTERIN CONVERTING FACTOR (SUBUNIT 1).
ID3133S BH4017 PROTEIN.
ID3134S PUTATIVE HSDS.
ID3135S ORF starting with TTG or GTG of length 534

ID3136S D-FRUCTOSE-1,6-BIPHOSPHATE ALDOLASE (FRAGMENT).
ID3137S BH1341PROTEIN.
ID3138S STAGE II SPORULATION PROTEIN P.
ID3139S BH176S PROTEIN.
ID3140S BH309S PROTEIN.
ID3141S YFNK.
ID3142S SPORE GERMINATION PROTEIN.
ID3143S ORF starting with ATG of length 336
ID3144S NA+/H+ ANTIPORTER.
ID3145S ORF starting with ATG of length 645
ID3146S PUTATIVE RESPONSE REGULATOR.
ID3147S ORF starting with ATG of length 558
ID3148S 2-KETO-3-DEOXYGLUCONATE PERMEASE (KDG PERMEASE).
ID3149S BH0802 PROTEIN.
ID3150S BH028S PROTEIN.
ID3151S ORF starting with ATG of length 287
ID3152S HYPOTHETICAL 30.6 KDA PROTEIN (ORF266).
ID3153S STAGE II SPORULATION PROTEIN M.
ID3154S YFNK.
ID3155S TRANSCRIPTION ANTITERMINATOR.
ID3156S Human secreted protein, SEQ ID NO: 7519.
ID3157S 5-AMINOLEVULINIC ACID DEHYDRATASE (EC 4.2.1.24).
ID3158S GLUCOSAMINE-6-PHOSPHATE ISOMERASE (EC 5.3.1.10) (GLUCOSAMINE
ID3159S PUTATIVE TETR-FAMILY TRANSCRIPTIONAL REGULATOR.
ID3160S ABC TRANSPORTER (ATP-BINDING PROTEIN).
ID3161S YLBM PROTEIN.
ID3162S GLYCINE BETAINE TRANSPORTER.
ID3163S INTEGRASE HOMOLOG.
ID3164S ORF starting with ATG of length 300
ID3165S ORF starting with ATG of length 259
ID3166S PUTATIVE XYLOSE OPERON REGULATORY PROTEIN.
ID3167S ORF starting with ATG of length 256
ID3168S CELL WALL LYTIC ACTIVITY.
ID3169S BH3591PROTEIN.
ID3170S YTOQ.
ID3171S SPORE GERMINATION PROTEIN.
ID3172S ORF starting with ATG of length 692
ID3173S ORF starting with ATG of length 459
ID3174S ALKYL HYDROPEROXIDE REDUCTASE LARGE SUBUNIT (EC 1.6.99.3) (P
ID3175S MOLYBDOPTERIN BIOSYNTHESIS.
ID3176S NA(+)/H(+) ANTIPORTER (SODIUM/PROTON ANTIPORTER).
ID3177S ORF starting with ATG of length 480
ID3178S OLIGOPEPTIDE ABC TRANSPORTER (PERMEASE).
ID3179S TWO-COMPONENT SENSOR HISTIDINE KINASE.
ID3180S ORF starting with TTG or GTG of length 1386
ID3181S HYPOTHETICAL 29.1 KDA PROTEIN.
ID3182S *Streptococcus pneumoniae* type 4 protein sequence #75.
ID3183S SPORE GERMINATION PROTEIN.
ID3184S ORF starting with ATG of length 351
ID3185S SPORE GERMINATION PROTEIN KA.
ID3186S ORF starting with ATG of length 274
ID3187S SOPRE GERMINATION PROTEIN.
ID3188S ORF starting with ATG of length 266
ID3189S ORF13.
ID3190S KYNURENINASE (EC 3.7.1.3) (L-KYNURENINE HYDROLASE).
ID3191S BH0970 PROTEIN.
ID3192S ORF starting with ATG of length 434
ID3193S ORF starting with ATG of length 735
ID3194S MLL3044 PROTEIN.
ID3195S HYPOTHETICAL OXIDOREDUCTASE IN RTP-PELB INTERGENIC REGION (E
ID3196S HYPOTHETICAL 47.4 KDA PROTEIN.
ID3197S ORF starting with ATG of length 554
ID3198S ORF starting with ATG of length 372
ID3199S ORF starting with ATG of length 300
ID3200S BH2631PROTEIN.
ID3201S HYPOTHETICAL 8.2 KDA PROTEIN IN NPRE-PYCA INTERGENIC REGION.
ID3202S ORF starting with ATG of length 279
ID3203S BH0602 PROTEIN.
ID3204S YFKK PROTEIN.
ID3205S HYPOTHETICAL 35.5 KDA PROTEIN.
ID3206S ORF starting with ATG of length 696
ID3207S BH0717 PROTEIN.
ID3208S BH3320 PROTEIN.
ID3209S ORF11.
ID3210S TRANSCRIPTIONAL ACTIVATOR OF THE GLUTAMATE SYNTHASE OPERON
ID3211S ORF starting with ATG of length 347
ID3212S FERRICHROME TRANSPORT PERMEASE.
ID3213S TRANSCRIPTIONAL REGULATOR.
ID3214S CELL DIVISION CYCLE CDC48 HOMOLOG (YJOB PROTEIN).
ID3215S PUTATIVE SECRETED PROTEIN.
ID3216S TYPE I RESTRICTION ENZYME ECOKI M PROTEIN (EC 2.1.1.72) (M.E
ID3217S A2-5A ORF1 (FRAGMENT).
ID3218S PHI PVL ORF 63 HOMOLOGUE.
ID3219S ORF starting with ATG of length 477
ID3220S ORF22.
ID3221S URIDINE KINASE (EC 2.7.1.48) (URIDINE MONOPHOSPHOKINASE).
ID3222S HYPOTHETICAL 30.7 KDA PROTEIN.
ID3223S BH3410 PROTEIN.
ID3224S PROBABLE AMINO-ACID ABC TRANSPORTER PERMEASE PROTEIN YCKA.
ID3225S HYPOTHETICAL PROTEIN.
ID3226S TRANSCRIPTION REGULATOR.
ID3227S SERINE/THREONINE PROTEIN KINASE.
ID3228S ORF starting with ATG of length 960
ID3229S ORF starting with TTG or GTG of length 561
ID3230S ORF11.
ID3231S PTS SYSTEM, SUCROSE PHOSPHOTRANSFERASE ENZYME II, BC COMPONE
ID3232S HYPOTHETICAL PROTEIN.
ID3233S GERMINATION PROTEIN.
ID3234S DIAMINOBUTYRIC ACID ACETYLTRANSFERASE.
ID3235S *Staphylococcus aureus* protein of unknown function.
ID3236S HYPOTHETICAL 38.4 KDA PROTEIN.
ID3237S RELATED TO A-AGGLUTININ CORE PROTEIN AGA1.
ID3238S DEACETYLASE, PUTATIVE.
ID3239S *E. coli* aspartokinase III variant No. 169 (T3521, S369F).
ID3240S BH1501PROTEIN.
ID3241S BH2389 PROTEIN.
ID3242S ORF starting with ATG of length 278
ID3243S PROBABLE TWO-COMPONENT SENSOR.

ID3244S BH0892 PROTEIN.
ID3245S BH1268 PROTEIN.
ID3246S BH1270 PROTEIN.
ID3247S ORF starting with ATG of length 969
ID3248S ORF starting with ATG of length 312
ID3249S ABC TRANSPORTER (ATP-BINDING PROTEIN) (DAUNORUBICIN RESISTAN
ID3250S *Streptococcus pneumoniae* SP0014 protein.
ID3251S L-ASPARTATE OXIDASE (EC 1.4.3.16) (QUINOLINATE SYNTHETASE B)
ID3252S BH290S PROTEIN.
ID3253S INNER SPORE COAT PROTEIN D.
ID3254S ORF starting with ATG of length 237
ID3255S ORF starting with ATG of length 452
ID3256S REGULATORY PROTEIN BLAR1.
ID3257S ORF starting with ATG of length 1200
ID3258S ORF starting with ATG of length 219
ID3259S BH1892 PROTEIN.
ID3260S ORF starting with ATG of length 624
ID3261S INTEGRASE HOMOLOG.
ID3262S HYPOTHETICAL 7.6 KDA PROTEIN.
ID3263S HYPOTHETICAL 40.9 KDA PROTEIN IN CCCA-SODA INTERGENIC REGION
ID3264S BH195S PROTEIN.
ID3265S TRANSCRIPTIONAL REGULATOR OF SPORE COAT PROTEIN (SPORE GERMI
ID3266S BH320S PROTEIN.
ID3267S BH1176 PROTEIN.
ID3268S BH1402 PROTEIN.
ID3269S LACZ ALPHA PEPTIDE.
ID3270S TRANSCRIPTIONAL REGULATOR OF SPORE COAT PROTEIN (SPORE GERMI
ID3271S BH2907 PROTEIN.
ID3272S BH2908 PROTEIN.
ID3273S STAGE II SPORULATION PROTEIN R.
ID3274S BH1678 PROTEIN.
ID3275S BICYCLOMYCIN RESISTANCE PROTEIN.
ID3276S *Synechocystis* sp phytochrome-related gene Cph1.
ID3277S ORF starting with ATG of length 222
ID3278S BH320S PROTEIN.
ID3279S BH053S PROTEIN.
ID3280S HYPOTHETICAL PROTEIN TC0114.
ID3281S Amino acid sequence of a *Chlamydia* pneumoniaeprotein.
ID3282S HYPOTHETICAL 14.9 KDA PROTEIN.
ID3283S *Streptococcus pneumoniae* encoded polypeptide.
ID3284S ORF starting with ATG of length 456
ID3285S HYPOTHETICAL 6.9 KDA PROTEIN APES063.
ID3286S *Chlamydia pneumoniae* lipoprotein sequence.
ID3287S ORF starting with ATG of length 411
ID3288S BH0407 PROTEIN.
ID3289S BH3604 PROTEIN.
ID3290S CAPSULAR POLYSACCHARIDE BIOSYNTHESIS.
ID3291S BH3874 PROTEIN.
ID3292S ORF starting with ATG of length 501
ID3293S BETA-N-ACETYLGLUCOSAMINIDASE PRECURSOR (EC 3.2.1.-).
ID3294S *Chlamydia pneumoniae* lipoprotein sequence.
ID3295S HYPOTHETICAL 6.9 KDA PROTEIN APES063.
ID3296S ORF starting with ATG of length 456
ID3297S *Streptococcus pneumoniae* encoded polypeptide.
ID3298S HYPOTHETICAL 14.9 KDA PROTEIN.
ID3299S Amino acid sequence of a *Chlamydia* pneumoniaeprotein.
ID3300S HYPOTHETICAL PROTEIN TC0114.
ID3301S *Chlamydia pneumoniae* lipoprotein sequence.
ID3302S YHCG (ABC TRANSPORTER) (ATP-BINDING PROTEIN).
ID3303S SPOIISA PROTEIN.
ID3304S BH1232 PROTEIN.
ID3305S TRANSPOSASE (11).
ID3306S ORF starting with ATG of length 462
ID3307S ORF starting with ATG of length 672
ID3308S RESPONSE REGULATOR ASPARTATE PHOSPHATASE.
ID3309S HYPOTHETICAL 56.9 KDA PROTEIN PH1047.
ID3310S BH0590 PROTEIN.
ID3311S RIBOFLAVIN BIOSYNTHESIS PROTEIN RIBA [INCLUDES: GTP CYCLOHYD
ID3312S HYPOTHETICAL 21.0 KDA PROTEIN IN CTAF 3'REGION (ORF1).
ID3313S HYPOTHETICAL 17.8 KDA PROTEIN IN CTAF 3'REGION (ORF3).
ID3314S BH1678 PROTEIN.
ID3315S ORF starting with ATG of length 384
ID3316S BH2622 PROTEIN.
ID3317S STAGE IV SPORULATION PROTEIN A (SPORE CORTEX FORMATION AND C
ID3318S ORF, HYPOTHETICAL PROTEIN.
ID3319S INTRACELLULAR PROTEINASE (EC 3.2.).
ID3320S RETINITIS PIGMENTOSA GTPASE REGULATOR-LIKE PROTEIN (FRAGMENT
ID3321S ORF22.
ID3322S BH1644 PROTEIN.
ID3323S BH0861PROTEIN.
ID3324S MEMBRANE-TYPE MOSAIC SERINE PROTEASE.
ID3325S ORF starting with ATG of length 488
ID3326S BH1720 PROTEIN.
ID3327S HYPOTHETICAL 20.5 KDA PROTEIN.
ID3328S YFIL.
ID3329S BH3604 PROTEIN.
ID3330S SPORE GERMINATION PROTEIN.
ID3331S ORF starting with ATG of length 1109
ID3332S BH0842 PROTEIN.
ID3333S AMINO ACID ABC TRANSPORTER PROTEIN, SOLUTE-BINDING COMPONENT
ID3334S BH0589 PROTEIN.
ID3335S YFKB PROTEIN.
ID3336S BH0883 PROTEIN.
ID3337S BH3772 PROTEIN.
ID3338S STAGE II SPORULATION PROTEIN R.
ID3339S ORF starting with ATG of length 255
ID3340S ORF26.
ID3341S ORF25.
ID3342S ORF16.
ID3343S ORF starting with ATG of length 1107
ID3344S BH1721PROTEIN.
ID3345S YJBK PROTEIN.
ID3346S BH2850 PROTEIN.
ID3347S GTP PYROPHOSPHOKINASE.
ID3348S NAD KINASE.
ID3349S BH2209 PROTEIN.
ID3350S BH2208 PROTEIN.
ID3351S YVMA.
ID3352S BH1114 PROTEIN.
ID3353S TRANSCRIPTION REGULATOR.
ID3354S FRUCTOSE 1-PHOSPHATE KINASE.
ID3355S ORF starting with ATG of length 782
ID3356S ORF starting with ATG of length 466
ID3357S HYPOTHETICAL 22.4 KDA PROTEIN IN RPMF-FTSL INTERGENIC REGION
ID3358S BH2580 PROTEIN.

ID3359S ORF starting with ATG of length 324
ID3360S HYPOTHETICAL 48.9 KDA PROTEIN PH0207.
ID3361S SPORE CORTEX-LYTIC ENZYME.
ID3362S HYPOTHETICAL 62.6 KDA PROTEIN IN RPMF-FTSL INTERGENIC REGION
ID3363S ORF starting with ATG of length 393
ID3364S ORF starting with ATG of length 405
ID3365S ORF starting with ATG of length 294
ID3366S BH4024 PROTEIN.
ID3367S RESOLVASE.
ID3368S BLMT.
ID3369S ORF starting with ATG of length 285
ID3370S BH0236 PROTEIN.
ID3371S BH0942 PROTEIN.
ID3372S ORF starting with ATG of length 339
ID3373S ORF starting with ATG of length 424
ID3374S PHAGE-RELATED PROTEIN.
ID3375S BH1913 PROTEIN.
ID3376S HYPOTHETICAL 19.4 KDA PROTEIN IN SPOIIR-GLYC INTERGENIC REGI
ID3377S BH1404 PROTEIN.
ID3378S OUTER SPORE COAT PROTEIN.
ID3379S HYPOTHETICAL 28.2 KDA PROTEIN IN BIOI 3'REGION (ORF2).
ID3380S ORF starting with ATG of length 537
ID3381S MLR2098PROTEIN.
ID3382S RELATED TO DIMERIC DIHYDRODIOL DEHYDROGENASE.
ID3383S PUTATIVE FRUCTOSE-SPECIFIC PERMEASE.
ID3384S TWO-COMPONENT SENSOR HISTIDINE KINASE.
ID3385S SIGMA 54 ACTIVATOR.
ID3386S ORF starting with ATG of length 331
ID3387S BH0913 PROTEIN.
ID3388S BH2208 PROTEIN.
ID3389S ORF starting with ATG of length 414
ID3390S HYPOTHETICAL TRANSCRIPTIONAL REGULATOR AF1627.
ID3391S BH1722 PROTEIN.
ID3392S HYPOTHETICAL 39.0 KDA PROTEIN.
ID3393S ORF starting with ATG of length 315
ID3394S BH3770 PROTEIN.
ID3395S BH1676 PROTEIN.
ID3396S ORF45.
ID3397S ORF starting with ATG of length 436
ID3398S PUTATIVE INTEGRAL MEMBRANE TRANSPORTER.
ID3399S BH1148 PROTEIN.
ID3400S BH1812 PROTEIN.
ID3401S TYROSYL-TRNA SYNTHETASE 2 (EC 6.1.1.1) (TYROSINE-TRNA LIGAS
ID3402S BH036S PROTEIN.
ID3403S BH2667 PROTEIN.
ID3404S PTS SYSTEM, GLUCITOL/SORBITOL-SPECIFIC IIBC COMPONENT (EIIBC
ID3405S ORF starting with ATG of length 702
ID3406S BH401S PROTEIN.
ID3407S BH0346 PROTEIN.
ID3408S ORF starting with ATG of length 335
ID3409S ORF starting with ATG of length 350
ID3410S ORF starting with ATG of length 506
ID3411S ORF starting with ATG of length 621
ID3412S HYPOTHETICAL TRANSCRIPTIONAL REGULATOR IN OPUE-RAPH INTERGEN
ID3413S BH1410 PROTEIN.
ID3414S ORF starting with ATG of length 346
ID3415S ORF starting with ATG of length 542
ID3416S DAUNORUBICIN RESISTANCE PROTEIN.
ID3417S BH2291PROTEIN.
ID3418S ORF starting with ATG of length 645
ID3419S BH3410 PROTEIN.
ID3420S PROBABLE AMINO-ACID ABC TRANSPORTER PERMEASE PROTEIN YCKA.
ID3421S ORF starting with ATG of length 696
ID3422S NITRIC OXIDE SYNTHASE.
ID3423S BH3568 PROTEIN.
ID3424S BH3567 PROTEIN.
ID3425S MLR2098PROTEIN.
ID3426S ORF starting with ATG of length 396
ID3427S ORF starting with ATG of length 945
ID3428S STAGE IV SPORULATION PROTEIN.
ID3429S BH2350 PROTEIN.
ID3430S DNA, COMPLETE SEQUENCE.
ID3431S ORF10.
ID3432S ORF starting with ATG of length 700
ID3433S ORF starting with ATG of length 801
ID3434S BH402S PROTEIN.
ID3435S UNKNOWN PROTEIN.
ID3436S HYPOTHETICAL 46.1 KDA PROTEIN IN PLSC 3'REGION.
ID3437S BH2390 PROTEIN.
ID3438S BH2389 PROTEIN.
ID3439S ORF starting with ATG of length 426
ID3440S TRANSPOSASE (22).
ID3441S ORF starting with ATG of length 588
ID3442S LPLC PROTEIN.
ID3443S ORF starting with ATG of length 2421
ID3444S BH0970 PROTEIN.
ID3445S CHORISMATE MUTASE (ISOZYMES1 AND 2).
ID3446S ORF starting with ATG of length 525
ID3447S ORF starting with ATG of length 486
ID3448S ORF starting with ATG of length 609
ID3449S HYPOTHETICAL 30.7 KDA PROTEIN.
ID3450S Human gene 8 encoded secreted protein HMAM121, SEQ ID NO:137
ID3451S BH1071PROTEIN.
ID3452S BH1089 PROTEIN.
ID3453S ORF starting with ATG of length 363
ID3454S *Staphylococcus aureus* protein homologous to subunit fmdE.
ID3455S MAGNESIUM CITRATE SECONDARY TRANSPORTER.
ID3456S BH0709 PROTEIN.
ID3457S UNKNOWN PROTEIN.
ID3458S ORF starting with ATG of length 483
ID3459S YJDC PROTEIN.
ID3460S BH2596 PROTEIN.
ID3461S BH2622 PROTEIN.
ID3462S ORF starting with ATG of length 662
ID3463S BH0236 PROTEIN.
ID3464S BH2637 PROTEIN.
ID3465S BH2638 PROTEIN.
ID3466S BH0424 PROTEIN.
ID3467S SUGAR TRANSPORT SYSTEM (PERMEASE).
ID3468S ENOYL-[ACYL-CARRIER PROTEIN] REDUCTASE.
ID3469S BH2840 PROTEIN.
ID3470S ORF starting with ATG of length 807
ID3471S BH2838 PROTEIN.
ID3472S BH2837 PROTEIN.
ID3473S GERMINATION (CORTEX HYDROLYSIS) AND SPORULATION (STAGE II, M
ID3474S REGULATORY PROTEIN.

ID3475S PUTATIVE GLYCOSYLTRANSFERASE CPSIVM.
ID3476S INNER SPORE COAT PROTEIN D.
ID3477S TWO-COMPONENT SENSOR HISTIDINE KINASE.
ID3478S YETF PROTEIN.
ID3479S SMALL, ACID-SOLUBLE SPORE PROTEIN D (SASP).
ID3480S Cyclohexanone monooxygenase sequence.
ID3481S KIAA165S PROTEIN (FRAGMENT).
ID3482S RIBONUCLEASE HII (EC 3.1.26.4) (RNASE HII) (FRAGMENT).
ID3483S CAPSID PROTEIN (F PROTEIN) (GPF).
ID3484S BH1804 PROTEIN.
ID3485S ORF starting with ATG of length 288
ID3486S ORF starting with ATG of length 417
ID3487S ORF starting with ATG of length 469
ID3488S BH3433 PROTEIN.
ID3489S BH3337 PROTEIN.
ID3490S BH3430 PROTEIN.
ID3491S ORF starting with ATG of length 809
ID3492S ORF starting with ATG of length 1188
ID3493S HYPOTHETICAL 15.7 KDA PROTEIN IN PBPD-COMA INTERGENIC REGION
ID3494S BH2622 PROTEIN.
ID3495S ORF15.
ID3496S TRANSCRIPTIONAL REGULATOR (LYSR FAMILY).
ID3497S ORF starting with ATG of length 478
ID3498S ORF starting with ATG of length 526
ID3499S TRANSPOSASE (22).
ID3500S Chlamydia pneumoniae lipoprotein sequence.
ID3501S BRANCHED-CHAIN ALPHA-KETO ACID DEHYDROGENASE E2.
ID3502S BH1247 PROTEIN.
ID3503S ORF starting with ATG of length 696
ID3504S ORF starting with ATG of length 384
ID3505S ORF starting with ATG of length 621
ID3506S HYPOTHETICAL 25.4 KDA PROTEIN IN DPPE-HMP INTERGENIC REGION.
ID3507S ORF starting with ATG of length 226
ID3508S ORF starting with ATG of length 233
ID3509S ORF starting with ATG of length 216
ID3510S ORF starting with ATG of length 396
ID3511S ORF starting with ATG of length 441
ID3512S ORF starting with ATG of length 298
ID3513S ORF starting with ATG of length 273
ID3514S ORF starting with ATG of length 339
ID3515S ORF starting with ATG of length 213
ID3516S ORF starting with ATG of length 271
ID3517S ORF starting with ATG of length 384
ID3518S ORF starting with ATG of length 267
ID3519S ORF starting with ATG of length 240
ID3520S ORF starting with ATG of length 249
ID3521S ORF starting with ATG of length 231
ID3522S ORF starting with ATG of length 270
ID3523S ORF starting with ATG of length 437
ID3524S ORF starting with ATG of length 474
ID3525S ORF starting with ATG of length 309
ID3526S ORF starting with ATG of length 273
ID3527S ORF starting with ATG of length 246
ID3528S ORF starting with ATG of length 543
ID3529S ORF starting with ATG of length 318
ID3530S ORF starting with ATG of length 249
ID3531S ORF starting with ATG of length 213
ID3532S ORF starting with ATG of length 260
ID3533S ORF starting with ATG of length 203
ID3534 S ORF starting with ATG of length 243
ID3535S ORF starting with ATG of length 218
ID3536S ORF starting with ATG of length 219
ID3537S ORF starting with ATG of length 219
ID3538S ORF starting with ATG of length 573
ID3539S ORF starting with ATG of length 648
ID3540S ORF starting with ATG of length 204
ID3541S ORF starting with ATG of length 351
ID3542S ORF starting with ATG of length 387
ID3543S ORF starting with ATG of length 267
ID3544 S ORF starting with ATG of length 285
ID3545S ORF starting with ATG of length 337
ID3546S ORF starting with ATG of length 441
ID3547S ORF starting with ATG of length 325
ID3548S ORF starting with ATG of length 226
ID3549S ORF starting with ATG of length 437
ID3550S ORF starting with ATG of length 288
ID3551S ORF starting with ATG of length 306
ID3552 S ORF starting with ATG of length 549
ID3553S ORF starting with ATG of length 375
ID3554 S ORF starting with ATG of length 326
ID3555S ORF starting with ATG of length 339
ID3556S ORF starting with ATG of length 453
ID3557S ORF starting with ATG of length 312
ID3558S ORF starting with ATG of length 354
ID3559S ORF starting with ATG of length 225
ID3560S ORF starting with ATG of length 370
ID3561S ORF starting with ATG of length 273
ID3562 S ORF starting with ATG of length 281
ID3563S ORF starting with ATG of length 240
ID3564 S ORF starting with ATG of length 258
ID3565S ORF starting with ATG of length 347
ID3566S ORF starting with ATG of length 204
ID3567S ORF starting with TTG or GTG of length 485
ID3568S ORF starting with ATG of length 448
ID3569S ORF starting with ATG of length 249
ID3570S ORF starting with ATG of length 366
ID3571S ORF starting with ATG of length 302
ID3572S ORF starting with TTG or GTG of length 408
ID3573S ORF starting with ATG of length 240
ID3574 S ORF starting with ATG of length 273
ID3575S ORF starting with ATG of length 249
ID3576S ORF starting with ATG of length 468
ID3577S ORF starting with ATG of length 339
ID3578S ORF starting with ATG of length 209
ID3579S ORF starting with ATG of length 293
ID3580S ORF starting with ATG of length 207
ID3581S ORF starting with ATG of length 246
ID3582 S ORF starting with ATG of length 258
ID3583S ORF starting with ATG of length 228
ID3584 S ORF starting with ATG of length 213
ID3585S ORF starting with ATG of length 204
ID3586S ORF starting with ATG of length 345
ID3587S ORF starting with ATG of length 561
ID3588S ORF starting with ATG of length 201
ID3589S ORF starting with ATG of length 417
ID3590S ORF starting with ATG of length 376
ID3591S ORF starting with ATG of length 294
ID3592S ORF starting with TTG or GTG of length 408
ID3593S ORF starting with ATG of length 279
ID3594 S ORF starting with ATG of length 427
ID3595S ORF starting with ATG of length 318
ID3596S ORF starting with ATG of length 477
ID3597S ORF starting with ATG of length 297
ID3598S ORF starting with ATG of length 222
ID3599S ORF starting with ATG of length 225
ID3600S ORF starting with ATG of length 270

ID3601S ORF starting with ATG of length 435
ID3602 S ORF starting with ATG of length 474
ID3603S ORF starting with ATG of length 525
ID3604S ORF starting with TTG or GTG of length 510
ID3605S ORF starting with ATG of length 207
ID3606S ORF starting with ATG of length 222
ID3607S ORF starting with ATG of length 474
ID3608S ORF starting with ATG of length 435
ID3609S ORF starting with ATG of length 261
ID3610S ORF starting with ATG of length 287
ID3611S ORF starting with ATG of length 288
ID3612 S ORF starting with ATG of length 212
ID3613S ORF starting with ATG of length 282
ID3614S ORF starting with ATG of length 241
ID3615S ORF starting with ATG of length 243
ID3616S ORF starting with ATG of length 210
ID3617S ORF starting with ATG of length 342
ID3618S ORF starting with ATG of length 250
ID3619S ORF starting with ATG of length 233
ID3620S ORF starting with ATG of length 272
ID3621S ORF starting with ATG of length 558
ID3622S ORF starting with ATG of length 290
ID3623S ORF starting with ATG of length 413
ID3624S ORF starting with ATG of length 213
ID3625S ORF starting with ATG of length 304
ID3626S ORF starting with ATG of length 702
ID3627S ORF starting with ATG of length 351
ID3628S ORF starting with ATG of length 654
ID3629S ORF starting with ATG of length 264
ID3630S ORF starting with ATG of length 264
ID3631S ORF starting with ATG of length 591
ID3632 S ORF starting with ATG of length 318
ID3633S ORF starting with ATG of length 268
ID3634 S ORF starting with ATG of length 525
ID3635S ORF starting with ATG of length 270
ID3636S ORF starting with ATG of length 609
ID3637S ORF starting with ATG of length 267
ID3638S ORF starting with ATG of length 444
ID3639S ORF starting with ATG of length 285
ID3640S ORF starting with ATG of length 307
ID3641S ORF starting with ATG of length 306
ID3642 S ORF starting with ATG of length 397
ID3643S ORF starting with ATG of length 220
ID3644S ORF starting with ATG of length 249
ID3645S ORF starting with TTG or GTG of length 423
ID3646S ORF starting with ATG of length 455
ID3647S ORF starting with ATG of length 227
ID3648S ORF starting with ATG of length 210
ID3649S ORF starting with ATG of length 363
ID3650S ORF starting with ATG of length 366
ID3651S ORF starting with ATG of length 273
ID3652S ORF starting with ATG of length 306
ID3653S ORF starting with TTG or GTG of length 402
ID3654S ORF starting with ATG of length 252
ID3655S ORF starting with ATG of length 231
ID3656S ORF starting with ATG of length 327
ID3657S ORF starting with ATG of length 287
ID3658S ORF starting with ATG of length 204
ID3659S ORF starting with ATG of length 1423
ID3660S ORF starting with ATG of length 309
ID3661S ORF starting with ATG of length 309
ID3662 S ORF starting with ATG of length 525
ID3663S ORF starting with ATG of length 225
ID3664 S ORF starting with ATG of length 360
ID3665S ORF starting with ATG of length 272
ID3666S ORF starting with ATG of length 201
ID3667S ORF starting with ATG of length 339
ID3668S ORF starting with ATG of length 483
ID3669S ORF starting with ATG of length 384
ID3670S ORF starting with ATG of length 225
ID3671S ORF starting with ATG of length 213
ID3672 S ORF starting with ATG of length 234
ID3673S ORF starting with ATG of length 397
ID3674 S ORF starting with ATG of length 348
ID3675S ORF starting with ATG of length 258
ID3676S ORF starting with ATG of length 471
ID3677S ORF starting with ATG of length 213
ID3678S ORF starting with ATG of length 285
ID3679S ORF starting with ATG of length 272
ID3680S ORF starting with ATG of length 357
ID3681S ORF starting with TTG or GTG of length 435
ID3682S ORF starting with ATG of length 729
ID3683S ORF starting with ATG of length 909
ID3684 S ORF starting with ATG of length 276
ID3685S ORF starting with ATG of length 270
ID3686S ORF starting with ATG of length 330
ID3687S ORF starting with ATG of length 310
ID3688S ORF starting with ATG of length 300
ID3689S ORF starting with ATG of length 615
ID3690S ORF starting with ATG of length 381
ID3691S ORF starting with ATG of length 291
ID3692 S ORF starting with ATG of length 207
ID3693S ORF starting with ATG of length 201
ID3694 S ORF starting with ATG of length 801
ID3695S ORF starting with ATG of length 501
ID3696S ORF starting with ATG of length 474
ID3697S ORF starting with ATG of length 255
ID3698S ORF starting with ATG of length 300
ID3699S ORF starting with TTG or GTG of length 558
ID3700S ORF starting with ATG of length 204
ID3701S ORF starting with ATG of length 222
ID3702 S ORF starting with ATG of length 276
ID3703S ORF starting with ATG of length 559
ID3704 S ORF starting with ATG of length 220
ID3705S ORF starting with ATG of length 213
ID3706S ORF starting with ATG of length 375
ID3707S ORF starting with ATG of length 255
ID3708S ORF starting with TTG or GTG of length 435
ID3709S ORF starting with ATG of length 621
ID3710S ORF starting with ATG of length 270
ID3711S ORF starting with ATG of length 204
ID3712 S ORF starting with ATG of length 207
ID3713S ORF starting with ATG of length 204
ID3714S ORF starting with ATG of length 309
ID3715S ORF starting with ATG of length 243
ID3716S ORF starting with ATG of length 819
ID3717S ORF starting with ATG of length 213
ID3718S ORF starting with ATG of length 364
ID3719S ORF starting with ATG of length 345
ID3720S ORF starting with ATG of length 207
ID3721S ORF starting with ATG of length 486
ID3722S ORF starting with ATG of length 351
ID3723S ORF starting with ATG of length 213
ID3724S ORF starting with ATG of length 663
ID3725S ORF starting with ATG of length 525
ID3726S ORF starting with ATG of length 228
ID3727S ORF starting with ATG of length 207
ID3728S ORF starting with ATG of length 375
ID3729S ORF starting with ATG of length 564
ID3730S ORF starting with ATG of length 369
ID3731S ORF starting with ATG of length 230
ID3732 S ORF starting with ATG of length 226
ID3733S ORF starting with ATG of length 654
ID3734 S ORF starting with ATG of length 463

ID3735S ORF starting with ATG of length 444
ID3736S ORF starting with ATG of length 375
ID3737S ORF starting with ATG of length 209
ID3738S ORF starting with ATG of length 236
ID3739S ORF starting with ATG of length 349
ID3740S ORF starting with ATG of length 210
ID3741S ORF starting with ATG of length 215
ID3742 S ORF starting with ATG of length 267
ID3743S ORF starting with ATG of length 220
ID3744S ORF starting with TTG or GTG of length 411
ID3745S ORF starting with ATG of length 231
ID3746S ORF starting with ATG of length 336
ID3747S ORF starting with ATG of length 320
ID3748S ORF starting with ATG of length 492
ID3749S ORF starting with ATG of length 358
ID3750S ORF starting with ATG of length 270
ID3751S ORF starting with ATG of length 441
ID3752 S ORF starting with ATG of length 279
ID3753S ORF starting with ATG of length 493
ID3754 S ORF starting with ATG of length 273
ID3755S ORF starting with ATG of length 384
ID3756S ORF starting with ATG of length 577
ID3757S ORF starting with ATG of length 216
ID3758S ORF starting with ATG of length 278
ID3759S ORF starting with TTG or GTG of length 612
ID3760S ORF starting with TTG or GTG of length 432
ID3761S ORF starting with ATG of length 605
ID3762 S ORF starting with ATG of length 243
ID3763S ORF starting with ATG of length 363
ID3764 S ORF starting with ATG of length 606
ID3765S ORF starting with ATG of length 376
ID3766S ORF starting with ATG of length 279
ID3767S ORF starting with ATG of length 318
ID3768S ORF starting with ATG of length 294
ID3769S ORF starting with ATG of length 557
ID3770S ORF starting with ATG of length 256
ID3771S ORF starting with ATG of length 253
ID3772 S ORF starting with ATG of length 408
ID3773S ORF starting with ATG of length 599
ID3774S ORF starting with ATG of length 259
ID3775S ORF starting with TTG or GTG of length 627
ID3776S ORF starting with ATG of length 492
ID3777S ORF starting with ATG of length 376
ID3778S ORF starting with ATG of length 300
ID3779S ORF starting with ATG of length 204
ID3780S ORF starting with ATG of length 1002
ID3781S ORF starting with ATG of length 325
ID3782S ORF starting with ATG of length 255
ID3783S ORF starting with TTG or GTG of length 633
ID3784S ORF starting with ATG of length 309
ID3785S ORF starting with ATG of length 276
ID3786S ORF starting with ATG of length 559
ID3787S ORF starting with ATG of length 231
ID3788S ORF starting with ATG of length 219
ID3789S ORF starting with ATG of length 216
ID3790S ORF starting with ATG of length 681
ID3791S ORF starting with ATG of length 345
ID3792S ORF starting with ATG of length 301
ID3793S ORF starting with ATG of length 202
ID3794S ORF starting with ATG of length 576
ID3795S ORF starting with ATG of length 327
ID3796S ORF starting with ATG of length 461
ID3797S ORF starting with ATG of length 231
ID3798S ORF starting with ATG of length 765
ID3799S ORF starting with ATG of length 210
ID3800S ORF starting with ATG of length 222
ID3801S ORF starting with ATG of length 300
ID3802S ORF starting with ATG of length 322
ID3803S ORF starting with ATG of length 213
ID3804S ORF starting with ATG of length 798
ID3805S ORF starting with ATG of length 537
ID3806S ORF starting with ATG of length 258
ID3807S ORF starting with ATG of length 216
ID3808S ORF starting with ATG of length 224
ID3809S ORF starting with ATG of length 426
ID3810S ORF starting with ATG of length 339
ID3811S ORF starting with ATG of length 218
ID3812S ORF starting with ATG of length 495
ID3813S ORF starting with ATG of length 309
ID3814S ORF starting with ATG of length 225
ID3815S ORF starting with ATG of length 210
ID3816S ORF starting with ATG of length 954
ID3817S ORF starting with ATG of length 243
ID3818S ORF starting with ATG of length 336
ID3819S ORF starting with ATG of length 388
ID3820S ORF starting with ATG of length 335
ID3821S ORF starting with ATG of length 226
ID3822S ORF starting with ATG of length 279
ID3823S ORF starting with ATG of length 237
ID3824S ORF starting with ATG of length 339
ID3825S ORF starting with ATG of length 447
ID3826S ORF starting with ATG of length 246
ID3827S ORF starting with ATG of length 366
ID3828S ORF starting with ATG of length 266
ID3829S ORF starting with ATG of length 243
ID3830S ORF starting with ATG of length 954
ID3831S ORF starting with ATG of length 270
ID3832S ORF starting with ATG of length 306
ID3833S ORF starting with ATG of length 366
ID3834S ORF starting with ATG of length 204
ID3835S ORF starting with ATG of length 342
ID3836S ORF starting with ATG of length 339
ID3837S ORF starting with ATG of length 243
ID3838S ORF starting with ATG of length 360
ID3839S ORF starting with ATG of length 301
ID3840S ORF starting with ATG of length 228
ID3841S ORF starting with ATG of length 465
ID3842S ORF starting with ATG of length 1182
ID3843S ORF starting with ATG of length 516
ID3844S ORF starting with ATG of length 204
ID3845S ORF starting with ATG of length 1000
ID3846S ORF starting with ATG of length 207
ID3847S ORF starting with ATG of length 285
ID3848S ORF starting with ATG of length 339
ID3849S ORF starting with ATG of length 447
ID3850S ORF starting with ATG of length 282
ID3851S ORF starting with ATG of length 819
ID3852T PUTATIVE SIGMA-B REGULATOR.
ID3853T NEGATIVE REGULATOR OF SIGMA-B ACTIVITY (ANTAGONIST OF RSBT).
ID3854T POSITIVE REGULATOR OF SIGMA-B ACTIVITY (SWITCH PROTEIN/SERIN
ID3855T ANTI-SIGMA F FACTOR (STAGE II SPORULATION PROTEIN AB).
ID3856T ANTI-SIGMA F FACTOR ANTAGONIST (STAGE II SPORULATION PROTEIN
ID3857T GENERAL STRESS PROTEIN 160 (GSP16O).
ID3858T TWO-COMPONENT SENSOR HISTIDINE KINASE INVOLVED IN DEGRADATIV
ID3859T TRANSCRIPTIONAL REGULATOR.
ID3860T TWO-COMPONENT SENSOR HISTIDINE KINASE INVOLVED IN PHOSPHATER
ID3861T SERINE PROTEIN KINASE.
ID3862T SERINE/THREONINE-PROTEIN KINASE.

ID3863T ARSENATE REDUCTASE (EC 1.).
ID3864T CONSERVED HYPOTHETICAL PROTEIN.
ID3865T CARBON STARVATION PROTEIN A HOMOLOG.
ID3866T POLAR FLAGELLAR PROTEIN.
ID3867T TWO-COMPONENT SENSOR HISTIDINE KINASE.
ID3868T CARBON STARVATION PROTEIN A HOMOLOG.
ID3869T CITS (TWO-COMPONENT SENSOR HISTIDINE KINASE).
ID3870T KIN1PROTEIN (PUTATIVE SENSORY TRANSDUCTION HISTIDINE KINASE
ID3871T TWO-COMPONENT SENSOR HISTIDINE KINASE.
ID3872T BH0289 PROTEIN.
ID3873T TWO-COMPONENT SENSOR HISTIDINE KINASE.
ID3874T ARSENATE REDUCTASE (ARSENICAL PUMP MODIFIER).
ID3875T BH1859 PROTEIN.
ID3876T TWO-COMPONENT RESPONSE REGULATOR INVOLVED IN MODULATION OF F
ID3877T ORF starting with ATG of length 709
ID3878T TRANSCRIPTIONAL REGULATOR.
ID3879T ORF starting with ATG of length 1347
ID3880T PUTATIVE INTEGRAL MEMBRANE PROTEIN (CSTA-LIKE).
ID3881T TWO-COMPONENT SENSOR HISTIDINE KINASE.
ID3882T CHEMOTAXIS CHEV PROTEIN (EC 2.7.3.-).
ID3883T SUBTILIN BIOSYNTHESIS SENSOR PROTEIN SPAK (EC 2.7.3.-).
ID3884T NEGATIVE REGULATOR OF SIGMA-B ACTIVITY (SWITCH PROTEIN/SERIN
ID3885T TWO-COMPONENT SENSOR HISTIDINE KINASE.
ID3886T BH3353 PROTEIN.
ID3887T SERINE PROTEIN KINASE.
ID3888T BH2734 PROTEIN.
ID3889T BH3833 PROTEIN.
ID3890T VPSR.
ID3891T NTRB, NTRC.
ID3892T ORF starting with ATG of length 1557
ID3893T YVQE PROTEIN.
ID3894T HYPOTHETICAL 40.2 KDA PROTEIN.
ID3895T TWO-COMPONENT SENSOR HISTIDINE KINASE.
ID3896T TRANSCRIPTIONAL REGULATOR.
ID3897T SERINE PROTEIN KINASE.
ID3898T HYPOTHETICAL 58.9 KDA PROTEIN.
ID3899T NEGATIVE REGULATOR OF SIGMA-B ACTIVITY (SWITCH PROTEIN/SERIN
ID3900T YLAK PROTEIN.
ID3901T TWO-COMPONENT RESPONSE REGULATOR.
ID3902T YTAB PROTEIN.
ID3903T SERINE/THREONINE PROTEIN KINASE.
ID3904T TWO-COMPONENT SENSOR HISTIDINE KINASE.
ID3905T CARBON STARVATION PROTEIN A, PUTATIVE.
ID3906T AUTOLYSIN RESPONSE REGULATOR.
ID3907T BH3353 PROTEIN.
ID3908T YLOO PROTEIN.
ID3909T YTAB PROTEIN.
ID3910T KIN1PROTEIN (PUTATIVE SENSORY TRANSDUCTION HISTIDINE KINASE
ID3911T ORF4 PROTEIN.
ID3912T BH2734 PROTEIN.
ID3913T TWO-COMPONENT SENSOR HISTIDINE KINASE.
ID3914T SUBTILIN BIOSYNTHESIS SENSOR PROTEIN SPAK (EC 2.7.3.-).
ID3915TK PUTATIVE TWO-COMPONENT RESPONSE REGULATOR.
ID3916TK GTP PYROPHOSPHOKINASE (STRINGENT RESPONSE).
ID3917TK TWO-COMPONENT RESPONSE REGULATOR INVOLVED IN PHOSPHATE REGUL
ID3918TK TRANSCRIPTIONAL REGULATORY PROTEIN DEGU.
ID3919TK STAGE II SPORULATION PROTEIN E.
ID3920TK *Mycobacterium bovis* regX3 protein.
ID3921TK TWO-COMPONENT RESPONSE REGULATOR.
ID3922TK TWO-COMPONENT RESPONSE REGULATOR.
ID3923TK TWO-COMPONENT RESPONSE REGULATOR.
ID3924TK TWO-COMPONENT RESPONSE REGULATOR.
ID3925TK STAGE II SPORULATION PROTEIN E.
ID3926TK TWO-COMPONENT RESPONSE REGULATOR.
ID3927TK TWO-COMPONENT RESPONSE REGULATOR.
ID3928TK SUBTILIN BIOSYNTHESIS REGULATORY PROTEIN SPAR.
ID3929TK INDIRECT POSITIVE REGULATOR OF SIGMA-B ACTIVITY (SERINE PHOS
ID3930TK TWO-COMPONENT RESPONSE REGULATOR.
ID3931TK TWO-COMPONENT RESPONSE REGULATOR.
ID3932TK TWO-COMPONENT RESPONSE REGULATOR.
ID3933TK PUTATIVE RESPONSE REGULATOR.
ID3934TK STAGE II SPORULATION PROTEIN E.
ID3935TK *Staphylococcus aureus* protein SEQ ID #5239.
ID3936TK GTP PYROPHOSPHOKINASE (STRINGENT RESPONSE).
ID3937TQ ORF starting with ATG of length 453
ID3938TQ ORF starting with ATG of length 636
ID3939TQ YUK[A,B,C,D,E,F], YUK[I,J,K,L,M] AND ALD GENES.
ID3940TQ BH2731PROTEIN.
ID3941TQ BH1735 PROTEIN.
ID3942TQ BH0757 PROTEIN.
ID3943TQ ORF starting with ATG of length 975
ID3944TQ YUK[A,B,C,D,E,F], YUK[I,J,K,L,M] AND ALD GENES.
ID3945TQ ORF starting with ATG of length 513
ID3946TQ ACETOIN DEHYDROGENASE.
ID3947TQ BH1735 PROTEIN.
ID3948Z transfer RNA-Ala
ID3949Z transfer RNA-Ile
ID3950Z transfer RNA-Ala
ID3951Z transfer RNA-Arg
ID3952Z transfer RNA-Asn
ID3953Z transfer RNA-Asp
ID3954Z transfer RNA-Glu
ID3955Z transfer RNA-Gly ID3956Z transfer RNA-Gly
ID3957Z transfer RNA-His
ID3958Z transfer RNA-Ile
ID3959Z transfer RNA-Leu
ID3960Z transfer RNA-Leu
ID3961Z transfer RNA-Lys
ID3962Z transfer RNA-Met
ID3963Z transfer RNA-Met
ID3964Z transfer RNA-Met
ID3965Z transfer RNA-Phe
ID3966Z transfer RNA-Pro
ID3967Z transfer RNA-Ser
ID3968Z transfer RNA-Ser
ID3969Z transfer RNA-Thr
ID3970Z transfer RNA-Val
ID3971Z transfer RNA-Asn
ID3972Z transfer RNA-Asp
ID3973Z transfer RNA-Cys
ID3974 Z transfer RNA-Gln
ID3975Z transfer RNA-Glu
ID3976Z transfer RNA-Gly
ID3977Z transfer RNA-His
ID3978Z transfer RNA-Leu
ID3979Z transfer RNA-Leu
ID3980Z transfer RNA-Met
ID3981Z transfer RNA-Phe
ID3982 Z transfer RNA-Ser
ID3983Z transfer RNA-Thr
ID3984 Z transfer RNA-Trp
ID3985Z transfer RNA-Val
ID3986Z transfer RNA-Arg
ID3987Z transfer RNA-Asp
ID3988Z transfer RNA-Gly
ID3989Z transfer RNA-Met
ID3990Z transfer RNA-Ala
ID3991Z transfer RNA-Arg
ID3992 Z transfer RNA-Asn
ID3993Z transfer RNA-Gly
ID3994 Z transfer RNA-Pro
ID3995Z transfer RNA-Thr
ID3996Z transfer RNA-Ala
ID3997Z transfer RNA-Arg
ID3998Z transfer RNA-Gly
ID3999Z transfer RNA-Leu
ID4000Z transfer RNA-Leu
ID4001Z transfer RNA-Lys
ID4002 Z transfer RNA-Pro
ID4003Z transfer RNA-Thr
ID4004 Z transfer RNA-Val
ID4005Z transfer RNA-Ala
ID4006Z transfer RNA-Ile
ID4007Z transfer RNA-Arg
ID4008Z transfer RNA-Asn
ID4009Z transfer RNA-Gln
ID4010Z transfer RNA-Glu
ID4011Z transfer RNA-Leu
ID4012Z transfer RNA-Leu
ID4013Z transfer RNA-Lys
ID4014Z transfer RNA-Ser
ID4015Z transfer RNA-Ala
ID4016Z transfer RNA-Arg
ID4017Z transfer RNA-Gln
ID4018Z transfer RNA-Gln
ID4019Z transfer RNA-Glu
ID4020Z transfer RNA-Glu
ID4021Z transfer RNA-Gly
ID4022 Z transfer RNA-Met
ID4023Z transfer RNA-Ser
ID4024Z transfer RNA-Thr
ID4025Z transfer RNA-Val
ID4026Z transfer RNA-Val
ID4027Z transfer RNA-Asp
ID4028Z transfer RNA-Glu
ID4029Z transfer RNA-Lys
ID4030Z transfer RNA-Phe
ID4031Z ribosomal RNA-16S
ID4032Z ribosomal RNA-23S
ID4033Z ribosomal RNA-5S

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08362221B2). An electronic copy of the "Sequence Listing" will also be available from the USPTO upon request and payment of the fee set forth in 37 CFR 1.19(b)(3).

What is claimed is:

1. An isolated nucleic acid which encodes a protein having aspartate 1-decarboxylase activity, wherein the nucleic acid sequence has at least 95% sequence homology to SEQ ID NO: 1042.

2. The isolated nucleic acid of claim 1, wherein the nucleic acid sequence comprises SEQ ID NO: 1042.

3. The isolated nucleic acid of claim 1, wherein the nucleic acid sequence is obtained from *Bacillus*.

4. The isolated nucleic acid of claim 3, wherein the nucleic acid sequence is obtained from *Bacillus licheniformis*.

5. A cell comprising the isolated nucleic acid of claim 1.

6. The cell of claim 5, wherein the isolated nucleic acid is transformed into the cell.

7. The cell of claim 5, wherein the cell exhibits increased aspartate 1-decarboxylase activity.

8. An isolated nucleic acid which encodes a protein having aspartate 1-decarboxylase activity, wherein the nucleic acid hybridizes under very high stringency conditions to the complementary strand of SEQ ID NO: 1042.

9. The isolated nucleic acid of claim 8, wherein the nucleic acid sequence is obtained from *Bacillus*.

10. The isolated nucleic acid of claim 8, wherein the nucleic acid sequence is obtained from *Bacillus licheniformis*.

11. A cell comprising the isolated nucleic acid of claim 8.

12. The cell of claim 11, wherein the isolated nucleic acid is transformed into the cell.

13. The cell of claim 11, wherein the cell exhibits increased aspartate 1-decarboxylase activity.

* * * * *